(12) United States Patent
Desai et al.

(10) Patent No.: US 9,149,455 B2
(45) Date of Patent: Oct. 6, 2015

(54) METHODS OF TREATING MELANOMA

(71) Applicant: Abraxis BioScience, LLC, Los Angeles, CA (US)

(72) Inventors: Neil P. Desai, Los Angeles, CA (US); Markus Renschler, San Francisco, CA (US)

(73) Assignee: ABRAXIS BIOSCIENCE, LLC, Los Angeles, CA (US)

( * ) Notice: Subject to any disclaimer, the term of this patent is extended or adjusted under 35 U.S.C. 154(b) by 32 days.

(21) Appl. No.: 13/791,841

(22) Filed: Mar. 8, 2013

(65) Prior Publication Data

US 2014/0134257 A1 May 15, 2014

Related U.S. Application Data

(60) Provisional application No. 61/724,892, filed on Nov. 9, 2012, provisional application No. 61/763,391, filed on Feb. 11, 2013.

(51) Int. Cl.

| | |
|---|---|
| A61K 31/337 | (2006.01) |
| A61K 38/38 | (2006.01) |
| A61P 35/00 | (2006.01) |
| C07K 16/22 | (2006.01) |
| C07K 16/28 | (2006.01) |
| C07K 16/30 | (2006.01) |
| A61K 9/00 | (2006.01) |
| A61K 9/51 | (2006.01) |
| A61K 39/00 | (2006.01) |

(52) U.S. Cl.
CPC .............. *A61K 31/337* (2013.01); *A61K 9/0019* (2013.01); *A61K 9/5169* (2013.01); *C07K 16/22* (2013.01); *C07K 16/2818* (2013.01); *C07K 16/3053* (2013.01); *A61K 2039/505* (2013.01)

(58) Field of Classification Search
CPC .. A61K 31/337; A61K 9/0019; A61K 9/5169
See application file for complete search history.

(56) References Cited

U.S. PATENT DOCUMENTS

| | | |
|---|---|---|
| 5,362,478 A | 11/1994 | Desai et al. |
| 5,439,686 A | 8/1995 | Desai et al. |
| 5,498,421 A | 3/1996 | Grinstaff et al. |
| 5,505,932 A | 4/1996 | Grinstaff et al. |
| 5,508,021 A | 4/1996 | Grinstaff et al. |
| 5,512,268 A | 4/1996 | Grinstaff et al. |
| 5,560,933 A | 10/1996 | Soon-Shiong et al. |

(Continued)

FOREIGN PATENT DOCUMENTS

| | | |
|---|---|---|
| WO | WO 94/18954 A1 | 9/1994 |
| WO | WO 98/14174 A1 | 4/1998 |

(Continued)

OTHER PUBLICATIONS

Si et al, "Prevalence of BRAF V600E Mutation in Chinese Melanoma Patients: Large Scale Analysis of BRAF and NRAS Mutations in a 432-Case Cohort", European Journal of Cancer 48, Jan. 2012, pp. 94-100, Available online: Jul. 23, 2011.*

(Continued)

*Primary Examiner* — Rachael E Bredefeld
(74) *Attorney, Agent, or Firm* — Morrison & Foerster LLP

(57) ABSTRACT

Provided herein are methods for the treatment of melanoma comprising administration of a composition comprising nanoparticles comprising taxane and a carrier protein.

16 Claims, 4 Drawing Sheets

(56) References Cited

U.S. PATENT DOCUMENTS

| | | |
|---|---|---|
| 5,635,207 A | 6/1997 | Grinstaff et al. |
| 5,639,473 A | 6/1997 | Grinstaff et al. |
| 5,650,156 A | 7/1997 | Grinstaff et al. |
| 5,665,382 A | 9/1997 | Grinstaff et al. |
| 5,665,383 A | 9/1997 | Grinstaff et al. |
| 5,916,596 A | 6/1999 | Desai et al. |
| 5,997,904 A | 12/1999 | Magdassi et al. |
| 6,096,331 A | 8/2000 | Desai et al. |
| 6,506,405 B1 | 1/2003 | Desai et al. |
| 6,528,067 B1 | 3/2003 | Magdassi et al. |
| 6,537,579 B1 | 3/2003 | Desai et al. |
| 6,565,842 B1 | 5/2003 | Desai et al. |
| 6,652,884 B2 | 11/2003 | Falciani |
| 6,749,868 B1 | 6/2004 | Desai et al. |
| 6,753,006 B1 | 6/2004 | Desai et al. |
| 7,758,891 B2 | 7/2010 | Desai et al. |
| 7,771,751 B2 | 8/2010 | Desai et al. |
| 7,780,984 B2 | 8/2010 | Desai et al. |
| 7,820,788 B2 | 10/2010 | Desai et al. |
| 7,923,536 B2 | 4/2011 | Desai et al. |
| 7,981,445 B2 | 7/2011 | De et al. |
| 8,034,375 B2 | 10/2011 | Desai et al. |
| 8,034,765 B2 | 10/2011 | De et al. |
| 8,137,684 B2 | 3/2012 | Desai et al. |
| 8,138,229 B2 | 3/2012 | Desai et al. |
| 8,257,733 B2 | 9/2012 | Desai et al. |
| 8,268,348 B2 | 9/2012 | Desai et al. |
| 8,314,156 B2 | 11/2012 | Desai et al. |
| 8,735,394 B2 | 5/2014 | Desai et al. |
| 8,846,771 B2 | 9/2014 | Desai et al. |
| 8,853,260 B2 | 10/2014 | Desai et al. |
| 8,911,786 B2 | 12/2014 | Desai et al. |
| 8,927,019 B2 | 1/2015 | Desai et al. |
| 8,999,396 B2 | 4/2015 | Desai et al. |
| 2003/0185894 A1 | 10/2003 | Zenoni et al. |
| 2003/0187062 A1 | 10/2003 | Zenoni et al. |
| 2003/0199425 A1 | 10/2003 | Desai et al. |
| 2005/0004002 A1 | 1/2005 | Desai et al. |
| 2006/0263434 A1 | 11/2006 | Desai et al. |
| 2007/0082838 A1 | 4/2007 | De et al. |
| 2007/0093547 A1 | 4/2007 | Desai et al. |
| 2008/0280987 A1 | 11/2008 | Desai et al. |
| 2009/0263483 A1 | 10/2009 | Desai et al. |
| 2009/0304805 A1 | 12/2009 | Desai et al. |
| 2010/0048499 A1 | 2/2010 | Desai et al. |
| 2010/0166869 A1 | 7/2010 | Desai et al. |
| 2010/0183728 A1 | 7/2010 | Desai et al. |
| 2010/0215751 A1 | 8/2010 | Desai et al. |
| 2010/0297243 A1 | 11/2010 | Desai et al. |
| 2011/0052708 A1 | 3/2011 | Soon-Shiong et al. |
| 2011/0118342 A1 | 5/2011 | De et al. |
| 2011/0151012 A1 | 6/2011 | Desai et al. |
| 2012/0070502 A1 | 3/2012 | Desai et al. |
| 2012/0076862 A1 | 3/2012 | Desai et al. |
| 2012/0128732 A1 | 5/2012 | Trieu et al. |
| 2012/0189701 A1 | 7/2012 | Desai et al. |
| 2012/0231082 A1 | 9/2012 | Desai et al. |
| 2012/0283205 A1 | 11/2012 | Desai et al. |
| 2012/0308612 A1 | 12/2012 | De et al. |
| 2013/0045240 A1 | 2/2013 | Tao et al. |
| 2013/0071438 A1 | 3/2013 | Desai et al. |
| 2013/0115296 A1 | 5/2013 | Yeo et al. |
| 2013/0195922 A1 | 8/2013 | Desai et al. |
| 2013/0195983 A1 | 8/2013 | Desai et al. |
| 2013/0195984 A1 | 8/2013 | Desai et al. |
| 2013/0202709 A1 | 8/2013 | Desai et al. |
| 2013/0209518 A1 | 8/2013 | Desai et al. |
| 2013/0244952 A1 | 9/2013 | Desai et al. |
| 2013/0266659 A1 | 10/2013 | Desai et al. |
| 2013/0280336 A1 | 10/2013 | Desai et al. |
| 2013/0280337 A1 | 10/2013 | Desai et al. |
| 2014/0017315 A1 | 1/2014 | Desai et al. |
| 2014/0017316 A1 | 1/2014 | Desai et al. |
| 2014/0017323 A1 | 1/2014 | Desai et al. |
| 2014/0023717 A1 | 1/2014 | Desai et al. |
| 2014/0039069 A1 | 2/2014 | Desai et al. |
| 2014/0039070 A1 | 2/2014 | Desai et al. |
| 2014/0056986 A1 | 2/2014 | Desai et al. |
| 2014/0072630 A1 | 3/2014 | Tao et al. |
| 2014/0072631 A1 | 3/2014 | Trieu et al. |
| 2014/0072643 A1 | 3/2014 | Desai et al. |
| 2014/0079787 A1 | 3/2014 | Yeo et al. |
| 2014/0079788 A1 | 3/2014 | Desai et al. |
| 2014/0079793 A1 | 3/2014 | Desai et al. |
| 2014/0080901 A1 | 3/2014 | Desai et al. |
| 2014/0155344 A1 | 6/2014 | Desai et al. |
| 2014/0170228 A1 | 6/2014 | Desai et al. |
| 2014/0186447 A1 | 7/2014 | Desai |
| 2014/0199403 A1 | 7/2014 | Desai et al. |
| 2014/0199404 A1 | 7/2014 | Heise |
| 2014/0199405 A1 | 7/2014 | Pierce et al. |
| 2014/0271871 A1 | 9/2014 | Desai et al. |
| 2014/0296279 A1 | 10/2014 | Seward et al. |
| 2014/0296353 A1 | 10/2014 | Desai et al. |
| 2014/0302157 A1 | 10/2014 | Desai et al. |
| 2015/0050356 A1 | 2/2015 | Desai et al. |
| 2015/0079181 A1 | 3/2015 | Desai et al. |

FOREIGN PATENT DOCUMENTS

| | | |
|---|---|---|
| WO | WO 98/14175 A1 | 4/1998 |
| WO | WO 99/00113 A1 | 1/1999 |
| WO | WO-00/64437 A1 | 11/2000 |
| WO | WO 00/71079 A2 | 11/2000 |
| WO | WO 00/71079 A3 | 11/2000 |
| WO | WO 01/89522 A1 | 11/2001 |
| WO | WO 02/087545 A1 | 11/2002 |
| WO | WO 03/096944 A1 | 11/2003 |
| WO | WO 2004/052401 A2 | 6/2004 |
| WO | WO 2004/052401 A3 | 6/2004 |
| WO | WO-2006/089290 A1 | 8/2006 |
| WO | WO 2007/027819 A2 | 3/2007 |
| WO | WO 2007/027819 A3 | 3/2007 |
| WO | WO 2007/027941 A2 | 3/2007 |
| WO | WO 2007/027941 A3 | 3/2007 |
| WO | WO-2007/139930 A2 | 12/2007 |
| WO | WO-2007/139930 A3 | 12/2007 |
| WO | WO 2008/027055 A1 | 3/2008 |
| WO | WO-2008/057562 A1 | 5/2008 |
| WO | WO 2008/076373 A1 | 6/2008 |
| WO | WO 2008/109163 A1 | 9/2008 |
| WO | WO-2008/137148 A2 | 11/2008 |
| WO | WO-2008/137148 A3 | 11/2008 |
| WO | WO 2008/150532 A1 | 12/2008 |
| WO | WO 2009/126175 A1 | 10/2009 |
| WO | WO 2009/126401 A1 | 10/2009 |
| WO | WO 2009/126938 A1 | 10/2009 |
| WO | WO-2010/068925 A1 | 6/2010 |
| WO | WO 2010/105172 A1 | 9/2010 |
| WO | WO 2010/118365 A1 | 10/2010 |
| WO | WO 2010/121000 A1 | 10/2010 |
| WO | WO-2011/025838 A1 | 3/2011 |
| WO | WO-2011/119988 A1 | 9/2011 |
| WO | WO-2011/123393 A1 | 10/2011 |
| WO | WO-2011/123395 A1 | 10/2011 |
| WO | WO-2011/153009 A1 | 12/2011 |
| WO | WO-2011/153010 A1 | 12/2011 |
| WO | WO-2011/156119 A1 | 12/2011 |
| WO | WO-2012/048223 A1 | 4/2012 |
| WO | WO-2012/149451 A1 | 11/2012 |
| WO | WO-2013/090634 A1 | 6/2013 |
| WO | WO-2014/105644 A1 | 7/2014 |
| WO | WO-2014/110345 A1 | 7/2014 |
| WO | WO-2014/110408 A1 | 7/2014 |
| WO | WO-2014/110443 A1 | 7/2014 |
| WO | WO-2014/123612 A1 | 8/2014 |
| WO | WO-2014/143613 A1 | 9/2014 |
| WO | WO-2014/151853 A1 | 9/2014 |
| WO | WO-2014/159171 A1 | 10/2014 |

OTHER PUBLICATIONS

Miele et al,"Albumin-Bound Formulation of Paclitaxel (Abraxane ABI-007) in the Treatment of Breast Cancer", International Journal of Nanomedicine, 2009: 4, pp. 99-105.*

(56) References Cited

OTHER PUBLICATIONS

Altmayer, P. et al. (Oct. 1995). "Propofol Binding to Human Blood Patients," *Arzneim.-Forsch./Drug Res.* 45:1053-1056.

Atkins, M et al. (Jul. 1999). "High-Dose Recombinant Interleukin 2 Therapy for Patients With Metastatic Melanoma: Analysis of 270 Patients Treated Between 1985 and 1993," *Journal of Clinical Oncology* 17(7):2105-2116.

Balch, C.M. et al. (Dec. 20, 2009). "Final Version of 2009 AJCC Melanoma Staging and Classification," *Journal of Clinical Oncology* 27(36):6199-6206.

Butte, M.J. et al. (Jul. 2007). "PD-L1 Interacts Specifically with B7-1 to Inhibit T Cell Proliferation," *Immunity* 27(1):111-122, 22 pages.

Carter, D.C. et al. (1994). "Structure of Serum Albumin," *Adv. Protein. Chem.* 45:153-203.

Chemnitz, J.M. et al. (2004). "SHP-1 and SHP-2 Associate With Immunoreceptor Tyrosine-Based Switch Motif of Programmed Death 1 Upon Primary Human T Cell Stimulation, but Only Receptor Ligation Prevents T Cell Activation," *J. Immunol.* 173:945-954.

Curry, S. et al. (Sep. 1998). "Crystal Structure of Human Serum Albumin Complexed With Fatty Acid Reveals an Asymmetric Distribution of Binding Sites," *Nat. Struct. Biol.* 5(9):827-835.

Davies, H. et al. (Jun. 2002). "Mutations of the *BRAF* Gene in Human Cancer," *Nature* 417:949-954.

Eisenhauer, E.A. et al. (2009). "New Response Evaluation Criteria in Solid Tumours: Revised RECIST Guideline (version 1.1)," *Eur. J Cancer* 45(2):228-247.

Fehske, K.J. et al. (1981). "The Location of Drug Binding Sites in Human Serum Albumin," *Biochem. Pharmcol.* 30(7):687-692.

Finlayson, J.S. (1980). "Albumin Products," *Seminars in Thrombosis and Hemostasis* 6(2):85-120.

Finn, L. et al. (2012). "Therapy for Metastatic Melanoma: The Past, Present, and Future," *BMC Medicine* 10(23):1-10.

Garrido, M.J. et al. (1994). "Binding Characteristics of Propofol to Plasma Proteins and Possible Interactions," *Rev. Esp. Anestestiol. Reanim.* 41:308-312.

Hauser, C.J. et al. (Jun. 1980). "Oxygen Transport Responses to Colloids and Crystalloids in Critically Ill Surgical Patients," *Surgery, Gynecology and Obstetrics* 150(6):811-816.

He, A.M. et al. (Jul. 16, 1992). "Atomic Structure and Chemistry of Human Serum Albumin," *Nature* 358:209-215.

Hersh, E.M. et al. (Jan. 1, 2010). "A Phase 2 Clinical Trial of nab-Paclitaxel in Previously Treated and Chemotherapy-Naive Patients With Metastatic Melanoma," *Cancer* 116:155-163.

Hill, G. et al. (Mar. 15, 1984). "Dimethyl Triazeno imidazole Carboxamide and Combination Therapy for Melanoma," *Cancer* 53(6):1299-1305.

Hurst, E.A. et al. (Aug. 2003). "Ocular Melanoma. A Review and the Relationship to Cutaneous Melanoma," *Archives of Dermatology Research* 139: 1067-1073.

Kottschade, L.A. et al. (Apr. 15, 2011, e-pub. Nov. 8, 2010). "A Phase II Trial of Nab-Paclitaxel (ABI-007) and Carboplatin in Patients With Unresectable Stage IV Melanoma,", *Cancer* 117:1704-1710.

Kottschade, L.A. et al. (Feb. 1, 2013, e-pub. Aug. 22, 2012). "A Randomized Phase 2 Study of Temozolomide and Bevacizumab or nab-Paclitaxel, Carboplatin, and Bevacizumab in Patients With Unresectable Stage IV Melanoma", *Cancer* 119(3):586-592.

Kragh-Hansen, U. (Feb. 1990). "Structure and Ligand Binding Properties of Human Serum Albumin," *Dan. Med. Bull.* 37(1):57-84.

Nishimura, H. et al. (1996). "Developmentally Regulated Expression of the PD-1 Protein on the Surface of Double-Negative (CD4⁻CD8⁻) Thymocytes," *Int. Immunol.* 8(5):773-780.

Nishimura, H. et al. (Aug. 1999). "Development of Lupus-Like Autoimmune Diseases by Disruption of the *PD-1* Gene Encoding an ITIM Motif-Carrying Immunoreceptor," *Immunity* 11:141.

Nishimura, H. et al. (Jan. 12, 2001). "Autoimmune Dilated Cardiomyopathy in PD-1 Receptor-Deficient Mice," *Science* 291:319-322.

Ott, P. A. et al. (2012, e-pub. Oct. 12, 2012). "Oblimersen in Combination With Temozolomide and Albumin-Bound Paclitaxel in Patients With Advanced Melanoma: A Phase I Trial," *Cancer Chemother. Pharmacol.* 71:183-191.

Paál, K. et al. (2001). "High Affinity Binding of Paclitaxel to Human Serum Albumin," *Eur. J. Biochem.* 268(7):2187-2191.

Phan, G. et al. (Aug. 1, 2001). "Factors Associated with Responses to High-Dose interleukin-2 in Patients With Metastatic Melanoma," *Journal of Clinical Oncology* 19(15): 3477-3482.

Purcell, M. et al. (2000). "Interaction of Taxol With Human Serum Albumin," *Biochim. Biophys. Acta* 1478:61-68.

SEER Cancer Statistics Review. (2012). Surveillance Epidemiology and End Results Cancer Statistics Review 2005-2009, last visited on Oct. 6, 2012, located at <http://seer.cancer.gov/csr/1975_2009_pops09/results_single/sect_01_table.01.pdf>, 1 page.

Spagnolo, F. et al. (2012). "Upcoming Strategies for the Treatment of Metastatic Melanoma," *Archives of Dermatology Research* 304:177-184.

Subudhi, S.K. et al. (Mar. 2004). "Local Expression of B7-H1 Promotes Organ-Specific Autoimmunity and Transplant Rejection," *J. Clin. Invest.* 113(5):694-700.

Sugio, S. et al. (1999). "Crystal Structure of Human Serum Albumin at 2.5 Å Resolution," *Protein. Eng.* 12(6):439-446.

Tamura, H. et al. (Mar. 2001)."B7-H1 Costimulation Preferentially Enhances CD28-Independent T-Helper Cell Function," *Blood* 97(6):1809-1816.

Tullis, J.L. (Jan. 24, 1977). "Albumin 1. Background and Use," *JAMA* 237(4):355-360.

Tullis, J.L. (Jan. 31, 1977). "Albumin 2. Guidelines for Clinical Use," *JAMA* 237(5):460-463.

Urien, S. et al. (May 1996). "Docetaxel Serum Protein Binding With High Affinity to Alpha$_1$-Acid Glycoprotein," *Invest. New Drugs* 14:147-151.

Villanueva, J. et al. (Dec. 14, 2010). "Acquired Resistance to BRAF Inhibitors Medicated by a RAF Kinase Switch in Melanoma Can be Overcome by Co-Targeting MEK and IGF-1R/PI3K," *Cell* 18(6): 683-695, 1-25 pages.

Vorum, H. (Nov. 1999). "Reversible Ligand Binding to Human Serum Albumin," *Dan. Med. Bull.* 5(46):379-399.

Yamazaki, T. et al. (2002). "Expression of Programmed Death 1 Ligands by Murine T Cells and APC," *J. Immunol.* 169:5538-5545.

Non-Final Office Action mailed on Feb. 13, 2014, for U.S. Appl. No. 13/781,479, filed Feb. 28, 2013, 39 Pages.

International Search Report mailed on Feb. 27, 2014, for PCT Patent Application No. PCT/US2013/072877, filed on Dec. 3, 2013, ten pages.

US 8,968,752, 3/2015, Desai et al. (withdrawn).

U.S. Appl. No. 14/273,319, filed May 8, 2014, for Desai et al.

U.S. Appl. No. 14/362,382, filed Jun. 2, 2014, for Foss et al.

U.S. Appl. No. 14/468,127, filed Aug. 25, 2014, for Desai et al. 2.

U.S. Appl. No. 14/505,452, filed Oct. 2, 2014, for Desai et al.

U.S. Appl. No. 14/626,678, filed Feb. 19, 2015, by Desai et al.

U.S. Appl. No. 14/631,671, filed Feb. 25, 2015, by Desai et al.

U.S. Appl. No. 14/660,872, filed Mar. 17, 2015, by Desai et al.

Non-Final Office Action mailed on Feb. 11, 2015, for U.S. Appl. No. 13/701,001, Internationally filed on May 20, 2011, 15 pages.

Non-Final Office Action mailed on Feb. 12, 2015, for U.S. Appl. No. 13/782,992, filed Mar. 1, 2013, 15 pages.

Final Office Action mailed on Jul. 10, 2015, for U.S. Appl. No. 13/263,723, filed May 4, 2012, 42 pages.

U.S. Appl. No. 14/714,131, filed May 15, 2015, by Seward et al.

\* cited by examiner

METHODS OF TREATING MELANOMA

RELATED APPLICATIONS

This application claims priority from U.S. Provisional Patent Application No. 61/724,892, filed Nov. 9, 2012, and U.S. Provisional Patent Application No. 61/763,391, filed Feb. 11, 2013, the contents of which are incorporated herein by reference in its entirety.

TECHNICAL FIELD

The present invention relates to methods, compositions, and kits for the treatment of melanoma by administering compositions comprising nanoparticles comprising taxane and a carrier protein.

BACKGROUND

Melanoma is a cancer characterized by the uncontrolled growth of pigment-producing cells (melanocytes). Malignant melanoma develops from a neoplastic transformation of melanocytes, which are predominantly found in the basal layer of the epidermis and the eye. Spagnolo F et al., Archives of Dermatology Research, 2012, 304: 177-184; Hurst E A et al., Archives of Dermatology Research, 2003, 139: 1067-1073. Malignant melanoma is the most aggressive form of skin cancer. It is estimated that 76,250 persons would be diagnosed with melanoma in 2012 and 9,180 persons would die from it. Spagnolo F et al., Archives of Dermatology Research, 2012, 304: 177-184; Surveillance Epidemiology and End Results Cancer Statistics Review 2005-2009 (accessed on Oct. 6, 2012 at http://seer.cancer.gov/csr/1975_2009_pops09/results_single/sect_01_table.01.pdf).

Although surgical removal of early melanoma lesions leads to a cure rate of 90%, advanced melanoma resists chemotherapy and tends to quickly metastasize (Spagnolo F et al., Archives of Dermatology Research, 2012, 304: 177-184); for these reasons, prognosis for advanced melanoma is poor, with 5-year survival rates of 78% for patients with stage IIIA, 59% for patients with stage IIIB, and 40% for patients with stage IIIC, respectively. Balch C M et al., Journal of Clinical Oncology, 2009, 27(36): 6199-6206. For patients with distant metastases, the prognosis significantly worsens, with 1 year survival rates of 62% for stage M1a, 53% for stage M1b and only 33% for stage M1c. Balch C M et al., Journal of Clinical Oncology, 2009, 27(36): 6199-6206.

The treatment options for metastatic melanoma are limited. Prior to 2011, only two therapies for metastatic melanoma had been approved by the FDA: dacarbazine and high dose interleukin 2 ("HD IL-2"), neither of which increased median overall survival. Hill G et al., Cancer, 1984, 53:1299-1305; Atkins M et al., Journal of Clinical Oncology, 1999, 17(7): 2105-2116; Phan G et al., Journal of Clinical Oncology, 2001, 19(15): 3477-3482. Moreover, dacarbazine is limited by a low response rate of 10% to 15%, while HD IL-2 has an even lower response rate of 6% to 10%. Finn L et al., BMC Medicine, 2012, 10:23. During 2011, the FDA approved two more therapies for advanced melanoma, vemurafenib (Zelboraf™) and ipilimumab. Finn L et al., BMC Medicine, 2012, 10:23. While vemurafenib has demonstrated good clinical activity with a high response rate and low toxicity, its applicability is limited to the 40%-60% of melanoma patients who harbor an activating mutation in the BRAF gene that leads to constitutive activation of the mitogen-activated protein kinase pathway ("MAPK"), which causes increased cellular proliferation as well as increased oncogenic activity. Finn L et al., BMC Medicine, 2012, 10:23. Additionally, most patients who initially respond to treatment with BRAF inhibitors relapse, indicating the development of drug resistance and demonstrating the limitations of targeting only one pathway to eradicate melanoma. Villanueva J et al., Cancer Cell, 2010, 18(6): 683-695; Spagnolo F et al., Archives of Dermatology Research, 2012, 304: 177-184. Ipilmumab can induce long-term responses in a subset of patients, but its utility is limited by its low response rate of 10% to 15% and by the fact that it improves median survival time by only two months. Finn L et al., BMC Medicine, 2012, 10:23. Thus, there remains a serious need for additional therapies for treatment of melanoma.

All references cited herein, including patent applications and publications, are incorporated by reference in their entirety.

SUMMARY OF THE INVENTION

Provided herein are methods of treating melanoma in an individual (e.g., human) comprising administering to the individual an effective amount of a composition comprising nanoparticles comprising a taxane (e.g., paclitaxel) and a carrier protein (e.g., albumin). In some embodiments, the melanoma is cutaneous melanoma. In some embodiments, the melanoma is metastatic melanoma. In some embodiments, the melanoma is metastatic malignant melanoma. In some embodiments, the melanoma is stage IV melanoma. In some embodiments, the individual has distant metastases. In some embodiments, the metastatic melanoma is at stage M1a. In some embodiments, the metastatic melanoma is at stage M1b. In some embodiments, the metastatic melanoma is at stage M1c. In some embodiments, the individual has measurable disease. In some embodiments, the individual has brain metastases. In some embodiments, the individual does not have brain metastases. In some embodiments, the taxane is paclitaxel. In some embodiments, the carrier protein is albumin such as human serum albumin or human albumin.

In some embodiments of any of the methods described herein, the individual has not been previously treated for melanoma. In some embodiments, the individual has not received prior cytotoxic chemotherapy for the metastatic malignant melanoma. In some embodiments, the individual has not received prior adjuvant cytotoxic chemotherapy. In some embodiments, the individual is a human. In some embodiments, the individual is a male. In some embodiments, the individual is a female. In some embodiments, the individual is under about 65 years old. In some embodiments, the individual is at least about 65 years old (for example at least about any of 70, 75, or 80 years old). In some embodiments, the individual has elevated serum lactate dehydrogenase ("LDH") level. In some embodiments, the individual has normal LDH level. In some embodiments, the individual has serum LDH of less than about 0.8× upper limit of normal ("ULN"). In some embodiments, the individual has serum LDH at about 0.8× to about 1.1×ULN. In some embodiments, the individual has serum LDH of between greater than about 1.1× to about 2.0×ULN. In some embodiments, the melanoma comprises wild-type BRAF. In some embodiments, the melanoma comprises a mutation in BRAF. In some embodiments, the melanoma comprises a V600E mutation in BRAF.

In some embodiments of any of the methods described herein, the composition comprising nanoparticles comprising taxane (e.g., paclitaxel) and a carrier protein (e.g., an albumin) is used as a monotherapy for treating the melanoma. In some embodiments of any of the methods described herein, the method further comprises a second therapy. In some embodiments, the second therapy is selected from the group consisting of chemotherapy, immunotherapy, surgery, radiation therapy, targeted therapy, or a combination thereof. In some embodiments, the method comprises administration of at least one other therapeutic agent. In some embodiments, the one other therapeutic agent is a BRAF inhibitor. In some embodiments, the one other therapeutic agent is ipilimumab. In some embodiments, the method is used as a first line therapy. In some embodiments, the method is used as a second line therapy.

In some embodiments of any of the methods described herein, the composition comprising nanoparticles comprising taxane (e.g., paclitaxel) and a carrier protein (e.g., albumin) is administered intravenously. In some embodiments, the dose of taxane (e.g., paclitaxel) in the nanoparticle composition is about 50 mg/m$^2$ to about 400 mg/m$^2$. In some embodiments, the dose of taxane (e.g., paclitaxel) in the nanoparticle composition is about 100 mg/m$^2$ to about 200 mg/m$^2$. In some embodiments, the dose of taxane (e.g., paclitaxel) in the nanoparticle composition is about 150 mg/m$^2$. In some embodiments, the composition comprising nanoparticles comprising taxane (e.g., paclitaxel) and a carrier protein (e.g., albumin) is administered weekly. In some embodiments, the method comprises at least one 28-day treatment cycle. In some embodiments, the composition comprising nanoparticles comprising taxane (e.g., paclitaxel) and a carrier protein (e.g., albumin) is administered on days 1, 8, and 15 of the 28-day treatment cycle. In some embodiments, the carrier protein is albumin. In some embodiments, the albumin is human serum albumin. In some embodiments, the albumin is human albumin. In some embodiments, the albumin is recombinant albumin. In some embodiments, the nanoparticles in the composition have an average diameter of no greater than about 200 nm. In some embodiments, the weight ratio of albumin and taxane (e.g., paclitaxel) in the nanoparticle composition is about 9:1 or less. In some embodiments, the weight ratio of albumin and taxane (e.g., paclitaxel) in the nanoparticle composition is about 9:1. In some embodiments, the taxane (e.g., paclitaxel) in the nanoparticles are coated with the albumin. In some embodiments, the taxane is paclitaxel. In some embodiments, there is provided a method of treating melanoma in an individual (e.g., human) comprising administering to the individual an effective amount of a composition comprising nanoparticles comprising paclitaxel and albumin (e.g., human albumin or human serum albumin).

In some embodiments, there is provided a method of treating melanoma in a human individual comprising administering to the individual an effective amount of a composition comprising nanoparticles comprising paclitaxel and an albumin. In some embodiments, the individual is selected for treatment based on the individual having metastatic melanoma at stage M1c. In some embodiments, the individual is selected for treatment based on the individual having a serum LDH level of between greater than about 1.1× to about 2.0× ULN. In some embodiments, the individual is selected for treatment based on the individual having a melanoma comprising wild-type BRAF. In some embodiments, the individual is selected for treatment based on the individual having a melanoma comprising a mutation in BRAF (such as a V600E mutation in BRAF).

In some embodiments, the method further comprises a second therapy, for example a second therapy comprising administration of at least one other therapeutic agent. In some embodiments, the other therapeutic agent is a BRAF inhibitor. In some embodiments, the other therapeutic agent is Ipilimumab.

In some embodiments, the method is used as a first line therapy. In some embodiments, the method is used as a second line therapy.

In some embodiments, the composition comprising nanoparticles comprising paclitaxel and an albumin is administered intravenously. In some embodiment, the dose of paclitaxel in the nanoparticle composition is about 80 mg/m$^2$ to about 200 mg/m$^2$ (for example about 150 mg/m$^2$). In some embodiments, the composition comprising nanoparticles comprising paclitaxel and an albumin is administered weekly, for example administered on days 1, 8, and 15 of the 28-day treatment cycle.

In some embodiments the albumin is human serum albumin. In some embodiments, the nanoparticles in the composition have an average diameter of no greater than about 200 nm. In some embodiments, the weight ratio of albumin and paclitaxel in the nanoparticle composition is about 9:1 or less. In some embodiments, the paclitaxel in the nanoparticles are coated with the albumin.

In some embodiments, there is provided a kit comprising (i) a composition comprising nanoparticles comprising paclitaxel and an albumin, and (ii) an instruction for administering the nanoparticle composition for treating melanoma.

It is to be understood that one, some, or all of the properties of the various embodiments described herein may be combined to form other embodiments of the present invention. These and other aspects of the invention will become apparent to one of skill in the art.

DETAILED DESCRIPTION

Figure 1:
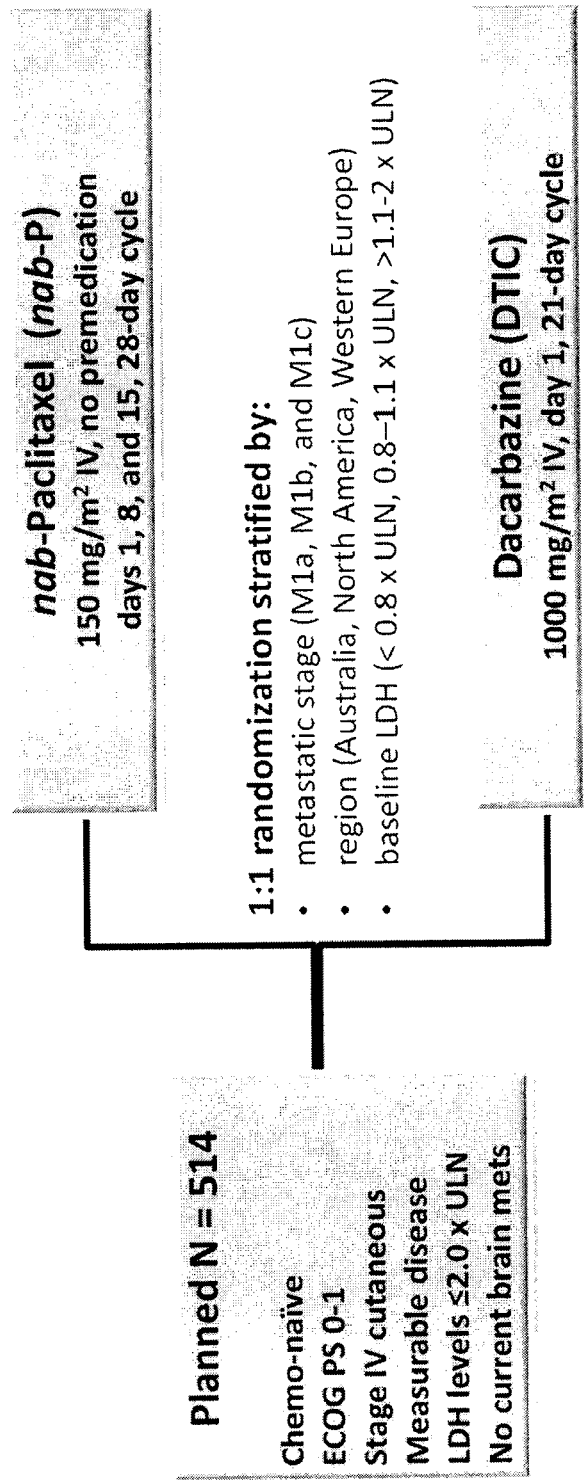
FIG. 1 shows the study design for the phase III study of Nab-paclitaxel (or Abraxane®) versus dacarbazine in chemotherapy-naive patients with metastatic malignant melanoma. DCR, disease control rate; ECOG, Eastern Cooperative Oncology Group; LDH, lactate dehydrogenase; ORR, objective response rate; OS, overall survival; PFS, progression-free survival; RECIST, Response Evaluation Criteria In Solid Tumors; ULN, upper limit of normal.

Provided herein are methods for treatment of melanoma (e.g., stage IV or metastatic cutaneous melanoma) in an individual using a composition comprising nanoparticles comprising a taxane and a carrier protein.

A phase III study using an albumin stabilized nanoparticle formulation of paclitaxel (Nab-paclitaxel, or Abraxane®) versus dacarbazine was conducted in chemotherapy-naive patients with metastatic malignant melanoma. Dacarbazine is the only FDA-approved chemotherapy since 1975 for metastatic melanoma. The study showed that Abraxane® almost doubled the progression-free survival ("PFS") compared to dacarbazine (PFS: 4.8 months for Abraxane® versus 2.5 months for dacarbazine, P=0.044). Abraxane® is the first single-agent chemotherapy to demonstrate a statistically significant improvement over dacarbazine in 37 years. The present invention thus provides methods, compositions, and kits for treatment of melanoma in an individual by administration of a composition comprising nanoparticles comprising a taxane and a carrier protein.

In some embodiments, there is provided a method of treating melanoma in an individual comprising administering to the individual a composition comprising nanoparticles comprising a taxane and a carrier protein. In some embodiments, the individual has stage IV or metastatic melanoma (e.g., stage IV or metastatic cutaneous melanoma). In some embodiments, the melanoma is metastatic malignant melanoma. In some embodiments, the metastatic melanoma is at stage M1a, stage M1b, or stage M1c. In some embodiments, the metastatic melanoma is at stage M1c. In some embodiments, the melanoma comprises a mutation in BRAF. In some embodiments, the melanoma does not comprise a mutation in BRAF. In some embodiments, the melanoma does not comprise BRAF mutant such as a BRAF mutant with increased activity (for example, increased kinase activity, and/or increased activity as compared to wild-type BRAF) or a BRAF gain-of-function mutant. In some embodiments, the melanoma does not comprise BRAF V600E mutation (e.g., the melanoma comprises wild-type BRAF). In some embodiments, the melanoma comprises a BRAF mutant such as a BRAF mutant with increased activity (for example, increased kinase activity, and/or increased activity as compared to wild-type BRAF) or a BRAF gain-of-function mutant. In some embodiments, the melanoma comprises BRAF V600E mutation. In some embodiments, the individual has elevated serum lactate dehydrogenase ("LDH") level (for example, elevated LDH level as compared to a normal level such as normal LDH level known in the art or normal LDH level in an individual without melanoma or cancer). In some embodiments, the individual has normal serum LDH level. In some embodiments, the individual has serum LDH of less than about 0.8× upper limit of normal ("ULN"). In some embodiments, the individual has serum LDH at about 0.8× to about 1.1×ULN. In some embodiments, the individual has serum LDH of between greater than about 1.1× to about 2.0×ULN. In some embodiments, the individual has serum LDH of between about 1.1× to about 2.0×ULN. In some embodiments, the individual is a human (e.g., male or female). In some embodiments, the taxane is paclitaxel. In some embodiments, the carrier protein is albumin.

Also provided herein are compositions (such as pharmaceutical compositions), articles of manufacture, medicines, kits, and unit dosages useful for the methods described herein. Also provided herein are certain combination therapies methods, kits, and compositions for the treatment of melanoma.

DEFINITIONS

The term "individual" refers to a mammal, including humans. An individual includes, but is not limited to, human, bovine, horse, feline, canine, rodent, or primate. In some embodiments, the individual is human. The term "individual" also includes human patients described in the Examples.

As used herein, "treatment" is an approach for obtaining beneficial or desired clinical results. Beneficial or desired clinical results may include, but are not limited to, any one or more of: alleviation of one or more symptoms, diminishment of extent of disease, stabilized (i.e., not worsening) state of disease, preventing or delaying spread (e.g., metastasis) of disease, preventing or delaying occurrence or recurrence of disease, delay or slowing of disease progression, ameliora-tion of the disease state, and remission (whether partial or total). Also encompassed by "treatment" is a reduction of pathological consequence of a proliferative disease such as cancer (e.g., melanoma). The methods provided herein contemplate any one or more of these aspects of treatment.

The term "effective amount" used herein refers to an amount of a compound or composition, when used alone or in combination with a second therapy, is sufficient to treat a specified disorder, condition or disease such as ameliorate, palliate, lessen, and/or delay one or more of its symptoms. In reference to cancers or other unwanted cell proliferation, an effective amount comprises an amount sufficient to cause a tumor to shrink and/or to decrease the growth rate of the tumor (such as to suppress tumor growth) or to prevent or delay other unwanted cell proliferation. An effective amount can be administered in one or more administrations. In the case of melanoma, the effective amount of the drug or composition may: (i) reduce the number of melanoma cells; (ii) reduce melanoma tumor size; (iii) inhibit, retard, slow to some extent and for example stop melanoma cell infiltration into peripheral organs; (iv) inhibit (i.e., slow to some extent and for example stop) melanoma tumor metastasis; (v) inhibit melanoma tumor growth; (vi) prevent or delay occurrence and/or recurrence of melanoma tumor; and/or (vii) relieve to some extent one or more of the symptoms associated with the melanoma.

As used herein, by "combination therapy" is meant that a first agent be administered in conjunction with another agent. "In conjunction with" refers to administration of one treatment modality in addition to another treatment modality, such as administration of a nanoparticle composition described herein in addition to administration of the other agent to the same individual. As such, "in conjunction with" refers to administration of one treatment modality before, during, or after delivery of the other treatment modality to the individual.

As used herein, by "pharmaceutically acceptable" or "pharmacologically compatible" is meant a material that is not biologically or otherwise undesirable, e.g., the material may be incorporated into a pharmaceutical composition administered to an individual or patient without causing any significant undesirable biological effects or interacting in a deleterious manner with any of the other components of the composition in which it is contained. Pharmaceutically acceptable carriers or excipients have for example met the required standards of toxicological and manufacturing testing and/or are included on the Inactive Ingredient Guide prepared by the U.S. Food and Drug administration.

As used herein and in the appended claims, the singular forms "a," "an," and "the" include plural reference unless the context clearly indicates otherwise.

Reference to "about" a value or parameter herein includes (and describes) embodiments that are directed to that value or parameter per se. For example, description referring to "about X" includes description of "X."

It is understood that aspect and variations of the invention described herein include "consisting" and/or "consisting essentially of" aspects and variations.

Methods of Treating Melanoma

The present invention provides methods for treatment of melanoma in an individual (e.g., human) using a composition comprising nanoparticles comprising a taxane and a carrier protein.

In some embodiments, the melanoma is cutaneous melanoma. In some embodiments, the melanoma is metastatic melanoma. In some embodiments, the melanoma is metastatic malignant melanoma. In some embodiments, the melanoma is stage IV melanoma (e.g., stage IV cutaneous melanoma). In some embodiments, the metastatic melanoma is at stage M1a. In some embodiments, the metastatic melanoma is at stage M1b. In some embodiments, the metastatic melanoma is at stage M1c. In some embodiments, the individual has not received prior therapy (e.g., prior cytotoxic chemotherapy) for the melanoma (e.g., metastatic melanoma). In some embodiments, the melanoma comprises a mutation in BRAF. In some embodiments, the melanoma comprises a BRAF V600E mutation. In some embodiments, the melanoma does not comprise a mutation in BRAF (e.g., the melanoma comprises wild-type BRAF). In some embodiments, the melanoma does not comprise BRAF mutant such as a BRAF mutant with increased activity (for example, increased kinase activity, and/or increased activity as compared to wild-type BRAF) or a BRAF gain-of-function mutant. In some embodiments, the melanoma does not comprise a constitutive active BRAF mutant. In some embodiments, the melanoma does not comprise BRAF V600E mutation (e.g., the melanoma comprises wild-type BRAF). In some embodiments, the melanoma comprises wild-type BRAF (e.g., the melanoma cells have wild-type BRAF). In some embodiments, the melanoma comprises a BRAF mutant such as a BRAF mutant with increased activity (for example, increased kinase activity, and/or increased activity as compared to wild-type BRAF) or a BRAF gain-of-function mutant. In some embodiments, the melanoma comprises a constitutive active BRAF mutant. In some embodiments, the melanoma comprises BRAF V600E mutation. In some embodiments, the individual has elevated serum lactate dehydrogenase ("LDH") level. In some embodiments, the individual has serum LDH of less than about 0.8× upper limit of normal ("ULN"). In some embodiments, the individual has serum LDH at about 0.8× to about 1.1×ULN. In some embodiments, the individual has serum LDH of between greater than about 1.1× to about 2.0×ULN. In some embodiments, the individual has serum LDH of between about 1.1× to about 2.0×ULN. In some embodiments, the individual is under about 65 years old. In some embodiments, the individual is at least about 65 years old (for example at least about any of 70, 75, or 80 years old). In some embodiments, the individual is a male. In some embodiments, the individual is a female. In some embodiments, the individual has one or more of the characteristics of the patients described in Examples 1 and 2 of the present disclosure. For example, the individual may have at least one (e.g., at least any of 2, 3, 4, 5, 6, or 7) of the following characteristics: (1) Histologically or cytologically confirmed cutaneous malignant melanoma with evidence of metastasis (Stage IV); (2) No prior cytotoxic chemotherapy for metastatic malignant melanoma; (3) No prior adjuvant cytotoxic chemotherapy; (4) Male or non-pregnant and non-lactating female ≥18 years of age; (5) No other current active malignancy within the past 3 years; (6) Radiographically-documented measurable disease (for example, the presence of at least 1 radiographically documented measurable lesion); and (7) ECOG performance status 0-1. In some embodiments, the individual does not have history or current evidence of brain metastases, including leptomeningeal involvement. In some embodiments, the individual does not have pre-existing peripheral neuropathy of NCI CTCAE Scale of Grade ≥2.

In some embodiments, the melanoma is cutaneous melanoma. In some embodiments, the melanoma is melanoma of the skin. In some embodiments, the melanoma is superficial spreading melanoma. In some embodiments, the melanoma is nodular melanoma. In some embodiments, the melanoma is acral lentiginous melanoma. In some embodiments, the melanoma is lentigo maligna melanoma. In some embodiments, the melanoma is mucosal melanoma (e.g., mucosal melanoma in nose, mouth, throat, or genital area). In some embodiments, the melanoma is ocular melanoma. In some embodiments, the melanoma is uveal melanoma. In some embodiments, the melanoma is choroidal melanoma. For example, in some embodiments, there is provided a method of treating cutaneous melanoma (e.g., metastatic or stage IV cutaneous melanoma) in an individual (e.g., human) comprising administering to the individual a composition comprising nanoparticles comprising a taxane (e.g., paclitaxel) and a carrier protein (e.g., albumin). In some embodiments, the individual has stage IV or metastatic melanoma. In some embodiments, the melanoma is metastatic malignant melanoma. In some embodiments, the metastatic melanoma is at stage M1a, stage M1b, or stage M1c. In some embodiments, the metastatic melanoma is at stage M1c. In some embodiments, the melanoma comprises a mutation in BRAF. In some embodiments, the melanoma does not comprise a mutation in BRAF. In some embodiments, the melanoma does not comprise BRAF mutant such as a BRAF mutant with increased activity (for example, increased kinase activity, and/or increased activity as compared to wild-type BRAF) or a BRAF gain-of-function mutant. In some embodiments, the melanoma does not comprise a constitutive active BRAF mutant. In some embodiments, the melanoma does not comprise BRAF V600E mutation (e.g., the melanoma comprises wild-type BRAF). In some embodiments, the melanoma comprises wild-type BRAF (e.g., the melanoma cells have wild-type BRAF). In some embodiments, the melanoma comprises a BRAF mutant such as a BRAF mutant with increased activity (for example, increased kinase activity, and/or increased activity as compared to wild-type BRAF) or a BRAF gain-of-function mutant. In some embodiments, the melanoma comprises BRAF V600E mutation. In some embodiments, the melanoma comprises a constitutively active BRAF mutant. In some embodiments, the melanoma does not comprise a constitutively active BRAF mutant. In some embodiments, the method of using taxane nanoparticles for treating melanoma is used as a monotherapy. In some embodiments, the method of treating melanoma using taxane nanoparticles does not further comprise one other therapeutic agent (such as one other chemotherapeutic agent or immunotherapeutic agent). In some embodiments, the method does not further comprise a cytotoxic chemotherapeutic agent.

Melanoma described herein may be any of the following: cutaneous melanoma, extracutaneous melanoma, superficial spreading melanoma, malignant melanoma, nodular malignant melanoma, nodular melanoma, polypoid melanoma, acral lentiginous melanoma, lentiginous malignant melanoma, amelanotic melanoma, lentigo maligna melanoma, mucosal lentignous melanoma, mucosal melanoma, soft-tissue melanoma, ocular melanoma, desmoplastic melanoma, or metastatic malignant melanoma.

In some embodiments, the melanoma to be treated is stage 0, stage I, stage II, stage III, or stage IV. In some embodiments, the melanoma to be treated is stage 0, stage IA, stage IB, stage IIA, stage IIB, stage IIC, stage IIIA, stage IIIB, stage IIIC, or stage IV. In some embodiments, the melanoma is metastatic melanoma. In some embodiments, the metastatic melanoma is at stage M1a. In some embodiments, the metastatic melanoma is at stage M1b. In some embodiments, the metastatic melanoma is at stage M1c. Staging of melanoma may be based on a method known to one skilled in the art. Staging of melanoma may be according to the criteria included in 2009 AJCC Melanoma Staging and Classification. See Balch C M et al., J Clin Oncol. 2009, 27(36):6199-206 (the contents disclosed therein are incorporated by reference in their entirety). For example, the staging of melanoma may be according to the criteria set forth in Tables 1 and 2.

TABLE 1

TNM Staging Categories for Cutaneous Melanoma

Classification

| T | Thickness (mm) | Ulceration Status/Mitoses |
|---|---|---|
| Tis | NA | NA |
| T1 | ≤1.00 | a: Without ulceration and mitosis <1/mm$^2$<br>b: With ulceration or mitoses ≥1/mm$^2$ |
| T2 | 1.01-2.00 | a: Without ulceration<br>b: With ulceration |
| T3 | 2.01-4.00 | a: Without ulceration<br>b: With ulceration |
| T4 | >4.00 | a: Without ulceration<br>b: With ulceration |

| N | No. of Metastatic Nodes | Nodal Metastatic Burden |
|---|---|---|
| N0 | 0 | NA |
| N1 | 1 | a: Micrometastasis*<br>b: Macrometastasis† |
| N2 | 2-3 | a: Micrometastasis*<br>b: Macrometastasis†<br>c: In transit metastases/satellites without metastatic nodes |
| N3 | 4+ metastatic nodes, or matted nodes, or in transit metastases/satellites with metastatic nodes | |

| M | Site | Serum LDH |
|---|---|---|
| M0 | No distant metastases | NA |
| M1a | Distant skin, subcutaneous, or nodal metastases | Normal |
| M1b | Lung metastases | Normal |
| M1c | All other visceral metastases | Normal |
| | Any distant metastasis | Elevated |

Abbreviations: NA, not applicable; LDH, lactate dehydrogenase.
*Micrometastases are diagnosed after sentinel lymph node biopsy.
†Macrometastases are defined as clinically detectable nodal metastases confirmed pathologically.

TABLE 2

Anatomic Stage Groupings for Cutaneous Melanoma

| Clinical Staging* | | | Pathologic Staging† | | |
|---|---|---|---|---|---|
| T | N | M | T | N | M |
| 0 Tis | N0 | M0 | 0 Tis | N0 | M0 |
| IA T1a | N0 | M0 | IA T1a | N0 | M0 |
| IB T1b | N0 | M0 | IB T1b | N0 | M0 |
| T2a | N0 | M0 | T2a | N0 | M0 |
| IIA T2b | N0 | M0 | IIA T2b | N0 | M0 |
| T3a | N0 | M0 | T3a | N0 | M0 |
| IIB T3b | N0 | M0 | IIB T3b | N0 | M0 |
| T4a | N0 | M0 | T4a | N0 | M0 |
| IIC T4b | N0 | M0 | IIC T4b | N0 | M0 |
| III Any T | N > N0 | M0 | IIIA T1-4a | N1a | M0 |
| | | | T1-4a | N2a | M0 |
| | | | IIIB T1-4b | N1a | M0 |
| | | | T1-4b | N2a | M0 |
| | | | T1-4a | N1b | M0 |
| | | | T1-4a | N2b | M0 |
| | | | T1-4a | N2c | M0 |
| | | | IIIC T1-4b | N1b | M0 |
| | | | T1-4b | N2b | M0 |
| | | | T1-4b | N2c | M0 |
| | | | Any T | N3 | M0 |
| IV Any T | Any N | M1 | IV Any T | Any N | M1 |

*Clinical staging includes microstaging of the primary melanoma and clinical/radiologic evaluation for metastases. By convention, it should be used after complete excision of the primary melanoma with clinical assessment for regional and distant metastases.
†Pathologic staging includes microstaging of the primary melanoma and pathologic information about the regional lymph nodes after partial (i.e., sentinel node biopsy) or complete lymphadenectomy. Pathologic stage 0 or stage IA patients are the exception; they do not require pathologic evaluation of their lymph nodes.

In some embodiments, the melanoma is early stage melanoma (e.g., early stage cutaneous melanoma). In some embodiments, the melanoma is late stage melanoma (e.g., late stage cutaneous melanoma). In some embodiments, the melanoma is advanced melanoma. In some embodiments, the individual has measurable disease. In some embodiments, the melanoma is metastatic melanoma (e.g., metastatic cutaneous melanoma). In some embodiments, the melanoma is metastatic malignant melanoma (e.g., metastatic malignant cutaneous melanoma). In some embodiments, the melanoma is stage IV melanoma (e.g., stage IV cutaneous melanoma). In some embodiments, the individual has measurable disease. A measurable disease may be determined using methods known to one skilled in the art. In some embodiments, a measurable disease refers to the presence of at least 1 radiographically documented measurable lesion. In some embodiments, the melanoma is a melanoma with one or more metastatic sites in the brain.

In some embodiments, the melanoma is non-metastatic melanoma. In some embodiments, the melanoma is metastatic melanoma. In some embodiments, the melanoma is a primary melanoma tumor. In some embodiments, the primary melanoma tumor has metastasized. In some embodiments, the melanoma is locally advanced melanoma. In some embodiments, the melanoma is recurrent melanoma. In some embodiments, the melanoma has reoccurred after remission. In some embodiments, the melanoma is progressive melanoma. In some embodiments, the melanoma is melanoma in remission. In some embodiments, the individual has distant metastases. Distant metastases may be based on methods known in the art, and may refer to distant skin, subcutaneous, or nodal metastases or metastases in distant organ such as lung metastases. In some embodiments, the individual does not have distant metastases. In some embodiments, the individual has locoregional cutaneous metastases. In some embodiments, the individual has distant skin, subcutaneous, or nodal metastases. In some embodiments, the individual has visceral metastases. In some embodiments, the individual does not have visceral metastases. In some embodiments, the individual has metastases of melanoma in lung, liver, bone or brain. In some embodiments, the individual does not have metastases of melanoma in brain. In some embodiments, the melanoma is localized resectable, localized unresectable, or unresectable. In some embodiments, the individual has previously been treated with a BRAF inhibitor such as, for example, Vemurafenib (Zelboraf) or Sorafenib (Nexavar).

For example, there is provided a method of treating stage IV melanoma (e.g., stage IV cutaneous melanoma) in an individual (e.g., human) comprising administering to the individual a composition comprising nanoparticles comprising a taxane (e.g., paclitaxel) and a carrier protein (e.g., albumin). In some embodiments, there is provided a method of treating metastatic melanoma (e.g., metastatic cutaneous melanoma) (such as melanoma at metastatic stage M1a, M1b, or M1c) in an individual (e.g., human) comprising administering to the individual a composition comprising nanoparticles comprising a taxane (e.g., paclitaxel) and a carrier protein (e.g., albumin). In some embodiments, the metastatic melanoma is at any of stage M1a, stage M1b, or stage M1c. In some embodiments, there is provided a method of treating metastatic cutaneous melanoma with metastatic stage M1c in an individual (e.g., human) comprising administering to the individual a composition comprising nanoparticles comprising a taxane (e.g., paclitaxel) and a carrier protein (e.g., albumin). In some embodiments, the melanoma comprises a mutation in BRAF. In some embodiments, the melanoma does not comprise a mutation in BRAF. In some embodiments, the melanoma does not comprise BRAF mutant such as a BRAF mutant with increased activity (for example, increased kinase activity, and/or increased activity as compared to wild-type BRAF) or a BRAF gain-of-function mutant. In some embodiments, the melanoma does not comprise BRAF V600E mutation (e.g., the melanoma comprises wild-type BRAF). In some embodiments, the melanoma comprises wild-type BRAF. In some embodiments, the melanoma comprises a BRAF mutant such as a BRAF mutant with increased activity (for example, increased kinase activity, and/or increased activity as compared to wild-type BRAF) or a BRAF gain-of-function mutant. In some embodiments, the melanoma comprises BRAF V600E mutation. In some embodiments, the method of using taxane nanoparticles for treating melanoma is used as a monotherapy. In some embodiments, the method of treating melanoma using taxane nanoparticles does not further comprise one other therapeutic agent (such as one other chemotherapeutic agent or immunotherapeutic agent). In some embodiments, the method does not further comprise a cytotoxic chemotherapeutic agent.

In some embodiments, the individual has melanoma tumor with thickness of less than about any of 0.5 millimeter ("mm"), 1 mm, 1.5 mm, 2 mm, 2.5 mm, 3 mm, 3.5 mm, 4 mm, 4.5 mm, 5 mm, 5.5 mm, 6 mm, 6.5 mm, 7 mm, 7.5 mm, or 8 mm. In some embodiments, the individual has melanoma tumor with thickness of at least about any of 0.5 mm, 1 mm, 1.5 mm, 2 mm, 2.5 mm, 3 mm, 3.5 mm, 4 mm, 4.5 mm, 5 mm, 5.5 mm, 6 mm, 6.5 mm, 7 mm, 7.5 mm, or 8 mm. In some embodiments, the individual has melanoma tumor with thickness of about any of 0.5 mm, 1 mm, 1.5 mm, 2 mm, 2.5 mm, 3 mm, 3.5 mm, 4 mm, 4.5 mm, 5 mm, 5.5 mm, 6 mm, 6.5 mm, 7 mm, 7.5 mm, or 8 mm. In some embodiments, the individual has melanoma tumor with thickness of about any of 0-1 mm, 1-2 mm, 2-3 mm, 3-4 mm, 4-5 mm, 5-6 mm, 1-4 mm, 1-6 mm, 2-4 mm, 2-6 mm, or 4-6 mm.

Any individual having melanoma (e.g., metastatic melanoma such as metastatic cutaneous melanoma) may be treated using a method described herein. In some embodiments, the individual is chemotherapy-naïve or has not been treated with chemotherapy. In some embodiments, the individual has not been previously treated for the melanoma. In some embodiments, the individual has not been previously treated for the metastatic melanoma. In some embodiments, the individual has not received prior therapy or prior chemotherapy (such as prior cytotoxic chemotherapy) for the melanoma (e.g., the metastatic malignant melanoma). In some embodiments, the individual has not received prior adjuvant therapy (e.g., adjuvant cytotoxic chemotherapy). In some embodiments, the individual has been previously treated with a kinase inhibitor. In some embodiments, the individual has been previously treated with a cytokine. In some embodiments, the individual has been previously treated with an adjuvant therapy (e.g., interferon, GM-CSF, or vaccine). For example, there is provided a method of treating melanoma (e.g., metastatic cutaneous melanoma) in an individual (e.g., human) comprising administering to the individual a composition comprising nanoparticles comprising a taxane (e.g., paclitaxel) and a carrier protein (e.g., albumin), wherein the individual has not received prior therapy or prior chemotherapy (such as prior cytotoxic chemotherapy) for the melanoma. In some embodiments, the melanoma comprises a mutation in BRAF. In some embodiments, the melanoma does not comprise a mutation in BRAF. In some embodiments, the melanoma does not comprise BRAF mutant such as a BRAF mutant with increased activity (for example, increased kinase activity, and/or increased activity as compared to wild-type BRAF) or a BRAF gain-of-function mutant. In some embodiments, the melanoma does not comprise BRAF V600E mutation (e.g., the melanoma comprises wild-type BRAF). In some embodiments, the melanoma comprises wild-type BRAF. In some embodiments, the melanoma comprises a BRAF mutant such as a BRAF mutant with increased activity (for example, increased kinase activity, and/or increased activity as compared to wild-type BRAF) or a BRAF gain-of-function mutant. In some embodiments, the melanoma comprises BRAF V600E mutation. In some embodiments, the method of using taxane nanoparticles for treating melanoma is used as a monotherapy. In some embodiments, the method of treating melanoma using taxane nanoparticles does not further comprise one other therapeutic agent (such as one other chemotherapeutic agent or immunotherapeutic agent). In some embodiments, the method does not further comprise a cytotoxic chemotherapeutic agent.

Any individual having normal or elevated lactate dehydrogenase ("LDH") level (such as normal or elevated serum LDH level) may be treated with a method described herein. In some embodiments, the individual has normal LDH level such as normal serum LDH level (e.g., a normal serum LDH baseline level or normal serum LDH at the time of diagnosis of melanoma). In some embodiments, the individual has elevated LDH level such as elevated serum LDH level (e.g., an elevated serum LDH baseline level or elevated serum LDH at the time of diagnosis of melanoma). In some embodiments, the individual has substantially elevated serum LDH level. In some embodiments, the individual has serum LDH level increased by at least about any of 10%, 20%, 30%, 40%, 50%, 60%, 70%, 80%, 90%, 100%, 120%, 140%, 150%, 175%, or 200% compared to the normal serum LDH value or serum LDH value for an individual without melanoma. The serum LDH level may be determined by a person skilled in the art using methods known in the art. In some embodiments, the serum LDH level can be determined via immunoassay, e.g., ELISA or sandwich ELISA. In some embodiments, the serum LDH level can be determined by a colorimetric assay in which either the reduction of NAD+ (oxidation of lactate to pyruvate) or the oxidation of NADH (reduction of pyruvate to lactate) is monitored by the change in absorbance at 340 nm. In some embodiments, LDH level can be determined via electrophoresis using a chromogenic LDH activity stain. In some embodiments, the LDH level described herein refers to baseline LDH level. In some embodiments, the LDH level described herein refers to the LDH level at the time of diagnosis of melanoma. In some embodiments, the LDH level described herein refers to the LDH level at the time of diagnosis of stage IV or metastatic melanoma. In some embodiments, the LDH level described herein is compared to an individual without melanoma. In some embodiments, the LDH level is elevated compared to a normal LDH level known in the art or a LDH level in an individual without melanoma or cancer. In some embodiments, the LDH level is elevated compared to a normal LDH level range known in the art or a LDH level in a healthy individual. In some embodiments, the LDH level refers to the total LDH level (LDH isoenzymes combined together).

In some embodiments, the individual has serum LDH level of at least about any of 0.6× upper limit of normal ("ULN"), 0.7×ULN, 0.8×ULN, 0.9×ULN, 1.0×ULN, 1.1×ULN, 1.2×ULN, 1.3×ULN, 1.4×ULN, 1.5×ULN, 1.6×ULN, 1.7×ULN, 1.8×ULN, 1.9×ULN, 2.0×ULN, 2.1×ULN, or 2.2×ULN. In some embodiments, the individual has serum LDH level of lower than about any of 0.6×ULN, 0.7×ULN, 0.8×ULN, 0.9×ULN, 1.0×ULN, 1.1×ULN, 1.2×ULN, 1.3×ULN, 1.4×ULN, 1.5×ULN, 1.6×ULN, 1.7×ULN, 1.8×ULN, 1.9×ULN, 2.0×ULN, 2.1×ULN, 2.2×ULN, 2.3×ULN, 2.4×ULN, 2.5×ULN, 2.6×ULN, 2.7×ULN, 2.8×ULN, or 3.0×ULN. In some embodiments, the individual has serum LDH level of about any of 0.6×ULN, 0.7×ULN, 0.8×ULN, 0.9×ULN, 1.0×ULN, 1.1×ULN, 1.2×ULN, 1.3×ULN, 1.4×ULN, 1.5×ULN, 1.6×ULN, 1.7×ULN, 1.8×ULN, 1.9×ULN, 2.0×ULN, 2.1×ULN, or 2.2×ULN. In some embodiments, the individual has serum LDH level of about any of 0.4×ULN-0.8×ULN, 0.6×ULN-2.5×ULN, 0.8×ULN-2.0×ULN, 0.8×ULN-1.5×ULN, 0.8×ULN-1.2×ULN, 0.8×ULN-1.1×ULN, 0.9×ULN-1.1×ULN, 0.8×ULN-1.2×ULN, 1.0×ULN-2.2×ULN, 1.1×ULN-2.0×ULN, >1.1×ULN-2.0×ULN, >1.2×ULN-2.0×ULN, 1.2×ULN-2.2×ULN, 1.2×ULN-2.0×ULN, 1.5×ULN-2.0×ULN, 1.2×ULN-5.0×ULN, 1.2×ULN-4.0×ULN, 2.0×ULN-4.0×ULN, 1.2×ULN-3.5×ULN, 1.2×ULN-3.0×ULN, 1.2×ULN-2.5×ULN, 1.1×ULN-1.8×ULN, 1.1×ULN-1.5×ULN, 1.2×ULN-1.5×ULN, 1.2×ULN-1.8×ULN, or 1.3×ULN-1.8×ULN. In some embodiments, the individual has serum LDH of less than about 0.8× upper limit of normal ("ULN"). In some embodiments, the individual has serum LDH at about 0.8× to about 1.1×ULN. In some embodiments, the individual has serum LDH of between greater than about 1.1× to about 2.0×ULN. In some embodiments, the individual has serum LDH of between about 1.1× to about 2.0×ULN. For example, there is provided a method of treating melanoma (e.g., metastatic cutaneous melanoma) in an individual (e.g., human) comprising administering to the individual a composition comprising nanoparticles comprising a taxane (e.g., paclitaxel) and a carrier protein (e.g., albumin), wherein the individual has normal serum LDH level. In some embodiments, the melanoma is metastatic malignant melanoma. In some embodiments, the metastatic melanoma is at stage M1a, stage M1b, or stage M1c. In some embodiments, the metastatic melanoma is at stage M1c. In some embodiments, the melanoma comprises a mutation in BRAF. In some embodiments, the melanoma does not comprise a mutation in BRAF. In some embodiments, the melanoma does not comprise BRAF mutant such as a BRAF mutant with increased activity (for example, increased kinase activity, and/or increased activity as compared to wild-type BRAF) or a BRAF gain-of-function mutant. In some embodiments, the melanoma does not comprise BRAF V600E mutation (e.g., the melanoma comprises wild-type BRAF). In some embodiments, the melanoma comprises wild-type BRAF. In some embodiments, the melanoma comprises a BRAF mutant such as a BRAF mutant with increased activity (for example, increased kinase activity, and/or increased activity as compared to wild-type BRAF) or a BRAF gain-of-function mutant. In some embodiments, the melanoma comprises BRAF V600E mutation. In some embodiments, the individual is a human (e.g., male or female). In some embodiments, the taxane is paclitaxel. In some embodiments, the carrier protein is albumin. In some embodiments, the method of using taxane nanoparticles for treating melanoma is used as a monotherapy. In some embodiments, the method of treating melanoma using taxane nanoparticles does not further comprise one other therapeutic agent (such as one other chemotherapeutic agent or immunotherapeutic agent). In some embodiments, the method does not further comprise a cytotoxic chemotherapeutic agent.

For another example, there is provided a method of treating melanoma (e.g., metastatic cutaneous melanoma) in an individual (e.g., human) comprising administering to the individual a composition comprising nanoparticles comprising a taxane (e.g., paclitaxel) and a carrier protein (e.g., albumin), wherein the individual has elevated serum LDH level. In some embodiments, the individual has serum LDH of one of the following: serum LDH level of less than about 0.8×ULN, serum LDH level of about 0.8× to about 1.1×ULN, or serum LDH of between greater than about 1.1× to about 2.0×ULN. In some embodiments, the individual has stage IV or metastatic melanoma (e.g., stage IV or metastatic cutaneous melanoma). In some embodiments, the melanoma is metastatic malignant melanoma. In some embodiments, the metastatic melanoma is at stage M1a, stage M1b, or stage M1c. In some embodiments, the metastatic melanoma is at stage M1c. In some embodiments, the melanoma comprises a mutation in BRAF. In some embodiments, the melanoma comprises a constitutively active BRAF mutant. In some embodiments, the melanoma comprises a BRAF mutant such as a BRAF mutant with increased activity (for example, increased kinase activity, and/or increased activity as compared to wild-type BRAF) or a BRAF gain-of-function mutant. In some embodiments, the melanoma comprises BRAF V600E mutation. In some embodiments, the individual is a human (e.g., male or female). In some embodiments, the taxane is paclitaxel. In some embodiments, the carrier protein is albumin. In some embodiments, the method of using taxane nanoparticles for treating melanoma is used as a monotherapy. In some embodiments, the method of treating melanoma using taxane nanoparticles does not further comprise one other therapeutic agent (such as one other chemotherapeutic agent or immunotherapeutic agent). In some embodiments, the method does not further comprise a cytotoxic chemotherapeutic agent.

BRAF is a protein encoded by BRAF gene. The gene may also be referred to as proto-oncogene B-Raf and v-Raf murine sarcoma viral oncogene homolog B1. Mutations in BRAF have been identified in melanomas, including a mutation at codon 600 (e.g., valine to glutamate mutation at codon 600). The V600E mutation was previously known as V599E mutation and was renamed based on additional sequence data. See Davies H et al., Nature 2002, 417:949-54. In some embodiments of the methods described herein, the melanoma comprises wild-type BRAF (e.g., the melanoma cells have wild-type BRAF). In some embodiments, the melanoma comprises a mutation in BRAF. In some embodiments, the melanoma does not comprise a mutation in BRAF. In some embodiments, the melanoma comprises a mutation at codon 600 in BRAF (such as Val mutated to Glu, Asp, Lys, or Arg). In some embodiments, the melanoma does not comprise a mutation V600E in BRAF (e.g., the melanoma cells are negative for BRAF V600E mutation). In some embodiments, the melanoma comprises BRAF V600E mutation. In some embodiments, the melanoma cells are characterized by homozygous V600E BRAF genotype. In some embodiments, the melanoma cells are characterized by heterozygous V600E BRAF genotype. In some embodiments a mutation in BRAF can be determined via allele-specific real-time PCR. In some embodiments, a mutation in BRAF can be determined via shifted termination assay (STA). In some embodiments, a mutation in BRAF can be determined via nucleic acid sequencing. In some embodiments, a mutation in BRAF can be determined using a commercially available kit, such as is available from, e.g., Roche, Neogenomics, Lab 2, or other companies.

In some embodiments, the melanoma does not comprise BRAF mutant such as a BRAF mutant with increased or elevated activity (for example, increased kinase activity, and/or increased activity as compared to wild-type BRAF) or a BRAF gain-of-function mutant. In some embodiments, the melanoma does not comprise a constitutive active BRAF mutant. In some embodiments, the melanoma does not comprise BRAF V600E mutation (e.g., the melanoma comprises wild-type BRAF). In some embodiments, the melanoma comprises wild-type BRAF. In some embodiments, the melanoma comprises a BRAF mutant such as a BRAF mutant with increased activity (for example, increased kinase activity, and/or increased activity as compared to wild-type BRAF) or a BRAF gain-of-function mutant. In some embodiments, the melanoma comprises a BRAF constitutive active mutant. In some embodiments, the mutant BRAF has elevated activity such as elevated kinase activity. In some embodiments, the mutant BRAF is a gain-of-function mutant. In some embodiments, the mutation in BRAF is in the kinase domain. In some embodiments, the melanoma comprise one or more of the following BRAF mutations: R461I, I462S, G463E, G463V, G465A, G465E, G465V, G468A, G468E, N580S, E585K, D593V, F594L, G595R, L596V, T598I, V599D, V599E, V599K, V599R, K600E, or A727V. In some embodiments, the melanoma comprises BRAF V600E mutation. Mutation(s) in BRAF may be identified using methods known in the art.

For example, there is provided a method of treating melanoma (e.g., metastatic cutaneous melanoma) in an individual (e.g., human) comprising administering to the individual a composition comprising nanoparticles comprising a taxane (e.g., paclitaxel) and a carrier protein (e.g., albumin), wherein the melanoma does not comprise BRAF mutant such as a BRAF mutant with increased activity (for example, increased kinase activity, and/or increased activity as compared to wild-type BRAF) or a BRAF gain-of-function mutant. In some embodiments, there is provided a method of treating melanoma (e.g., metastatic cutaneous melanoma) in an individual (e.g., human) comprising administering to the individual a composition comprising nanoparticles comprising a taxane (e.g., paclitaxel) and a carrier protein (e.g., albumin), wherein the melanoma does not comprise BRAF V600E mutation (e.g., the melanoma comprises wild-type BRAF). In some embodiments, there is provided a method of treating melanoma (e.g., metastatic cutaneous melanoma) in an individual (e.g., human) comprising administering to the individual a composition comprising nanoparticles comprising a taxane (e.g., paclitaxel) and a carrier protein (e.g., albumin), wherein the melanoma comprises wild-type BRAF. In some embodiments, there is provided a method of treating melanoma (e.g., metastatic cutaneous melanoma) in an individual (e.g., human) comprising administering to the individual a composition comprising nanoparticles comprising a taxane (e.g., paclitaxel) and a carrier protein (e.g., albumin), wherein the melanoma comprises a BRAF mutant such as a BRAF mutant with increased activity (for example, increased kinase activity, and/or increased activity as compared to wild-type BRAF) or a BRAF gain-of-function mutant. In some embodiments, there is provided a method of treating melanoma (e.g., metastatic cutaneous melanoma) in an individual (e.g., human) comprising administering to the individual a composition comprising nanoparticles comprising a taxane (e.g., paclitaxel) and a carrier protein (e.g., albumin), wherein the melanoma comprises BRAF V600E mutation. In some embodiments, the individual has stage IV or metastatic melanoma (e.g., stage IV or metastatic cutaneous melanoma). In some embodiments, the melanoma is metastatic malignant melanoma. In some embodiments, the metastatic melanoma is at stage M1a, stage M1b, or stage M1c. In some embodiments, the metastatic melanoma is at stage M1c. In some embodiments, the individual has elevated serum LDH level. In some embodiments, the individual has serum LDH of about any of the following: <0.8×ULN, 0.4-0.8×ULN, 0.8-1.1×ULN, 0.9-1.1×ULN, 0.8-1.2×ULN, 1.1-1.5×ULN, 1.2-1.5×ULN, 1.1-2×ULN, or 1.5-2×ULN. In some embodiments, the individual has serum LDH of less than about 0.8×ULN. In some embodiments, the individual has serum LDH at about 0.8× to about 1.1×ULN. In some embodiments, the individual has serum LDH of between greater than about 1.1× to about 2.0×ULN. In some embodiments, the individual has serum LDH of between about 1.1× to about 2.0×ULN. In some embodiments, the individual is a human (e.g., male or female). In some embodiments, the taxane is paclitaxel. In some embodiments, the carrier protein is albumin. In some embodiments, the method of using taxane nanoparticles for treating melanoma is used as a monotherapy. In some embodiments, the method of treating melanoma using taxane nanoparticles does not further comprise one other therapeutic agent (such as one other chemotherapeutic agent or immunotherapeutic agent). In some embodiments, the method does not further comprise a cytotoxic chemotherapeutic agent.

In some embodiments of any of the methods described herein, the melanoma comprises a mutation in BRAF. In some embodiments, the melanoma comprises a V600E BRAF mutation. In some embodiments, the melanoma does not comprise a mutation in BRAF or is negative for BRAF mutation. In some embodiments, the melanoma comprises wild-type BRAF. In some embodiments of any of the methods described herein, the melanoma comprises a mutation in neuroblastoma RAS viral (v-ras) oncogene homolog ("NRAS"). In some embodiments, the melanoma does not comprise a mutation in NRAS or is negative for NRAS mutation. In some embodiments, the melanoma comprises wild-type NRAS. In some embodiments of any of the methods described herein, the melanoma comprises a mutation in phosphatase and tensin homolog ("PTEN"). In some embodiments, the melanoma does not comprise a mutation in PTEN or is negative for PTEN mutation. In some embodiments, the melanoma comprises wild-type PTEN. In some embodiments, the melanoma comprises (i) wild-type BRAF or a mutation in BRAF; (ii) wild-type NRAS or a mutation in NRAS; and/or (iii) wild-type PTEN or a mutation in PTEN. In some embodiments, the melanoma is triple negative melanoma or comprises wild-type BRAF, wild-type NRAS, and wild-type PTEN. Methods known in the art may be used to determine whether the melanoma or an individual having the melanoma comprises wild-type for a gene or protein or mutation(s) in a gene or protein described herein.

An individual described herein in some embodiments is a human. In some embodiments, the individual is a male. In some embodiments, the individual is a female. In some embodiments, the individual is at least about any of 25, 30, 35, 40, 45, 50, 55, 60, 65, 70, 75, 80, 85, or 90 years old. In some embodiments, the individual is under about any of 25, 30, 35, 40, 45, 50, 55, 60, 65, 70, 75, 80, 85, or 90 years old. In some embodiments, the individual is about any of 25, 30, 35, 40, 45, 50, 55, 60, 65, 70, 75, 80, 85, or 90 years old. In some embodiments, the individual is under about 65 years old. In some embodiments, the individual is at least about 65 years old (for example at least about any of 70, 75, or 80 years old). In some embodiments, the individual has a single lesion at presentation. In some embodiments, the individual has multiple lesions at presentation. An individual that may be treated with a method described herein may be any one of the following: Caucasian ethnicity or race, Asian ethnicity or race, African or African American ethnicity or race, Hispanic ethnicity or race, Latino ethnicity or race, or Hawaiian or Pacific Islander ethnicity or race.

In some embodiments, the individual is a human who exhibits one or more symptoms associated with having melanoma (e.g., stage IV or metastatic melanoma). In some embodiments, the individual is genetically or otherwise predisposed (e.g., having a risk factor) to developing melanoma. These risk factors include, but are not limited to, age, sex, race, diet, history of previous disease, life style or habit, genetic (e.g., hereditary) considerations, and environmental exposure (such as exposure to sunlight). In some embodiments, the individual is positive for SPARC expression (for example based on IHC standard). In some embodiments, the individual is negative for SPARC expression.

The methods provided herein may be practiced in an adjuvant setting. Adjuvant setting may refer to a clinical setting in which an individual has had a history of a cancer described herein, and generally (but not necessarily) been responsive to therapy, which includes, but is not limited to, surgery (e.g., surgery resection), radiotherapy, and chemotherapy; however, because of their history of cancer, these individuals are considered at risk of development of the disease. Treatment or administration in the adjuvant setting refers to a subsequent mode of treatment. The degree of risk (e.g., when an individual in the adjuvant setting is considered as "high risk" or "low risk") depends upon several factors, most usually the extent of disease when first treated.

In some embodiments, the method is practiced in a neoadjuvant setting, i.e., the method may be carried out before the primary/definitive therapy. In some embodiments, the method is used to treat an individual who has previously been treated. Any of the methods of treatment provided herein may be used to treat an individual who has not previously been treated.

Methods described herein may be used to treat an individual having melanoma who has previously been treated for the melanoma. The prior treatment may include a chemotherapy agent such as dacarbazine or DTIC (also known as DIC, DTIC-Dome, or Imidazole Carboxamide). In some embodiments, the prior treatment comprises Oblimersen (or Genasense, available from Genta Inc.). In some embodiments, the prior treatment comprises an immunotherapy (such as interleukin-2 (IL-2) or interferon (IFN)). In some embodiments, the prior treatment comprises a BRAF inhibitor, such as Vemurafenib (or Zelboraf, available from Genentech USA, Inc.), GDC-0879 (available from Tocris Bioscience), PLX-4720 (available from Symansis), Dabrafenib (or GSK2118436), LGX 818, CEP-32496, UI-152, RAF 265, Regorafenib (BAY 73-4506), CCT239065, or Sorafenib (or Sorafenib Tosylate or Nexavar®, available from Bayer Pharmaceuticals Corp.). In some embodiments, the prior treatment comprises Ipilimumab (or MDX-010, MDX-101, or Yervoy, available from Bristol-Myers Squibb). In some embodiments, the individual has been previously treated for the melanoma and the individual is substantially refractory to the prior treatment. In some embodiments, the individual has been previously treated for the melanoma and is no longer or only partially responsive to the prior treatment. In some embodiments, the individual is initially responsive to the prior treatment but has progressed on the prior treatment. In some embodiments, the individual is not responsive to the prior treatment.

Methods described herein may be used as a first line therapy. Methods described herein may also be used as a second line or third line therapy after the prior treatment for melanoma has failed or has substantially failed, or the melanoma is substantially refractory to the first line therapy. In some embodiments, the melanoma is substantially refractory to first line therapy with a BRAF inhibitor. In some embodiments, the individual has received at least one line of therapy (e.g., chemotherapy or immunotherapy) for treating melanoma (e.g., stage IV or metastatic melanoma) prior to receiving the treatment described herein. In some embodiments, the patient has received 1 line of therapy or 2 lines of therapy (e.g., 1 line of chemotherapy or immunotherapy or 2 lines of chemotherapy or immunotherapy). Thus, the treatment described herein may be used as a second line therapy or a third line therapy. The prior line of therapy described herein may be prior line of chemotherapy or immunotherapy. The first line of therapy may comprise any of the following: dacarbazine or DTIC (also known as DIC, DTIC-Dome, or Imidazole Carboxamide), Oblimersen (or Genasense), an immunotherapy (such as interleukin-2 (IL-2) or interferon (IFN), a BRAF inhibitor (such as Vemurafenib (or Zelboraf), GDC-0879, PLX-4720, (available from Symansis), Dabrafenib (or GSK2118436), LGX 818, CEP-32496, UI-152, RAF 265, Regorafenib (BAY 73-4506), CCT239065, or Sorafenib (or Sorafenib Tosylate, or Nexavar®)), or Ipilimumab (or MDX-010, MDX-101, or Yervoy).

In some embodiments, there is provided a method of treating melanoma (e.g., metastatic cutaneous melanoma) in an individual comprising administering to the individual an effective amount of a composition comprising nanoparticles comprising a taxane (e.g., paclitaxel) and a carrier protein (e.g., albumin), wherein the method is used as a second line or third line therapy. In some embodiments, there is provided a method of treating melanoma in an individual comprising administering to the individual an effective amount of a composition comprising nanoparticles comprising a taxane (e.g., paclitaxel) and a carrier protein (e.g., albumin), wherein the method is used in an adjuvant setting. In some embodiments, there is provided a method of treating melanoma in an individual comprising administering to the individual an effective amount of a composition comprising nanoparticles comprising a taxane (e.g., paclitaxel) and a carrier protein (e.g., albumin), wherein the method is used in a neoadjuvant setting. In some embodiments, the individual has stage IV or metastatic melanoma (e.g., stage IV or metastatic cutaneous melanoma). In some embodiments, the melanoma is metastatic malignant melanoma. In some embodiments, the metastatic melanoma is at stage M1a, stage M1b, or stage M1c. In some embodiments, the metastatic melanoma is at stage M1c. In some embodiments, the melanoma comprises a mutation in BRAF. In some embodiments, the melanoma does not comprise a mutation in BRAF. In some embodiments, the melanoma does not comprise BRAF mutant such as a BRAF mutant with increased activity (for example, increased kinase activity, and/or increased activity as compared to wild-type BRAF) or a BRAF gain-of-function mutant. In some embodiments, the melanoma does not comprise BRAF V600E mutation (e.g., the melanoma comprises wild-type BRAF). In some embodiments, the melanoma comprises wild-type BRAF. In some embodiments, the melanoma comprises a BRAF mutant such as a BRAF mutant with increased activity (for example, increased kinase activity, and/or increased activity as compared to wild-type BRAF) or a BRAF gain-of-function mutant. In some embodiments, the melanoma comprises BRAF V600E mutation. In some embodiments, the individual has elevated serum LDH level. In some embodiments, the individual has serum LDH of about any of the following: <0.8×ULN, 0.4-0.8×ULN, 0.8-1.1×ULN, 0.9-1.1×ULN, 0.8-1.2×ULN, 1.1-1.5×ULN, 1.2-1.5×ULN, 1.1-2×ULN, or 1.5-2×ULN. In some embodiments, the individual has serum LDH of less than about 0.8×ULN. In some embodiments, the individual has serum LDH at about 0.8× to about 1.1×ULN. In some embodiments, the individual has serum LDH of between greater than about 1.1× to about 2.0×ULN. In some embodiments, the individual has serum LDH of between about 1.1× to about 2.0×ULN. In some embodiments, the individual is a human (e.g., male or female). In some embodiments, the taxane is paclitaxel. In some embodiments, the carrier protein is albumin. In some embodiments, the method of using taxane nanoparticles for treating melanoma is used as a monotherapy. In some embodiments, the method of treating melanoma using taxane nanoparticles does not further comprise one other therapeutic agent (such as one other chemotherapeutic agent or immunotherapeutic agent). In some embodiments, the method does not further comprise a cytotoxic chemotherapeutic agent.

In some embodiments, there is provided a method of treating stage IV or metastatic melanoma (e.g., stage IV or metastatic cutaneous melanoma) in an individual (e.g., human) comprising administering to the individual a composition comprising nanoparticles comprising a taxane (e.g., paclitaxel) and a carrier protein (e.g., albumin), wherein the melanoma does not comprise BRAF mutant such as a BRAF mutant with increased activity (for example, increased kinase activity, and/or increased activity as compared to wild-type BRAF) or a BRAF gain-of-function mutant. In some embodiments, there is provided a method of treating stage IV or metastatic melanoma (e.g., stage IV or metastatic cutaneous melanoma) in an individual (e.g., human) comprising administering to the individual a composition comprising nanoparticles comprising a taxane (e.g., paclitaxel) and a carrier protein (e.g., albumin), wherein the melanoma comprises wild-type BRAF. In some embodiments, there is provided a method of treating stage IV or metastatic melanoma (e.g., stage IV or metastatic cutaneous melanoma) in an individual (e.g., human) comprising administering to the individual a composition comprising nanoparticles comprising a taxane (e.g., paclitaxel) and a carrier protein (e.g., albumin), wherein the melanoma comprises a BRAF mutant such as a BRAF mutant with increased activity (for example, increased kinase activity, and/or increased activity as compared to wild-type BRAF) or a BRAF gain-of-function mutant. In some embodiments, there is provided a method of treating stage IV or metastatic melanoma (e.g., stage IV or metastatic cutaneous melanoma) in an individual (e.g., human) comprising administering to the individual a composition comprising nanoparticles comprising a taxane (e.g., paclitaxel) and a carrier protein (e.g., albumin), wherein the melanoma comprises BRAF V600E mutation. In some embodiments, the taxane in the nanoparticles is coated with the carrier protein. In some embodiments, the average or mean particle size of the nanoparticles in the composition is no greater than about 200 nm (such as less than about 200 nm). In some embodiments, the taxane is paclitaxel. In some embodiments, the carrier protein is albumin such as human serum albumin or human albumin.

In some embodiments, there is provided a method of treating stage IV or metastatic melanoma (e.g., stage IV or metastatic cutaneous melanoma) in an individual (e.g., human) comprising administering to the individual a composition comprising nanoparticles comprising paclitaxel and albumin, wherein the melanoma comprises wild-type BRAF. In some embodiments, there is provided a method of treating stage IV or metastatic melanoma (e.g., stage IV or metastatic cutaneous melanoma) in an individual (e.g., human) comprising administering to the individual a composition comprising nanoparticles comprising paclitaxel and albumin, wherein the melanoma comprises wild-type BRAF, wherein the paclitaxel in the nanoparticles is coated with the albumin. In some embodiments, there is provided a method of treating stage IV or metastatic melanoma (e.g., stage IV or metastatic cutaneous melanoma) in an individual (e.g., human) comprising administering to the individual a composition comprising nanoparticles comprising paclitaxel and albumin, wherein the melanoma comprises wild-type BRAF, wherein the paclitaxel in the nanoparticles is coated with the albumin, wherein the average or mean particle size of the nanoparticles in the composition is no greater than about 200 nm (such as less than about 200 nm). In some embodiments, the albumin is human albumin. In some embodiments, the albumin is human serum albumin. In some embodiments, the albumin is recombinant albumin. In some embodiments, the method of using taxane nanoparticles for treating melanoma is used as a monotherapy. In some embodiments, the method of treating melanoma using taxane nanoparticles does not further comprise one other therapeutic agent (such as one other chemotherapeutic agent or immunotherapeutic agent). In some embodiments, the method does not further comprise a cytotoxic chemotherapeutic agent.

In some embodiments, there is provided a method of treating stage IV or metastatic melanoma (e.g., stage IV or metastatic cutaneous melanoma) in an individual (e.g., human) comprising administering to the individual a composition comprising nanoparticles comprising paclitaxel and albumin, wherein the melanoma comprises a BRAF mutation such as BRAF V600E mutation. In some embodiments, there is provided a method of treating stage IV or metastatic melanoma (e.g., stage IV or metastatic cutaneous melanoma) in an individual (e.g., human) comprising administering to the individual a composition comprising nanoparticles comprising paclitaxel and albumin, wherein the melanoma comprises a BRAF mutation such as BRAF V600E mutation, wherein the paclitaxel in the nanoparticles is coated with the albumin. In some embodiments, there is provided a method of treating stage IV or metastatic melanoma (e.g., stage IV or metastatic cutaneous melanoma) in an individual (e.g., human) comprising administering to the individual a composition comprising nanoparticles comprising paclitaxel and albumin, wherein the melanoma comprises a BRAF mutation such as BRAF V600E mutation, wherein the paclitaxel in the nanoparticles is coated with the albumin, wherein the average or mean particle size of the nanoparticles in the composition is no greater than about 200 nm (such as less than about 200 nm). In some embodiments, the albumin is human albumin. In some embodiments, the albumin is human serum albumin. In some embodiments, the albumin is recombinant albumin. In some embodiments, the method of using taxane nanoparticles for treating melanoma is used as a monotherapy. In some embodiments, the method of treating melanoma using taxane nanoparticles does not further comprise one other therapeutic agent (such as one other chemotherapeutic agent or immunotherapeutic agent). In some embodiments, the method does not further comprise a cytotoxic chemotherapeutic agent.

In some embodiments, there is provided a method of treating stage IV or metastatic melanoma (e.g., stage IV or metastatic cutaneous melanoma) with metastatic stage M1c in an individual (e.g., human) comprising administering to the individual a composition comprising nanoparticles comprising a taxane (e.g., paclitaxel) and a carrier protein (e.g., albumin), wherein the melanoma does not comprise BRAF mutant such as a BRAF mutant with increased activity (for example, increased kinase activity, and/or increased activity as compared to wild-type BRAF) or a BRAF gain-of-function mutant. In some embodiments, there is provided a method of treating stage IV or metastatic melanoma (e.g., stage IV or metastatic cutaneous melanoma) with metastatic stage M1c in an individual (e.g., human) comprising administering to the individual a composition comprising nanoparticles comprising a taxane (e.g., paclitaxel) and a carrier protein (e.g., albumin), wherein the melanoma comprises wild-type BRAF. In some embodiments, there is provided a method of treating stage IV or metastatic melanoma (e.g., stage IV or metastatic cutaneous melanoma) with metastatic stage M1c in an individual (e.g., human) comprising administering to the individual a composition comprising nanoparticles comprising a taxane (e.g., paclitaxel) and a carrier protein (e.g., albumin), wherein the melanoma comprises a BRAF mutant such as a BRAF mutant with increased activity (for example, increased kinase activity, and/or increased activity as compared to wild-type BRAF) or a BRAF gain-of-function mutant. In some embodiments, there is provided a method of treating stage IV or metastatic melanoma (e.g., stage IV or metastatic cutaneous melanoma) with metastatic stage M1c in an individual (e.g., human) comprising administering to the individual a composition comprising nanoparticles comprising a taxane (e.g., paclitaxel) and a carrier protein (e.g., albumin), wherein the melanoma comprises BRAF V600E mutation. In some embodiments, the taxane in the nanoparticles is coated with the carrier protein. In some embodiments, the average or mean particle size of the nanoparticles in the composition is no greater than about 200 nm (such as less than about 200 nm). In some embodiments, the taxane is paclitaxel. In some embodiments, the carrier protein is albumin such as human serum albumin or human albumin. In some embodiments, there is provided a method of treating stage IV or metastatic melanoma (e.g., stage IV or metastatic cutaneous melanoma) with metastatic stage M1c in an individual (e.g., human) comprising administering to the individual a composition comprising nanoparticles comprising paclitaxel and albumin, wherein the melanoma comprises wild-type BRAF. In some embodiments, there is provided a method of treating stage IV or metastatic melanoma (e.g., stage IV or metastatic cutaneous melanoma) with metastatic stage M1c in an individual (e.g., human) comprising administering to the individual a composition comprising nanoparticles comprising paclitaxel and albumin, wherein the melanoma comprises wild-type BRAF, wherein the paclitaxel in the nanoparticles is coated with the albumin. In some embodiments, there is provided a method of treating stage IV or metastatic melanoma (e.g., stage IV or metastatic cutaneous melanoma) with metastatic stage M1c in an individual (e.g., human) comprising administering to the individual a composition comprising nanoparticles comprising paclitaxel and albumin, wherein the melanoma comprises wild-type BRAF, wherein the paclitaxel in the nanoparticles is coated with the albumin, wherein the average or mean particle size of the nanoparticles in the composition is no greater than about 200 nm (such as less than about 200 nm). In some embodiments, there is provided a method of treating stage IV or metastatic melanoma (e.g., stage IV or metastatic cutaneous melanoma) with metastatic stage M1c in an individual (e.g., human) comprising administering to the individual a composition comprising nanoparticles comprising paclitaxel and albumin, wherein the melanoma comprises a BRAF mutation such as BRAF V600E mutation. In some embodiments, there is provided a method of treating stage IV or metastatic melanoma (e.g., stage IV or metastatic cutaneous melanoma) with metastatic stage M1c in an individual (e.g., human) comprising administering to the individual a composition comprising nanoparticles comprising paclitaxel and albumin, wherein the melanoma comprises a BRAF mutation such as BRAF V600E mutation, wherein the paclitaxel in the nanoparticles is coated with the albumin. In some embodiments, there is provided a method of treating stage IV or metastatic melanoma (e.g., stage IV or metastatic cutaneous melanoma) with metastatic stage M1c in an individual (e.g., human) comprising administering to the individual a composition comprising nanoparticles comprising paclitaxel and albumin, wherein the melanoma comprises a BRAF mutation such as BRAF V600E mutation, wherein the paclitaxel in the nanoparticles is coated with the albumin, wherein the average or mean particle size of the nanoparticles in the composition is no greater than about 200 nm (such as less than about 200 nm). In some embodiments, the albumin is human albumin. In some embodiments, the albumin is human serum albumin. In some embodiments, the albumin is recombinant albumin. In some embodiments, the method of using taxane nanoparticles for treating melanoma is used as a monotherapy. In some embodiments, the method of treating melanoma using taxane nanoparticles does not further comprise one other therapeutic agent (such as one other chemotherapeutic agent or immunotherapeutic agent). In some embodiments, the method does not further comprise a cytotoxic chemotherapeutic agent.

In some embodiments, there is provided a method of treating melanoma (such as metastatic melanoma) in a human individual, comprising administering to the individual a) an effective amount of a composition comprising nanoparticles comprising paclitaxel and an albumin, wherein the individual has been previously treated for the melanoma with at least one BRAF inhibitor (such as, for example, Vemurafenib (Zelboraf) or Sorafenib). In some embodiments, there is provided a method of treating melanoma (such as metastatic melanoma) in a human individual, comprising administering to the individual a) an effective amount of a composition comprising nanoparticles comprising paclitaxel and an albumin, wherein the dose of the nanoparticle composition is between about 50 mg/m$^2$ to about 200 mg/m$^2$ (such as, for example, about 100 mg/m$^2$ to about 150 mg/m$^2$, for example about 100 mg/m$^2$), wherein the individual has been previously treated for the melanoma with at least one BRAF inhibitor (such as, for example, Vemurafenib (Zelboraf) or Sorafenib), and wherein the individual is substantially refractory to prior treatment with a BRAF inhibitor. In some embodiments, there is provided a method of treating melanoma (such as metastatic melanoma) in a human individual, comprising administering to the individual a) an effective amount of a composition comprising nanoparticles comprising paclitaxel and an albumin, wherein the dose of the nanoparticle composition is about 100 mg/m$^2$, wherein the individual has been previously treated for the melanoma with at least one BRAF inhibitor (such as, for example, Vemurafenib (Zelboraf) or Sorafenib), and wherein the individual is substantially refractory to prior treatment with a BRAF inhibitor.

In some embodiments, there is provided a method of treating stage IV or metastatic melanoma (e.g., stage IV or metastatic cutaneous melanoma) in an individual (e.g., human) comprising administering to the individual a composition comprising nanoparticles comprising a taxane (e.g., paclitaxel) and a carrier protein (e.g., albumin), wherein the melanoma does not comprise BRAF mutant such as a BRAF mutant with increased activity (for example, increased kinase activity, and/or increased activity as compared to wild-type BRAF) or a BRAF gain-of-function mutant, wherein the individual has serum LDH of any one of: less than about 0.8× ULN, about 0.8× to about 1.1×ULN, between greater than about 1.1× to about 2.0×ULN, or between about 1.1× to about 2.0×ULN. In some embodiments, there is provided a method of treating stage IV or metastatic melanoma (e.g., stage IV or metastatic cutaneous melanoma) in an individual (e.g., human) comprising administering to the individual a composition comprising nanoparticles comprising a taxane (e.g., paclitaxel) and a carrier protein (e.g., albumin), wherein the melanoma comprises wild-type BRAF, wherein the individual has serum LDH of any one of the following: less than about 0.8×ULN, about 0.8× to about 1.1×ULN, between greater than about 1.1× to about 2.0×ULN, or between about 1.1× to about 2.0×ULN. In some embodiments, there is provided a method of treating stage IV or metastatic melanoma (e.g., stage IV or metastatic cutaneous melanoma) in an individual (e.g., human) comprising administering to the individual a composition comprising nanoparticles comprising a taxane (e.g., paclitaxel) and a carrier protein (e.g., albumin), wherein the melanoma comprises a BRAF mutant such as a BRAF mutant with increased activity (for example, increased kinase activity, and/or increased activity as compared to wild-type BRAF) or a BRAF gain-of-function mutant, wherein the individual has serum LDH of any one of the following: less than about 0.8×ULN, about 0.8× to about 1.1×ULN, between greater than about 1.1× to about 2.0×ULN, or between about 1.1× to about 2.0×ULN. In some embodiments, there is provided a method of treating stage IV or metastatic melanoma (e.g., stage IV or metastatic cutaneous melanoma) in an individual (e.g., human) comprising administering to the individual a composition comprising nanoparticles comprising a taxane (e.g., paclitaxel) and a carrier protein (e.g., albumin), wherein the melanoma comprises BRAF V600E mutation, wherein the individual has serum LDH of any one of the following: less than about 0.8×ULN, about 0.8× to about 1.1×ULN, between greater than about 1.1× to about 2.0× ULN, or between about 1.1× to about 2.0×ULN.

In some embodiments, there is provided a method of treating stage IV or metastatic melanoma (e.g., stage IV or metastatic cutaneous melanoma) in an individual (e.g., human) comprising administering to the individual a composition comprising nanoparticles comprising a taxane (e.g., paclitaxel) and a carrier protein (e.g., albumin), wherein the melanoma comprises wild-type BRAF, wherein the individual has serum LDH of less than about 0.8×ULN. In some embodiments, there is provided a method of treating stage IV or metastatic melanoma (e.g., stage IV or metastatic cutaneous melanoma) in an individual (e.g., human) comprising administering to the individual a composition comprising nanoparticles comprising a taxane (e.g., paclitaxel) and a carrier protein (e.g., albumin), wherein the melanoma comprises wild-type BRAF, wherein the individual has serum LDH of about 0.8× to about 1.1×ULN. In some embodiments, there is provided a method of treating stage IV or metastatic melanoma (e.g., stage IV or metastatic cutaneous melanoma) in an individual (e.g., human) comprising administering to the individual a composition comprising nanoparticles comprising a taxane (e.g., paclitaxel) and a carrier protein (e.g., albumin), wherein the melanoma comprises wild-type BRAF, wherein the individual has serum LDH of between greater than about 1.1× to about 2.0×ULN or between about 1.1× to about 2.0× ULN. In some embodiments, the taxane in the nanoparticles is coated with the carrier protein. In some embodiments, the average or mean particle size of the nanoparticles in the composition is no greater than about 200 nm (such as less than about 200 nm). In some embodiments, the taxane is pacli-taxel. In some embodiments, the carrier protein is albumin such as human serum albumin or human albumin. In some embodiments, there is provided a method of treating stage IV or metastatic melanoma (e.g., stage IV or metastatic cutaneous melanoma) in an individual (e.g., human) comprising administering to the individual a composition comprising nanoparticles comprising paclitaxel and albumin, wherein the melanoma comprises wild-type BRAF, wherein the individual has serum LDH of any one of: less than about 0.8× ULN, about 0.8× to about 1.1×ULN, between greater than about 1.1× to about 2.0×ULN, or between about 1.1× to about 2.0×ULN.

In some embodiments, there is provided a method of treating stage IV or metastatic melanoma (e.g., stage IV or metastatic cutaneous melanoma) in an individual (e.g., human) comprising administering to the individual a composition comprising nanoparticles comprising paclitaxel and albumin, wherein the melanoma comprises wild-type BRAF, wherein the paclitaxel in the nanoparticles is coated with the albumin, wherein the individual has serum LDH of any one of: less than about 0.8×ULN, about 0.8× to about 1.1×ULN, between greater than about 1.1× to about 2.0×ULN, or between about 1.1× to about 2.0×ULN. In some embodiments, there is provided a method of treating stage IV or metastatic melanoma (e.g., stage IV or metastatic cutaneous melanoma) in an individual (e.g., human) comprising administering to the individual a composition comprising nanoparticles comprising paclitaxel and albumin, wherein the melanoma comprises wild-type BRAF, wherein the paclitaxel in the nanoparticles is coated with the albumin, wherein the average or mean particle size of the nanoparticles in the composition is no greater than about 200 nm (such as less than about 200 nm), wherein the individual has serum LDH of any one of: less than about 0.8×ULN, about 0.8× to about 1.1×ULN, between greater than about 1.1× to about 2.0×ULN, or between about 1.1× to about 2.0×ULN. In some embodiments, there is provided a method of treating stage IV or metastatic melanoma (e.g., stage IV or metastatic cutaneous melanoma) in an individual (e.g., human) comprising administering to the individual a composition comprising nanoparticles comprising paclitaxel and albumin, wherein the melanoma comprises a BRAF mutation such as BRAF V600E mutation, wherein the individual has serum LDH of any one of: less than about 0.8×ULN, about 0.8× to about 1.1×ULN, between greater than about 1.1× to about 2.0×ULN, or between about 1.1× to about 2.0×ULN. In some embodiments, there is provided a method of treating stage IV or metastatic melanoma (e.g., stage IV or metastatic cutaneous melanoma) in an individual (e.g., human) comprising administering to the individual a composition comprising nanoparticles comprising paclitaxel and albumin, wherein the melanoma comprises a BRAF mutation such as BRAF V600E mutation, wherein the paclitaxel in the nanoparticles is coated with the albumin, wherein the individual has serum LDH of any one of: less than about 0.8×ULN, about 0.8× to about 1.1×ULN, between greater than about 1.1× to about 2.0×ULN, or between about 1.1× to about 2.0×ULN.

In some embodiments, there is provided a method of treating stage IV or metastatic melanoma (e.g., stage IV or metastatic cutaneous melanoma) in an individual (e.g., human) comprising administering to the individual a composition comprising nanoparticles comprising paclitaxel and albumin, wherein the melanoma comprises a BRAF mutation such as BRAF V600E mutation, wherein the paclitaxel in the nanoparticles is coated with the albumin, wherein the average or mean particle size of the nanoparticles in the composition is no greater than about 200 nm (such as less than about 200 nm), wherein the individual has serum LDH of any one of: less than about 0.8×ULN, about 0.8× to about 1.1×ULN, between greater than about 1.1× to about 2.0×ULN, or between about 1.1× to about 2.0×ULN. In some embodiments, the individual has serum LDH of less than about 0.8×ULN. In some embodiments, the individual has serum LDH of less than about 0.8×ULN about 0.8× to about 1.1× ULN. In some embodiments, the individual has serum LDH of between greater than about 1.1× to about 2.0×ULN, or between about 1.1× to about 2.0×ULN. In some embodiments, the albumin is human albumin. In some embodiments, the albumin is human serum albumin. In some embodiments, the albumin is recombinant albumin. In some embodiments, the method of using taxane nanoparticles for treating melanoma is used as a monotherapy. In some embodiments, the method of treating melanoma using taxane nanoparticles does not further comprise one other therapeutic agent (such as one other chemotherapeutic agent or immunotherapeutic agent). In some embodiments, the method does not further comprise a cytotoxic chemotherapeutic agent.

In some embodiments, there is provided a method of treating stage IV or metastatic melanoma (e.g., stage IV or metastatic cutaneous melanoma) in an individual (e.g., human) comprising administering to the individual a composition comprising nanoparticles comprising a taxane (e.g., paclitaxel) and a carrier protein (e.g., albumin), wherein the individual has serum LDH of any one of the following: less than about 0.8×ULN, about 0.8× to about 1.1×ULN, between greater than about 1.1× to about 2.0×ULN, or between about 1.1× to about 2.0×ULN. In some embodiments, there is provided a method of treating stage IV or metastatic melanoma (e.g., stage IV or metastatic cutaneous melanoma) in an individual (e.g., human) comprising administering to the individual a composition comprising nanoparticles comprising a taxane (e.g., paclitaxel) and a carrier protein (e.g., albumin), wherein the individual has serum LDH of less than about 0.8×ULN. In some embodiments, there is provided a method of treating stage IV or metastatic melanoma (e.g., stage IV or metastatic cutaneous melanoma) in an individual (e.g., human) comprising administering to the individual a composition comprising nanoparticles comprising a taxane (e.g., paclitaxel) and a carrier protein (e.g., albumin), wherein the individual has serum LDH of about 0.8× to about 1.1×ULN. In some embodiments, there is provided a method of treating stage IV or metastatic melanoma (e.g., stage IV or metastatic cutaneous melanoma) in an individual (e.g., human) comprising administering to the individual a composition comprising nanoparticles comprising a taxane (e.g., paclitaxel) and a carrier protein (e.g., albumin), wherein the individual has serum LDH of between greater than about 1.1× to about 2.0×ULN or between about 1.1× to about 2.0×ULN. In some embodiments, the taxane in the nanoparticles is coated with the carrier protein. In some embodiments, the average or mean particle size of the nanoparticles in the composition is no greater than about 200 nm (such as less than about 200 nm). In some embodiments, the taxane is paclitaxel. In some embodiments, the carrier protein is albumin such as human serum albumin or human albumin. In some embodiments, there is provided a method of treating stage IV or metastatic melanoma (e.g., stage IV or metastatic cutaneous melanoma) in an individual (e.g., human) comprising administering to the individual a composition comprising nanoparticles comprising paclitaxel and an albumin, wherein the individual has serum LDH of any one of the following: less than about 0.8×ULN, about 0.8× to about 1.1×ULN, between greater than about 1.1× to about 2.0×ULN, or between about 1.1× to about 2.0×ULN. In some embodiments, there is provided a method of treating stage IV or metastatic melanoma (e.g., stage IV or metastatic cutaneous melanoma) in an individual (e.g., human) comprising administering to the individual a composition comprising nanoparticles comprising paclitaxel and an albumin, wherein the individual has serum LDH of any one of the following: less than about 0.8×ULN, about 0.8× to about 1.1×ULN, between greater than about 1.1× to about 2.0×ULN, or between about 1.1× to about 2.0×ULN, wherein the paclitaxel in the nanoparticles is coated with the albumin. In some embodiments, there is provided a method of treating stage IV or metastatic melanoma (e.g., stage IV or metastatic cutaneous melanoma) in an individual (e.g., human) comprising administering to the individual a composition comprising nanoparticles comprising paclitaxel and an albumin, wherein the individual has serum LDH of any one of the following: less than about 0.8×ULN, about 0.8× to about 1.1×ULN, between greater than about 1.1× to about 2.0×ULN, or between about 1.1× to about 2.0×ULN, wherein the paclitaxel in the nanoparticles is coated with the albumin, wherein the average or mean particle size of the nanoparticles in the composition is no greater than about 200 nm (such as less than about 200 nm). In some embodiments, the individual has serum LDH of less than about 0.8×ULN. In some embodiments, the individual has serum LDH of less than about 0.8×ULN about 0.8× to about 1.1×ULN. In some embodiments, the individual has serum LDH of between greater than about 1.1× to about 2.0×ULN, or between about 1.1× to about 2.0×ULN. In some embodiments, the albumin is human albumin. In some embodiments, the albumin is human serum albumin. In some embodiments, the albumin is recombinant albumin. In some embodiments, the method of using taxane nanoparticles for treating melanoma is used as a monotherapy. In some embodiments, the method of treating melanoma using taxane nanoparticles does not further comprise one other therapeutic agent (such as one other chemotherapeutic agent or immunotherapeutic agent). In some embodiments, the method does not further comprise a cytotoxic chemotherapeutic agent.

In some embodiments, there is provided a method of treating stage IV or metastatic melanoma (e.g., stage IV or metastatic cutaneous melanoma) in an individual (e.g., human) comprising administering to the individual a composition comprising nanoparticles comprising a taxane (e.g., paclitaxel) and a carrier protein (e.g., albumin), wherein the melanoma does not comprise BRAF mutant such as a BRAF mutant with increased activity (for example, increased kinase activity, and/or increased activity as compared to wild-type BRAF) or a BRAF gain-of-function mutant, wherein the individual is a human (female or male). In some embodiments, there is provided a method of treating stage IV or metastatic melanoma (e.g., stage IV or metastatic cutaneous melanoma) in an individual (e.g., human) comprising administering to the individual a composition comprising a taxane (e.g., paclitaxel) and a carrier protein (e.g., albumin), wherein the melanoma comprises a BRAF V600E mutation, wherein the individual is a human (female or male).

In some embodiments, there is provided a method of treating stage IV or metastatic melanoma (e.g., stage IV or metastatic cutaneous melanoma) in an individual (e.g., human) comprising administering to the individual a composition comprising nanoparticles comprising a taxane (e.g., paclitaxel) and a carrier protein (e.g., albumin), wherein the melanoma comprises wild-type BRAF, wherein the individual is a human (female or male). In some embodiments, there is provided a method of treating stage IV or metastatic melanoma (e.g., stage IV or metastatic cutaneous melanoma) in an individual (e.g., human) comprising administering to the individual a composition comprising nanoparticles comprising a taxane (e.g., paclitaxel) and a carrier protein (e.g., albumin), wherein the melanoma comprises a BRAF mutant such as a BRAF mutant with increased activity (for example, increased kinase activity, and/or increased activity as compared to wild-type BRAF) or a BRAF gain-of-function mutant, wherein the individual is a human (female or male). In some embodiments, there is provided a method of treating stage IV or metastatic melanoma (e.g., stage IV or metastatic cutaneous melanoma) in an individual (e.g., human) comprising administering to the individual a composition comprising nanoparticles comprising a taxane (e.g., paclitaxel) and a carrier protein (e.g., albumin), wherein the melanoma comprises BRAF V600E mutation, wherein the individual is a human (female or male). In some embodiments, there is provided a method of treating stage IV or metastatic melanoma (e.g., stage IV or metastatic cutaneous melanoma) in an individual (e.g., human) comprising administering to the individual a composition comprising nanoparticles comprising a taxane (e.g., paclitaxel) and a carrier protein (e.g., albumin), wherein the melanoma comprises wild-type BRAF, wherein the individual is a human female. In some embodiments, there is provided a method of treating stage IV or metastatic melanoma (e.g., stage IV or metastatic cutaneous melanoma) in an individual (e.g., human) comprising administering to the individual a composition comprising nanoparticles comprising a taxane (e.g., paclitaxel) and a carrier protein (e.g., albumin), wherein the melanoma comprises wild-type BRAF, wherein the individual is a human male. In some embodiments, the taxane in the nanoparticles is coated with the carrier protein. In some embodiments, the average or mean particle size of the nanoparticles in the composition is no greater than about 200 nm (such as less than about 200 nm). In some embodiments, the taxane is paclitaxel. In some embodiments, the carrier protein is albumin such as human serum albumin or human albumin. In some embodiments, there is provided a method of treating stage IV or metastatic melanoma (e.g., stage IV or metastatic cutaneous melanoma) in an individual comprising administering to the individual a composition comprising nanoparticles comprising paclitaxel and albumin, wherein the melanoma comprises wild-type BRAF, wherein the individual is a human (female or male). In some embodiments, there is provided a method of treating stage IV or metastatic melanoma (e.g., stage IV or metastatic cutaneous melanoma) in an individual comprising administering to the individual a composition comprising nanoparticles comprising paclitaxel and albumin, wherein the melanoma comprises wild-type BRAF, wherein the paclitaxel in the nanoparticles is coated with the albumin, wherein the individual is a human (female or male). In some embodiments, there is provided a method of treating stage IV or metastatic melanoma (e.g., stage IV or metastatic cutaneous melanoma) in an individual comprising administering to the individual a composition comprising nanoparticles comprising paclitaxel and albumin, wherein the melanoma comprises wild-type BRAF, wherein the paclitaxel in the nanoparticles is coated with the albumin, wherein the average or mean particle size of the nanoparticles in the composition is no greater than about 200 nm (such as less than about 200 nm), wherein the individual is a human (female or male). In some embodiments, there is provided a method of treating stage IV or metastatic melanoma (e.g., stage IV or metastatic cutaneous melanoma) in an individual comprising administering to the individual a composition comprising nanoparticles comprising paclitaxel and albumin, wherein the melanoma comprises a BRAF mutation such as BRAF V600E mutation, wherein the individual is a human (female or male). In some embodiments, there is provided a method of treating stage IV or metastatic melanoma (e.g., stage IV or metastatic cutaneous melanoma) in an individual comprising administering to the individual a composition comprising nanoparticles comprising paclitaxel and albumin, wherein the melanoma comprises a BRAF mutation such as BRAF V600E mutation, wherein the paclitaxel in the nanoparticles is coated with the albumin, wherein the individual is a human (female or male). In some embodiments, there is provided a method of treating stage IV or metastatic melanoma (e.g., stage IV or metastatic cutaneous melanoma) in an individual comprising administering to the individual a composition comprising nanoparticles comprising paclitaxel and albumin, wherein the melanoma comprises a BRAF mutation such as BRAF V600E mutation, wherein the paclitaxel in the nanoparticles is coated with the albumin, wherein the average or mean particle size of the nanoparticles in the composition is no greater than about 200 nm (such as less than about 200 nm), wherein the individual is a human (female or male). In some embodiments, the albumin is human albumin. In some embodiments, the albumin is human serum albumin. In some embodiments, the albumin is recombinant albumin. In some embodiments, the individual is a human male. In some embodiments, the individual is a human female. In some embodiments, the method of using taxane nanoparticles for treating melanoma is used as a monotherapy. In some embodiments, the method of treating melanoma using taxane nanoparticles does not further comprise one other therapeutic agent (such as one other chemotherapeutic agent or immunotherapeutic agent). In some embodiments, the method does not further comprise a cytotoxic chemotherapeutic agent.

In some embodiments, there is provided a method of treating stage IV or metastatic melanoma (e.g., stage IV or metastatic cutaneous melanoma) in an individual (e.g., human) comprising administering to the individual a composition comprising nanoparticles comprising a taxane (e.g., paclitaxel) and a carrier protein (e.g., albumin), wherein the melanoma does not comprise BRAF mutant such as a BRAF mutant with increased activity (for example, increased kinase activity, and/or increased activity as compared to wild-type BRAF) or a BRAF gain-of-function mutant, wherein the individual is a human (female or male), wherein the individual is under about 65 years old or at least about 65 years old (for example at least about any of 70, 75, or 80 years old). In some embodiments, there is provided a method of treating stage IV or metastatic melanoma (e.g., stage IV or metastatic cutaneous melanoma) in an individual (e.g., human) comprising administering to the individual a composition comprising nanoparticles comprising a taxane (e.g., paclitaxel) and a carrier protein (e.g., albumin), wherein the melanoma comprises wild-type BRAF, wherein the individual is a human (female or male), wherein the individual is under about 65 years old or at least about 65 years old (for example at least about any of 70, 75, or 80 years old). In some embodiments, there is provided a method of treating stage IV or metastatic melanoma (e.g., stage IV or metastatic cutaneous melanoma) in an individual (e.g., human) comprising administering to the individual a composition comprising nanoparticles comprising a taxane (e.g., paclitaxel) and a carrier protein (e.g., albumin), wherein the melanoma comprises a BRAF mutant such as a BRAF mutant with increased activity (for example, increased kinase activity, and/or increased activity as compared to wild-type BRAF) or a BRAF gain-of-function mutant, wherein the individual is a human (female or male), wherein the individual is under about 65 years old or at least about 65 years old (for example at least about any of 70, 75, or 80 years old). In some embodiments, there is provided a method of treating stage IV or metastatic melanoma (e.g., stage IV or metastatic cutaneous melanoma) in an individual (e.g., human) comprising administering to the individual a composition comprising nanoparticles comprising a taxane (e.g., paclitaxel) and a carrier protein (e.g., albumin), wherein the melanoma comprises BRAF V600E mutation, wherein the individual is a human (female or male), wherein the individual is under about 65 years old or at least about 65 years old (for example at least about any of 70, 75, or 80 years old). In some embodiments, there is provided a method of treating stage IV or metastatic melanoma (e.g., stage IV or metastatic cutaneous melanoma) in an individual (e.g., human) comprising administering to the individual a composition comprising nanoparticles comprising a taxane (e.g., paclitaxel) and a carrier protein (e.g., albumin), wherein the melanoma comprises wild-type BRAF, wherein the individual is a human (female or male), wherein the individual is under about 65 years old. In some embodiments, there is provided a method of treating stage IV or metastatic melanoma (e.g., stage IV or metastatic cutaneous melanoma) in an individual (e.g., human) comprising administering to the individual a composition comprising nanoparticles comprising a taxane (e.g., paclitaxel) and a carrier protein (e.g., albumin), wherein the melanoma comprises wild-type BRAF, wherein the individual is a human (female or male), wherein the individual is at least about 65 years old (for example at least about any of 70, 75, or 80 years old). In some embodiments, the average or mean particle size of the nanoparticles in the composition is no greater than about 200 nm (such as less than about 200 nm). In some embodiments, the taxane is paclitaxel. In some embodiments, the carrier protein is albumin such as human serum albumin or human albumin. In some embodiments, the method of using taxane nanoparticles for treating melanoma is used as a monotherapy. In some embodiments, the method of treating melanoma using taxane nanoparticles does not further comprise one other therapeutic agent (such as one other chemotherapeutic agent or immunotherapeutic agent). In some embodiments, the method does not further comprise a cytotoxic chemotherapeutic agent.

In some embodiments, there is provided a method of treating stage IV or metastatic melanoma (e.g., stage IV or metastatic cutaneous melanoma) in an individual (e.g., human) comprising administering to the individual a composition comprising nanoparticles comprising a taxane (e.g., paclitaxel) and a carrier protein (e.g., albumin), wherein the individual has serum LDH of any one of the following: less than about 0.8×ULN, about 0.8× to about 1.1×ULN, between greater than about 1.1× to about 2.0×ULN, or between about 1.1× to about 2.0×ULN, wherein the individual is a human (female or male) (e.g., under about 65 years old or at least about 65 years old). In some embodiments, there is provided a method of treating stage IV or metastatic melanoma (e.g., stage IV or metastatic cutaneous melanoma) in an individual (e.g., human) comprising administering to the individual a composition comprising nanoparticles comprising a taxane (e.g., paclitaxel) and a carrier protein (e.g., albumin), wherein the individual has serum LDH of less than about 0.8×ULN, wherein the individual is a human (female or male) (e.g., under about 65 years old or at least about 65 years old). In some embodiments, there is provided a method of treating stage IV or metastatic melanoma (e.g., stage IV or metastatic cutaneous melanoma) in an individual (e.g., human) comprising administering to the individual a composition comprising nanoparticles comprising a taxane (e.g., paclitaxel) and a carrier protein (e.g., albumin), wherein the individual has serum LDH of between 0.8× to about 1.1×ULN, wherein the individual is a human (female or male) (e.g., under about 65 years old or at least about 65 years old). In some embodiments, there is provided a method of treating stage IV or metastatic melanoma (e.g., stage IV or metastatic cutaneous melanoma) in an individual (e.g., human) comprising administering to the individual a composition comprising nanoparticles comprising a taxane (e.g., paclitaxel) and a carrier protein (e.g., albumin), wherein the individual has serum LDH of between greater than about 1.1× to about 2.0×ULN or between about 1.1× to about 2.0×ULN, wherein the individual is a human (female or male) (e.g., under about 65 years old or at least about 65 years old). In some embodiments, the taxane in the nanoparticles is coated with the carrier protein. In some embodiments, the average or mean particle size of the nanoparticles in the composition is no greater than about 200 nm (such as less than about 200 nm). In some embodiments, the taxane is paclitaxel. In some embodiments, the carrier protein is albumin such as human serum albumin or human albumin. In some embodiments, the method of using taxane nanoparticles for treating melanoma is used as a monotherapy. In some embodiments, the method of treating melanoma using taxane nanoparticles does not further comprise one other therapeutic agent (such as one other chemotherapeutic agent or immunotherapeutic agent). In some embodiments, the method does not further comprise a cytotoxic chemotherapeutic agent.

The methods described herein are useful for various aspects of melanoma treatment. In some embodiments, there is provided a method for treatment of melanoma in an individual (e.g., human) using an effective amount of a composition comprising nanoparticles comprising a taxane and a carrier protein. In some embodiments, an effective amount is an amount sufficient to delay development of melanoma. In some embodiments, an effective amount is an amount sufficient to prevent or delay occurrence and/or recurrence of melanoma. In some embodiments, an effective amount comprises an amount sufficient to produce a complete response when an individual is treated with any of the methods described herein for melanoma. In some embodiments, an effective amount comprises an amount sufficient to produce a partial response when an individual is treated with any of the methods described herein for melanoma.

In some embodiments, the effective amount of a composition comprising nanoparticles comprising taxane (e.g., paclitaxel) and a carrier protein (e.g., albumin) produces a complete response, a partial response, reduction in size of a melanoma tumor, reduction in metastasis, stable disease, and/or an increase in overall response rate. In some embodiments, the taxane is paclitaxel. In some embodiments, the carrier protein is albumin. The efficacy parameters (such as complete response or partial response) described herein may be determined by any of the methods known to one skilled in the art. For example, the efficacy parameters may be determined according to RECIST such as RECIST version 1.0 or 1.1 criteria. RECIST version 1.1 criteria are described in Eisenhauer E A et al. 2009, Eur J Cancer., 45(2):228-47, the disclosure of which is incorporated herein by reference in its entirety.

In some embodiments, there is provided a method of inhibiting melanoma cell proliferation in an individual, comprising administering to the individual an effective amount of a composition comprising nanoparticles comprising a taxane (e.g., paclitaxel) and a carrier protein (e.g., albumin). In some embodiments, the taxane is paclitaxel. In some embodiments, the carrier protein is albumin. In some embodiments, there is provided a method of inhibiting melanoma cell proliferation in an individual, comprising administering to the individual an effective amount of a composition comprising nanoparticles comprising paclitaxel and albumin. In some embodiments, at least about 10% (including for example at least about any of 20%, 30%, 40%, 60%, 70%, 80%, 90%, 91%, 92%, 93%, 94%, 95%, 96%, 97%, 98%, 99%, or 100%) cell proliferation is inhibited. In some embodiments, the individual has stage IV or metastatic melanoma (e.g., stage IV or metastatic cutaneous melanoma). In some embodiments, the melanoma is metastatic malignant melanoma. In some embodiments, the metastatic melanoma is at stage M1a, stage M1b, or stage M1c. In some embodiments, the metastatic melanoma is at stage M1c. In some embodiments, the melanoma comprises a mutation in BRAF. In some embodiments the melanoma comprises a BRAF V600E mutation. In some embodiments, the melanoma does not comprise a mutation in BRAF. In some embodiments, the melanoma does not comprise BRAF mutant such as a BRAF mutant with increased activity (for example, increased kinase activity, and/or increased activity as compared to wild-type BRAF) or a BRAF gain-of-function mutant. In some embodiments, the melanoma does not comprise a BRAF V600E mutation (e.g., the melanoma comprises wild-type BRAF). In some embodiments, the melanoma comprises wild-type BRAF. In some embodiments, the melanoma comprises a BRAF mutant such as a BRAF mutant with increased activity (for example, increased kinase activity, and/or increased activity as compared to wild-type BRAF) or a BRAF gain-of-function mutant. In some embodiments, the melanoma comprises BRAF V600E mutation. In some embodiments, the individual has elevated serum LDH level. In some embodiments, the individual has normal serum LDH level. In some embodiments, the individual has serum LDH of about any of the following: <0.8×ULN, 0.4-0.8×ULN, 0.8-1.1×ULN, 0.9-1.1×ULN, 0.8-1.2×ULN, 1.1-1.5×ULN, 1.2-1.5×ULN, 1.1-2×ULN, or 1.5-2×ULN. In some embodiments, the individual has serum LDH of less than about 0.8×ULN. In some embodiments, the individual has serum LDH at about 0.8× to about 1.1×ULN. In some embodiments, the individual has serum LDH of between greater than about 1.1× to about 2.0×ULN. In some embodiments, the individual has serum LDH of between about 1.1× to about 2.0×ULN. In some embodiments, the individual is a human (e.g., male or female).

In some embodiments, there is provided a method of preventing or inhibiting metastasis of melanoma in an individual, comprising administering to the individual an effective amount of a composition comprising nanoparticles comprising a taxane (e.g., paclitaxel) and a carrier protein (e.g., albumin). In some embodiments, the taxane is paclitaxel. In some embodiments, the carrier protein is albumin. In some embodiments, there is provided a method of preventing or inhibiting metastasis of melanoma in an individual, comprising administering to the individual an effective amount of a composition comprising nanoparticles comprising paclitaxel and albumin. In some embodiments, at least about 10% (including for example at least about any of 20%, 30%, 40%, 60%, 70%, 80%, 90%, 95%, or 100%) metastasis is inhibited. In some embodiments, there is provided a method of delaying or slowing metastasis of melanoma in an individual, comprising administering to the individual an effective amount of a composition comprising nanoparticles comprising a taxane and a carrier protein (e.g., albumin). In some embodiments, the individual has stage IV or metastatic melanoma (e.g., stage IV or metastatic cutaneous melanoma). In some embodiments, the melanoma is metastatic malignant melanoma. In some embodiments, the metastatic melanoma is at stage M1a, stage M1b, or stage M1c. In some embodiments, the metastatic melanoma is at stage M1c. In some embodiments, the melanoma comprises a mutation in BRAF. In some embodiments, the melanoma comprises a BRAF V600E mutation. In some embodiments, the melanoma does not comprise a mutation in BRAF. In some embodiments, the melanoma does not comprise BRAF mutant such as a BRAF mutant with increased activity (for example, increased kinase activity, and/or increased activity as compared to wild-type BRAF) or a BRAF gain-of-function mutant. In some embodiments, the melanoma does not comprise BRAF V600E mutation (e.g., the melanoma comprises wild-type BRAF). In some embodiments, the melanoma comprises wild-type BRAF. In some embodiments, the melanoma comprises a BRAF mutant such as a BRAF mutant with increased activity (for example, increased kinase activity, and/or increased activity as compared to wild-type BRAF) or a BRAF gain-of-function mutant. In some embodiments, the melanoma comprises BRAF V600E mutation. In some embodiments, the individual has elevated serum LDH level. In some embodiments, the individual has normal serum LDH level. In some embodiments, the individual has serum LDH of about any of the following: <0.8×ULN, 0.4-0.8×ULN, 0.8-1.1×ULN, 0.9-1.1×ULN, 0.8-1.2×ULN, 1.1-1.5×ULN, 1.2-1.5×ULN, 1.1-2×ULN, or 1.5-2×ULN. In some embodiments, the individual has serum LDH of less than about 0.8×ULN. In some embodiments, the individual has serum LDH at about 0.8× to about 1.1×ULN. In some embodiments, the individual has serum LDH of between greater than about 1.1× to about 2.0×ULN. In some embodiments, the individual has serum LDH of between about 1.1× to about 2.0×ULN. In some embodiments, the individual is a human (e.g., male or female).

In some embodiments, there is provided a method of reducing size of a melanoma tumor or reducing melanoma tumor volume in an individual, comprising administering to the individual an effective amount of a composition comprising nanoparticles comprising a taxane (e.g., paclitaxel) and a carrier protein (e.g., albumin). In some embodiments, the taxane is paclitaxel. In some embodiments, the carrier protein is albumin. In some embodiments, there is provided a method of reducing size of a melanoma tumor or reducing melanoma tumor volume in an individual, comprising administering to the individual an effective amount of a composition comprising nanoparticles comprising paclitaxel and albumin. In some embodiments, the tumor size or tumor volume is reduced at least about 10% (including for example at least about any of 20%, 30%, 40%, 60%, 70%, 80%, 90%, 95%, or 100%). In some embodiments, the individual has stage IV or metastatic melanoma (e.g., stage IV or metastatic cutaneous melanoma). In some embodiments, the melanoma is metastatic malignant melanoma. In some embodiments, the metastatic melanoma is at stage M1a, stage M1b, or stage M1c. In some embodiments, the metastatic melanoma is at stage M1c. In some embodiments, the melanoma comprises a mutation in BRAF. In some embodiments, the melanoma comprises a BRAF V600E mutation. In some embodiments, the melanoma does not comprise a mutation in BRAF. In some embodiments, the melanoma does not comprise BRAF mutant such as a BRAF mutant with increased activity (for example, increased kinase activity, and/or increased activity as compared to wild-type BRAF) or a BRAF gain-of-function mutant. In some embodiments, the melanoma does not comprise BRAF V600E mutation (e.g., the melanoma comprises wild-type BRAF). In some embodiments, the melanoma comprises wild-type BRAF. In some embodiments, the melanoma comprises a BRAF mutant such as a BRAF mutant with increased activity (for example, increased kinase activity, and/or increased activity as compared to wild-type BRAF) or a BRAF gainof-function mutant. In some embodiments, the melanoma comprises BRAF V600E mutation. In some embodiments, the individual has elevated serum LDH level. In some embodiments, the individual has normal serum LDH level. In some embodiments, the individual has serum LDH of about any of the following: <0.8×ULN, 0.4-0.8×ULN, 0.8-1.1× ULN, 0.9-1.1×ULN, 0.8-1.2×ULN, 1.1-1.5×ULN, 1.2-1.5× ULN, 1.1-2×ULN, or 1.5-2×ULN. In some embodiments, the individual has serum LDH of less than about 0.8×ULN. In some embodiments, the individual has serum LDH at about 0.8× to about 1.1×ULN. In some embodiments, the individual has serum LDH of between greater than about 1.1× to about 2.0×ULN. In some embodiments, the individual has serum LDH of between about 1.1× to about 2.0×ULN. In some embodiments, the individual is a human (e.g., male or female).

In some embodiments, there is provided a method of prolonging time to disease progression of melanoma in an individual, comprising administering to the individual an effective amount of a composition comprising nanoparticles comprising a taxane (e.g., paclitaxel) and a carrier protein (e.g., albumin). In some embodiments, the taxane is paclitaxel. In some embodiments, the carrier protein is albumin. In some embodiments, there is provided a method of prolonging time to disease progression of melanoma in an individual, comprising administering to the individual an effective amount of a composition comprising nanoparticles comprising paclitaxel and albumin. In some embodiments, the method prolongs the time to disease progression by at least about any of 1, 2, 3, 4, 5, 6, 7, 8, 9, 10, 11, 12, 13, 14, 15, 16, 17, 18, 19, 20, 2, 24, 26, 28, 30, 35, 40, 45, or 50 weeks. In some embodiments, the individual has stage IV or metastatic melanoma (e.g., stage IV or metastatic cutaneous melanoma). In some embodiments, the melanoma is metastatic malignant melanoma. In some embodiments, the metastatic melanoma is at stage M1a, stage M1b, or stage M1c. In some embodiments, the metastatic melanoma is at stage M1c. In some embodiments, the melanoma comprises a mutation in BRAF. In some embodiments, the melanoma comprises a V600E BRAF mutation. In some embodiments, the melanoma does not comprise a mutation in BRAF. In some embodiments, the melanoma does not comprise BRAF mutant such as a BRAF mutant with increased activity (for example, increased kinase activity, and/or increased activity as compared to wild-type BRAF) or a BRAF gain-of-function mutant. In some embodiments, the melanoma does not comprise a BRAF V600E mutation (e.g., the melanoma comprises wild-type BRAF). In some embodiments, the melanoma comprises wild-type BRAF. In some embodiments, the melanoma comprises a BRAF mutant such as a BRAF mutant with increased activity (for example, increased kinase activity, and/or increased activity as compared to wild-type BRAF) or a BRAF gain-of-function mutant. In some embodiments, the melanoma comprises BRAF V600E mutation. In some embodiments, the individual has elevated serum LDH level. In some embodiments, the individual has normal serum LDH level. In some embodiments, the individual has serum LDH of about any of the following: <0.8×ULN, 0.4-0.8×ULN, 0.8-1.1× ULN, 0.9-1.1×ULN, 0.8-1.2×ULN, 1.1-1.5×ULN, 1.2-1.5× ULN, 1.1-2×ULN, or 1.5-2×ULN. In some embodiments, the individual has serum LDH of less than about 0.8×ULN. In some embodiments, the individual has serum LDH at about 0.8× to about 1.1×ULN. In some embodiments, the individual has serum LDH of between greater than about 1.1× to about 2.0×ULN. In some embodiments, the individual has serum LDH of between about 1.1× to about 2.0×ULN. In some embodiments, the individual is a human (e.g., male or female).

In some embodiments, there is provided a method of prolonging survival of an individual having melanoma, comprising administering to the individual an effective amount of a composition comprising nanoparticles comprising a taxane (e.g., paclitaxel) and a carrier protein (e.g., albumin). In some embodiments, the taxane is paclitaxel. In some embodiments, the carrier protein is albumin. In some embodiments, there is provided a method of prolonging survival of an individual having melanoma, comprising administering to the individual an effective amount of a composition comprising nanoparticles comprising a paclitaxel and albumin. In some embodiments, the method prolongs the survival of the individual by at least about any of 1, 2, 3, 4, 5, 6, 7, 8, 9, 10, 11, 12, 18, or 24 months. In some embodiments, the individual has stage IV or metastatic melanoma (e.g., stage IV or metastatic cutaneous melanoma). In some embodiments, the melanoma is metastatic malignant melanoma. In some embodiments, the metastatic melanoma is at stage M1a, stage M1b, or stage M1c. In some embodiments, the metastatic melanoma is at stage M1c. In some embodiments, the melanoma comprises a mutation in BRAF. In some embodiments, the melanoma comprises a BRAF V600E mutation. In some embodiments, the melanoma does not comprise a mutation in BRAF. In some embodiments, the melanoma does not comprise BRAF mutant such as a BRAF mutant with increased activity (for example, increased kinase activity, and/or increased activity as compared to wild-type BRAF) or a BRAF gain-of-function mutant. In some embodiments, the melanoma does not comprise BRAF V600E mutation (e.g., the melanoma comprises wild-type BRAF). In some embodiments, the melanoma comprises wild-type BRAF. In some embodiments, the melanoma comprises a BRAF mutant such as a BRAF mutant with increased activity (for example, increased kinase activity, and/or increased activity as compared to wild-type BRAF) or a BRAF gain-of-function mutant. In some embodiments, the melanoma comprises BRAF V600E mutation. In some embodiments, the individual has elevated serum LDH level. In some embodiments, the individual has normal serum LDH level. In some embodiments, the individual has serum LDH of about any of the following: <0.8×ULN, 0.4-0.8×ULN, 0.8-1.1×ULN, 0.9-1.1×ULN, 0.8-1.2×ULN, 1.1-1.5×ULN, 1.2-1.5×ULN, 1.1-2×ULN, or 1.5-2×ULN. In some embodiments, the individual has serum LDH of less than about 0.8×ULN. In some embodiments, the individual has serum LDH at about 0.8× to about 1.1×ULN. In some embodiments, the individual has serum LDH of between greater than about 1.1× to about 2.0×ULN. In some embodiments, the individual has serum LDH of between about 1.1× to about 2.0×ULN. In some embodiments, the individual is a human (e.g., male or female). In some embodiments, the taxane is paclitaxel. In some embodiments, the carrier protein is albumin.

The method of using taxane nanoparticles for treating melanoma may be used as a monotherapy. In some embodiments, there is provide a method of treating melanoma in an individual (e.g., human) comprising administering to the individual an effective amount of a composition comprising nanoparticles comprising a taxane (e.g., paclitaxel) and a carrier protein (e.g., albumin), wherein the method is used as a monotherapy. In some embodiments, a method described herein does not further comprise one other therapeutic agent (such as one other chemotherapeutic agent or immunotherapeutic agent). In some embodiments, a method described herein does not further comprise a cytotoxic chemotherapeutic agent.

In some embodiments, there is provided a method of treating melanoma in an individual (e.g., human) comprising administering (such as intravenously administering) to the individual an effective amount of a composition comprising nanoparticles comprising paclitaxel and albumin (such as Nab-paclitaxel, for example about 5 mg/ml Nab-paclitaxel), wherein the dose of paclitaxel in the nanoparticle composition is between about 80 mg/m$^2$ to about 175 mg/m$^2$ (such as between about 90 mg/m$^2$ to about 150 mg/m$^2$). In some embodiments, there is provided a method of treating melanoma in an individual (e.g., human) comprising administering (such as intravenously administering) to the individual an effective amount of a composition comprising nanoparticles comprising paclitaxel and albumin (such as Nab-paclitaxel, for example about 5 mg/ml Nab-paclitaxel), wherein the dose of paclitaxel in the nanoparticle composition is between about 90 mg/m$^2$ to about 150 mg/m$^2$ (for example about 90 mg/m$^2$, about 120 mg/m$^2$, or about 150 mg/m$^2$), wherein the nanoparticle composition is administered weekly. In some embodiments, there is provided a method of treating melanoma in an individual (e.g., human) comprising administering (such as intravenously administering) to the individual an effective amount of a composition comprising nanoparticles comprising paclitaxel and albumin (such as Nab-paclitaxel, for example about 5 mg/ml Nab-paclitaxel), wherein the dose of paclitaxel in the nanoparticle composition is between about 90 mg/m$^2$ to about 150 mg/m$^2$ (for example about 90 mg/m$^2$, about 120 mg/m$^2$, or about 150 mg/m$^2$), wherein the nanoparticle composition is administered weekly, three out of four weeks. In some embodiments, there is provided a method of treating melanoma in human individual who has previously been treated for melanoma, comprising administering (such as intravenously administering) to the individual an effective amount of a composition comprising nanoparticles comprising paclitaxel and albumin (such as Nab-paclitaxel, for example about 5 mg/ml Nab-paclitaxel), wherein the dose of paclitaxel in the nanoparticle composition is between about 90 mg/m$^2$ to about 150 mg/m$^2$ (for example about 90 mg/m$^2$, about 120 mg/m$^2$, or about 150 mg/m$^2$), wherein the nanoparticle composition is administered weekly, three out of four weeks. In some embodiments, there is provided a method of treating melanoma in human individual who is chemotherapy naïve, comprising administering (such as intravenously administering) to the individual an effective amount of a composition comprising nanoparticles comprising paclitaxel and albumin (such as Nab-paclitaxel, for example about 5 mg/ml Nab-paclitaxel), wherein the dose of paclitaxel in the nanoparticle composition is between about 90 mg/m$^2$ to about 150 mg/m$^2$ (for example about 90 mg/m$^2$, about 120 mg/m$^2$, or about 150 mg/m$^2$), wherein the nanoparticle composition is administered weekly, three out of four weeks. In some embodiments, the individual is a male. In some embodiments, the individual is a female. In some embodiment, the individual is a human who is at least 65 years old (including for example at least 70, 75, or 80 years old). In some embodiments, the individual is a human who is less than 65 years old (including for example less than 60, 50, or 40 years old).

In some embodiments, there is provided a method of treating metastatic melanoma (such as stage IV metastatic melanoma or M1c melanoma) in an individual (e.g., human) comprising administering (such as intravenously administering) to the individual an effective amount of a composition comprising nanoparticles comprising paclitaxel and albumin (such as Nab-paclitaxel, for example about 5 mg/ml Nab-paclitaxel), wherein the dose of paclitaxel in the nanoparticle composition is between about 80 mg/m$^2$ to about 175 mg/m$^2$ (such as between about 90 mg/m$^2$ to about 150 mg/m$^2$). In some embodiments, there is provided a method of treating metastatic melanoma (such as stage IV melanoma or M1c melanoma) in an individual (e.g., human) comprising administering (such as intravenously administering) to the individual an effective amount of a composition comprising nanoparticles comprising paclitaxel and albumin (such as Nab-paclitaxel, for example about 5 mg/ml Nab-paclitaxel), wherein the dose of paclitaxel in the nanoparticle composition is between about 90 mg/m$^2$ to about 150 mg/m$^2$ (for example about 90 mg/m$^2$, about 120 mg/m$^2$, or about 150 mg/m$^2$), wherein the nanoparticle composition is administered weekly. In some embodiments, there is provided a method of treating metastatic melanoma (such as stage IV metastatic melanoma or M1c melanoma) in an individual (e.g., human) comprising administering (such as intravenously administering) to the individual an effective amount of a composition comprising nanoparticles comprising paclitaxel and albumin (such as Nab-paclitaxel, for example about 5 mg/ml Nab-paclitaxel), wherein the dose of paclitaxel in the nanoparticle composition is between about 90 mg/m$^2$ to about 150 mg/m$^2$ (for example about 90 mg/m$^2$, about 120 mg/m$^2$, or about 150 mg/m$^2$), wherein the nanoparticle composition is administered weekly, three out of four weeks. In some embodiments, there is provided a method of treating metastatic melanoma (such as stage IV metastatic melanoma or M1c melanoma) in human individual who has previously been treated for melanoma, comprising administering (such as intravenously administering) to the individual an effective amount of a composition comprising nanoparticles comprising paclitaxel and albumin (such as Nab-paclitaxel, for example about 5 mg/ml Nab-paclitaxel), wherein the dose of paclitaxel in the nanoparticle composition is between about 90 mg/m$^2$ to about 150 mg/m$^2$ (for example about 90 mg/m$^2$, about 120 mg/m$^2$, or about 150 mg/m$^2$), wherein the nanoparticle composition is administered weekly, three out of four weeks. In some embodiments, there is provided a method of treating metastatic melanoma (such as stage IV metastatic melanoma or M1c melanoma) in human individual who is chemotherapy naïve, comprising administering (such as intravenously administering) to the individual an effective amount of a composition comprising nanoparticles comprising paclitaxel and albumin (such as Nab-paclitaxel, for example about 5 mg/ml Nab-paclitaxel), wherein the dose of paclitaxel in the nanoparticle composition is between about 90 mg/m$^2$ to about 150 mg/m$^2$ (for example about 90 mg/m$^2$, about 120 mg/m$^2$, or about 150 mg/m$^2$), wherein the nanoparticle composition is administered weekly, three out of four weeks. In some embodiments, the individual is a male. In some embodiments, the individual is a female. In some embodiment, the individual is a human who is at least 65 years old (including for example at least 70, 75, or 80 years old). In some embodiments, the individual is a human who is less than 65 years old (including for example less than 60, 50, or 40 years old).

In some embodiments, there is provided a method of treating melanoma in an individual (e.g., human) who comprises wild-type BRAF, comprising administering (such as intravenously administering) to the individual an effective amount of a composition comprising nanoparticles comprising paclitaxel and albumin (such as Nab-paclitaxel, for example about 5 mg/ml Nab-paclitaxel), wherein the dose of paclitaxel in the nanoparticle composition is between about 80 mg/m$^2$ to about 175 mg/m$^2$ (such as between about 90 mg/m$^2$ to about 150 mg/m$^2$). In some embodiments, there is provided a method of treating melanoma in an individual (e.g., human) who comprises wild-type BRAF, comprising administering (such as intravenously administering) to the individual an effective amount of a composition comprising nanoparticles comprising paclitaxel and albumin (such as Nab-paclitaxel, for example about 5 mg/ml Nab-paclitaxel), wherein the dose of paclitaxel in the nanoparticle composition is between about 90 mg/m² to about 150 mg/m² (for example about 90 mg/m², about 120 mg/m², or about 150 mg/m²), wherein the nanoparticle composition is administered weekly. In some embodiments, there is provided a method of treating melanoma in an individual (e.g., human) who comprises wild-type BRAF, comprising administering (such as intravenously administering) to the individual an effective amount of a composition comprising nanoparticles comprising paclitaxel and albumin (such as Nab-paclitaxel, for example about 5 mg/ml Nab-paclitaxel), wherein the dose of paclitaxel in the nanoparticle composition is between about 90 mg/m² to about 150 mg/m² (for example about 90 m g/m², about 120 mg/m², or about 150 mg/m²), wherein the nanoparticle composition is administered weekly, three out of four weeks. In some embodiments, there is provided a method of treating melanoma in an individual (e.g., human) who comprises wild-type BRAF and has previously been treated for melanoma, comprising administering (such as intravenously administering) to the individual an effective amount of a composition comprising nanoparticles comprising paclitaxel and albumin (such as Nab-paclitaxel, for example about 5 mg/ml Nab-paclitaxel), wherein the dose of paclitaxel in the nanoparticle composition is between about 90 mg/m² to about 150 mg/m² (for example about 90 mg/m², about 120 mg/m², or about 150 mg/m²), wherein the nanoparticle composition is administered weekly, three out of four weeks. In some embodiments, there is provided a method of treating melanoma in an individual (e.g., human) who comprises wild-type BRAF and is chemotherapy naïve, comprising administering (such as intravenously administering) to the individual an effective amount of a composition comprising nanoparticles comprising paclitaxel and albumin (such as Nab-paclitaxel, for example about 5 mg/ml Nab-paclitaxel), wherein the dose of paclitaxel in the nanoparticle composition is between about 90 mg/m² to about 150 mg/m² (for example about 90 mg/m², about 120 mg/m², or about 150 mg/m²), wherein the nanoparticle composition is administered weekly, three out of four weeks. In some embodiments, the individual is a male. In some embodiments, the individual is a female. In some embodiment, the individual is a human who is at least 65 years old (including for example at least 70, 75, or 80 years old). In some embodiments, the individual is a human who is less than 65 years old (including for example less than 60, 50, or 40 years old).

In some embodiments, there is provided a method of treating melanoma in an individual (e.g., human) who comprises a BRAF V600E mutation, comprising administering (such as intravenously administering) to the individual an effective amount of a composition comprising nanoparticles comprising paclitaxel and albumin (such as Nab-paclitaxel, for example about 5 mg/ml Nab-paclitaxel), wherein the dose of paclitaxel in the nanoparticle composition is between about 80 mg/m² to about 175 mg/m² (such as between about 90 mg/m² to about 150 mg/m²). In some embodiments, there is provided a method of treating melanoma in an individual (e.g., human) who comprises a BRAF V600E mutation, comprising administering (such as intravenously administering) to the individual an effective amount of a composition comprising nanoparticles comprising paclitaxel and albumin (such as Nab-paclitaxel, for example about 5 mg/ml Nab-paclitaxel), wherein the dose of paclitaxel in the nanoparticle composition is between about 90 mg/m² to about 150 mg/m² (for example about 90 mg/m², about 120 mg/m², or about 150 mg/m²), wherein the nanoparticle composition is administered weekly. In some embodiments, there is provided a method of treating melanoma in an individual (e.g., human) who comprises a BRAF V600E mutation, comprising administering (such as intravenously administering) to the individual an effective amount of a composition comprising nanoparticles comprising paclitaxel and albumin (such as Nab-paclitaxel, for example about 5 mg/ml Nab-paclitaxel), wherein the dose of paclitaxel in the nanoparticle composition is between about 90 mg/m² to about 150 mg/m² (for example about 90 mg/m², about 120 mg/m², or about 150 mg/m²), wherein the nanoparticle composition is administered weekly, three out of four weeks. In some embodiments, there is provided a method of treating melanoma in an individual (e.g., human) who comprises a BRAF V600E mutation and has previously been treated for melanoma, comprising administering (such as intravenously administering) to the individual an effective amount of a composition comprising nanoparticles comprising paclitaxel and albumin (such as Nab-paclitaxel, for example about 5 mg/ml Nab-paclitaxel), wherein the dose of paclitaxel in the nanoparticle composition is between about 90 mg/m² to about 150 mg/m² (for example about 90 mg/m², about 120 mg/m², or about 150 mg/m²), wherein the nanoparticle composition is administered weekly, three out of four weeks. In some embodiments, there is provided a method of treating melanoma in an individual (e.g., human) who comprises a BRAF V600E mutation and is chemotherapy naïve, comprising administering (such as intravenously administering) to the individual an effective amount of a composition comprising nanoparticles comprising paclitaxel and albumin (such as Nab-paclitaxel, for example about 5 mg/ml Nab-paclitaxel), wherein the dose of paclitaxel in the nanoparticle composition is between about 90 mg/m² to about 150 mg/m² (for example about 90 mg/m², about 120 mg/m², or about 150 mg/m²), wherein the nanoparticle composition is administered weekly, three out of four weeks. In some embodiments, the individual is a male. In some embodiments, the individual is a female. In some embodiment, the individual is a human who is at least 65 years old (including for example at least 70, 75, or 80 years old). In some embodiments, the individual is a human who is less than 65 years old (including for example less than 60, 50, or 40 years old).

In some embodiments, there is provided a method of treating metastatic melanoma (such as stage IV metastatic melanoma or M1c melanoma) in an individual (e.g., human) who comprises wild-type BRAF, comprising administering (such as intravenously administering) to the individual an effective amount of a composition comprising nanoparticles comprising paclitaxel and albumin (such as Nab-paclitaxel, for example about 5 mg/ml Nab-paclitaxel), wherein the dose of paclitaxel in the nanoparticle composition is between about 80 mg/m² to about 175 mg/m² (such as between about 90 mg/m² to about 150 mg/m²). In some embodiments, there is provided a method of treating metastatic melanoma (such as stage IV metastatic melanoma or M1c melanoma) in an individual (e.g., human) who comprises wild-type BRAF, comprising administering (such as intravenously administering) to the individual an effective amount of a composition comprising nanoparticles comprising paclitaxel and albumin (such as Nab-paclitaxel, for example about 5 mg/ml Nab-paclitaxel), wherein the dose of paclitaxel in the nanoparticle composition is between about 90 mg/m² to about 150 mg/m² (for example about 90 mg/m², about 120 mg/m², or about 150 mg/m²), wherein the nanoparticle composition is administered weekly. In some embodiments, there is provided a method of treating metastatic melanoma (such as stage IV metastatic melanoma or M1c melanoma) in an individual (e.g., human) who comprises wild-type BRAF, comprising administering (such as intravenously administering) to the individual an effective amount of a composition comprising nanoparticles comprising paclitaxel and albumin (such as Nab-paclitaxel, for example about 5 mg/ml Nab-paclitaxel), wherein the dose of paclitaxel in the nanoparticle composition is between about 90 mg/m² to about 150 mg/m² (for example about 90 mg/m², about 120 mg/m², or about 150 mg/m²), wherein the nanoparticle composition is administered weekly, three out of four weeks. In some embodiments, there is provided a method of treating metastatic melanoma (such as stage IV metastatic melanoma or M1c melanoma) in an individual (e.g., human) who comprises wild-type BRAF and has previously been treated for melanoma, comprising administering (such as intravenously administering) to the individual an effective amount of a composition comprising nanoparticles comprising paclitaxel and albumin (such as Nab-paclitaxel, for example about 5 mg/ml Nab-paclitaxel), wherein the dose of paclitaxel in the nanoparticle composition is between about 90 mg/m² to about 150 mg/m² (for example about 90 mg/m², about 120 mg/m², or about 150 mg/m²), wherein the nanoparticle composition is administered weekly, three out of four weeks. In some embodiments, there is provided a method of treating metastatic melanoma (such as stage IV metastatic melanoma or M1c melanoma) in an individual (e.g., human) who comprises wild-type BRAF and is chemotherapy naïve, comprising administering (such as intravenously administering) to the individual an effective amount of a composition comprising nanoparticles comprising paclitaxel and albumin (such as Nab-paclitaxel, for example about 5 mg/ml Nab-paclitaxel), wherein the dose of paclitaxel in the nanoparticle composition is between about 90 mg/m² to about 150 mg/m² (for example about 90 mg/m², about 120 mg/m², or about 150 mg/m²), wherein the nanoparticle composition is administered weekly, three out of four weeks. In some embodiments, the individual is a male. In some embodiments, the individual is a female. In some embodiment, the individual is a human who is at least 65 years old (including for example at least 70, 75, or 80 years old). In some embodiments, the individual is a human who is less than 65 years old (including for example less than 60, 50, or 40 years old).

In some embodiments, there is provided a method of treating metastatic melanoma (such as stage IV metastatic melanoma or M1c melanoma) in an individual (e.g., human) who comprises a BRAF V600E mutation, comprising administering (such as intravenously administering) to the individual an effective amount of a composition comprising nanoparticles comprising paclitaxel and albumin (such as Nab-paclitaxel, for example about 5 mg/ml Nab-paclitaxel), wherein the dose of paclitaxel in the nanoparticle composition is between about 80 mg/m² to about 175 mg/m² (such as between about 90 mg/m² to about 150 mg/m²). In some embodiments, there is provided a method of treating metastatic melanoma (such as stage IV metastatic melanoma or M1c melanoma) in an individual (e.g., human) who comprises a BRAF V600E mutation, comprising administering (such as intravenously administering) to the individual an effective amount of a composition comprising nanoparticles comprising paclitaxel and albumin (such as Nab-paclitaxel, for example about 5 mg/ml Nab-paclitaxel), wherein the dose of paclitaxel in the nanoparticle composition is between about 90 mg/m² to about 150 mg/m² (for example about 90 mg/m², about 120 mg/m², or about 150 mg/m²), wherein the nanoparticle composition is administered weekly. In some embodiments, there is provided a method of treating metastatic melanoma (such as stage IV metastatic melanoma or M1c melanoma) in an individual (e.g., human) who comprises a BRAF V600E mutation, comprising administering (such as intravenously administering) to the individual an effective amount of a composition comprising nanoparticles comprising paclitaxel and albumin (such as Nab-paclitaxel, for example about 5 mg/ml Nab-paclitaxel), wherein the dose of paclitaxel in the nanoparticle composition is between about 90 mg/m² to about 150 mg/m² (for example about 90 mg/m², about 120 mg/m², or about 150 mg/m²), wherein the nanoparticle composition is administered weekly, three out of four weeks. In some embodiments, there is provided a method of treating metastatic melanoma (such as stage IV metastatic melanoma or M1c melanoma) in an individual (e.g., human) who comprises a BRAF V600E mutation and has previously been treated for melanoma, comprising administering (such as intravenously administering) to the individual an effective amount of a composition comprising nanoparticles comprising paclitaxel and albumin (such as Nab-paclitaxel, for example about 5 mg/ml Nab-paclitaxel), wherein the dose of paclitaxel in the nanoparticle composition is between about 90 mg/m² to about 150 mg/m² (for example about 90 mg/m², about 120 mg/m², or about 150 mg/m²), wherein the nanoparticle composition is administered weekly, three out of four weeks. In some embodiments, there is provided a method of treating metastatic melanoma (such as stage IV metastatic melanoma or M1c melanoma) in an individual (e.g., human) who comprises a BRAF V600E mutation and is chemotherapy naïve, comprising administering (such as intravenously administering) to the individual an effective amount of a composition comprising nanoparticles comprising paclitaxel and albumin (such as Nab-paclitaxel, for example about 5 mg/ml Nab-paclitaxel), wherein the dose of paclitaxel in the nanoparticle composition is between about 90 mg/m² to about 150 mg/m² (for example about 90 mg/m², about 120 mg/m², or about 150 mg/m²), wherein the nanoparticle composition is administered weekly, three out of four weeks. In some embodiments, the individual is a male. In some embodiments, the individual is a female. In some embodiment, the individual is a human who is at least 65 years old (including for example at least 70, 75, or 80 years old). In some embodiments, the individual is a human who is less than 65 years old (including for example less than 60, 50, or 40 years old).

In some embodiments, there is provided a method of treating metastatic melanoma (such as stage IV metastatic melanoma or M1c melanoma) in the liver in an individual (e.g., human) comprising administering (such as administering by hepatic arterial infusion) to the individual an effective amount of a composition comprising nanoparticles comprising paclitaxel and albumin (such as Nab-paclitaxel, for example about 5 mg/ml Nab-paclitaxel), wherein the dose of paclitaxel in the nanoparticle composition is between about 80 mg/m² to about 175 mg/m² (such as between about 90 mg/m² to about 150 mg/m²). In some embodiments, there is provided a method of treating metastatic melanoma (such as stage IV metastatic melanoma or M1c melanoma) in the liver in an individual (e.g., human) who comprises wild-type BRAF, comprising administering (such as administering by hepatic arterial infusion) to the individual an effective amount of a composition comprising nanoparticles comprising paclitaxel and albumin (such as Nab-paclitaxel, for example about 5 mg/ml Nab-paclitaxel), wherein the dose of paclitaxel in the nanoparticle composition is between about 80 mg/m² to about 175 mg/m² (such as between about 90 mg/m² to about 150 mg/m²). In some embodiments, the nanoparticle composition is administered weekly. In some embodiments, the nanoparticle composition is administered weekly, three out of four weeks. In some embodiments, the individual is a male. In some embodiments, the individual is a female. In some embodiment, the individual is a human who is at least 65 years old (including for example at least 70, 75, or 80 years old). In some embodiments, the individual is a human who is less than 65 years old (including for example less than 60, 50, or 40 years old).

In some embodiments, there is provided a method of treating metastatic melanoma (such as stage IV metastatic melanoma or M1c melanoma) in the liver in an individual (e.g., human) who comprises wild-type BRAF, comprising administering (such as administering by hepatic arterial infusion) to the individual an effective amount of a composition comprising nanoparticles comprising paclitaxel and albumin (such as Nab-paclitaxel, for example about 5 mg/ml Nab-paclitaxel), wherein the Nab-paclitaxel dose is between about 130 mg/m$^2$ to about 285 mg/m$^2$ (such as, for example, about 130 mg/m$^2$, about 170 mg/m$^2$, about 220 mg/m$^2$, or about 285 mg/m$^2$). In some embodiments, there is provided a method of treating metastatic melanoma (such as stage IV metastatic melanoma or M1c melanoma) in the liver in an individual (e.g., human) who comprises a BRAF V600E mutation, comprising administering (such as administering by hepatic arterial infusion) to the individual an effective amount of a composition comprising nanoparticles comprising paclitaxel and albumin (such as Nab-paclitaxel, for example about 5 mg/ml Nab-paclitaxel), wherein the Nab-paclitaxel dose is between about 130 mg/m$^2$ to about 285 mg/m$^2$ (such as, for example, about 130 mg/m$^2$, about 170 mg/m$^2$, about 220 mg/m$^2$, or about 285 mg/m$^2$). In some embodiments, the nanoparticle composition is administered via hepatic artery one day every three weeks. In some embodiments, the nanoparticle composition is administered via hepatic arterial infusion over 30 minutes every three weeks. In some embodiments, the individual is a human who is at least 65 years old (including for example at least 70, 75 or 80 years old). In some embodiments, the individual is a human who is less than 65 years old (including, for example, less than 60, 50, or 40 years old).

In some embodiments, there is provided a method of treating metastatic melanoma (such as stage IV metastatic melanoma or M1c melanoma) in the liver in an individual (e.g., human) comprising administering (such as administering by hepatic arterial infusion) to the individual an effective amount of a composition comprising nanoparticles comprising paclitaxel and albumin (such as Nab-paclitaxel, for example about 5 mg/ml Nab-paclitaxel), wherein the dose of paclitaxel in the nanoparticle composition is between about 80 mg/m$^2$ to about 175 mg/m$^2$ (such as between about 100 mg/m$^2$ to about 150 mg/m$^2$). In some embodiments, there is provided a method of treating metastatic melanoma (such as stage IV metastatic melanoma or M1c melanoma) in the liver in an individual (e.g., human) who comprises a BRAF V600E mutation, comprising administering (such as administering by hepatic arterial infusion) to the individual an effective amount of a composition comprising nanoparticles comprising paclitaxel and albumin (such as Nab-paclitaxel, for example about 5 mg/ml Nab-paclitaxel), wherein the dose of paclitaxel in the nanoparticle composition is between about 80 mg/m$^2$ to about 175 mg/m$^2$ (such as between about 100 mg/m$^2$ to about 150 mg/m$^2$). In some embodiments, the nanoparticle composition is administered weekly. In some embodiments, the nanoparticle composition is administered weekly, three out of four weeks. In some embodiments, the individual is a male. In some embodiments, the individual is a female. In some embodiment, the individual is a human who is at least 65 years old (including for example at least 70, 75, or 80 years old). In some embodiments, the individual is a human who is less than 65 years old (including for example less than 60, 50, or 40 years old).

In some embodiments, there is provided a method of treating uveal melanoma (such as unresectable uveal melanoma or metastatic uveal melanoma) in an individual (e.g., human) comprising administering (such as intravenous administration) to the individual an effective amount of a composition comprising nanoparticles comprising paclitaxel and albumin (such as Nab-paclitaxel, for example about 5 mg/ml Nab-paclitaxel). In some embodiments, the uveal melanoma is any of Choroidal melanoma, ciliary body melanoma, or iris melanoma. In some embodiments, the uveal melanoma is Posterior uveal melanoma.

In some embodiments, there is provided a method of treating uveal melanoma in an individual (e.g., human) comprising administering (such as intravenous administration) to the individual an effective amount of a composition comprising nanoparticles comprising paclitaxel and albumin (such as Nab-paclitaxel, for example about 5 mg/ml Nab-paclitaxel), wherein the dose of paclitaxel in the nanoparticle composition is between about 80 mg/m$^2$ to about 175 mg/m$^2$ (such as between about 100 mg/m$^2$ to about 150 mg/m$^2$). In some embodiments, there is provided a method of treating metastatic uveal melanoma in an individual (e.g., human) comprising administering (such as intravenous administration) to the individual an effective amount of a composition comprising nanoparticles comprising paclitaxel and albumin (such as Nab-paclitaxel, for example about 5 mg/ml Nab-paclitaxel), wherein the dose of paclitaxel in the nanoparticle composition is between about 80 mg/m$^2$ to about 175 mg/m$^2$ (such as between about 100 mg/m$^2$ to about 150 mg/m$^2$). In some embodiments, there is provided a method of treating unresectable uveal melanoma in an individual (e.g., human) comprising administering (such as intravenous administration) to the individual an effective amount of a composition comprising nanoparticles comprising paclitaxel and albumin (such as Nab-paclitaxel, for example about 5 mg/ml Nab-paclitaxel), wherein the dose of paclitaxel in the nanoparticle composition is between about 80 mg/m$^2$ to about 175 mg/m$^2$ (such as between about 100 mg/m$^2$ to about 150 mg/m$^2$). In some embodiments, the nanoparticle composition is administered weekly. In some embodiments, the nanoparticle composition is administered weekly, three out of four weeks. In some embodiments, the nanoparticle composition is administered intravenously. In some embodiments, the nanoparticle composition is administered intravenously over 30 minutes at a dose of 150 mg/m$^2$ weekly. In some embodiments, the nanoparticle composition is administered intravenously over 30 minutes at a dose of 150 mg/m$^2$ weekly for three out of four weeks. In some embodiments, the individual comprises wild-type BRAF. In some embodiments, the individual comprises a BRAF mutation. In some embodiments, the individual comprises a BRAF V600E mutation. In some embodiments, the individual is a male. In some embodiments, the individual is a female. In some embodiment, the individual is a human who is at least 65 years old (including for example at least 70, 75, or 80 years old). In some embodiments, the individual is a human who is less than 65 years old (including for example less than 60, 50, or 40 years old).

In some embodiments, there is provided a method of treating uveal melanoma in an individual (e.g., human) comprising administering (such as intravenous administration) to the individual an effective amount of a composition comprising nanoparticles comprising paclitaxel and albumin (such as Nab-paclitaxel, for example about 5 mg/ml Nab-paclitaxel), wherein the dose of paclitaxel in the nanoparticle composition is between about 80 mg/m$^2$ to about 175 mg/m$^2$ (such as between about 100 mg/m$^2$ to about 150 mg/m$^2$). In some embodiments, there is provided a method of treating metastatic uveal melanoma in an individual (e.g., human) comprising administering (such as intravenous administration) to the individual an effective amount of a composition comprising nanoparticles comprising paclitaxel and albumin (such as Nab-paclitaxel, for example about 5 mg/ml Nab-paclitaxel), wherein the dose of paclitaxel in the nanoparticle composition is between about 80 mg/m$^2$ to about 175 mg/m$^2$ (such as between about 100 mg/m$^2$ to about 150 mg/m$^2$). In some embodiments, there is provided a method of treating unresectable uveal melanoma in an individual (e.g., human) comprising administering (such as intravenous administration) to the individual an effective amount of a composition comprising nanoparticles comprising paclitaxel and albumin (such as Nab-paclitaxel, for example about 5 mg/ml Nab-paclitaxel), wherein the dose of paclitaxel in the nanoparticle composition is between about 80 mg/m$^2$ to about 175 mg/m$^2$ (such as between about 100 mg/m$^2$ to about 150 mg/m$^2$). In some embodiments, the nanoparticle composition is administered weekly. In some embodiments, the nanoparticle composition is administered weekly, three out of four weeks. In some embodiments, the individual comprises a BRAF V600E mutation. In some embodiments, the individual is a male. In some embodiments, the individual is a female. In some embodiment, the individual is a human who is at least 65 years old (including for example at least 70, 75, or 80 years old). In some embodiments, the individual is a human who is less than 65 years old (including for example less than 60, 50, or 40 years old).

In some embodiments, there is provided a method of treating melanoma in a human individual, comprising administering (such as intravenously administering) to the individual an effective amount of a composition comprising nanoparticles comprising paclitaxel and albumin (such as Nab-paclitaxel, for example about 5 mg/ml Nab-paclitaxel), wherein the dose of paclitaxel in the nanoparticle composition is between about 80 mg/m$^2$ to about 175 mg/m$^2$ (such as between about 100 mg/m$^2$ to about 150 mg/m$^2$, for example 150 mg/m$^2$), wherein the nanoparticle composition is administered weekly, three out of four weeks. In some embodiments, there is provided a method of treating stage IV cutaneous melanoma in a human individual, comprising administering (such as intravenously administering) to the individual an effective amount of a composition comprising nanoparticles comprising paclitaxel and albumin (such as Nab-paclitaxel, for example about 5 mg/ml Nab-paclitaxel), wherein the dose of paclitaxel in the nanoparticle composition is between about 100 mg/m$^2$ to about 150 mg/m$^2$ (for example 150 mg/m$^2$), wherein the nanoparticle composition is administered weekly, three out of four weeks. In some embodiments, there is provided a method of treating stage IV cutaneous melanoma in a human individual who is chemotherapy naïve, comprising administering (such as intravenously administering) to the individual an effective amount of a composition comprising nanoparticles comprising paclitaxel and albumin (such as Nab-paclitaxel, for example about 5 mg/ml Nab-paclitaxel), wherein the dose of paclitaxel in the nanoparticle composition is between about 100 mg/m$^2$ to about 150 mg/m$^2$ (for example 150 mg/m$^2$), wherein the nanoparticle composition is administered weekly, three out of four weeks. In some embodiments, there is provided a method of treating stage IV cutaneous melanoma in a human individual who is chemotherapy naïve, wherein the individual has radiographically-documented measurable disease (for example defined by the presence of at least one radiographically documented measurable lesion), comprising administering (such as intravenously administering) to the individual an effective amount of a composition comprising nanoparticles comprising paclitaxel and albumin (such as Nab-paclitaxel, for example about 5 mg/ml Nab-paclitaxel), wherein the dose of paclitaxel in the nanoparticle composition is between about 100 mg/m$^2$ to about 150 mg/m$^2$ (for example 150 mg/m$^2$), wherein the nanoparticle composition is administered weekly, three out of four weeks. In some embodiments, the individual has metastatic melanoma of stage M1c. In some embodiments, the individual has metastatic melanoma of stage M1c or M1b. In some embodiments, the individual has metastatic melanoma at stage M1a, M1b, or M1c. In some embodiments, the individual has LDH level of no greater than about 2.0×ULN (such as LDH of <about 0.8×ULN, about 0.8 to about 1.1×ULN, or >about 1.1-2×ULN). In some embodiments, the individual comprises wild-type BRAF. In some embodiments, the individual has a BRAF mutation. In some embodiments, the individual has a BRAF V600E mutation. In some embodiments, the individual is a male. In some embodiments, the individual is a female. In some embodiment, the individual is a human who is at least 65 years old (including for example at least 70, 75, or 80 years old). In some embodiments, the individual is a human who is less than 65 years old (including for example less than 60, 50, or 40 years old).

In some embodiments, there is provided a method of treating melanoma in a human individual, comprising administering (such as intravenously administering) to the individual an effective amount of a composition comprising nanoparticles comprising paclitaxel and albumin (such as Nab-paclitaxel, for example about 5 mg/ml Nab-paclitaxel), wherein the dose of paclitaxel in the nanoparticle composition is between about 80 mg/m$^2$ to about 175 mg/m$^2$ (such as between about 100 mg/m$^2$ to about 150 mg/m$^2$, for example 150 mg/m$^2$), wherein the nanoparticle composition is administered weekly, three out of four weeks, and wherein the individual is substantially refractory to prior treatment with a BRAF inhibitor. In some embodiments, there is provided a method of treating stage IV cutaneous melanoma in a human individual, comprising administering (such as intravenously administering) to the individual an effective amount of a composition comprising nanoparticles comprising paclitaxel and albumin (such as Nab-paclitaxel, for example about 5 mg/ml Nab-paclitaxel), wherein the dose of paclitaxel in the nanoparticle composition is between about 100 mg/m$^2$ to about 150 mg/m$^2$ (for example 150 mg/m$^2$), wherein the nanoparticle composition is administered weekly, three out of four weeks, and wherein the individual is substantially refractory to prior treatment with a BRAF inhibitor.

In some embodiments, there is provided a method of treating metastatic melanoma in a human individual who comprises wild-type BRAF, comprising administering (such as intravenously administering) to the individual an effective amount of a composition comprising nanoparticles comprising paclitaxel and albumin (such as Nab-paclitaxel, for example about 5 mg/ml Nab-paclitaxel), wherein the dose of paclitaxel in the nanoparticle composition is between about 80 m g/m$^2$ to about 175 mg/m$^2$ (such as between about 100 mg/m$^2$ to about 150 mg/m$^2$, for example 150 mg/m$^2$), wherein the nanoparticle composition is administered weekly, three out of four weeks. In some embodiments, there is provided a method of treating unresectable stage IIIc or stage IV metastatic melanoma in a human individual having a wild-type BRAF, comprising administering (such as intravenously administering) to the individual an effective amount of a composition comprising nanoparticles comprising paclitaxel and albumin (such as Nab-paclitaxel, for example about 5 mg/ml Nab-paclitaxel), wherein the dose of paclitaxel in the nanoparticle composition is between about 100 mg/m² to about 150 mg/m² (for example 150 mg/m²), wherein the nanoparticle composition is administered weekly, three out of four weeks. In some embodiments, there is provided a method of treating unresectable stage Inc or stage IV metastatic melanoma in a human individual having a wild-type BRAF, wherein the individual has failed treatment with ipilimumab, comprising administering (such as intravenously administering) to the individual an effective amount of a composition comprising nanoparticles comprising paclitaxel and albumin (such as Nab-paclitaxel, for example about 5 mg/ml Nab-paclitaxel), wherein the dose of paclitaxel in the nanoparticle composition is between about 100 mg/m² to about 150 mg/m² (for example 150 mg/m²), wherein the nanoparticle composition is administered weekly, three out of four weeks. In some embodiments, the individual has metastatic melanoma of stage M1c. In some embodiments, the individual has metastatic melanoma of stage M1c or M1b. In some embodiments, the individual has metastatic melanoma at stage M1a, M1b, or M1c. In some embodiments, the individual has LDH level of no greater than about 2.0×ULN (such as LDH of <about 0.8×ULN, about 0.8 to about 1.1×ULN, or >about 1.1-2× ULN). In some embodiments, the individual is a male. In some embodiments, the individual is a female. In some embodiment, the individual is a human who is at least 65 years old (including for example at least 70, 75, or 80 years old). In some embodiments, the individual is a human who is less than 65 years old (including for example less than 60, 50, or 40 years old).

In some embodiments, there is provided a method of treating melanoma by following any one of the dosing regimens provided in Table 3.

TABLE 3

Clinical Studies with Nab-paclitaxel Monotherapy

| Melanoma Patient Setting | Line of Treatment | Clinical Trial Title | Study Design |
|---|---|---|---|
| Metastatic | First line | Phase I/II Study of Hepatic Arterial Infusion of Nab-paclitaxel (or Abraxane ®) in Patients with Metastatic Melanoma in the Liver | Abraxane ® Dose Escalation: 100 mg/m², 135 mg/m², 170 mg/m², 260 mg/m² - Cycle q21 days. Treatment duration: to progression or unacceptable toxicity. |
| Metastatic | Chemo-naïve, previously treated | A Phase 2 Clinical Trial of Nab-paclitaxel (or Abraxane ®) in Previously Treated and Chemotherapy-Naïve Patients With Metastatic Melanoma | Nab-paclitaxel Dose: Weekly for 3 of 4 weeks at 100 mg/m² (in previously treated patients) or 150 mg/m² (in chemotherapy-naive patients). |
| Metastatic | First line | An open-label, multicenter, phase III trial of Nab-paclitaxel (or Abraxane ®) (NP) versus dacarbazine (DTIC) in previously untreated patients (PTs) with metastatic malignant melanoma (MMM) | Dosing Regimen: Nab-paclitaxel at 150 mg/m² weekly X 3/4 weeks or Dacarbazine 1000 mg/m² Q 3 W. Dosage reductions of Nab-paclitaxel to 120 and 90 mg/m² and of Dacarbazine to 800 and 600 mg/m² and the use of filgrastim for neutropenic fever allowed. |
| Unresectable, Metastatic | Chemo-naïve, previously treated | A Phase 2 Study Of Weekly Infusion Nab-paclitaxel (Paclitaxel Protein-bound Particles for Injectable Suspension) (or Abraxane ®) In Patients With Unresectable And Metastatic Uveal Melanoma | Nab-paclitaxel Dose: 150 mg/m² weekly for 3 of 4 weeks every 28 days. |
| Unresectable Stage III, Unresectable Stage IV | Chemo-naïve, previously treated | An Open-Label, Multicenter, Phase II Trial of NAB-PACLITAXEL (or Nab-paclitaxel or Abraxane ®) (A Cremophor ® -Free, Protein Stabilized, Nanoparticle Paclitaxel) in Previously Treated Patients With Metastatic Melanoma | NAB-PACLITAXEL Dose: Cohort I (previously treated) received NAB-PACLITAXEL on days 1, 8, and 15. Cohort II (chemotherapy-naïve) received NAB-PACLITAXEL at a higher dose than Cohort I. Treatment Duration: every 4 weeks in the absence of disease progression or unacceptable toxicity. |
| Metastatic malignant melanoma; stage IV | Chemotherapy naïve | Phase III study of Nab-paclitaxel v. dacarbazine in chemotherapy-naïve patients with metastatic malignant melanoma | Arm I: Nab-paclitaxel at 150 mg/m² on days 1, 8, and 15, 28 day cycle Arm II: Dacarbazine at 1000 mg/m², day 1, 21 day cycle |

TABLE 3-continued

Clinical Studies with Nab-paclitaxel Monotherapy

| Melanoma Patient Setting | Line of Treatment | Clinical Trial Title | Study Design |
|---|---|---|---|
| Second line metastatic melanoma unresectable stage IIIc & IV | Wildtype BRAF metastatic melanoma patients who failed treatment with ipilimumab | Abraxane ® v. DTIC in wild-type BRAF metastatic melanoma patients who failed treatment with ipilimumab | Arm 1: Nab-paclitaxel at 150 mg/m² days 1, 8, 15<br>Arm 2: DTIC 1000 mg/m² every 3 weeks |

The methods described herein may further comprise selecting patients for treatment (e.g., identifying an individual who is suitable for treatment for melanoma). Thus, for example, in some embodiments, a method described herein further comprises identifying the individual having one of the characteristics described herein, such as melanoma subtype or staging characteristics, LDH level, or BRAF status described herein. In some embodiments, there is provided a method of treating melanoma in an individual (e.g., human) comprising the steps of (a) determining whether the individual has melanoma such as a melanoma described herein, and (b) administering to the individual an effective amount of a composition comprising nanoparticles comprising a taxane (e.g., paclitaxel) and a carrier protein (e.g., albumin). In some embodiments, there is provided a method of treating melanoma in an individual (e.g., human) comprising the steps of (a) determining whether the individual has a BRAF status described herein, and (b) administering to the individual an effective amount of a composition comprising nanoparticles comprising a taxane (e.g., paclitaxel) and a carrier protein (e.g., albumin). In some embodiments, there is provided a method of treating melanoma in an individual (e.g., human) comprising the steps of (a) determining whether the individual has a LDH level described herein, and (b) administering to the individual an effective amount of a composition comprising nanoparticles comprising a taxane (e.g., paclitaxel) and a carrier protein (e.g., albumin).

In some embodiments, there is provided a method of treating melanoma (for example metastatic melanoma) in an individual comprising administering to the individual an effective amount of a composition comprising nanoparticles comprising paclitaxel and albumin (such as Nab-paclitaxel, for example about 5 mg/ml Nab-paclitaxel), wherein the individual is selected for treatment based on melanoma subtype or staging characteristics (such as stages M1a, M1b, M1c). In some embodiments, there is provided a method of treating melanoma (for example metastatic melanoma) in an individual comprising: a) determining the melanoma subtype or staging characteristics (such as stages M1a, M1b, M1c) of the individual; and b) administering to the individual an effective amount of a composition comprising nanoparticles comprising paclitaxel and albumin (such as Nab-paclitaxel, for example about 5 mg/ml Nab-paclitaxel). In some embodiments, there is provided a method of treating melanoma (for example metastatic melanoma) in an individual comprising: a) selecting the individual for treatment based on the melanoma subtype or staging characteristics (such as stages M1a, M1b, M1c) of the individual; and b) administering to the individual an effective amount of a composition comprising nanoparticles comprising paclitaxel and albumin (such as Nab-paclitaxel, for example about 5 mg/ml Nab-paclitaxel).

In some embodiments, there is provided a method of treating melanoma (for example metastatic melanoma) in an individual comprising: a) determining the melanoma subtype or staging characteristics (such as stages M1a, M1b, M1c) of the individual; b) selecting the individual for treatment based on the melanoma subtype or staging characteristics (such as stages M1a, M1b, M1c) of the individual; and c) administering to the individual an effective amount of a composition comprising nanoparticles comprising paclitaxel and albumin (such as Nab-paclitaxel, for example about 5 mg/ml Nab-paclitaxel). In some embodiments, an individual who has stage M1a melanoma is treated. In some embodiments, an individual who has stage M1b melanoma is treated. In some embodiments, an individual who has stage M1c melanoma is treated. In some embodiments, an individual who has cutaneous metastatic melanoma is treated. Treatment decision can also be based on the subtype of the melanoma, such as any subtype of the melanoma described herein. In some embodiments, the method comprises intravenously administering (for example over a period of about 30 to about 40 minutes) to the individual an effective amount of Nab-paclitaxel (such as about 5 mg/ml Nab-paclitaxel), wherein the dose of paclitaxel in the nanoparticle composition is about 80 to about 200 mg/m² (including for example about 90 mg/m², about 120 mg/m², or about 150 mg/m²) on days 1, 8, 15 of every 28 day cycle. In some embodiments, the individual is treated for at least about 2 months, including for example at least about any of 3, 4, 5, 6, 7, 8, 9, 10, 11, or 12 months.

In some embodiments, there is provided a method of treating melanoma (for example metastatic melanoma) in an individual comprising administering to the individual an effective amount of a composition comprising nanoparticles comprising paclitaxel and albumin (such as Nab-paclitaxel, for example about 5 mg/ml Nab-paclitaxel), wherein the individual is selected for treatment based on melanoma subtype or staging characteristics being stage M1c. In some embodiments, there is provided a method of treating melanoma (for example metastatic melanoma) in an individual comprising: a) determining the melanoma subtype or staging characteristics (such as stages M1a, M1b, M1c) of the individual; and b) administering to the individual an effective amount of a composition comprising nanoparticles comprising paclitaxel and albumin (such as Nab-paclitaxel, for example about 5 mg/ml Nab-paclitaxel), wherein the individual is selected for treatment if the individual has a melanoma at stage M1c. In some embodiments, there is provided a method of treating melanoma (for example metastatic melanoma) in an individual comprising: a) selecting the individual for treatment based on the melanoma subtype being at stage M1c; and b) administering to the individual an effective amount of a composition comprising nanoparticles comprising paclitaxel and albumin (such as Nab-paclitaxel, for example about 5 mg/ml Nab-paclitaxel). In some embodiments, there is provided a method of treating melanoma (for example metastatic melanoma) in an individual comprising: a) determining the melanoma subtype or staging characteristics (such as stages M1a, M1b, M1c) of the individual; b) selecting the individual for treatment based on the melanoma subtype being at stage M1c; and c) administering to the individual an effective amount of a composition comprising nanoparticles comprising paclitaxel and albumin (such as Nab-paclitaxel, for example about 5 mg/ml Nab-paclitaxel). In some embodiments, an individual who has cutaneous metastatic melanoma is treated. In some embodiments, the method comprises intravenously administering (for example over a period of about 30 to about 40 minutes) to the individual an effective amount of Nab-paclitaxel (such as about 5 mg/ml Nab-paclitaxel), wherein the dose of paclitaxel in the nanoparticle composition is about 80 to about 200 mg/m$^2$ (including for example about 90 mg/m$^2$, about 120 mg/m$^2$, or about 150 mg/m$^2$) on days 1, 8, 15 of every 28 day cycle. In some embodiments, the individual is treated for at least about 2 months, including for example at least about any of 3, 4, 5, 6, 7, 8, 9, 10, 11, or 12 months.

In some embodiments, there is provided a method of treating melanoma (for example metastatic melanoma) in an individual comprising administering to the individual an effective amount of a composition comprising nanoparticles comprising paclitaxel and albumin (such as Nab-paclitaxel, for example about 5 mg/ml Nab-paclitaxel), wherein the individual is selected for treatment based on BRAF status of the individual. In some embodiments, there is provided a method of treating melanoma (for example metastatic melanoma) in an individual comprising: a) determining the BRAF status of the individual; and b) administering to the individual an effective amount of a composition comprising nanoparticles comprising paclitaxel and albumin (such as Nab-paclitaxel, for example about 5 mg/ml Nab-paclitaxel). In some embodiments, there is provided a method of treating melanoma (for example metastatic melanoma) in an individual comprising: a) determining the BRAF status of the individual; b) selecting the individual for treatment based on the BRAF status of the individual; and c) administering to the individual an effective amount of a composition comprising nanoparticles comprising paclitaxel and albumin (such as Nab-paclitaxel, for example about 5 mg/ml Nab-paclitaxel). In some embodiments, there is provided a method of treating melanoma (for example metastatic melanoma) in an individual comprising: a) selecting the individual for treatment based on the BRAF status of the individual; and b) administering to the individual an effective amount of a composition comprising nanoparticles comprising paclitaxel and albumin (such as Nab-paclitaxel, for example about 5 mg/ml Nab-paclitaxel). In some embodiments, an individual who comprises wild-type BRAF is treated. In some embodiments, an individual who comprises a BRAF mutation (such as a BRAF V600E mutation) is treated. Treatments based on any other BRAF status described herein are also contemplated. In some embodiments, the method comprises intravenously administering (for example over a period of about 30 to about 40 minutes) to the individual an effective amount of Nab-paclitaxel (such as about 5 mg/ml Nab-paclitaxel), wherein the dose of paclitaxel in the nanoparticle composition is about 80 to about 200 mg/m$^2$ (including for example about 90 mg/m$^2$, about 120 mg/m$^2$, or about 150 mg/m$^2$) on days 1, 8, 15 of every 28 day cycle. In some embodiments, the individual is treated for at least about 2 months, including for example at least about any of 3, 4, 5, 6, 7, 8, 9, 10, 11, or 12 months.

In some embodiments, there is provided a method of treating melanoma (for example metastatic melanoma) in an individual comprising administering to the individual an effective amount of a composition comprising nanoparticles comprising paclitaxel and albumin (such as Nab-paclitaxel, for example about 5 mg/ml Nab-paclitaxel), wherein the individual is selected for treatment if the individual comprises a wild-type BRAF. In some embodiments, there is provided a method of treating melanoma (for example metastatic melanoma) in an individual comprising: a) determining the BRAF status of the individual; and b) administering to the individual an effective amount of a composition comprising nanoparticles comprising paclitaxel and albumin (such as Nab-paclitaxel, for example about 5 mg/ml Nab-paclitaxel), wherein the individual is selected for treatment if the individual comprises a wild-type BRAF. In some embodiments, there is provided a method of treating melanoma (for example metastatic melanoma) in an individual comprising: a) selecting the individual for treatment based on the individual comprising a wild-type BRAF; and b) administering to the individual an effective amount of a composition comprising nanoparticles comprising paclitaxel and albumin (such as Nab-paclitaxel, for example about 5 mg/ml Nab-paclitaxel). In some embodiments, there is provided a method of treating melanoma (for example metastatic melanoma) in an individual comprising: a) determining the BRAF status of the individual; b) selecting the individual for treatment based on the individual comprising a wild-type BRAF; and c) administering to the individual an effective amount of a composition comprising nanoparticles comprising paclitaxel and albumin (such as Nab-paclitaxel, for example about 5 mg/ml Nab-paclitaxel). In some embodiments, the method comprises intravenously administering (for example over a period of about 30 to about 40 minutes) to the individual an effective amount of Nab-paclitaxel (such as about 5 mg/ml Nab-paclitaxel), wherein the dose of paclitaxel in the nanoparticle composition is about 80 to about 200 mg/m$^2$ (including for example about 90 mg/m$^2$, about 120 mg/m$^2$, or about 150 mg/m$^2$) on days 1, 8, 15 of every 28 day cycle. In some embodiments, the individual is treated for at least about 2 months, including for example at least about any of 3, 4, 5, 6, 7, 8, 9, 10, 11, or 12 months.

In some embodiments, there is provided a method of treating melanoma (for example metastatic melanoma) in an individual comprising administering to the individual an effective amount of a composition comprising nanoparticles comprising paclitaxel and albumin (such as Nab-paclitaxel, for example about 5 mg/ml Nab-paclitaxel), wherein the individual is selected for treatment if the individual comprises a BRAF mutation (such as a BRAF V600E mutation). In some embodiments, there is provided a method of treating melanoma (for example metastatic melanoma) in an individual comprising: a) determining the BRAF status of the individual; and b) administering to the individual an effective amount of a composition comprising nanoparticles comprising paclitaxel and albumin (such as Nab-paclitaxel, for example about 5 mg/ml Nab-paclitaxel), wherein the individual is selected for treatment if the individual comprises a BRAF mutation (such as a BRAF V600E mutation). In some embodiments, there is provided a method of treating melanoma (for example metastatic melanoma) in an individual comprising: a) selecting the individual for treatment based on the individual comprising a BRAF mutation (such as a BRAF V600E mutation); and b) administering to the individual an effective amount of a composition comprising nanoparticles comprising paclitaxel and albumin (such as Nab-paclitaxel, for example about 5 mg/ml Nab-paclitaxel). In some embodiments, there is provided a method of treating melanoma (for example metastatic melanoma) in an individual comprising: a) determining the BRAF status of the individual; b) selecting the individual for treatment based on the individual comprising a BRAF mutation (such as a BRAF V600E mutation); and c) administering to the individual an effective amount of a composition comprising nanoparticles comprising paclitaxel and albumin (such as Nab-paclitaxel, for example about 5 mg/ml Nab-paclitaxel). In some embodiments, the method comprises intravenously administering (for example over a period of about 30 to about 40 minutes) to the individual an effective amount of Nab-paclitaxel (such as about 5 mg/ml Nab-paclitaxel), wherein the dose of paclitaxel in the nanoparticle composition is about 80 to about 200 mg/m$^2$ (including for example about 90 mg/m$^2$, about 120 mg/m$^2$, or about 150 mg/m$^2$) on days 1, 8, 15 of every 28 day cycle. In some embodiments, the individual is treated for at least about 2 months, including for example at least about any of 3, 4, 5, 6, 7, 8, 9, 10, 11, or 12 months.

In some embodiments, there is provided a method of treating melanoma (for example metastatic melanoma) in an individual comprising administering to the individual an effective amount of a composition comprising nanoparticles comprising paclitaxel and albumin (such as Nab-paclitaxel, for example about 5 mg/ml Nab-paclitaxel), wherein the individual is selected for treatment based on LDH level of the individual. In some embodiments, there is provided a method of treating melanoma (for example metastatic melanoma) in an individual comprising: a) determining the LDH level of the individual; and b) administering to the individual an effective amount of a composition comprising nanoparticles comprising paclitaxel and albumin (such as Nab-paclitaxel, for example about 5 mg/ml Nab-paclitaxel). In some embodiments, there is provided a method of treating melanoma (for example metastatic melanoma) in an individual comprising: a) selecting the individual for treatment based on the LDH level of the individual; and b) administering to the individual an effective amount of a composition comprising nanoparticles comprising paclitaxel and albumin (such as Nab-paclitaxel, for example about 5 mg/ml Nab-paclitaxel). In some embodiments, there is provided a method of treating melanoma (for example metastatic melanoma) in an individual comprising: a) determining the LDH level of the individual; b) selecting the individual for treatment based on the LDH level of the individual; and c) administering to the individual an effective amount of a composition comprising nanoparticles comprising paclitaxel and albumin (such as Nab-paclitaxel, for example about 5 mg/ml Nab-paclitaxel). In some embodiments, an individual whose LDH level is greater than about 1.1 to about 2.0×ULN is treated. In some embodiments, an individual whose LDH level is between about 0.8× to about 1.1×ULN is treated. In some embodiments, an individual whose LDH level is less than about 0.8×ULN is treated. Treatments of individuals having any other LDH levels described herein are also contemplated. In some embodiments, the method comprises intravenously administering (for example over a period of about 30 to about 40 minutes) to the individual an effective amount of Nab-paclitaxel (such as about 5 mg/ml Nab-paclitaxel), wherein the dose of paclitaxel in the nanoparticle composition is about 80 to about 200 mg/m$^2$ (including for example about 90 mg/m$^2$, about 120 mg/m$^2$, or about 150 mg/m$^2$) on days 1, 8, 15 of every 28 day cycle. In some embodiments, the individual is treated for at least about 2 months, including for example at least about any of 3, 4, 5, 6, 7, 8, 9, 10, 11, or 12 months.

In some embodiments, there is provided a method of treating melanoma (for example metastatic melanoma) in an individual comprising administering to the individual an effective amount of a composition comprising nanoparticles comprising paclitaxel and albumin (such as Nab-paclitaxel, for example about 5 mg/ml Nab-paclitaxel), wherein the individual is selected for treatment based on the individual having an elevated LDH level. In some embodiments, there is provided a method of treating melanoma (for example metastatic melanoma) in an individual comprising: a) determining the LDH level of the individual; and b) administering to the individual an effective amount of a composition comprising nanoparticles comprising paclitaxel and albumin (such as Nab-paclitaxel, for example about 5 mg/ml Nab-paclitaxel), wherein the individual is selected for treatment based on having an elevated LDH level. In some embodiments, there is provided a method of treating melanoma (for example metastatic melanoma) in an individual comprising: a) selecting the individual for treatment based on the individual having an elevated LDH level; and b) administering to the individual an effective amount of a composition comprising nanoparticles comprising paclitaxel and albumin (such as Nab-paclitaxel, for example about 5 mg/ml Nab-paclitaxel). In some embodiments, there is provided a method of treating melanoma (for example metastatic melanoma) in an individual comprising: a) determining the LDH level of the individual; b) selecting the individual for treatment based on the individual having an elevated LDH level; and c) administering to the individual an effective amount of a composition comprising nanoparticles comprising paclitaxel and albumin (such as Nab-paclitaxel, for example about 5 mg/ml Nab-paclitaxel). In some embodiments, an individual whose LDH level is greater than about 1.1 to about 2.0×ULN is treated. In some embodiments, the method comprises intravenously administering (for example over a period of about 30 to about 40 minutes) to the individual an effective amount of Nab-paclitaxel (such as about 5 mg/ml Nab-paclitaxel), wherein the dose of paclitaxel in the nanoparticle composition is about 80 to about 200 mg/m$^2$ (including for example about 90 mg/m$^2$, about 120 mg/m$^2$, or about 150 mg/m$^2$) on days 1, 8, 15 of every 28 day cycle. In some embodiments, the individual is treated for at least about 2 months, including for example at least about any of 3, 4, 5, 6, 7, 8, 9, 10, 11, or 12 months.

In some embodiments, an individual is identified for treatment based on two or more of the following characteristics: melanoma subtype or staging characteristics, BRAF status, and LDH level. For example, in some embodiments, there is provided a method of treating melanoma (for example metastatic melanoma) in an individual comprising administering to the individual an effective amount of a composition comprising nanoparticles comprising paclitaxel and albumin (such as Nab-paclitaxel, for example about 5 mg/ml Nab-paclitaxel), wherein the individual is selected for treatment based on melanoma subtype or staging characteristics (such as stages M1a, M1b, M1c) and BRAF status. In some embodiments, there is provided a method of treating melanoma (for example metastatic melanoma) in an individual comprising: a) determining the melanoma subtype or staging characteristics (such as stages M1a, M1b, M1c) and BRAF status of the individual; and b) administering to the individual an effective amount of a composition comprising nanoparticles comprising paclitaxel and albumin (such as Nab-paclitaxel, for example about 5 mg/ml Nab-paclitaxel). In some embodiments, there is provided a method of treating melanoma (for example metastatic melanoma) and BRAF status in an individual comprising: a) selecting the individual for treatment based on the melanoma subtype or staging characteristics (such as stages M1a, M1b, M1c) of the individual; and b) administering to the individual an effective amount of a composition comprising nanoparticles comprising paclitaxel and albumin (such as Nab-paclitaxel, for example about 5 mg/ml Nab-paclitaxel). In some embodiments, there is provided a method of treating melanoma (for example metastatic melanoma) and BRAF status in an individual comprising: a) determining the melanoma subtype or staging characteristics (such as stages M1a, M1b, M1c) and BRAF status of the individual; b) selecting the individual for treatment based on the melanoma subtype or staging characteristics (such as stages M1a, M1b, M1c) of the individual; and c) administering to the individual an effective amount of a composition comprising nanoparticles comprising paclitaxel and albumin (such as Nab-paclitaxel, for example about 5 mg/ml Nab-paclitaxel). In some embodiments, an individual who has stage M1a melanoma and comprises wild-type BRAF is treated. In some embodiments, an individual who has stage M1b melanoma and comprises wild-type BRAF is treated. In some embodiments, an individual who has stage M1c melanoma and comprises wild-type BRAF is treated. In some embodiments, an individual who has cutaneous metastatic melanoma and wild-type BRAF is treated. Treatment decision can also be based on the subtype of the melanoma, such as any subtype of the melanoma described herein, and other BRAF status, such as any of the BRAF status described herein, are also contemplated. In some embodiments, the method comprises intravenously administering (for example over a period of about 30 to about 40 minutes) to the individual an effective amount of Nab-paclitaxel (such as about 5 mg/ml Nab-paclitaxel), wherein the dose of paclitaxel in the nanoparticle composition is about 80 to about 200 mg/m$^2$ (including for example about 90 mg/m$^2$, about 120 mg/m$^2$, or about 150 mg/m$^2$) on days 1, 8, 15 of every 28 day cycle. In some embodiments, the individual is treated for at least about 2 months, including for example at least about any of 3, 4, 5, 6, 7, 8, 9, 10, 11, or 12 months.

In some embodiments, the method of using taxane nanoparticles for treating melanoma described herein is used as a monotherapy. In some embodiments, the method of treating melanoma using taxane nanoparticles does not further comprise one other therapeutic agent (such as one other chemotherapeutic agent or immunotherapeutic agent). In some embodiments, the method does not further comprise a cytotoxic chemotherapeutic agent.

It is understood that reference to and description of methods of treating melanoma as described herein is exemplary and that this description applies equally to and includes methods of treating melanoma using combination therapy.

Methods of Combination Therapies

The present invention further provides combination therapy for treating melanoma. Provided herein are methods of treating melanoma comprising administering to an individual an effective amount of a composition comprising nanoparticles comprising a taxane (e.g., paclitaxel) and a carrier protein (e.g., albumin) and a second therapy. The second therapy may be surgery, radiation, gene therapy, immunotherapy, bone marrow transplantation, stem cell transplantation, hormone therapy, targeted therapy, cryotherapy, ultrasound therapy, photodynamic therapy, and/or chemotherapy (e.g., one or more compounds or pharmaceutically acceptable salts thereof useful for treating melanoma). The nanoparticle composition is administered either prior to or after the administration of the second therapy.

In some embodiments, there is provided a method of treating melanoma in an individual (e.g., human) comprising administering to the individual a) an effective amount of a composition comprising nanoparticles comprising a taxane (e.g., paclitaxel) and a carrier protein (e.g., albumin), and b) an effective amount of at least one other agent (such as a chemotherapeutic agent or immunotherapeutic agent). In some embodiments, the individual has stage IV or metastatic melanoma (e.g., stage IV or metastatic cutaneous melanoma). In some embodiments, the melanoma is metastatic malignant melanoma. In some embodiments, the metastatic melanoma is at stage M1a, stage M1b, or stage M1c. In some embodiments, the metastatic melanoma is at stage M1c. In some embodiments, the melanoma comprises a mutation in BRAF. In some embodiments, the melanoma does not comprise a mutation in BRAF. In some embodiments, the melanoma does not comprise BRAF mutant such as a BRAF mutant with increased activity (for example, increased kinase activity, and/or increased activity as compared to wild-type BRAF) or a BRAF gain-of-function mutant. In some embodiments, the melanoma does not comprise BRAF V600E mutation (e.g., the melanoma comprises wild-type BRAF). In some embodiments, the melanoma comprises wild-type BRAF. In some embodiments, the melanoma comprises a BRAF mutant such as a BRAF mutant with increased activity (for example, increased kinase activity, and/or increased activity as compared to wild-type BRAF) or a BRAF gain-of-function mutant. In some embodiments, the melanoma comprises BRAF V600E mutation. In some embodiments, the individual has elevated serum LDH level. In some embodiments, the individual has serum LDH of about any of the following: <0.8×ULN, 0.4-0.8×ULN, 0.8-1.1×ULN, 0.9-1.1×ULN, 0.8-1.2×ULN, 1.1-1.5×ULN, 1.2-1.5×ULN, 1.1-2×ULN, or 1.5-2×ULN. In some embodiments, the individual has serum LDH of less than about 0.8×ULN. In some embodiments, the individual has serum LDH at about 0.8× to about 1.1×ULN. In some embodiments, the individual has serum LDH of between greater than about 1.1× to about 2.0×ULN. In some embodiments, the individual has serum LDH of between about 1.1× to about 2.0×ULN. In some embodiments, the individual is a human (e.g., male or female). In some embodiments, the taxane is paclitaxel. In some embodiments, the carrier protein is albumin. In some embodiments, the one other agent is a chemotherapeutic agent or immunotherapeutic agent. In some embodiments, the one other agent is a platinum-based agent such as carboplatin.

An exemplary and non-limiting list of chemotherapeutic agents contemplated is provided herein. Suitable chemotherapeutic agents include, for example, platinum-based agents (such as carboplatin), vinca alkaloids, agents that disrupt microtubule formation, anti-angiogenic agents, therapeutic antibodies, EGFR targeting agents, tyrosine kinase targeting agent (such as tyrosine kinase inhibitors), transitional metal complexes, proteasome inhibitors, antimetabolites (such as nucleoside analogs), alkylating agents, anthracycline antibiotics, topoisomerase inhibitors, macrolides, therapeutic antibodies, retinoids; geldanamycin or a derivative thereof, and other standard chemotherapeutic agents well recognized in the art.

In some embodiments, the other agent is one of the following: a platinum-based agent (e.g., carboplatin or cisplatin), an anti-VEGF antibody (e.g., bevacizumab), dacarbazine or DTIC (also known as DIC, DTIC-Dome, or Imidazole Carboxamide), Oblimersen (or Genasense), interleukin-2 (IL-2), interferon (IFN), Interferon α-2b, a BRAF inhibitor (such as Vemurafenib (or Zelboraf), GDC-0879 (available from Tocris Bioscience), PLX-4720 (available from Symansis), or Sorafenib (or Sorafenib Tosylate or Nexavar (available from Bayer Pharmaceuticals Corp.,)), Dabrafenib (GSK2118436), LGX-818, CEP-32496, UI-152, RAF 265, Regorafenib (BAY 73-4506), or CCT239065), an antibody against the Programmed Death 1 (PD-1) receptor (such as BMS-936558, available from Bristol Myers Squibb), an antibody against the PD-1 Ligand (anti-PD-L1 antibody), or anti-CTLA-4 antibody such as Ipilimumab (or MDX-010, MDX-101, or Yervoy), or a DNA alkylating agent such as Temozolomide.

Programmed Death Receptor 1 (PD-I) is a member of the CD28/CTLA4 family that is expressed on activated, but not resting T cells (Nishimura et al. (1996) Int. Immunol. 8:773). Ligation of PD-I by its ligands mediates an inhibitory signal that results in reduced cytokine production, and reduced T cell survival (Nishimura et al. (1999) Immunity 11:141; Nishimura et al. (2001) Science 291:319; Chemnitz et al. (2004) J. Immunol. 173:945).

Programmed Death Receptor Ligand 1 (PD-L1) is a B7 family member that is expressed on many cell types, including APCs and activated T cells (Yamazaki et al. (2002) J. Immunol. 169:5538). PD-L1 binds to both PD-I and B7-1. Both binding of T-cell-expressed B7-1 by PD-L1 and binding of T-cell-expressed PD-L1 by B7-1 result in T cell inhibition (Butte et al. (2007) Immunity 27: 111). There is also evidence that, like other B7 family members, PD-L1 can also provide costimulatory signals to T cells (Subudhi et al. (2004) J. Clin. Invest. 113:694; Tamura et al. (2001) Blood 97:1809).

Trametinib (GSK1120212) is an orally bioavailable inhibitor of mitogen-activated protein kinase kinase (MEK MAPK/ERK kinase). National Cancer Institute, Drug Dictionary (World Wide Web at—cancer.gov/drugdictionary-?cdrid=599034, accessed on Feb. 11, 2013). Trametinib specifically binds to and inhibits MEK 1 and 2, resulting in an inhibition of growth factor-mediated cell signaling and cellular proliferation in various cancers. Id. MEK 1 and 2 are dual specificity threonine/tyrosine kinases which are often upregulated in various cancer cell types and play a key role in the activation of the RAS/RAF/MEK/ERK signaling pathway that regulates cell growth. Id.

TH-302 is a hypoxia-activated prodrug consisting of a 2-nitroimidazole phosphoramidate conjugate with potential antineoplastic activity. National Cancer Institute, Drug Dictionary (World Wide Web at—cancer.gov/drugdictionary-?CdrID=560194 accessed on Feb. 11, 2013). The 2-nitroimidazole moiety of hypoxia-activated prodrug TH-302 acts as a hypoxic trigger, releasing the DNA-alkylating dibromo isophosphoramide mustard moiety within hypoxic regions of tumors. Id. The hypoxia-specific activity of this agent reduces systemic toxicity. Id.

The present application thus in some embodiments provides methods of combination therapy. In some embodiments, there is provided a method of treating melanoma (such as metastatic melanoma, stage III melanoma, or stage IV melanoma) in an individual (such as a human individual), comprising administering to the individual a) an effective amount of a composition comprising nanoparticles comprising a taxane (e.g., paclitaxel) and a carrier protein (e.g., albumin), and b) an effective amount of a chemotherapeutic agent. In some embodiments, there is provided a method of treating melanoma (such as metastatic melanoma, stage III melanoma, or stage IV melanoma) in a human individual, comprising administering to the individual a) an effective amount of a composition comprising nanoparticles comprising paclitaxel and albumin (such as Nab-paclitaxel, for example about 5 mg/ml Nab-paclitaxel), and b) an effective amount of a chemotherapeutic agent.

Thus, for example, in some embodiments, there is provided a method of treating melanoma (such as metastatic melanoma, stage III melanoma, or stage IV melanoma) in a human individual, comprising administering to the individual a) an effective amount of a composition comprising nanoparticles comprising paclitaxel and albumin (such as Nab-paclitaxel, for example about 5 mg/ml Nab-paclitaxel), and b) an effective amount of a platinum-based agent (such as carboplatin or cisplatin). In some embodiments, there is provided a method of treating unresectable stage IV melanoma in a human individual (including a chemotherapy naïve individual and an individual who has previously been treated for melanoma), comprising administering (such as intravenously administering) to the individual a) an effective amount of a composition comprising nanoparticles comprising paclitaxel and albumin (such as Nab-paclitaxel, for example about 5 mg/ml Nab-paclitaxel), and b) an effective amount of carboplatin. In some embodiments, there is provided a method of treating unresectable stage IV melanoma in a human individual (including a chemotherapy naïve individual and an individual who has previously been treated for melanoma), comprising administering (such as intravenously administering) to the individual a) an effective amount of a composition comprising nanoparticles comprising paclitaxel and albumin (such as Nab-paclitaxel, for example about 5 mg/ml Nab-paclitaxel), wherein the dose of paclitaxel in the nanoparticle composition is between about 80 mg/m$^2$ to about 175 mg/m$^2$ (such as between about 100 mg/m$^2$ to about 150 mg/m$^2$); and b) an effective amount of carboplatin. In some embodiments, there is provided a method of treating unresectable stage IV melanoma in a human individual (including a chemotherapy naïve individual and an individual who has previously been treated for melanoma), comprising administering (such as intravenously administering) to the individual a) an effective amount of a composition comprising nanoparticles comprising paclitaxel and albumin (such as Nab-paclitaxel, for example about 5 mg/ml Nab-paclitaxel), wherein the dose of paclitaxel in the nanoparticle composition is between about 80 mg/m$^2$ to about 175 mg/m$^2$ (such as between about 100 mg/m$^2$ to about 150 mg/m$^2$); and b) an effective amount of carboplatin (for example carboplatin at the dose of AUC2, AUC3, AUC4, AUC5, or AUC6). In some embodiments, the nanoparticle composition and the carboplatin are administered on days 1, 8, 15 of a 28 day cycle. In some embodiments, the nanoparticle composition is administered on days 1, 8, 15 of a 28 day cycle, and the carboplatin is administered on day 1. In some embodiments, the method further comprises administering to the individual an effective amount of sorafenib (for example sorafenib at the daily dose of about 400 mg). In some embodiments, the method further comprises administering to the individual an effective amount of bevacizumab (for example between about 5 mg/kg to about 15 mg/kg, such as about 10 mg/kg bevacizumab). In some embodiments, the method further comprises administering to the individual one or more of the following: temozolomide, interleukin-2, interferon (such as interferon α-2b), and oblimersen. In some embodiments, the individual is chemotherapy naïve. In some embodiments, the individual has previously been treated for melanoma. In some embodiments, the individual is at stage IV melanoma. In some embodiments, the individual is at stage M1c melanoma. In some embodiments, the individual comprises wild-type BRAF. In some embodiments, the individual comprises a BRAF mutation (such as a BRAF V600E mutation). In some embodiments, the individual is a male. In some embodiments, the individual is a female. In some embodiments, the individual is a human who is at least 65 years old (including for example at least 70, 75, or 80 years old). In some embodiments, the individual is a human who is less than 65 years old (including for example less than 60, 50, or 40 years old). In some embodiments, the individual has a normal LDH level. In some embodiments, the individual has an elevated LDH level.

In some embodiments, there is provided a method of treating melanoma (such as metastatic melanoma, stage III melanoma, or stage IV melanoma) in a human individual, comprising administering to the individual a) an effective amount of a composition comprising nanoparticles comprising paclitaxel and albumin (such as Nab-paclitaxel, for example about 5 mg/ml Nab-paclitaxel), and b) an effective amount of a therapeutic antibody (such as an anti-VEGF antibody, for example bevacizumab). In some embodiments, there is provided a method of treating stage III or stage IV melanoma in a human individual (including a chemotherapy naïve individual and an individual who has previously been treated for melanoma), comprising administering (such as intravenously administering) to the individual a) an effective amount of a composition comprising nanoparticles comprising paclitaxel and albumin (such as Nab-paclitaxel, for example about 5 mg/ml Nab-paclitaxel), and b) an effective amount of bevacizumab. In some embodiments, there is provided a method of treating stage III or stage IV melanoma in a human individual (including a chemotherapy naïve individual and an individual who has previously been treated for melanoma), comprising administering (such as intravenously administering) to the individual a) an effective amount of a composition comprising nanoparticles comprising paclitaxel and albumin (such as Nab-paclitaxel, for example about 5 mg/ml Nab-paclitaxel), wherein the dose of paclitaxel in the nanoparticle composition is between about 80 mg/m$^2$ to about 175 mg/m$^2$ (such as between about 100 mg/m$^2$ to about 150 mg/m$^2$); and b) an effective amount of bevacizumab (for example about 5 mg/kg to about 15 mg/kg, such as about 10 mg/kg bevacizumab). In some embodiments, the method further comprises administering to the individual an effective amount of carboplatin. In some embodiments, the individual is chemotherapy naïve. In some embodiments, the individual has previously been treated for melanoma. In some embodiments, the individual is at stage IV melanoma. In some embodiments, the individual is at stage M1c melanoma. In some embodiments, the individual comprises wild-type BRAF. In some embodiments, the individual comprises a BRAF mutation (such as a BRAF V600E mutation). In some embodiments, the individual is a male. In some embodiments, the individual is a female. In some embodiments, the individual is a human who is at least 65 years old (including for example at least 70, 75, or 80 years old). In some embodiments, the individual is a human who is less than 65 years old (including for example less than 60, 50, or 40 years old). In some embodiments, the individual has a normal LDH level. In some embodiments, the individual has an elevated LDH level.

In some embodiments, there is provided a method of treating melanoma (such as metastatic melanoma, stage III melanoma, or stage IV melanoma) in a human individual (such as an individual having wild-type BRAF), comprising administering (such as intravenously administering) to the individual a) an effective amount of a composition comprising nanoparticles comprising paclitaxel albumin (such as Nab-paclitaxel, for example about 5 mg/ml Nab-paclitaxel), wherein the dose of paclitaxel in the nanoparticle composition is between about 100 mg/m$^2$ to about 150 mg/m$^2$ (such as 150 mg/m$^2$), and b) an effective amount of bevacizumab, wherein the dose of bevacizumab is between about 5 mg/kg to about 15 mg/kg (such as about 10 mg/kg). In some embodiments, there is provided a method of treating melanoma (such as metastatic melanoma, stage III melanoma, or stage IV melanoma) in a human individual (such as an individual having wild-type BRAF), comprising administering (such as intravenously administering) to the individual a) an effective amount of a composition comprising nanoparticles comprising paclitaxel albumin (such as Nab-paclitaxel, for example about 5 mg/ml Nab-paclitaxel), wherein the dose of paclitaxel in the nanoparticle composition is between about 100 mg/m$^2$ to about 150 mg/m$^2$ (such as 150 mg/m$^2$), wherein the nanoparticle composition is administered on days 1, 8, 15 of a 28 day cycle, and b) an effective amount of bevacizumab, wherein the dose of bevacizumab is between about 5 mg/kg to about 15 mg/kg (such as about 10 mg/kg), wherein the bevacizumab is administered on days 1 and 15 of a 28 day cycle. In some embodiments, there is provided a method of treating unresectable stage IIIc or stage IV metastatic melanoma in a human individual having wild-type BRAF, comprising intravenously administering to the individual a) an effective amount of a composition comprising nanoparticles comprising paclitaxel albumin (such as Nab-paclitaxel, for example about 5 mg/ml Nab-paclitaxel), wherein the dose of paclitaxel in the nanoparticle composition is between about 100 mg/m$^2$ to about 150 mg/m$^2$ (such as 150 mg/m$^2$), wherein the nanoparticle composition is administered on days 1, 8, 15 of a 28 day cycle, and b) an effective amount of bevacizumab, wherein the dose of bevacizumab is between about 5 mg/kg to about 15 mg/kg (such as about 10 mg/kg), wherein the bevacizumab is administered on days 1 and 15 of a 28 day cycle. In some embodiments, the individual is chemotherapy naïve. In some embodiments, the individual has previously been treated for melanoma. In some embodiments, the individual is at stage IV melanoma. In some embodiments, the individual is at stage M1c melanoma. In some embodiments, the individual comprises wild-type BRAF. In some embodiments, the individual comprises a BRAF mutation (such as a BRAF V600E mutation). In some embodiments, the individual is a male. In some embodiments, the individual is a female. In some embodiments, the individual is a human who is at least 65 years old (including for example at least 70, 75, or 80 years old). In some embodiments, the individual is a human who is less than 65 years old (including for example less than 60, 50, or 40 years old). In some embodiments, the individual has a normal LDH level. In some embodiments, the individual has an elevated LDH level.

In some embodiments, there is provided a method of treating melanoma (such as metastatic melanoma, stage III melanoma, or stage IV melanoma) in a human individual, comprising administering to the individual a) an effective amount of a composition comprising nanoparticles comprising paclitaxel and albumin (such as Nab-paclitaxel, for example about 5 mg/ml Nab-paclitaxel), and b) an effective amount of a temozolomide. In some embodiments, there is provided a method of treating metastatic melanoma in a human individual (including a chemotherapy naïve individual and an individual who has previously been treated for melanoma), comprising administering (such as intravenously administering) to the individual a) an effective amount of a composition comprising nanoparticles comprising paclitaxel and albumin (such as Nab-paclitaxel, for example about 5 mg/ml Nab-paclitaxel), and b) an effective amount of temozolomide. In some embodiments, there is provided a method of treating metastatic melanoma in a human individual (including a chemotherapy naïve individual and an individual who has previously been treated for melanoma), comprising administering (such as intravenously administering) to the individual a) an effective amount of a composition comprising nanoparticles comprising paclitaxel and albumin (such as Nab-paclitaxel, for example about 5 mg/ml Nab-paclitaxel), wherein the dose of paclitaxel in the nanoparticle composition is between about 80 mg/m$^2$ to about 175 mg/m$^2$ (such as between about 100 mg/m$^2$ to about 150 mg/m$^2$); and b) an effective amount of tomozolomide. In some embodiments, the method further comprises administering to the individual an effective amount of oblimersen. In some embodiments, the individual is chemotherapy naïve. In some embodiments, the individual has previously been treated for melanoma. In some embodiments, the individual is at stage M1c melanoma. In some embodiments, the individual comprises wild-type BRAF. In some embodiments, the individual comprises a BRAF mutation (such as a BRAF V600E mutation). In some embodiments, the individual is a male. In some embodiments, the individual is a female. In some embodiments, the individual is a human who is at least 65 years old (including for example at least 70, 75, or 80 years old). In some embodiments, the individual is a human who is less than 65 years old (including for example less than 60, 50, or 40 years old). In some embodiments, the individual has a normal LDH level. In some embodiments, the individual has an elevated LDH level.

In some embodiments, there is provided a method of treating melanoma (such as metastatic melanoma, stage III melanoma, or stage IV melanoma) in a human individual, comprising administering to the individual a) an effective amount of a composition comprising nanoparticles comprising paclitaxel and albumin (such as Nab-paclitaxel, for example about 5 mg/ml Nab-paclitaxel), and b) an effective amount of a MEK inhibitor (such as Trametinib (GSK1120212)). In some embodiments, there is provided a method of treating stage III or stage IV melanoma in a human individual (including a chemotherapy naïve individual and an individual who has previously been treated for melanoma), comprising administering (such as intravenously administering) to the individual a) an effective amount of a composition comprising nanoparticles comprising paclitaxel and albumin (such as Nab-paclitaxel, for example about 5 mg/ml Nab-paclitaxel), and b) an effective amount of a MEK inhibitor (such as Trametinib (GSK1120212)). In some embodiments, there is provided a method of treating stage III or stage IV melanoma in a human individual (including a chemotherapy naïve individual and an individual who has previously been treated for melanoma), comprising administering (such as intravenously administering) to the individual a) an effective amount of a composition comprising nanoparticles comprising paclitaxel and albumin (such as Nab-paclitaxel, for example about 5 mg/ml Nab-paclitaxel), wherein the dose of paclitaxel in the nanoparticle composition is between about 80 mg/m$^2$ to about 175 mg/m$^2$ (such as between about 100 mg/m$^2$ to about 150 mg/m$^2$); and b) an effective amount of a MEK inhibitor (such as Trametinib (GSK1120212)). In some embodiments, the individual is chemotherapy naïve. In some embodiments, the individual has previously been treated for melanoma. In some embodiments, the individual is at stage IV melanoma. In some embodiments, the individual is at stage M1c melanoma. In some embodiments, the individual comprises wild-type BRAF. In some embodiments, the individual comprises a BRAF mutation (such as a BRAF V600E mutation). In some embodiments, the individual is a male. In some embodiments, the individual is a female. In some embodiments, the individual is a human who is at least 65 years old (including for example at least 70, 75, or 80 years old). In some embodiments, the individual is a human who is less than 65 years old (including for example less than 60, 50, or 40 years old). In some embodiments, the individual has a normal LDH level. In some embodiments, the individual has an elevated LDH level.

In some embodiments, there is provided a method of treating melanoma (such as metastatic melanoma, stage III melanoma, or stage IV melanoma) in a human individual, comprising administering to the individual a) an effective amount of a composition comprising nanoparticles comprising paclitaxel and albumin (such as Nab-paclitaxel, for example about 5 mg/ml Nab-paclitaxel), and b) an effective amount of TH-302. In some embodiments, there is provided a method of treating stage III or stage IV melanoma in a human individual (including a chemotherapy naïve individual and an individual who has previously been treated for melanoma), comprising administering (such as intravenously administering) to the individual a) an effective amount of a composition comprising nanoparticles comprising paclitaxel and albumin (such as Nab-paclitaxel, for example about 5 mg/ml Nab-paclitaxel), and b) an effective amount of TH-302. In some embodiments, there is provided a method of treating stage III or stage IV melanoma in a human individual (including a chemotherapy naïve individual and an individual who has previously been treated for melanoma), comprising administering (such as intravenously administering) to the individual a) an effective amount of a composition comprising nanoparticles comprising paclitaxel and albumin (such as Nab-paclitaxel, for example about 5 mg/ml Nab-paclitaxel), wherein the dose of paclitaxel in the nanoparticle composition is between about 80 mg/m$^2$ to about 175 mg/m$^2$ (such as between about 100 mg/m$^2$ to about 150 mg/m$^2$); and b) an effective amount of TH-302. In some embodiments, the individual is chemotherapy naïve. In some embodiments, the individual has previously been treated for melanoma. In some embodiments, the individual is at stage IV melanoma. In some embodiments, the individual is at stage M1c melanoma. In some embodiments, the individual comprises wild-type BRAF. In some embodiments, the individual comprises a BRAF mutation (such as a BRAF V600E mutation). In some embodiments, the individual is a male. In some embodiments, the individual is a female. In some embodiments, the individual is a human who is at least 65 years old (including for example at least 70, 75, or 80 years old). In some embodiments, the individual is a human who is less than 65 years old (including for example less than 60, 50, or 40 years old). In some embodiments, the individual has a normal LDH level. In some embodiments, the individual has an elevated LDH level.

In some embodiments, there is provided a method of treating melanoma (such as metastatic melanoma, stage III melanoma, or stage IV melanoma) in a human individual, comprising administering to the individual a) an effective amount of a composition comprising nanoparticles comprising paclitaxel and albumin (such as Nab-paclitaxel, for example about 5 mg/ml Nab-paclitaxel), and b) an effective amount of oblimersen. In some embodiments, there is provided a method of treating metastatic melanoma in a human individual (including a chemotherapy naïve individual and an individual who has previously been treated for melanoma), comprising administering (such as intravenously administering) to the individual a) an effective amount of a composition comprising nanoparticles comprising paclitaxel and albumin (such as Nab-paclitaxel, for example about 5 mg/ml Nab-paclitaxel), and b) an effective amount of oblimersen. In some embodiments, there is provided a method of treating metastatic melanoma in a human individual (including a chemotherapy naïve individual and an individual who has previously been treated for melanoma), comprising administering (such as intravenously administering) to the individual a) an effective amount of a composition comprising nanoparticles comprising paclitaxel and albumin (such as Nab-paclitaxel, for example about 5 mg/ml Nab-paclitaxel), wherein the dose of paclitaxel in the nanoparticle composition is between about 80 mg/m$^2$ to about 175 mg/m$^2$ (such as between about 100 mg/m$^2$ to about 150 mg/m$^2$); and b) an effective amount of oblimersen. In some embodiments, the method further comprises administering to the individual an effective amount of temozolomide. In some embodiments, the individual is chemotherapy naïve. In some embodiments, the individual has previously been treated for melanoma. In some embodiments, the individual is at stage IV melanoma. In some embodiments, the individual is at stage M1c melanoma. In some embodiments, the individual comprises wild-type BRAF. In some embodiments, the individual comprises a BRAF mutation (such as a BRAF V600E mutation). In some embodiments, the individual is a male. In some embodiments, the individual is a female. In some embodiments, the individual is a human who is at least 65 years old (including for example at least 70, 75, or 80 years old). In some embodiments, the individual is a human who is less than 65 years old (including for example less than 60, 50, or 40 years old). In some embodiments, the individual has a normal LDH level. In some embodiments, the individual has an elevated LDH level.

In some embodiments, the method of treating melanoma comprises any one of the dosing regimens provided in Table 4.

TABLE 4

Clinical studies with Nab-paclitaxel (or Abraxane ®)

| Melanoma Patient Setting | Line of Treatment | Clinical Trial Title | Study Design | Combination Treatment |
|---|---|---|---|---|
| Unresectable, Stage IV | Chemo-naïve, Previously treated | A Phase II Trial of Carboplatin and Abraxane ® in Patients with Unresectable Stage IV Melanoma (NCCTG Study N057E) | Dosing Regimen: 28 day cycle: Abraxane ® at 100 mg/m$^2$ in combination with Carboplatin area under the curve (AUC2) on days 1, 8, and 15. | Carboplatin |
| Stage III, Stage IV | First line | Phase II trial of Nab-paclitaxel and bevacizumab as first line therapy in patients with unresectable melanoma | Dosing Regimen: 28 day cycle: Nab-paclitaxel at 150 mg/m$^2$ on days 1, 8, 15 in combination with Bevacizumab at 10 mg/kg on days 1, 15. Treatment Duration: treated to progression or dose limiting toxicity. If the subject had a CR, dosed with 2 more cycles; if the subject had a PR or SD for 4 months, dosed with 4 more cycles then discontinue treatment with Nab-paclitaxel and continue bevacizumab. If the subject had disease progression after discontinuing Nab-paclitaxel because of clinical benefit, restart Nab-paclitaxel and continue combination therapy. | Bevacizumab |
| Metastatic, Stage IV, Unresectable Stage III | Chemo-naïve, previously treated | Phase II Study of ABX, Carboplatin, and Sorafenib in Metastatic Melanoma | Dosing Regimen: 28 day cycle: Nab-paclitaxel at 100 mg/m$^2$ on days 1, 8, and 15 in combination with Carboplatin AUC = 6 on day 1, and Sorafenib at 400 mg bid po daily from day 2 to day 27. Treatment Duration: continued until progression or unacceptable toxicity. | Carboplatin Sorafenib |
| Stage IV, Unresectable | Chemo-naïve | A randomized phase II study of temozolomide and bevacizumab or Nab-paclitaxel, carboplatin, and bevacizumab in patients with unresectable stage IV melanoma: A North Central Cancer Treatment Group Study, N0775 Nab-paclitaxel, carboplatin, and bevacizumab in N077 | Dosing Regimen: 28 day cycle: (Arm A) Temozolomide at 200 mg/m$^2$ on days 1 to 5 and Bevacizumab at 10 mg/kg on days 1 to 15 vs. (Arm B) Nab-paclitaxel at 100 mg/m$^2$ [80 mg/m$^2$ post addendum 5] on days 1, 8, and 15 in combination with Carboplatin at AUC 6 on day 1 [AUC 5 post addendum 5], and Bevacizumab at 10 mg/kg on days 1and 15. | Carboplatin Bevacizumab |

TABLE 4-continued

Clinical studies with Nab-paclitaxel (or Abraxane ®)

| Melanoma Patient Setting | Line of Treatment | Clinical Trial Title | Study Design | Combination Treatment |
|---|---|---|---|---|
| Metastatic | Chemo-naïve | Abraxane ®, temozolomide, and oblimersen (The ATG Trial): A final report of toxicity and clinical efficacy in metastatic melanoma patients with normal lactate dehydrogenase (LDH) | Dosing Regimen: 56 day cycle: (Cohort 1) Abraxane ® at 175 mg/m$^2$ on days 7 and 28 in combination with Oblimersen at 7 mg/kg/d continuous IV infusion on days 1 to 7 and 22 to 28, and Temozolomide at 75/m$^2$/d on days 1 to 42; (Cohort 2) Abraxane ® at 260 mg/m$^2$ on days 7 and 28 in combination with Oblimersen at 7 mg/kg/d continuous IV infusion on days 1 to 7 and 22 to 28, and Temozolomide at 75/m$^2$/d on days 1 to 42; (Cohort 3) Abraxane ® at 175 mg/m$^2$ on days 7 and 28 in combination with Oblimersen at 900 mg fixed dose, twice weekly in weeks 1 to 2, 4 to 5 [days 1, 4, 8, 11, 22, 25, 29, 32], and Temozolomide at 75/m$^2$/d on days 1 to 42. | Temozolomide Oblimersen |
| Metastatic | Chemo-naïve | Abraxane ®, temozolomide, and oblimersen (The ATG Trial): A final report of toxicity and clinical efficacy in metastatic melanoma patients with normal lactate dehydrogenase (LDH) | Dosing Regimen: 56 day cycle: (Cohort 1) Abraxane ® at 175 mg/m$^2$ on days 8 and 29 in combination with Oblimersen at 7 mg/kg/d continuous IV infusion on days 1 to 7 and 22 to 28, and Temozolomide at 75/m$^2$/d on days 1 to 42; (Cohort 2) Abraxane ® at 260 mg/m$^2$ on days 8 and 29 in combination with Oblimersen at 7 mg/kg/d continuous IV infusion on days 1 to 7 and 22 to 28, and Temozolomide at 75/m$^2$/d on days 1 to 42; (Cohort 3) Abraxane ® at 175 mg/m$^2$ on days 8 and 29 in combination with Oblimersen at 900 mg fixed dose, twice weekly in weeks 1 to 2, 4 to 5 [days 1, 4, 8, 11, 22, 25, 29, 32], and Temozolomide at 75/m$^2$/d on days 1 to 42. | Temozolomide Oblimersen |
| Stage IV, Unresectable Stage III | Chemo-naïve, Previously treated with radiation | Phase I Biochemotherapy With Cisplatin, Temozolomide, With Increasing Doses of Abraxane ®, Combined With Interleukin-2 and Interferon in Patients With Metastatic Melanoma | Dosing Regimen: 21 day cycle: Abraxane ® at 100 mg/m$^2$ on day 1 and at 70 mg/m$^2$ on day 2 in combination with Temozolomide at 250 mg/m$^2$ on days 1, 2, and 3, Cisplatin at 20 mg/m$^2$ on days 1, 2, 3, and 4, Interleukin-2 at 9 MIU/m$^2$ on days 1, 2, 3, and 4, and Interferon α-2b at 5 MIU/m$^2$ on days 1, 2, 3, 4, and 5. | Cisplatin Temozolomide Interleukin-2 Interferon α-2b |

TABLE 4-continued

Clinical studies with Nab-paclitaxel (or Abraxane ®)

| Melanoma Patient Setting | Line of Treatment | Clinical Trial Title | Study Design | Combination Treatment |
|---|---|---|---|---|
| Unresectable stage IIIc & IV metastatic melanoma | First line therapy | Abraxane ® in combination with bevacizumab vs. ipilimumab in patients with unresectable wild-type BRAF metastatic melanoma | Arm I: Nab-paclitaxel at 150 mg/m$^2$ days 1, 8, 15 of a 28 day cycle, treatment until PD or unacceptable toxicity Arm II: ipilimumab on day 1 every three weeks, 21-day cycle, 4 doses | Bevacizumab |
| Metastatic, Stage III, Stage IV | Chemo-naive | Safety, efficacy, and immunological effect of Abraxane ® plus Ipilimumab in patients with metastatic melanoma | Dosage Regimen: 28 day cycle: Abraxane ® at 150 mg/m$^2$ on days 1, 8, and 15 in combination with Ipilimumab at 3 mg/kg every 21 days for a total of four doses. Treatment Duration: Until disease progression. | Ipilimumab |
| Metastatic | Previously treated | Phase II trial of Abraxane ® plus Avastin in 1$^{st}$ line BRAF wild type patient with metastatic melanoma | Dosage Regimen: (Arm 1) Abraxane ® at 150 mg/m$^2$ on days 1, 8, and 15 in combination with Bevacizumab at 10 mg/kg on days 1 and 8 for every 28 day cycle vs. (Arm 2) Ipilimumab at 3 mg/kg on day 1 every 3 weeks for a total of four doses. Treatment Duration: Abraxane ® and Bevacizumab treatment until disease progression. | |
| Metastatic | N/A | A pilot study of the combination of Nab-paclitaxel, Temozolomide and Bevacizumab in patients with metastatic melanoma with brain metastases | Dosage Regimen: 28 day cycle: Abraxane ® on days 1, 8, and 15 in combination with Temozolomide on days 1 to 5, and Bevacizumab at 10 mg/kg every 2 weeks. Treatment Duration: Until disease progression or intolerance. | Temozolomide Bevacizumab |
| | N/A | A phase II randomized, open-label, trial of Ipilimumab and Nab-paclitaxel in treatment of naïve patients with unresectable or metastatic melanoma | Dosage Regimen: (Cohort 1) Abraxane ® at 150 mg/m$^2$ on days 1 and 8 every three weeks for a total of two cycles followed by Ipilimumab at 10 mg/kg every three weeks for a total of four cycles; (Cohort 2) Ipilimumab at 10 mg/kg every three weeks for a total of two cycles followed by Abraxane ® at 150 mg/m$^2$ on days 1 and 8 for a total of two cycles followed by Ipilimumab at 10 mg/kg every three weeks for a total of two cycles. | Ipilimumab |
| Stage IV | N/A | | Dosage Regimen: 28 day cycle: Abraxane ® at 100 mg/m$^2$ on days 1, 8, and 15 in combination with Vemurafenib at 960 mg twice a day. Treatment Duration: Until disease progression. | Vemurafenib |

TABLE 4-continued

Clinical studies with Nab-paclitaxel (or Abraxane ®)

| Melanoma Patient Setting | Line of Treatment | Clinical Trial Title | Study Design | Combination Treatment |
|---|---|---|---|---|
| Stage IV | N/A | Phase I/II trial of GSK1120212 and Nab-paclitaxel in metastatic melanoma | Dosage Regimen: Abraxane ® in combination with Trametinib. | Trametinib |
| Stage IV | N/A | A Phase I/II trial of Abraxane ® in combination with TH-302 in patients with advanced melanoma | Dosage Regimen: Abraxane ® in combination with TH-302 | TH-302 |
| Stage IV | Previously Treated | Targeted nanoparticle therapy for advanced melanoma: Nab-paclitaxel (Abraxane ®/Bevacizumab complex (nanoAB)) | Dosage Regimen: 28 day cycle (+/−3 days): Abraxane ® at 125 mg/m2 in combination with bevacizumab 50 mg/m2 on days 1, 8, and 15. Treatment Duration: Until disease progression, patient refusal, or unacceptable toxicity. Dosage Escalation Regimen: 28 day cycle (+/−days): Abraxane ® at 75, 100, 125, 150, or 175 mg/m2 in combination with Bevacizumab 30, 40, 50, 60, or 70 mg/m2 on days 1, 8, and 15, respectively. Treatment Duration: Until disease progression, patient refusal, or unacceptable toxicity. | Bevacizumab |

In some embodiments, there is provided a method of treating melanoma in an individual (e.g., human) comprising administering to the individual a) an effective amount of a composition comprising nanoparticles comprising a taxane (e.g., paclitaxel) and a carrier protein (e.g., albumin), and b) surgery, radiation therapy, or a combination of surgery and radiation therapy. In some embodiments, the individual has stage IV or metastatic melanoma (e.g., stage IV or metastatic cutaneous melanoma). In some embodiments, the melanoma is metastatic malignant melanoma. In some embodiments, the metastatic melanoma is at stage M1a, stage M1b, or stage M1c. In some embodiments, the metastatic melanoma is at stage M1c. In some embodiments, the melanoma comprises a mutation in BRAF. In some embodiments, the melanoma does not comprise a mutation in BRAF. In some embodiments, the melanoma does not comprise BRAF mutant such as a BRAF mutant with increased activity (for example, increased kinase activity, and/or increased activity as compared to wild-type BRAF) or a BRAF gain-of-function mutant. In some embodiments, the melanoma does not comprise BRAF V600E mutation (e.g., the melanoma comprises wild-type BRAF). In some embodiments, the melanoma comprises wild-type BRAF. In some embodiments, the melanoma comprises a BRAF mutant such as a BRAF mutant with increased activity (for example, increased kinase activity, and/or increased activity as compared to wild-type BRAF) or a BRAF gain-of-function mutant. In some embodiments, the melanoma comprises BRAF V600E mutation. In some embodiments, the individual has elevated serum LDH level. In some embodiments, the individual has serum LDH of about any of the following: <0.8×ULN, 0.4-0.8×ULN, 0.8-1.1×ULN, 0.9-1.1×ULN, 0.8-1.2×ULN, 1.1-1.5×ULN, 1.2-1.5×ULN, 1.1-2×ULN, or 1.5-2×ULN. In some embodiments, the individual has serum LDH of less than about 0.8×ULN. In some embodiments, the individual has serum LDH at about 0.8× to about 1.1×ULN. In some embodiments, the individual has serum LDH of between greater than about 1.1× to about 2.0×ULN. In some embodiments, the individual has serum LDH of between about 1.1× to about 2.0×ULN. In some embodiments, the individual is a human (e.g., male or female). In some embodiments, the taxane is paclitaxel. In some embodiments, the carrier protein is albumin.

In some embodiments, there is a method of treating melanoma (such as metastatic melanoma) in a human individual, comprising administering to the individual a) an effective amount of a composition comprising nanoparticles comprising paclitaxel and an albumin, and b) an effective amount of bevacizumab. In some embodiments, there is a method of treating melanoma (such as metastatic melanoma) in a human individual, comprising administering to the individual a) an effective amount of a composition comprising nanoparticles comprising paclitaxel and an albumin, and b) an effective amount of bevacizumab, wherein the dose of the nanoparticle composition is between about 50 mg/m$^2$ to about 200 mg/m$^2$ (such as, for example, between about 100 mg/m$^2$ to about 150 mg/m$^2$, and for example about 100 mg/m$^2$), and wherein the dose of bevacizumab is between about 5 mg/kg to about 15 mg/kg (such as, for example, between about 8 mg/kg to about 12 mg/kg, and for example about 10 mg/kg). In some embodiments, there is a method of treating melanoma (such as metastatic melanoma) in a human individual, comprising administering to the individual a) an effective amount of a composition comprising nanoparticles comprising paclitaxel and an albumin, and b) an effective amount of bevacizumab, wherein the dose of the nanoparticle composition is between about 50 mg/m² to about 200 mg/m² (such as, for example, between about 100 mg/m² to about 150 mg/m², and for example about 100 mg/m²), wherein the dose of the nanoparticle composition is administered on days 1, 8, and 15 of a 28 day cycle, wherein the dose of bevacizumab is between about 5 mg/kg to about 15 mg/kg (such as, for example, between about 8 mg/kg to about 12 mg/kg, and for example about 10 mg/kg), and wherein the dose of bevacizumab is administered on days 1 and 15 of a 28 day cycle. In some embodiments, there is a method of treating melanoma (such as metastatic melanoma) in a human individual, comprising administering to the individual a) an effective amount of a composition comprising nanoparticles comprising paclitaxel and an albumin, and b) an effective amount of bevacizumab, wherein the dose of the nanoparticle composition is about 100 mg/m² and is administered intravenously on days 1, 8, and 15 of a 28 day cycle, and wherein the dose of bevacizumab is about 10 mg/kg and is administered intravenously on days 1 and 15 of a 28 day cycle. In some embodiments, there is a method of treating melanoma (such as metastatic melanoma) in a human individual, comprising administering to the individual a) an effective amount of a composition comprising nanoparticles comprising paclitaxel and an albumin, and b) an effective amount of bevacizumab, wherein the dose of the nanoparticle composition is about 100 mg/m² and is administered intravenously over 30 minutes on days 1, 8, and 15 of a 28 day cycle, wherein the dose of bevacizumab is about 10 mg/kg and is administered intravenously over 90 minutes on days 1 and 15 of a 28 day cycle. In some embodiments, the individual is chemotherapy naïve. In some embodiments, the individual has previously been treated for melanoma. In some embodiments, the individual is at stage IV melanoma. In some embodiments, the individual is at stage M1c melanoma. In some embodiments, the individual comprises wild-type BRAF. In some embodiments, the individual comprises a BRAF mutation (such as a BRAF V600E mutation). In some embodiments, the individual is a male. In some embodiments, the individual is a female. In some embodiments, the individual is a human who is at least 65 years old (including for example at least 70, 75, or 80 years old). In some embodiments, the individual is a human who is less than 65 years old (including for example less than 60, 50, or 40 years old). In some embodiments, the individual has a normal LDH level. In some embodiments, the individual has an elevated LDH level.

In some embodiments, there is provided a method of treating melanoma (such as metastatic melanoma) in a human individual, comprising administering to the individual a) an effective amount of a composition comprising nanoparticles comprising paclitaxel and an albumin, and b) an effective amount of a BRAF inhibitor. Suitable BRAF inhibitors include, for example, Vemurafenib (Zelboraf), GDC-0879, PLX-4720, Dabrafenib (or GSK2118436), LGX 818, CEP-32496, UI-152, RAF 265, Regorafenib (BAY 73-4506), CCT239065, or Sorafenib (or Sorafenib Tosylate, or Nexavar®). In some embodiments, there is provided a method of treating melanoma (such as metastatic melanoma) in a human individual, comprising administering to the individual a) an effective amount of a composition comprising nanoparticles comprising paclitaxel and an albumin, wherein the dose of the nanoparticle composition is between about 50 mg/m² to about 200 mg/m², and b) an effective amount of a BRAF inhibitor (such as, for example, Vemurafenib (Zelboraf), Dabrafenib, Regorafenib, or Sorafenib). In some embodiments, there is provided a method of treating melanoma (such as metastatic melanoma) in a human individual, comprising administering to the individual a) an effective amount of a composition comprising nanoparticles comprising paclitaxel and an albumin, wherein the dose of the nanoparticle composition is between about 100 mg/m² to about 150 mg/m², and b) an effective amount of a BRAF inhibitor (such as, for example, Vemurafenib (Zelboraf)). In some embodiments, there is provided a method of treating melanoma (such as metastatic melanoma) in a human individual, comprising administering to the individual a) an effective amount of a composition comprising nanoparticles comprising paclitaxel and an albumin, wherein the dose of the nanoparticle composition is about 100 mg/m², and b) an effective amount of a BRAF inhibitor (such as, for example, Vemurafenib). In some embodiments, there is provided a method of treating melanoma (such as metastatic melanoma) in a human individual, comprising administering to the individual a) an effective amount of a composition comprising nanoparticles comprising paclitaxel and an albumin, wherein the dose of the nanoparticle composition is about 100 mg/m², wherein the nanoparticle composition is administered on days 1, 8, and 15 of a 28 day cycle, and b) an effective amount of a BRAF inhibitor (such as, for example, Vemurafenib). In some embodiments, there is provided a method of treating melanoma (such as metastatic melanoma) in a human individual, comprising administering to the individual a) an effective amount of a composition comprising nanoparticles comprising paclitaxel and an albumin, wherein the dose of the nanoparticle composition is about 100 mg/m², wherein the nanoparticle composition is administered intravenously over 30 minutes on days 1, 8, and 15 of a 28 day cycle, and b) an effective amount of a BRAF inhibitor (such as, for example, Vemurafenib). In some embodiments, the individual is chemotherapy naïve. In some embodiments, the individual has previously been treated for melanoma. In some embodiments, the individual is at stage IV melanoma. In some embodiments, the individual is at stage M1c melanoma. In some embodiments, the individual comprises wild-type BRAF. In some embodiments, the individual comprises a BRAF mutation (such as a BRAF V600E mutation). In some embodiments, the individual is a male. In some embodiments, the individual is a female. In some embodiments, the individual is a human who is at least 65 years old (including for example at least 70, 75, or 80 years old). In some embodiments, the individual is a human who is less than 65 years old (including for example less than 60, 50, or 40 years old). In some embodiments, the individual has a normal LDH level. In some embodiments, the individual has an elevated LDH level.

In some embodiments, there is provided a method of treating melanoma (such as metastatic melanoma) in a human individual, comprising administering to the individual a) an effective amount of a composition comprising nanoparticles comprising paclitaxel and an albumin, and b) an effective amount of another chemotherapeutic agent, wherein the individual has been previously treated for the melanoma with at least one BRAF inhibitor (such as, for example, Vemurafenib (Zelboraf) or Sorafenib), and wherein the individual is substantially refractory to prior treatment with a BRAF inhibitor. In some embodiments, there is provided a method of treating melanoma (such as metastatic melanoma) in a human individual, comprising administering to the individual a) an effective amount of a composition comprising nanoparticles comprising paclitaxel and an albumin, wherein the dose of the nanoparticle composition is between about 50 mg/m² to about 200 mg/m², and b) an effective amount of another chemotherapeutic agent, wherein the individual has been previously treated for the melanoma with at least one BRAF inhibitor (such as, for example, Vemurafenib (Zelboraf) or Sorafenib), and wherein the individual is substantially refractory to prior treatment with a BRAF inhibitor. In some embodiments, there is provided a method of treating melanoma (such as metastatic melanoma) in a human individual, comprising administering to the individual a) an effective amount of a composition comprising nanoparticles comprising paclitaxel and an albumin, wherein the dose of the nanoparticle composition is between about 100 mg/m² to about 150 mg/m², and b) an effective amount of another chemotherapeutic agent, wherein the individual has been previously treated for the melanoma with at least one BRAF inhibitor (such as, for example, Vemurafenib (Zelboraf) or Sorafenib), and wherein the individual is substantially refractory to prior treatment with a BRAF inhibitor. In some embodiments, there is provided a method of treating melanoma (such as metastatic melanoma) in a human individual, comprising administering to the individual a) an effective amount of a composition comprising nanoparticles comprising paclitaxel and an albumin, wherein the dose of the nanoparticle composition is about 100 mg/m², and b) an effective amount another chemotherapeutic agent, wherein the individual has been previously treated for the melanoma with at least one BRAF inhibitor (such as, for example, Vemurafenib (Zelboraf) or Sorafenib), and wherein the individual is substantially refractory to prior treatment with a BRAF inhibitor. In some embodiments, there is provided a method of treating melanoma (such as metastatic melanoma) in a human individual, comprising administering to the individual a) an effective amount of a composition comprising nanoparticles comprising paclitaxel and an albumin, wherein the dose of the nanoparticle composition is about 100 mg/m², wherein the nanoparticle composition is administered on days 1, 8, and 15 of a 28 day cycle, and b) an effective amount of another chemotherapeutic agent, wherein the individual has been previously treated for the melanoma with at least one BRAF inhibitor (such as, for example, Vemurafenib (Zelboraf) or Sorafenib), and wherein the individual is substantially refractory to prior treatment with a BRAF inhibitor. In some embodiments, the individual is at stage IV melanoma. In some embodiments, the individual is at stage M1c melanoma. In some embodiments, the individual comprises wild-type BRAF. In some embodiments, the individual comprises a BRAF mutation (such as a BRAF V600E mutation). In some embodiments, the individual is a male. In some embodiments, the individual is a female. In some embodiments, the individual is a human who is at least 65 years old (including for example at least 70, 75, or 80 years old). In some embodiments, the individual is a human who is less than 65 years old (including for example less than 60, 50, or 40 years old). In some embodiments, the individual has a normal LDH level. In some embodiments, the individual has an elevated LDH level.

In some embodiments, there is provided a method of treating melanoma (such as metastatic melanoma) in a human individual, comprising administering to the individual an effective amount of a composition comprising nanoparticles comprising paclitaxel and an albumin, wherein the individual has been previously treated for the melanoma with at least one BRAF inhibitor (such as, for example, Vemurafenib (Zelboraf) or Sorafenib), and wherein the individual is substantially refractory to prior treatment with a BRAF inhibitor. In some embodiments, there is provided a method of treating melanoma (such as metastatic melanoma) in a human individual, comprising administering to the individual an effective amount of a composition comprising nanoparticles comprising paclitaxel and an albumin, wherein the dose of the nanoparticle composition is between about 50 mg/m² to about 200 mg/m², wherein the individual has been previously treated for the melanoma with at least one BRAF inhibitor (such as, for example, Vemurafenib (Zelboraf) or Sorafenib), and wherein the individual is substantially refractory to prior treatment with a BRAF inhibitor. In some embodiments, there is provided a method of treating melanoma (such as metastatic melanoma) in a human individual, comprising administering to the individual an effective amount of a composition comprising nanoparticles comprising paclitaxel and an albumin, wherein the dose of the nanoparticle composition is between about 100 mg/m² to about 150 mg/m², wherein the individual has been previously treated for the melanoma with at least one BRAF inhibitor (such as, for example, Vemurafenib (Zelboraf) or Sorafenib), and wherein the individual is substantially refractory to prior treatment with a BRAF inhibitor. In some embodiments, there is provided a method of treating melanoma (such as metastatic melanoma) in a human individual, comprising administering to the individual an effective amount of a composition comprising nanoparticles comprising paclitaxel and an albumin, wherein the dose of the nanoparticle composition is about 100 mg/m², wherein the individual has been previously treated for the melanoma with at least one BRAF inhibitor (such as, for example, Vemurafenib (Zelboraf) or Sorafenib), and wherein the individual is substantially refractory to prior treatment with a BRAF inhibitor. In some embodiments, there is provided a method of treating melanoma (such as metastatic melanoma) in a human individual, comprising administering to the individual an effective amount of a composition comprising nanoparticles comprising paclitaxel and an albumin, wherein the dose of the nanoparticle composition is about 100 mg/m², wherein the nanoparticle composition is administered on days 1, 8, and 15 of a 28 day cycle, wherein the individual has been previously treated for the melanoma with at least one BRAF inhibitor (such as, for example, Vemurafenib (Zelboraf) or Sorafenib), and wherein the individual is substantially refractory to prior treatment with a BRAF inhibitor. In some embodiments, the individual is at stage IV melanoma. In some embodiments, the individual is at stage M1c melanoma. In some embodiments, the individual comprises wild-type BRAF. In some embodiments, the individual comprises a BRAF mutation (such as a BRAF V600E mutation). In some embodiments, the individual is a male. In some embodiments, the individual is a female. In some embodiments, the individual is a human who is at least 65 years old (including for example at least 70, 75, or 80 years old). In some embodiments, the individual is a human who is less than 65 years old (including for example less than 60, 50, or 40 years old). In some embodiments, the individual has a normal LDH level. In some embodiments, the individual has an elevated LDH level.

In some embodiments, there is provided a method of treating melanoma (such as metastatic melanoma) in a human individual, comprising administering to the individual a) an effective amount of a composition comprising nanoparticles comprising paclitaxel and an albumin, and b) an effective amount of Ipilimumab. In some embodiments, there is provided a method of treating melanoma (such as metastatic melanoma) in a human individual, comprising administering to the individual a) an effective amount of a composition comprising nanoparticles comprising paclitaxel and an albumin, wherein the dose of the nanoparticle composition is between about 50 mg/m² to about 200 mg/m², and b) an effective amount of Ipilimumab, wherein the dose of Ipilimumab is between about 1 mg/kg to about 5 mg/kg. In some embodiments, there is provided a method of treating melanoma (such as metastatic melanoma) in a human individual, comprising administering to the individual a) an effective amount of a composition comprising nanoparticles comprising paclitaxel and an albumin, wherein the dose of the nanoparticle composition is between about 100 mg/m² to about 150 mg/m², and b) an effective amount of Ipilimumab, wherein the dose of Ipilimumab is between about 2 mg/kg to about 4 mg/kg. In some embodiments, there is provided a method of treating melanoma (such as metastatic melanoma) in a human individual, comprising administering to the individual a) an effective amount of a composition comprising nanoparticles comprising paclitaxel and an albumin, wherein the dose of the nanoparticle composition is about 100 mg/m², and b) an effective amount of Ipilimumab, wherein the dose of Ipilimumab is about 3 mg/kg. In some embodiments, there is provided a method of treating melanoma (such as metastatic melanoma) in a human individual, comprising administering to the individual a) an effective amount of a composition comprising nanoparticles comprising paclitaxel and an albumin, wherein the dose of the nanoparticle composition is about 100 mg/m², wherein the nanoparticle composition is administered on days 1, 8, and 15 of a 28 day cycle, and b) an effective amount of Ipilimumab, wherein the dose of Ipilimumab is about 3 mg/kg, and wherein the Ipilimumab is administered on day 1 of a 21 day cycle. In some embodiments, there is provided a method of treating melanoma (such as metastatic melanoma) in a human individual, comprising administering to the individual a) an effective amount of a composition comprising nanoparticles comprising paclitaxel and an albumin, wherein the dose of the nanoparticle composition is about 100 mg/m², wherein the nanoparticle composition is administered intravenously over 30 minutes on days 1, 8, and 15 of a 28 day cycle, and b) an effective amount of Ipilimumab, wherein the dose of Ipilimumab is about 3 mg/kg, wherein the Ipilimumab is administered intravenously over 30 minutes on day 1 of a 21 day cycle. In some embodiments, the individual is chemotherapy naïve. In some embodiments, the individual has previously been treated for melanoma. In some embodiments, the individual is at stage IV melanoma. In some embodiments, the individual is at stage M1c melanoma. In some embodiments, the individual comprises wild-type BRAF. In some embodiments, the individual comprises a BRAF mutation (such as a BRAF V600E mutation). In some embodiments, the individual is a male. In some embodiments, the individual is a female. In some embodiments, the individual is a human who is at least 65 years old (including for example at least 70, 75, or 80 years old). In some embodiments, the individual is a human who is less than 65 years old (including for example less than 60, 50, or 40 years old). In some embodiments, the individual has a normal LDH level. In some embodiments, the individual has an elevated LDH level.

In some embodiments, there is provided a method of treating melanoma (such as metastatic melanoma) in a human individual, comprising administering to the individual a) an effective amount of a composition comprising nanoparticles comprising paclitaxel and an albumin, and b) an effective amount of anti-PD-1 antibody. In some embodiments, there is provided a method of treating melanoma (such as metastatic melanoma) in a human individual, comprising administering to the individual a) an effective amount of a composition comprising nanoparticles comprising paclitaxel and an albumin, wherein the dose of the nanoparticle composition is between about 50 mg/m² to about 200 mg/m² (such as, for example, between about 100 mg/m² and about 150 mg/m², for example about 100 mg/m²) and b) an effective amount of anti-PD-1 antibody, wherein the dose of anti-PD-1 antibody is between about 0.1 mg/kg to about 15 mg/kg (such as, for example, between about 2 mg/kg to about 12 mg/kg, for example about 10 mg/kg). In some embodiments, there is provided a method of treating melanoma (such as metastatic melanoma) in a human individual, comprising administering to the individual a) an effective amount of a composition comprising nanoparticles comprising paclitaxel and an albumin, wherein the dose of the nanoparticle composition is about 100 mg/m², and b) an effective amount of anti-PD-1 antibody, wherein the dose of anti-PD-1 antibody is about 10 mg/kg. In some embodiments, the individual is chemotherapy naïve. In some embodiments, the individual has previously been treated for melanoma. In some embodiments, the individual is at stage IV melanoma. In some embodiments, the individual is at stage M1c melanoma. In some embodiments, the individual comprises wild-type BRAF. In some embodiments, the individual comprises a BRAF mutation (such as a BRAF V600E mutation). In some embodiments, the individual is a male. In some embodiments, the individual is a female. In some embodiments, the individual is a human who is at least 65 years old (including for example at least 70, 75, or 80 years old). In some embodiments, the individual is a human who is less than 65 years old (including for example less than 60, 50, or 40 years old). In some embodiments, the individual has a normal LDH level. In some embodiments, the individual has an elevated LDH level.

In some embodiments, there is provided a method of treating melanoma (such as metastatic melanoma) in a human individual, comprising administering to the individual a) an effective amount of a composition comprising nanoparticles comprising paclitaxel and an albumin, and b) an effective amount of anti-PD-L1 antibody. In some embodiments, there is provided a method of treating melanoma (such as metastatic melanoma) in a human individual, comprising administering to the individual a) an effective amount of a composition comprising nanoparticles comprising paclitaxel and an albumin, wherein the dose of the nanoparticle composition is between about 50 mg/m² to about 200 mg/m² (such as, for example, between about 100 mg/m² and about 150 mg/m², for example about 100 mg/m²) and b) an effective amount of anti-PD-L1 antibody, wherein the dose of anti-PD-L1 antibody is between about 0.3 mg/kg to about 15 mg/kg (such as, for example, between about 2 mg/kg to about 12 mg/kg, for example about 10 mg/kg). In some embodiments, there is provided a method of treating melanoma (such as metastatic melanoma) in a human individual, comprising administering to the individual a) an effective amount of a composition comprising nanoparticles comprising paclitaxel and an albumin, wherein the dose of the nanoparticle composition is about 100 mg/m², and b) an effective amount of anti-PD-L1 antibody, wherein the dose of anti-PD-L1 antibody is about 10 mg/kg. In some embodiments, the individual is chemotherapy naïve. In some embodiments, the individual has previously been treated for melanoma. In some embodiments, the individual is at stage IV melanoma. In some embodiments, the individual is at stage M1c melanoma. In some embodiments, the individual comprises wild-type BRAF. In some embodiments, the individual comprises a BRAF mutation (such as a BRAF V600E mutation). In some embodiments, the individual is a male. In some embodiments, the individual is a female. In some embodiments, the individual is a human who is at least 65 years old (including for example at least 70, 75, or 80 years old). In some embodiments, the individual is a human who is less than 65 years old (including for example less than 60, 50, or 40 years old). In some embodiments, the individual has a normal LDH level. In some embodiments, the individual has an elevated LDH level.

In some embodiments, there is provided a method of treating melanoma (such as metastatic melanoma) in a human individual, comprising administering to the individual a) an effective amount of a composition comprising nanoparticles comprising paclitaxel and an albumin, b) an effective amount of Ipilimumab, and c) an effective amount of bevacizumab. In some embodiments, there is provided a method of treating melanoma (such as metastatic melanoma) in a human individual, comprising administering to the individual a) an effective amount of a composition comprising nanoparticles comprising paclitaxel and an albumin, b) an effective amount of Ipilimumab, and c) an effective amount of bevacizumab, wherein the dose of the nanoparticle composition is between about 50 mg/m$^2$ to about 200 mg/m$^2$, wherein the dose of Ipilimumab is between about 1 mg/kg to about 5 mg/kg, and wherein the dose of bevacizumab is between about 5 mg/kg to 15 mg/kg. In some embodiments, there is provided a method of treating melanoma (such as metastatic melanoma) in a human individual, comprising administering to the individual a) an effective amount of a composition comprising nanoparticles comprising paclitaxel and an albumin, b) an effective amount of Ipilimumab, and c) an effective amount of bevacizumab, wherein the dose of the nanoparticle composition is between about 100 mg/m$^2$ to about 150 mg/m$^2$, wherein the dose of Ipilimumab is between about 2 mg/kg to about 4 mg/kg, and wherein the dose of bevacizumab is between about 8 mg/kg to 12 mg/kg. In some embodiments, there is provided a method of treating melanoma (such as metastatic melanoma) in a human individual, comprising administering to the individual a) an effective amount of a composition comprising nanoparticles comprising paclitaxel and an albumin, b) an effective amount of Ipilimumab, and c) an effective amount of bevacizumab, wherein the dose of the nanoparticle composition is about 100 mg/m$^2$, wherein the dose of Ipilimumab is about 3 mg/kg, and wherein the dose of the bevacizumab is about 10 mg/kg. In some embodiments, there is provided a method of treating melanoma (such as metastatic melanoma) in a human individual, comprising administering to the individual a) an effective amount of a composition comprising nanoparticles comprising paclitaxel and an albumin, b) an effective amount of Ipilimumab, and c) an effective amount of bevacizumab, wherein the dose of the nanoparticle composition is about 100 mg/m$^2$ and is administered on days 1, 8, and 15 of a 28 day cycle, wherein the dose of Ipilimumab is about 3 mg/kg and is administered on day 1 of a 21 day cycle, and wherein the dose of bevacizumab is about 10 mg/kg and is administered on days 1 and 15 of a 28 day cycle. In some embodiments, there is provided a method of treating melanoma (such as metastatic melanoma) in a human individual, comprising administering to the individual a) an effective amount of a composition comprising nanoparticles comprising paclitaxel and an albumin, b) an effective amount of Ipilimumab, and c) an effective amount of bevacizumab, wherein the dose of the nanoparticle composition is about 100 mg/m$^2$ and is administered intravenously on days 1, 8, and 15 of a 28 day cycle, wherein the dose of Ipilimumab is about 3 mg/kg and is administered intravenously on day 1 of a 21 day cycle, and wherein the dose of bevacizumab is about 10 mg/kg and is administered intravenously on days 1 and 15 of a 28 day cycle. In some embodiments, the individual is chemotherapy naïve. In some embodiments, the individual has previously been treated for melanoma. In some embodiments, the individual is at stage IV melanoma. In some embodiments, the individual is at stage M1c melanoma. In some embodiments, the individual comprises wild-type BRAF. In some embodiments, the individual comprises a BRAF mutation (such as a BRAF V600E mutation). In some embodiments, the individual is a male. In some embodiments, the individual is a female. In some embodiments, the individual is a human who is at least 65 years old (including for example at least 70, 75, or 80 years old). In some embodiments, the individual is a human who is less than 65 years old (including for example less than 60, 50, or 40 years old). In some embodiments, the individual has a normal LDH level. In some embodiments, the individual has an elevated LDH level.

In some embodiments, there is provided a method of treating melanoma (such as metastatic melanoma) in a human individual, comprising administering to the individual a) an effective amount of a composition comprising nanoparticles comprising paclitaxel and an albumin, b) an effective amount of Ipilimumab, c) an effective amount of bevacizumab, and d) an effective amount of temozolomide. In some embodiments, there is provided a method of treating melanoma (such as metastatic melanoma) in a human individual, comprising administering to the individual a) an effective amount of a composition comprising nanoparticles comprising paclitaxel and an albumin, b) an effective amount of Ipilimumab, c) an effective amount of bevacizumab, and d) an effective amount of temozolomide, wherein the dose of the nanoparticle composition is between about 50 mg/m$^2$ to about 200 mg/m$^2$, (such as, for example, between about 100 mg/m$^2$ to about 150 mg/m$^2$, and for example about 100 mg/m$^2$), wherein the dose of Ipilimumab is between about 1 mg/kg to about 5 mg/kg, (such as, for example, between about 2 mg/kg to about 4 mg/kg, and for example about 3 mg/kg), wherein the dose of bevacizumab is between about 5 mg/kg to 15 mg/kg, (such as, for example, between about 7 mg/kg and 12 mg/kg, and for example about 10 mg/kg), and wherein the dose of temozolomide is between about 25 mg/m$^2$ and 125 mg/m$^2$, (such as, for example, between about 50 mg/m$^2$ to about 100 mg/m$^2$, and for example about 75 mg/m$^2$). In some embodiments, there is provided a method of treating melanoma (such as metastatic melanoma) in a human individual, comprising administering to the individual a) an effective amount of a composition comprising nanoparticles comprising paclitaxel and an albumin, b) an effective amount of Ipilimumab, c) an effective amount of bevacizumab, and d) an effective amount of temozolomide, wherein the dose of the nanoparticle composition is about 100 mg/m$^2$, wherein the dose of Ipilimumab is about 3 mg/kg, wherein the dose of the bevacizumab is about 10 mg/kg, and wherein the dose of temozolomide is about 75 mg/m$^2$. In some embodiments, there is provided a method of treating melanoma (such as metastatic melanoma) in a human individual, comprising administering to the individual a) an effective amount of a composition comprising nanoparticles comprising paclitaxel and an albumin, b) an effective amount of Ipilimumab, c) an effective amount of bevacizumab, and d) an effective amount of temozolomide, wherein the dose of the nanoparticle composition is about 100 mg/m$^2$ and is administered on days 1, 8, and 15 of a 28 day cycle, wherein the dose of Ipilimumab is about 3 mg/kg and is administered on day 1 of a 21 day cycle, wherein the dose of bevacizumab is about 10 mg/kg and is administered on days 1 and 15 of a 28 day cycle, and wherein the dose of temozolomide is about 75 mg/m$^2$ and is administered on days 1 to 42. In some embodiments, there is provided a method of treating melanoma (such as metastatic melanoma) in a human individual, comprising administering to the individual a) an effective amount of a composition comprising nanoparticles comprising paclitaxel and an albumin, b) an effective amount of Ipilimumab, c) an effective amount of bevacizumab, and d) an effective amount of temozolomide, wherein the dose of the nanoparticle composition is about 100 mg/m$^2$ and is administered intravenously on days 1, 8, and 15 of a 28 day cycle, wherein the dose of Ipilimumab is about 3 mg/kg and is administered intravenously on day 1 of a 21 day cycle, wherein the dose of bevacizumab is about 10 mg/kg and is administered intravenously on days 1 and 15 of a 28 day cycle, and wherein the dose of temozolomide is about 75 mg/m² and is administered on days 1 to 42. In some embodiments, the individual is chemotherapy naïve. In some embodiments, the individual has previously been treated for melanoma. In some embodiments, the individual is at stage IV melanoma. In some embodiments, the individual is at stage M1c melanoma. In some embodiments, the individual comprises wild-type BRAF. In some embodiments, the individual comprises a BRAF mutation (such as a BRAF V600E mutation). In some embodiments, the individual is a male. In some embodiments, the individual is a female. In some embodiments, the individual is a human who is at least 65 years old (including for example at least 70, 75, or 80 years old). In some embodiments, the individual is a human who is less than 65 years old (including for example less than 60, 50, or 40 years old). In some embodiments, the individual has a normal LDH level. In some embodiments, the individual has an elevated LDH level.

In some embodiments, the individual has stage IV or metastatic melanoma (e.g., stage IV or metastatic cutaneous melanoma). In some embodiments, the melanoma is metastatic malignant melanoma. In some embodiments, the metastatic melanoma is at stage M1a, stage M1b, or stage M1c. In some embodiments, the metastatic melanoma is at stage M1c. In some embodiments, the melanoma comprises a mutation in BRAF. In some embodiments, the melanoma comprises one or more of the following BRAF mutations: R461I, I462S, G463E, G463V, G465A, G465E, G465V, G468A, G468E, N580S, E585K, D593V, F594L, G595R, L596V, T598I, V599D, V599E, V599K, V599R, K600E, or A727V. In some embodiments, the melanoma does not comprise a mutation in BRAF. In some embodiments, the melanoma comprises a BRAF mutant such as a BRAF mutant with increased activity (for example, increased kinase activity, and/or increased activity as compared to wild-type BRAF) or a BRAF gain-of-function mutant. In some embodiments, the melanoma does not comprise BRAF mutant such as a BRAF mutant with increased activity (for example, increased kinase activity, and/or increased activity as compared to wild-type BRAF) or a BRAF gain-of-function mutant. In some embodiments, the melanoma comprises a BRAF mutant such as a BRAF mutant with decreased activity (for example, decreased kinase activity, and/or decreased activity as compared to wild-type BRAF) or a BRAF loss-of-function mutant. In some embodiments, the melanoma comprises a constitutively active BRAF. In some embodiments, the melanoma does not comprise a constitutively active BRAF. In some embodiments, the melanoma comprises a BRAF V600E mutation. In some embodiments, the melanoma does not comprise a BRAF V600E mutation (e.g., the melanoma comprises wild-type BRAF). In some embodiments, the melanoma comprises wild-type BRAF.

Modes of Administration

The dose of the taxane nanoparticle compositions administered to an individual (such as a human) may vary with the particular composition, the mode of administration, and the type of melanoma described herein being treated. The dose of the taxane nanoparticle compositions administered to an individual (such as a human) may also be adjusted (such as reduced) based on an individual's symptoms (such as adverse reactions). In some embodiments, the amount of the composition is effective to result in a response. In some embodiments, the amount of the composition is effective to result in an objective response (such as a partial response or a complete response). In some embodiments, the amount of the taxane nanoparticle composition administered (for example when administered alone) is sufficient to produce an overall response rate of more than about any of 20%, 25%, 30%, 35%, 40%, 45%, 50%, 55%, 60%, 64%, 65%, 70%, 75%, 80%, 85%, or 90% among a population of individuals treated with the taxane nanoparticle composition. Responses of an individual to the treatment of the methods described herein can be determined using methods known in the field.

In some embodiments, the amount of the composition is sufficient to prolong progression-free survival of the individual. In some embodiments, the amount of the composition is sufficient to prolong survival of the individual. In some embodiments, the amount of the composition is sufficient to improve quality of life of the individual. In some embodiments, the amount of the composition (for example when administered alone) is sufficient to produce clinical benefit of more than about any of 50%, 60%, 70%, or 77% among a population of individuals treated with the taxane nanoparticle composition.

In some embodiments, the amount of the composition, first therapy, second therapy, or combination therapy is an amount sufficient to decrease the size of a melanoma tumor, decrease the number of melanoma tumor cells, or decrease the growth rate of a melanoma tumor by at least about any of 10%, 20%, 30%, 40%, 50%, 60%, 70%, 80%, 90%, 95% or 100% compared to the corresponding tumor size, number of melanoma tumor cells, or tumor growth rate in the same individual prior to treatment or compared to the corresponding activity in other individuals not receiving the treatment. Methods that can be used to measure the magnitude of this effect are known in the field.

In some embodiments, the amount of the taxane (e.g., paclitaxel) in the composition is below the level that induces a toxicological effect (i.e., an effect above a clinically acceptable level of toxicity) or is at a level where a potential side effect can be controlled or tolerated when the composition is administered to the individual.

In some embodiments, the amount of the composition is close to a maximum tolerated dose (MTD) of the composition following the same dosing regimen. In some embodiments, the amount of the composition is more than about any of 80%, 90%, 95%, or 98% of the MTD.

In some embodiments, the amount of a taxane (e.g., paclitaxel) in the composition is included in any of the following ranges: about 0.1 mg to about 500 mg, about 0.1 mg to about 2.5 mg, about 0.5 to about 5 mg, about 5 to about 10 mg, about 10 to about 15 mg, about 15 to about 20 mg, about 20 to about 25 mg, about 20 to about 50 mg, about 25 to about 50 mg, about 50 to about 75 mg, about 50 to about 100 mg, about 75 to about 100 mg, about 100 to about 125 mg, about 125 to about 150 mg, about 150 to about 175 mg, about 175 to about 200 mg, about 200 to about 225 mg, about 225 to about 250 mg, about 250 to about 300 mg, about 300 to about 350 mg, about 350 to about 400 mg, about 400 to about 450 mg, or about 450 to about 500 mg. In some embodiments, the amount of a taxane (e.g., paclitaxel) in the effective amount of the composition (e.g., a unit dosage form) is in the range of about 5 mg to about 500 mg, such as about 30 mg to about 300 mg or about 50 mg to about 200 mg. In some embodiments, the concentration of the taxane (e.g., paclitaxel) in the composition is dilute (about 0.1 mg/ml) or concentrated (about 100 mg/ml), including for example any of about 0.1 to about 50 mg/ml, about 0.1 to about 20 mg/ml, about 1 to about 10 mg/ml, about 2 mg/ml to about 8 mg/ml, about 4 to about 6 mg/ml, or about 5 mg/ml. In some embodiments, the concentration of the taxane (e.g., paclitaxel) is at least about any of 0.5 mg/ml, 1.3 mg/ml, 1.5 mg/ml, 2 mg/ml, 3 mg/ml, 4 mg/ml, 5 mg/ml, 6 mg/ml, 7 mg/ml, 8 mg/ml, 9 mg/ml, 10 mg/ml, 15 mg/ml, 20 mg/ml, 25 mg/ml, 30 mg/ml, 40 mg/ml, or 50 mg/ml. In some embodiments, the concentration of the taxane (e.g., paclitaxel) is no more than about any of 100 mg/ml, 90 mg/ml, 80 mg/ml, 70 mg/ml, 60 mg/ml, 50 mg/ml, 40 mg/ml, 30 mg/ml, 20 mg/ml, 10 mg/ml, or 5 mg/ml.

Exemplary effective amounts of a taxane (e.g., paclitaxel) in the nanoparticle composition include, but are not limited to, at least about any of 25 mg/m$^2$, 30 mg/m$^2$, 50 mg/m$^2$, 60 mg/m$^2$, 75 mg/m$^2$, 80 mg/m$^2$, 90 mg/m$^2$, 100 mg/m$^2$, 120 mg/m$^2$, 125 mg/m$^2$, 150 mg/m$^2$, 160 mg/m$^2$, 175 mg/m$^2$, 180 mg/m$^2$, 200 mg/m$^2$, 210 mg/m$^2$, 220 mg/m$^2$, 250 mg/m$^2$, 260 mg/m$^2$, 300 mg/m$^2$, 350 mg/m$^2$, 400 mg/m$^2$, 500 mg/m$^2$, 540 mg/m$^2$, 750 mg/m$^2$, 1000 mg/m$^2$, or 1080 mg/m$^2$ of a taxane (e.g., paclitaxel). In various embodiments, the composition includes less than about any of 350 mg/m$^2$, 300 mg/m$^2$, 250 mg/m$^2$, 200 mg/m$^2$, 150 mg/m$^2$, 120 mg/m$^2$, 100 mg/m$^2$, 90 mg/m$^2$, 50 mg/m$^2$, or 30 mg/m$^2$ of a taxane (e.g., paclitaxel). In some embodiments, the amount of the taxane (e.g., paclitaxel) per administration is less than about any of 25 mg/m$^2$, 22 mg/m$^2$, 20 mg/m$^2$, 18 mg/m$^2$, 15 mg/m$^2$, 14 mg/m$^2$, 13 mg/m$^2$, 12 mg/m$^2$, 11 mg/m$^2$, 10 mg/m$^2$, 9 mg/m$^2$, 8 mg/m$^2$, 7 mg/m$^2$, 6 mg/m$^2$, 5 mg/m$^2$, 4 mg/m$^2$, 3 mg/m$^2$, 2 mg/m$^2$, or 1 mg/m$^2$. In some embodiments, the effective amount of a taxane (e.g., paclitaxel) in the composition is included in any of the following ranges: about 1 to about 5 mg/m$^2$, about 5 to about 10 mg/m$^2$, about 10 to about 25 mg/m$^2$, about 25 to about 50 m g/m$^2$, about 50 to about 75 mg/m$^2$, about 75 to about 100 mg/m$^2$, about 100 to about 125 mg/m$^2$, about 100 to about 200 mg/m$^2$, about 125 to about 150 mg/m$^2$, about 125 to about 175 mg/m$^2$, about 150 to about 175 mg/m$^2$, about 175 to about 200 mg/m$^2$, about 200 to about 225 mg/m$^2$, about 225 to about 250 mg/m$^2$, about 250 to about 300 mg/m$^2$, about 300 to about 350 mg/m$^2$, or about 350 to about 400 mg/m$^2$. In some embodiments, the effective amount of a taxane (e.g., paclitaxel) in the composition is included in any of the following ranges: about 10 mg/m$^2$ to about 400 mg/m$^2$, about 25 mg/m$^2$ to about 400 mg/m$^2$, about 50 mg/m$^2$ to about 400 mg/m$^2$, about 75 mg/m$^2$ to about 350 mg/m$^2$, about 75 mg/m$^2$ to about 300 mg/m$^2$, about 75 mg/m$^2$ to about 250 mg/m$^2$, about 75 mg/m$^2$ to about 200 mg/m$^2$, about 75 mg/m$^2$ to about 150 mg/m$^2$, about 75 mg/m$^2$ to about 125 mg/m$^2$, about 100 mg/m$^2$ to about 260 mg/m$^2$, about 100 mg/m$^2$ to about 250 mg/m$^2$, about 100 mg/m$^2$ to about 200 mg/m$^2$, or about 125 mg/m$^2$ to about 175 mg/m$^2$. In some embodiments, the effective amount of a taxane (e.g., paclitaxel) in the composition is about 5 to about 300 mg/m$^2$, about 100 to about 200 mg/m$^2$, about 100 to about 150 mg/m$^2$, about 50 to about 150 mg/m$^2$, about 75 to about 150 mg/m$^2$, about 75 to about 125 mg/m$^2$, or about 70 mg/m$^2$, about 80 mg/m$^2$, about 90 mg/m$^2$, about 100 mg/m$^2$, about 110 mg/m$^2$, about 120 mg/m$^2$, about 130 mg/m$^2$, about 140 mg/m$^2$, about 150 mg/m$^2$, about 160 mg/m$^2$, about 170 mg/m$^2$, about 180 mg/m$^2$, about 190 mg/m$^2$, about 200 mg/m$^2$, about 250 mg/m$^2$, about 260 mg/m$^2$, or about 300 mg/m$^2$.

In some embodiments of any of the above aspects, the effective amount of a taxane (e.g., paclitaxel) in the composition includes at least about any of 1 mg/kg, 2.5 mg/kg, 3.5 mg/kg, 5 mg/kg, 6.5 mg/kg, 7.5 mg/kg, 10 mg/kg, 15 mg/kg, 20 mg/kg, 25 mg/kg, 30 mg/kg, 35 mg/kg, 40 mg/kg, 45 mg/kg, 50 mg/kg, 55 mg/kg, or 60 mg/kg. In various embodiments, the effective amount of a taxane (e.g., paclitaxel) in the composition includes less than about any of 350 mg/kg, 300 mg/kg, 250 mg/kg, 200 mg/kg, 150 mg/kg, 100 mg/kg, 50 mg/kg, 25 mg/kg, 20 mg/kg, 10 mg/kg, 7.5 mg/kg, 6.5 mg/kg, 5 mg/kg, 3.5 mg/kg, 2.5 mg/kg, or 1 mg/kg of a taxane (e.g., paclitaxel).

Exemplary dosing frequencies for the administration of the nanoparticle compositions include, but are not limited to, daily, every two days, every three days, every four days, every five days, every six days, weekly without break, weekly for three out of four weeks, once every three weeks, once every two weeks, or two out of three weeks. In some embodiments, the composition is administered about once every 2 weeks, once every 3 weeks, once every 4 weeks, once every 6 weeks, or once every 8 weeks. In some embodiments, the composition is administered at least about any of 1×, 2×, 3×, 4×, 5×, 6×, or 7× (i.e., daily) a week. In some embodiments, the intervals between each administration are less than about any of 6 months, 3 months, 1 month, 20 days, 15, days, 14 days, 13 days, 12 days, 11 days, 10 days, 9 days, 8 days, 7 days, 6 days, 5 days, 4 days, 3 days, 2 days, or 1 day. In some embodiments, the intervals between each administration are more than about any of 1 month, 2 months, 3 months, 4 months, 5 months, 6 months, 8 months, or 12 months. In some embodiments, there is no break in the dosing schedule. In some embodiments, the interval between each administration is no more than about a week.

In some embodiments, the dosing frequency is once every two days for one time, two times, three times, four times, five times, six times, seven times, eight times, nine times, ten times, and eleven times. In some embodiments, the dosing frequency is once every two days for five times. In some embodiments, the taxane (e.g., paclitaxel) is administered over a period of at least ten days, wherein the interval between each administration is no more than about two days, and wherein the dose of the taxane (e.g., paclitaxel) at each administration is about 0.25 mg/m$^2$ to about 250 mg/m$^2$, about 0.25 mg/m$^2$ to about 150 mg/m$^2$, about 0.25 mg/m$^2$ to about 75 mg/m$^2$, such as about 0.25 mg/m$^2$ to about 25 mg/m$^2$, about 25 mg/m$^2$ to about 50 mg/m$^2$, or about 50 mg/m$^2$ to about 100 mg/m$^2$.

The administration of the composition can be extended over an extended period of time, such as from about a month up to about seven years. In some embodiments, the composition is administered over a period of at least about any of 2, 3, 4, 5, 6, 7, 8, 9, 10, 11, 12, 18, 24, 30, 36, 48, 60, 72, or 84 months.

In some embodiments, the dosage of a taxane (e.g., paclitaxel) in a nanoparticle composition can be in the range of 5-400 mg/m$^2$ when given on a 3 week schedule, or 5-250 mg/m$^2$ (such as 75-200 mg/m$^2$, 100-200 mg/m$^2$, for example 125-175 mg/m$^2$) when given on a weekly schedule. For example, the amount of a taxane (e.g., paclitaxel) is about 60 to about 300 mg/m$^2$ (e.g., about 100 mg/m$^2$, 125 mg/m$^2$, 150 mg/m$^2$, 175 mg/m$^2$, 200 mg/m$^2$, 225 mg/m$^2$, 250 mg/m$^2$, or 260 mg/m$^2$) on a three week schedule. In some embodiments, the amount of a taxane (e.g., paclitaxel) is about 60 to about 300 mg/m$^2$ (e.g., about 100 mg/m$^2$, 125 mg/m$^2$, 150 m g/m$^2$, 175 mg/m$^2$, 200 mg/m$^2$, 225 mg/m$^2$, 250 mg/m$^2$, or 260 mg/m$^2$) administered weekly. In some embodiments, the amount of a taxane (e.g., paclitaxel) is about 60 to about 300 mg/m$^2$ (e.g., about 100 mg/m$^2$, 125 mg/m$^2$, 150 mg/m$^2$, 175 mg/m$^2$, 200 mg/m$^2$, 225 mg/m$^2$, 250 mg/m$^2$, or 260 mg/m$^2$) administered weekly for three out of a four week schedule.

Other exemplary dosing schedules for the administration of the nanoparticle composition (e.g., paclitaxel/albumin nanoparticle composition) include, but are not limited to, 100 mg/m$^2$, weekly, without break; 75 mg/m$^2$ weekly, 3 out of four weeks; 100 mg/m$^2$, weekly, 3 out of 4 weeks; 125 mg/m$^2$, weekly, 3 out of 4 weeks; 150 mg/m$^2$, weekly, 3 out of 4 weeks; 175 mg/m$^2$, weekly, 3 out of 4 weeks; 125 mg/m$^2$, weekly, 2 out of 3 weeks; 130 mg/m$^2$, weekly, without break; 175 mg/m$^2$, once every 2 weeks; 260 mg/m$^2$, once every 2 weeks; 260 mg/m$^2$, once every 3 weeks; 180-300 mg/m$^2$, every three weeks; 60-175 mg/m$^2$, weekly, without break;

20-150 mg/m² twice a week; and 150-250 mg/m² twice a week. The dosing frequency of the composition may be adjusted over the course of the treatment based on the judgment of the administering physician.

In some embodiments, the individual is treated for at least about any of one, two, three, four, five, six, seven, eight, nine, or ten treatment cycles.

The compositions described herein allow infusion of the composition to an individual over an infusion time that is shorter than about 24 hours. For example, in some embodiments, the composition is administered over an infusion period of less than about any of 24 hours, 12 hours, 8 hours, 5 hours, 3 hours, 2 hours, 1 hour, 30 minutes, 20 minutes, or 10 minutes. In some embodiments, the composition is administered over an infusion period of about 30 minutes.

Other exemplary doses of the taxane (in some embodiments paclitaxel) in the nanoparticle composition include, but is not limited to, about any of 50 mg/m², 60 mg/m², 75 mg/m², 80 mg/m², 90 mg/m², 100 mg/m², 120 mg/m², 140 mg/m², 150 mg/m², 160 mg/m², 175 mg/m², 200 mg/m², 210 mg/m², 220 mg/m², 260 mg/m², and 300 mg/m². For example, the dosage of paclitaxel in a nanoparticle composition can be in the range of about 100-400 mg/m² when given on a 3 week schedule, or about 50-250 mg/m² when given on a weekly schedule.

In some embodiments, there is provided a method of treating melanoma in an individual (e.g., human) comprising administering to the individual an effective amount of a composition comprising nanoparticles comprising a taxane (e.g., paclitaxel) and a carrier protein (e.g., albumin such as human serum albumin or human albumin), wherein the dose of taxane in the nanoparticle composition is between about 50 m g/m² to about 400 mg/m² (including for example about 100 mg/m² to about 300 mg/m², about 100 mg/m² to about 200 mg/m², or about 125 mg/m² to about 175 mg/m²). In some embodiments, the effective amount of taxane in the nanoparticle composition is between about 100 mg/m² to about 300 mg/m² (e.g., about 100 mg/m² to about 200 mg/m²). In some embodiments, the effective amount of taxane in the nanoparticle composition is between about 125 mg/m² to about 175 mg/m² (e.g., about 100 mg/m² or about 150 mg/m²). In some embodiments, the nanoparticle composition is administered weekly for three weeks of four weeks or weekly. In some embodiments, the carrier protein is albumin such as human serum albumin or human albumin. In some embodiments, the taxane is paclitaxel.

In some embodiments, there is provided a method of treating melanoma in an individual (e.g., human) comprising administering to the individual an effective amount of a composition comprising nanoparticles comprising a taxane (e.g., paclitaxel) and a carrier protein (e.g., albumin such as human serum albumin or human albumin), wherein the dose of taxane in the nanoparticle composition is between about 50 m g/m² to about 400 mg/m² (including for example about 100 mg/m² to about 300 mg/m², about 100 mg/m² to about 200 mg/m², or about 125 mg/m² to about 175 mg/m²). In some embodiments, the effective amount of taxane in the nanoparticle composition is between about 100 mg/m² to about 300 mg/m² (e.g., about 100 mg/m² to about 200 mg/m² such as about 100 mg/m² or about 150 mg/m²). In some embodiments, the effective amount of taxane in the nanoparticle composition is between about 100 mg/m² to about 200 mg/m² (e.g., about 100 mg/m² or about 150 mg/m²). In some embodiments, the nanoparticle composition is administered weekly for three weeks of four weeks or weekly. In some embodiments, the individual has stage IV or metastatic melanoma (e.g., stage IV or metastatic cutaneous melanoma). In some embodiments, the melanoma is metastatic malignant melanoma. In some embodiments, the metastatic melanoma is at stage M1a, stage M1b, or stage M1c. In some embodiments, the metastatic melanoma is at stage M1c. In some embodiments, the melanoma comprises a mutation in BRAF. In some embodiments, the melanoma does not comprise a mutation in BRAF. In some embodiments, the melanoma does not comprise BRAF mutant such as a BRAF mutant with increased activity (for example, increased kinase activity, and/or increased activity as compared to wild-type BRAF) or a BRAF gain-of-function mutant. In some embodiments, the melanoma does not comprise BRAF V600E mutation (e.g., the melanoma comprises wild-type BRAF). In some embodiments, the melanoma comprises wild-type BRAF. In some embodiments, the melanoma comprises a BRAF mutant such as a BRAF mutant with increased activity (for example, increased kinase activity, and/or increased activity as compared to wild-type BRAF) or a BRAF gain-of-function mutant. In some embodiments, the melanoma comprises BRAF V600E mutation. In some embodiments, the individual has elevated serum LDH level. In some embodiments, the individual has serum LDH of about any of the following: <0.8×ULN, 0.4-0.8×ULN, 0.8-1.1×ULN, 0.9-1.1×ULN, 0.8-1.2×ULN, 1.1-1.5×ULN, 1.2-1.5×ULN, 1.1-2×ULN, or 1.5-2×ULN. In some embodiments, the individual has serum LDH of less than about 0.8×ULN. In some embodiments, the individual has serum LDH at about 0.8× to about 1.1×ULN. In some embodiments, the individual has serum LDH of between greater than about 1.1× to about 2.0×ULN. In some embodiments, the individual has serum LDH of between about 1.1× to about 2.0×ULN. In some embodiments, the individual is a human (e.g., male or female). In some embodiments, the taxane is paclitaxel. In some embodiments, the carrier protein is albumin.

The nanoparticle compositions can be administered to an individual (such as human) via various routes, including, for example, parenteral, intravenous, intraventricular, intra-arterial, intraperitoneal, intrapulmonary, oral, inhalation, intravesicular, intramuscular, intra-tracheal, subcutaneous, intraocular, intrathecal, transmucosal, and transdermal. In some embodiments, sustained continuous release formulation of the composition may be used. In some embodiments, the composition is administered intravenously. In some embodiments, the composition is administered intraportally. In some embodiments, the composition is administered intraarterially. In some embodiments, the composition is administered intraperitoneally. In some embodiments, the composition is administered intrathecally. In some embodiments, the composition is administered through a ported catheter to spinal fluid. In some embodiments, the composition is administered intraventricularly. In some embodiments, the composition is administered systemically. In some embodiments, the composition is administered by infusion. In some embodiments, the composition is administered by infusion through implanted pump. In some embodiments, the composition is administered by a ventricular catheter. In some embodiments, the composition is administered through a port or portacath. In some embodiments, the port or portacath is inserted into a vein (such as jugular vein, subclavian vein, or superior vena cava).

The dosing regimens described herein apply to both monotherapy and combination therapy settings. The modes of administration for combination therapy methods are further described below.

Modes of Administration for Combination Therapy

Provided herein are modes and administrations for treatment melanoma using combination therapy. In some embodiments, there is provided a method of treating melanoma in an individual (e.g., human) comprising administering to the individual a) an effective amount of a composition comprising nanoparticles comprising a taxane (e.g., paclitaxel) and a carrier protein (e.g., albumin), and b) an effective amount of at least one other agent (such as a chemotherapeutic agent or immunotherapeutic agent). The modes and administrations for using a composition comprising nanoparticles comprising a taxane (e.g., paclitaxel) and a carrier protein (e.g., albumin) and the other agent are described herein.

The composition comprising nanoparticles comprising taxane (also referred to as "nanoparticle composition") and the other agent can be administered simultaneously (i.e., simultaneous administration) and/or sequentially (i.e., sequential administration).

In some embodiments, the nanoparticle composition and the other agent (including the specific agents described herein) are administered simultaneously. The term "simultaneous administration," as used herein, means that the nanoparticle composition and the other agent are administered with a time separation of no more than about 15 minute(s), such as no more than about any of 10, 5, or 1 minutes. When the drugs are administered simultaneously, the drug in the nanoparticles and the other agent may be contained in the same composition (e.g., a composition comprising both the nanoparticles and the other agent) or in separate compositions (e.g., the nanoparticles are contained in one composition and the other agent is contained in another composition).

In some embodiments, the nanoparticle composition and the other agent are administered sequentially. The term "sequential administration" as used herein means that the drug in the nanoparticle composition and the other agent are administered with a time separation of more than about 15 minutes, such as more than about any of 20, 30, 40, 50, 60 or more minutes. Either the nanoparticle composition or the other agent may be administered first. The nanoparticle composition and the other agent are contained in separate compositions, which may be contained in the same or different packages.

In some embodiments, the administration of the nanoparticle composition and the other agent are concurrent, i.e., the administration period of the nanoparticle composition and that of the other agent overlap with each other. In some embodiments, the nanoparticle composition is administered for at least one cycle (for example, at least any of 2, 3, or 4 cycles) prior to the administration of the other agent. In some embodiments, the other agent is administered for at least any of one, two, three, or four weeks. In some embodiments, the administrations of the nanoparticle composition and the other agent are initiated at about the same time (for example, within any one of 1, 2, 3, 4, 5, 6, or 7 days). In some embodiments, the administrations of the nanoparticle composition and the other agent are terminated at about the same time (for example, within any one of 1, 2, 3, 4, 5, 6, or 7 days). In some embodiments, the administration of the other agent continues (for example for about any one of 1, 2, 3, 4, 5, 6, 7, 8, 9, 10, 11, or 12 months) after the termination of the administration of the nanoparticle composition. In some embodiments, the administration of the other agent is initiated after (for example after about any one of 1, 2, 3, 4, 5, 6, 7, 8, 9, 10, 11, or we months) the initiation of the administration of the nanoparticle composition. In some embodiments, the administrations of the nanoparticle composition and the other agent are initiated and terminated at about the same time. In some embodiments, the administrations of the nanoparticle composition and the other agent are initiated at about the same time and the administration of the other agent continues (for example for about any one of 1, 2, 3, 4, 5, 6, 7, 8, 9, 10, 11, or 12 months) after the termination of the administration of the nanoparticle composition. In some embodiments, the administration of the nanoparticle composition and the other agent stop at about the same time and the administration of the other agent is initiated after (for example after about any one of 1, 2, 3, 4, 5, 6, 7, 8, 9, 10, 11, or we months) the initiation of the administration of the nanoparticle composition.

In some embodiments, the administration of the nanoparticle composition and the other agent (e.g., carboplatin) are concurrent, i.e., the administration period of the nanoparticle composition and that of the other agent overlap with each other. In some embodiments, the administrations of the nanoparticle composition and the other agent are initiated at about the same time (for example, within any one of 1, 2, 3, 4, 5, 6, or 7 days). In some embodiments, the administration of the nanoparticle composition and the other agent are terminated at about the same time (for example, within any one of 1, 2, 3, 4, 5, 6, or 7 days). In some embodiments, the administration of the other agent continues (for example for about any one of 1, 2, 3, 4, 5, 6, 7, 8, 9, 10, 11, or 12 months) after the termination of the administration of the nanoparticle composition. In some embodiments, the administration of the other agent is initiated after (for example after about any one of 1, 2, 3, 4, 5, 6, 7, 8, 9, 10, 11, or 12 months) the initiation of the administration of the nanoparticle composition. In some embodiments, the administrations of the nanoparticle composition and the other agent are initiated and terminated at about the same time. In some embodiments, the administrations of the nanoparticle composition and the other agent are initiated at about the same time and the administration of the other agent continues (for example for about any one of 1, 2, 3, 4, 5, 6, 7, 8, 9, 10, 11, or 12 months) after the termination of the administration of the nanoparticle composition. In some embodiments, the administration of the nanoparticle composition and the other agent stop at about the same time and the administration of the other agent is initiated after (for example after about any one of 1, 2, 3, 4, 5, 6, 7, 8, 9, 10, 11, or 12 months) the initiation of the administration of the nanoparticle composition. In some embodiments, the method comprises more than one treatment cycles, wherein at least one of the treatment cycles comprise the administration of (a) an effective amount of a composition comprising nanoparticles comprising a taxane (such as paclitaxel) and a carrier protein (e.g., albumin); and (b) an effective amount of at least one other agent. In some embodiments, the treatment cycle comprises no less than about (such as about) 21 days (e.g., 4 weeks). In some embodiments, the treatment cycle comprises less than about 21 days (for example weekly or daily). In some embodiments, the treatment cycle comprises about 28 days.

In some embodiments, the administration of the nanoparticle composition and the other agent are non-concurrent. For example, in some embodiments, the administration of the nanoparticle composition is terminated before the other agent is administered. In some embodiments, the administration of the other agent is terminated before the nanoparticle composition is administered. The time period between these two non-concurrent administrations can range from about two to eight weeks, such as about four weeks.

The dosing frequency of the drug-containing nanoparticle composition and the other agent may be adjusted over the course of the treatment, based on the judgment of the administering physician. When administered separately, the drug-containing nanoparticle composition and the other agent can be administered at different dosing frequency or intervals. For example, the drug-containing nanoparticle composition can be administered weekly, while another agent can be administered more or less frequently. In some embodiments, sustained continuous release formulation of the drug-containing nanoparticle and/or other agent may be used. Various formulations and devices for achieving sustained release are known in the art. Exemplary dosing frequencies are further provided herein.

The nanoparticle composition and the other agent can be administered using the same route of administration or different routes of administration. Exemplary administration routes are further provided herein. In some embodiments (for both simultaneous and sequential administrations), the taxane in the nanoparticle composition and the other agent are administered at a predetermined ratio. For example, in some embodiments, the ratio by weight of the taxane in the nanoparticle composition and the other agent is about 1 to 1. In some embodiments, the weight ratio may be between about 0.001 to about 1 and about 1000 to about 1, or between about 0.01 to about 1 and 100 to about 1. In some embodiments, the ratio by weight of the taxane in the nanoparticle composition and the other agent is less than about any of 100:1, 50:1, 30:1, 10:1, 9:1, 8:1, 7:1, 6:1, 5:1, 4:1, 3:1, 2:1, and 1:1 In some embodiments, the ratio by weight of the taxane in the nanoparticle composition and the other agent is more than about any of 1:1, 2:1, 3:1, 4:1, 5:1, 6:1, 7:1, 8:1, 9:1, 30:1, 50:1, 100:1. Other ratios are contemplated.

The doses required for the taxane and/or the other agent may (but not necessarily) be lower than what is normally required when each agent is administered alone. Thus, in some embodiments, a subtherapeutic amount of the drug in the nanoparticle composition and/or the other agent are administered. "Subtherapeutic amount" or "subtherapeutic level" refer to an amount that is less than therapeutic amount, that is, less than the amount normally used when the drug in the nanoparticle composition and/or the other agent are administered alone. The reduction may be reflected in terms of the amount administered at a given administration and/or the amount administered over a given period of time (reduced frequency).

In some embodiments, enough other agent is administered so as to allow reduction of the normal dose of the drug in the nanoparticle composition required to effect the same degree of treatment by at least about any of 5%, 10%, 20%, 30%, 50%, 60%, 70%, 80%, 90%, or more. In some embodiments, enough drug in the nanoparticle composition is administered so as to allow reduction of the normal dose of the other agent required to effect the same degree of treatment by at least about any of 5%, 10%, 20%, 30%, 50%, 60%, 70%, 80%, 90%, or more.

In some embodiments, the dose of both the taxane in the nanoparticle composition and the other agent are reduced as compared to the corresponding normal dose of each when administered alone. In some embodiments, both the taxane in the nanoparticle composition and the other agent are administered at a subtherapeutic, i.e., reduced, level. In some embodiments, the dose of the nanoparticle composition and/or the other agent is substantially less than the established maximum toxic dose (MTD). For example, the dose of the nanoparticle composition and/or the other agent is less than about 50%, 40%, 30%, 20%, or 10% of the MTD.

In some embodiments, the dose of taxane and/or the dose of the other agent is higher than what is normally required when each agent is administered alone. For example, in some embodiments, the dose of the nanoparticle composition and/ or the other agent is substantially higher than the established maximum toxic dose (MTD). For example, the dose of the nanoparticle composition and/or the other agent is more than about 50%, 40%, 30%, 20%, or 10% of the MTD of the agent when administered alone.

In some embodiments, the amount of a taxane (e.g., paclitaxel) in the composition is included in any of the following ranges: about 0.5 to about 5 mg, about 5 to about 10 mg, about 10 to about 15 mg, about 15 to about 20 mg, about 20 to about 25 mg, about 20 to about 50 mg, about 25 to about 50 mg, about 50 to about 75 mg, about 50 to about 100 mg, about 75 to about 100 mg, about 100 to about 125 mg, about 125 to about 150 mg, about 150 to about 175 mg, about 175 to about 200 mg, about 200 to about 225 mg, about 225 to about 250 mg, about 250 to about 300 mg, about 300 to about 350 mg, about 350 to about 400 mg, about 400 to about 450 mg, or about 450 to about 500 mg. In some embodiments, the amount of a taxane (e.g., paclitaxel) or derivative thereof in the effective amount of the composition (e.g., a unit dosage form) is in the range of about 5 mg to about 500 mg, such as about 30 mg to about 300 mg or about 50 mg to about 200 mg. In some embodiments, the concentration of the taxane (e.g., paclitaxel) in the composition is dilute (about 0.1 mg/ml) or concentrated (about 100 mg/ml), including for example any of about 0.1 to about 50 mg/ml, about 0.1 to about 20 mg/ml, about 1 to about 10 mg/ml, about 2 mg/ml to about 8 mg/ml, about 4 to about 6 mg/ml, about 5 mg/ml. In some embodiments, the concentration of the taxane (e.g., paclitaxel) is at least about any of 0.5 mg/ml, 1.3 mg/ml, 1.5 mg/ml, 2 mg/ml, 3 mg/ml, 4 mg/ml, 5 mg/ml, 6 mg/ml, 7 mg/ml, 8 mg/ml, 9 mg/ml, 10 mg/ml, 15 mg/ml, 20 mg/ml, 25 mg/ml, 30 mg/ml, 40 mg/ml, or 50 mg/ml.

Exemplary effective amounts of a taxane (e.g., paclitaxel) in the nanoparticle composition include, but are not limited to, at least about any of 25 mg/m$^2$, 30 mg/m$^2$, 50 mg/m$^2$, 60 mg/m$^2$, 75 mg/m$^2$, 80 mg/m$^2$, 90 mg/m$^2$, 100 mg/m$^2$, 120 mg/m$^2$, 125 mg/m$^2$, 150 mg/m$^2$, 160 mg/m$^2$, 175 mg/m$^2$, 180 mg/m$^2$, 200 mg/m$^2$, 210 mg/m$^2$, 220 mg/m$^2$, 250 mg/m$^2$, 260 mg/m$^2$, 300 mg/m$^2$, 350 mg/m$^2$, 400 mg/m$^2$, 500 mg/m$^2$, 540 mg/m$^2$, 750 mg/m$^2$, 1000 mg/m$^2$, or 1080 mg/m$^2$ of a taxane (e.g., paclitaxel). In various embodiments, the composition includes less than about any of 350 mg/m$^2$, 300 mg/m$^2$, 250 mg/m$^2$, 200 mg/m$^2$, 150 mg/m$^2$, 120 mg/m$^2$, 100 mg/m$^2$, 90 mg/m$^2$, 50 mg/m$^2$, or 30 mg/m$^2$ of a taxane (e.g., paclitaxel). In some embodiments, the amount of the taxane (e.g., paclitaxel) per administration is less than about any of 25 mg/m$^2$, 22 mg/m$^2$, 20 mg/m$^2$, 18 mg/m$^2$, 15 mg/m$^2$, 14 mg/m$^2$, 13 mg/m$^2$, 12 mg/m$^2$, 11 mg/m$^2$, 10 mg/m$^2$, 9 mg/m$^2$, 8 mg/m$^2$, 7 mg/m$^2$, 6 mg/m$^2$, 5 mg/m$^2$, 4 mg/m$^2$, 3 mg/m$^2$, 2 mg/m$^2$, or 1 mg/m$^2$. In some embodiments, the effective amount of a taxane (e.g., paclitaxel) in the composition is included in any of the following ranges: about 1 to about 5 mg/m$^2$, about 5 to about 10 mg/m$^2$, about 10 to about 25 mg/m$^2$, about 25 to about 50 m g/m$^2$, about 50 to about 75 mg/m$^2$, about 75 to about 100 mg/m$^2$, about 100 to about 125 mg/m$^2$, about 125 to about 150 mg/m$^2$, about 150 to about 175 mg/m$^2$, about 175 to about 200 mg/m$^2$, about 200 to about 225 mg/m$^2$, about 225 to about 250 mg/m$^2$, about 250 to about 300 mg/m$^2$, about 300 to about 350 mg/m$^2$, or about 350 to about 400 mg/m$^2$. In some embodiments, the effective amount of a taxane (e.g., paclitaxel) in the composition is about 5 to about 300 mg/m$^2$, such as about 20 to about 300 mg/m$^2$, about 50 to about 250 mg/m$^2$, about 100 to about 150 mg/m$^2$, about 120 mg/m$^2$, about 130 mg/m$^2$, or about 140 mg/m$^2$, or about 260 mg/m$^2$.

In some embodiments of any of the above aspects, the effective amount of a taxane (e.g., paclitaxel) in the composition includes at least about any of 1 mg/kg, 2.5 mg/kg, 3.5 mg/kg, 5 mg/kg, 6.5 mg/kg, 7.5 mg/kg, 10 mg/kg, 15 mg/kg, or 20 mg/kg. In various embodiments, the effective amount of a taxane (e.g., paclitaxel) in the composition includes less than about any of 350 mg/kg, 300 mg/kg, 250 mg/kg, 200 mg/kg, 150 mg/kg, 100 mg/kg, 50 mg/kg, 25 mg/kg, 20 mg/kg, 10 mg/kg, 7.5 mg/kg, 6.5 mg/kg, 5 mg/kg, 3.5 mg/kg, 2.5 mg/kg, or 1 mg/kg of a taxane (e.g., paclitaxel).

Exemplary dosing frequencies for the nanoparticle composition (and as indicated below for the other agent) include, but are not limited to, weekly without break; weekly, three out of four weeks; once every three weeks; once every two weeks; weekly, two out of three weeks. In some embodiments, the composition is administered about once every 2 weeks, once every 3 weeks, once every 4 weeks, once every 6 weeks, or once every 8 weeks. In some embodiments, the composition is administered at least about any of 1×, 2×, 3×, 4×, 5×, 6×, or 7× (i.e., daily) a week, or three times daily, two times daily. In some embodiments, the intervals between each administration are less than about any of 6 months, 3 months, 1 month, 20 days, 15 days, 12 days, 10 days, 9 days, 8 days, 7 days, 6 days, 5 days, 4 days, 3 days, 2 days, or 1 day. In some embodiments, the intervals between each administration are more than about any of 1 month, 2 months, 3 months, 4 months, 5 months, 6 months, 8 months, or 12 months. In some embodiments, there is no break in the dosing schedule. In some embodiments, the interval between each administration is no more than about a week.

In some embodiments, the taxane in the nanoparticle composition is administered weekly. In some embodiments, the taxane in a nanoparticle composition is administered every two weeks. In some embodiments, the taxane in the nanoparticle composition is administered every three weeks. In some embodiments, the other agent is administered 1×, 2×, 3×, 4×, 5×, 6×, or 7 times a week. In some embodiments, the other agent is administered every two weeks or two out of three weeks. In some embodiments, the taxane is paclitaxel. In some embodiment, the other agent is a platinum-based agent (such as carboplatin). In some embodiments of the above dosages and/or administrations, the taxane is paclitaxel and the other agent is carboplatin.

The administration of the nanoparticle composition (and for the other agent) can be extended over an extended period of time, such as from about a month up to about seven years. In some embodiments, the composition is administered over a period of at least about any of 2, 3, 4, 5, 6, 7, 8, 9, 10, 11, 12, 18, 24, 30, 36, 48, 60, 72, or 84 months. In some embodiments, the taxane (e.g., paclitaxel) is administered over a period of at least one month, wherein the interval between each administration is no more than about a week, and wherein the dose of the taxane (e.g., paclitaxel) at each administration is about 0.25 mg/m$^2$ to about 75 mg/m$^2$, such as about 0.25 mg/m$^2$ to about 25 mg/m$^2$ or about 25 mg/m$^2$ to about 50 mg/m$^2$.

The dosing frequency of the other agent (e.g., a platinum-based agent such as carboplatin) can be the same or different from that of the nanoparticle composition. Exemplary frequencies are provided above. As further example, the other agent can be administered three times a day, two times a day, daily, 6 times a week, 5 times a week, 4 times a week, 3 times a week, two times a week, weekly, weekly for two weeks of three weeks, or weekly for three weeks of four weeks. In some embodiments, the other agent is administered twice daily or three times daily.

In some embodiments, the dosage of a taxane (e.g., paclitaxel) in a nanoparticle composition can be in the range of 5-400 mg/m$^2$ when given on a 3 week schedule, or 5-250 mg/m$^2$ when given on a weekly schedule. For example, the amount of a taxane (e.g., paclitaxel) can be about 60 to about 300 mg/m$^2$ (e.g., about 260 mg/m$^2$) when given on a three week schedule.

Other exemplary dosing schedules for the administration of the nanoparticle composition (e.g., paclitaxel/albumin nanoparticle composition) include, but are not limited to, 100 mg/m$^2$, weekly, without break; 75 mg/m$^2$ weekly, 3 out of four weeks; 100 mg/m$^2$, weekly, 3 out of 4 weeks; 125 mg/m$^2$, weekly, 3 out of 4 weeks; 125 mg/m$^2$, weekly, 2 out of 3 weeks; 130 mg/m$^2$, weekly, without break; 175 mg/m$^2$, once every 2 weeks; 260 mg/m$^2$, once every 2 weeks; 260 mg/m$^2$, once every 3 weeks; 180-300 mg/m$^2$, every three weeks; 60-175 mg/m$^2$, weekly, without break; 20-150 mg/m$^2$, twice a week; and 150-250 mg/m$^2$ twice a week. The dosing frequency of the composition may be adjusted over the course of the treatment based on the judgment of the administering physician.

In some embodiments, the individual is treated for at least about any of one, two, three, four, five, six, seven, eight, nine, or ten treatment cycles. The compositions described herein allow infusion of the composition to an individual over an infusion time that is shorter than about 24 hours. For example, in some embodiments, the composition is administered over an infusion period of less than about any of 24 hours, 12 hours, 8 hours, 5 hours, 3 hours, 2 hours, 1 hour, 30 minutes, 20 minutes, or 10 minutes. In some embodiments, the composition is administered over an infusion period of about 30 minutes.

Other exemplary dose of the taxane (in some embodiments paclitaxel) in the nanoparticle composition include, but is not limited to, about any of 50 mg/m$^2$, 60 mg/m$^2$, 75 mg/m$^2$, 80 mg/m$^2$, 90 mg/m$^2$, 100 mg/m$^2$, 120 mg/m$^2$, 160 mg/m$^2$, 175 mg/m$^2$, 200 mg/m$^2$, 210 mg/m$^2$, 220 mg/m$^2$, 260 mg/m$^2$, and 300 mg/m$^2$. For example, the dosage of paclitaxel in a nanoparticle composition can be in the range of about 100-400 mg/m$^2$ when given on a 3 week schedule, or about 50-250 mg/m$^2$ when given on a weekly schedule.

The dosage of the other agent (e.g., a platinum-based agent such as carboplatin) may be determined using methods known in the field. For example, the dosage of the other agent may be determined by calculating the area under the blood plasma concentration curve (AUC) by methods known in the field, taking into account the individual's creatinine clearance rate. The dosage of the other agent may be adjusted (e.g., reduced) based on the individual's symptoms (such as adverse reactions). In some embodiments, the dosage of the other agent for combination treatment along with the taxane nanoparticles is calculated to provide an AUC of about 0.1-10 mg/ml min, about 1-8 mg/ml min, about 1.5 to about 7.5 mg/ml min, about 2 to about 6 mg/ml min or about any of 1, 2, 3, 4, 5, 6, or 7 mg/ml min. The other agent such as carboplatin may be administered systematically. The other agent may be administered intravenously. The other agent may be administered over a period of about 10 to about 300 minutes, about 30 to about 180 minutes, about 45 to about 120 minutes or about 60 minutes.

Other exemplary amounts of the other agent (e.g., a platinum-based agent such as carboplatin) include, but are not limited to, any of the following ranges: about 0.5 to about 5 mg, about 5 to about 10 mg, about 10 to about 15 mg, about 15 to about 20 mg, about 20 to about 25 mg, about 20 to about 50 mg, about 25 to about 50 mg, about 50 to about 75 mg, about 50 to about 100 mg, about 75 to about 100 mg, about 100 to about 125 mg, about 125 to about 150 mg, about 150 to about 175 mg, about 175 to about 200 mg, about 200 to about 225 mg, about 225 to about 250 mg, about 250 to about 300 mg, about 300 to about 350 mg, about 350 to about 400 mg, about 400 to about 450 mg, or about 450 to about 500 mg. For example, the other agent can be administered at a dose of about 1 mg/kg to about 200 mg/kg (including for example about 1 mg/kg to about 20 mg/kg, about 20 mg/kg to about 40 mg/kg, about 40 mg/kg to about 60 mg/kg, about 60 mg/kg to about 80 mg/kg, about 80 mg/kg to about 100 mg/kg, about 100 mg/kg to about 120 mg/kg, about 120 mg/kg to about 140 mg/kg, about 140 mg/kg to about 200 mg/kg).

The dosage of the other agent (e.g., carboplatin) may be determined by calculating the area under the blood plasma concentration curve (AUC) by methods known in the field, taking into account the individual's creatinine clearance rate. The dosage of the other agent may be adjusted (e.g., reduced) based on the individual's symptoms (such as adverse reactions). In some embodiments, the dosage of the other agent such as carboplatin for combination treatment along with the taxane nanoparticles is calculated to provide an AUC of about 0.1-10 mg/ml min, about 1-8 mg/ml min, about 1.5 to about 7.5 mg/ml min, about 2 to about 6 mg/ml min or about any of 1, 2, 3, 4, 5, 6, or 7 mg/ml min. The other agent such as carboplatin may be administered systematically. The other agent such as carboplatin may be administered intravenously. The other agent such as carboplatin may be administered via portacath. The other agent such as carboplatin may be administered over a period of about 10 to about 300 minutes, about 30 to about 180 minutes, about 45 to about 120 minutes or about 60 minutes.

The dosing frequency of the other agent can be the same or different from that of the nanoparticle composition. Exemplary frequencies are provided above. As further example, the other agent can be administered three times a day, two times a day, daily, 6 times a week, 5 times a week, 4 times a week, 3 times a week, two times a week, weekly. In some embodiments, the other agent is administered twice daily or three times daily.

In some embodiments, the effective amount of taxane in the nanoparticle composition is between about 45 mg/m$^2$ to about 350 mg/m$^2$ and the effective amount of the other agent is about 1 mg/kg to about 200 mg/kg (including for example about 1 mg/kg to about 20 mg/kg, about 20 mg/kg to about 40 mg/kg, about 40 mg/kg to about 60 mg/kg, about 60 mg/kg to about 80 mg/kg, about 80 mg/kg to about 100 mg/kg, about 100 mg/kg to about 120 mg/kg, about 120 mg/kg to about 140 mg/kg, about 140 mg/kg to about 200 mg/kg). In some embodiments, the effective amount of taxane in the nanoparticle composition is between about 80 mg/m$^2$ to about 350 mg/m$^2$ and the effective amount of the other agent is about 1 mg/kg to about 200 mg/kg (including for example about 1 mg/kg to about 20 mg/kg, about 20 mg/kg to about 40 mg/kg, about 40 mg/kg to about 60 mg/kg, about 60 mg/kg to about 80 mg/kg, about 80 mg/kg to about 100 mg/kg, about 100 mg/kg to about 120 mg/kg, about 120 mg/kg to about 140 mg/kg, about 140 mg/kg to about 200 mg/kg). In some embodiments, the effective amount of taxane in the nanoparticle composition is between about 80 mg/m$^2$ to about 300 mg/m$^2$ and the effective amount of the other agent is about 1 mg/kg to about 200 mg/kg (including for example about 1 mg/kg to about 20 mg/kg, about 20 mg/kg to about 40 mg/kg, about 40 mg/kg to about 60 mg/kg, about 60 mg/kg to about 80 mg/kg, about 80 mg/kg to about 100 mg/kg, about 100 mg/kg to about 120 mg/kg, about 120 mg/kg to about 140 mg/kg, about 140 mg/kg to about 200 mg/kg). In some embodiments, the effective amount of taxane in the nanoparticle composition is between about 150 m g/m$^2$ to about 350 mg/m$^2$ and the effective amount of the other agent is about 1 mg/kg to about 200 mg/kg (including for example about 1 mg/kg to about 20 mg/kg, about 20 mg/kg to about 40 mg/kg, about 40 mg/kg to about 60 mg/kg, about 60 mg/kg to about 80 mg/kg, about 80 mg/kg to about 100 mg/kg, about 100 mg/kg to about 120 mg/kg, about 120 mg/kg to about 140 mg/kg, about 140 mg/kg to about 200 mg/kg). In some embodiments, the effective amount of taxane in the nanoparticle composition is between about 80 mg/m$^2$ to about 150 mg/m$^2$ and the effective amount of the other agent is about 1 mg/kg to about 200 mg/kg (including for example about 1 mg/kg to about 20 mg/kg, about 20 mg/kg to about 40 mg/kg, about 40 mg/kg to about 60 mg/kg, about 60 mg/kg to about 80 mg/kg, about 80 mg/kg to about 100 mg/kg, about 100 mg/kg to about 120 mg/kg, about 120 mg/kg to about 140 mg/kg, about 140 mg/kg to about 200 mg/kg). In some embodiments, the effective amount of taxane (e.g., paclitaxel) in the nanoparticle composition is about 100 mg/m$^2$. In some embodiments, the effective amount of taxane in the nanoparticle composition is between about 170 mg/m$^2$ to about 200 mg/m$^2$ and the effective amount of the other agent is about 1 mg/kg to about 200 mg/kg (including for example about 1 mg/kg to about 20 mg/kg, about 20 mg/kg to about 40 mg/kg, about 40 mg/kg to about 60 mg/kg, about 60 mg/kg to about 80 mg/kg, about 80 mg/kg to about 100 mg/kg, about 100 mg/kg to about 120 mg/kg, about 120 mg/kg to about 140 mg/kg, about 140 mg/kg to about 200 mg/kg). In some embodiments, the effective amount of taxane in the nanoparticle composition is between about 200 mg/m$^2$ to about 350 mg/m$^2$ and the effective amount of the other agent is about 1 mg/kg to about 200 mg/kg (including for example about 1 mg/kg to about 20 mg/kg, about 20 mg/kg to about 40 mg/kg, about 40 mg/kg to about 60 mg/kg, about 60 mg/kg to about 80 mg/kg, about 80 mg/kg to about 100 mg/kg, about 100 mg/kg to about 120 mg/kg, about 120 mg/kg to about 140 mg/kg, about 140 mg/kg to about 200 mg/kg). In some embodiments, the effective amount of taxane (e.g., paclitaxel) in the nanoparticle composition is about 260 mg/m$^2$. In some embodiments of any of the above methods, the effective amount of the other agent is about 20-30 mg/kg, about 30-40 mg/kg, about 40-50 mg/kg, about 50-60 mg/kg, about 60-70 mg/kg, about 70-80 mg/kg, about 80-100 mg/kg, or about 100-120 mg/kg.

In some embodiments, the effective amount of taxane in the nanoparticle composition is between about 45 mg/m$^2$ to about 350 mg/m$^2$ and the effective amount of the other agent is about 80 mg to about 1000 mg (including for example about 80 to about 100 mg, about 100 to about 200 mg, about 200 to about 300 mg, about 300 to about 400 mg, about 400 to about 500 mg, about 500 to about 600 mg, about 600 to about 700 mg, about 700 to about 800 mg, about 800 to about 900 mg, about 900 mg to about 1000 mg). In some embodiments, the effective amount of taxane in the nanoparticle composition is between about 80 mg/m$^2$ to about 350 mg/m$^2$ and the effective amount of the other agent is about 80 mg to about 1000 mg (including for example about 80 to about 100 mg, about 100 to about 200 mg, about 200 to about 300 mg, about 300 to about 400 mg, about 400 to about 500 mg, about 500 to about 600 mg, about 600 to about 700 mg, about 700 to about 800 mg, about 800 to about 900 mg, about 900 mg to about 1000 mg). In some embodiments, the effective amount of taxane in the nanoparticle composition is between about 80 mg/m$^2$ to about 300 mg/m$^2$ and the effective amount of the other agent is about 80 mg to about 1000 mg (including for example about 80 to about 100 mg, about 100 to about 200 mg, about 200 to about 300 mg, about 300 to about 400 mg, about 400 to about 500 mg, about 500 to about 600 mg, about 600 to about 700 mg, about 700 to about 800 mg, about 800 to about 900 mg, about 900 mg to about 1000 mg). In some embodiments, the effective amount of taxane in the nanoparticle composition is between about 150 mg/m² to about 350 mg/m² and the effective amount of the other agent is about 80 mg to about 1000 mg (including for example about 80 to about 100 mg, about 100 to about 200 mg, about 200 to about 300 mg, about 300 to about 400 mg, about 400 to about 500 mg, about 500 to about 600 mg, about 600 to about 700 mg, about 700 to about 800 mg, about 800 to about 900 mg, about 900 mg to about 1000 mg). In some embodiments, the effective amount of taxane in the nanoparticle composition is between about 80 mg/m² to about 150 mg/m² and the effective amount of the other agent is about 80 mg to about 1000 mg (including for example about 80 to about 100 mg, about 100 to about 200 mg, about 200 to about 300 mg, about 300 to about 400 mg, about 400 to about 500 mg, about 500 to about 600 mg, about 600 to about 700 mg, about 700 to about 800 mg, about 800 to about 900 mg, about 900 mg to about 1000 mg). In some embodiments, the effective amount of taxane in the nanoparticle composition is between about 170 mg/m² to about 200 mg/m² and the effective amount of the other agent is about 80 mg to about 1000 mg (including for example about 80 to about 100 mg, about 100 to about 200 mg, about 200 to about 300 mg, about 300 to about 400 mg, about 400 to about 500 mg, about 500 to about 600 mg, about 600 to about 700 mg, about 700 to about 800 mg, about 800 to about 900 mg, about 900 mg to about 1000 mg). In some embodiments, the effective amount of taxane in the nanoparticle composition is between about 200 mg/m² to about 350 mg/m² and the effective amount of the other agent is about 80 mg to about 1000 mg (including for example about 80 to about 100 mg, about 100 to about 200 mg, about 200 to about 300 mg, about 300 to about 400 mg, about 400 to about 500 mg, about 500 to about 600 mg, about 600 to about 700 mg, about 700 to about 800 mg, about 800 to about 900 mg, about 900 mg to about 1000 mg). In some embodiments, the effective amount of taxane (e.g., paclitaxel) in the nanoparticle composition is about 100 mg/m². In some embodiments of any of the above methods, the effective amount of the other agent is about 100-200 mg, about 200-300 mg, about 300-400 mg, about 400-500 mg.

In some embodiments, the effective amount of taxane in the nanoparticle composition is between about 50 mg/m² to about 400 mg/m² (including for example about 100 mg/m² to about 300 mg/m², about 75 mg/m² to about 150 mg/m², or about 100 mg/m² to about 150 mg/m²) and the effective amount of the other agent (e.g., carboplatin) is about AUC1 to about AUC7 (including for example about AUC2 to about AUC6, or about any of AUC1, AUC2, AUC3, AUC4, AUC5, or AUC6). In some embodiments, the effective amount of taxane in the nanoparticle composition is between about 100 mg/m² to about 300 mg/m² (e.g., about 100 mg/m² to about 150 mg/m²) and the effective amount of the other agent is about AUC2 to about AUC6 (e.g., about any of AUC2, AUC3, AUC4, AUC5, or AUC6). In some embodiments, the effective amount of taxane in the nanoparticle composition is between about 100 mg/m² to about 150 mg/m² and the effective amount of the other agent is about AUC4 to about AUC6 (e.g., about any of AUC4, AUC5, or AUC6).

In some embodiments, there is provided a method of treating melanoma in an individual (e.g., human) comprising administering to the individual (a) an effective amount of a composition comprising nanoparticles comprising a taxane (e.g., paclitaxel) and a carrier protein (e.g., albumin such as human serum albumin or human albumin) and (b) an effective amount of at least one other agent (e.g., carboplatin), wherein the dose of taxane in the nanoparticle composition is between about 50 mg/m² to about 400 mg/m² (including for example about 100 mg/m² to about 300 mg/m², about 100 mg/m² to about 200 mg/m², or about 100 mg/m² to about 150 mg/m², or about 100 mg/m², or about 150 mg/m²) and the effective amount of the other agent (e.g., carboplatin) is about AUC1 to about AUC7 (including for example about AUC2 to about AUC6, or about any of AUC1, AUC2, AUC3, AUC4, AUC5, or AUC6). In some embodiments, the nanoparticle composition is administered weekly for three weeks of four weeks or weekly. In some embodiments, the other agent is administered weekly for three weeks of four weeks or weekly. In some embodiments, the carrier protein is albumin such as human serum albumin or human albumin. In some embodiments, the taxane is paclitaxel. In some embodiments, the one other agent is a platinum-based agent. In some embodiments, the one other agent is carboplatin.

The nanoparticle composition (and the other agent) described herein can be administered to an individual (such as human) via various routes, including, for example, intravenous, intra-arterial, intraperitoneal, intrapulmonary, oral, inhalation, intravesicular, intramuscular, intra-tracheal, subcutaneous, intraocular, intrathecal, transmucosal, and transdermal. In some embodiments, sustained continuous release formulation of the composition may be used. In one variation of the invention, nanoparticles (such as albumin nanoparticles) can be administered by any acceptable route including, but not limited to, orally, intramuscularly, transdermally, intravenously, through an inhaler or other air borne delivery systems and the like. Any of the routes that may be used to administer a nanoparticle composition described herein may be used to administer the other agent. The other agent described herein can be administered to an individual (such as human) via various routes, such as parenterally, including intravenous, intraventricular, intra-arterial, intraperitoneal, intrapulmonary, oral, inhalation, intravesicular, intramuscular, intra-tracheal, subcutaneous, intraocular, intrathecal, or transdermal. In some embodiments, the other agent is administrated systemically. In some embodiments, the other agent is administrated intravenously. In some embodiments, the other agent is administered by infusion. In some embodiments, the other agent is administered by a port or portacath. In some embodiments, the nanoparticle composition is administered orally.

As will be understood by those of ordinary skill in the art, the appropriate doses of other agents will be approximately those already employed in clinical therapies wherein the other agent are administered alone or in combination with other agents. Variation in dosage will likely occur depending on the condition being treated. As described above, in some embodiments, the other agents may be administered at a reduced level.

A combination of the administration configurations described herein can be used. The combination therapy methods described herein may be performed alone or in conjunction with an additional therapy, such as chemotherapy, radiation therapy (e.g., whole brain radiation therapy), surgery, hormone therapy, gene therapy, immunotherapy, chemoimmunotherapy, cryotherapy, ultrasound therapy, liver transplantation, local ablative therapy, radiofrequency ablation therapy, photodynamic therapy, and the like. Additionally, a person having a greater risk of developing the proliferative disease may receive treatments to inhibit and/or delay the development of the disease.

Nanoparticle Compositions

The nanoparticle compositions described herein comprise nanoparticles comprising (in various embodiments consisting essentially of) a taxane (such as paclitaxel) and a carrier protein (e.g., an albumin such as human serum albumin or human albumin) Nanoparticles of poorly water soluble drugs (such as taxane) have been disclosed in, for example, U.S.

Pat. Nos. 5,916,596; 6,506,405; 6,749,868, 6,537,579, 7,820,788, and also in U.S. Pat. Pub. Nos. 2006/0263434, and 2007/0082838; PCT Patent Application WO08/137148, each of which is incorporated by reference in their entirety.

In some embodiments, the composition comprises nanoparticles with an average or mean diameter of no greater than about 1000 nanometers (nm), such as no greater than about (or less than about) any of 900, 800, 700, 600, 500, 400, 300, 200, and 100 nm. In some embodiments, the average or mean diameters of the nanoparticles is no greater than about 200 nm (such as less than about 200 nm). In some embodiments, the average or mean diameters of the nanoparticles is no greater than about 150 nm. In some embodiments, the average or mean diameters of the nanoparticles is no greater than about 100 nm. In some embodiments, the average or mean diameter of the nanoparticles is about 20 to about 400 nm. In some embodiments, the average or mean diameter of the nanoparticles is about 40 to about 200 nm. In some embodiments, the nanoparticles are sterile-filterable.

In some embodiments, the nanoparticles in the composition described herein have an average diameter of no greater than about 200 nm, including for example no greater than about any one of 190, 180, 170, 160, 150, 140, 130, 120, 110, 100, 90, 80, 70, or 60 nm. In some embodiments, at least about 50% (for example at least about any one of 60%, 70%, 80%, 90%, 95%, or 99%) of the nanoparticles in the composition have a diameter of no greater than about 200 nm, including for example no greater than about any one of 190, 180, 170, 160, 150, 140, 130, 120, 110, 100, 90, 80, 70, or 60 nm. In some embodiments, at least about 50% (for example at least any one of 60%, 70%, 80%, 90%, 95%, or 99%) of the nanoparticles in the composition fall within the range of about 20 to about 400 nm, including for example about 20 to about 200 nm, about 40 to about 200 nm, about 30 to about 180 nm, and any one of about 40 to about 150, about 50 to about 120, and about 60 to about 100 nm.

In some embodiments, the carrier protein (e.g., albumin) has sulfhydral groups that can form disulfide bonds. In some embodiments, at least about 5% (including for example at least about any one of 10%, 15%, 20%, 25%, 30%, 40%, 50%, 60%, 70%, 80%, or 90%) of carrier protein (e.g., albumin) in the nanoparticle portion of the composition are crosslinked (for example crosslinked through one or more disulfide bonds).

In some embodiments, the nanoparticles comprise the taxane (such as paclitaxel) coated with a carrier protein (e.g., an albumin such as human albumin or human serum albumin). In some embodiments, the composition comprises a taxane in both nanoparticle and non-nanoparticle forms (e.g., in the form of paclitaxel solutions or in the form of soluble carrier protein/nanoparticle complexes), wherein at least about any one of 50%, 60%, 70%, 80%, 90%, 95%, or 99% of the taxane in the composition are in nanoparticle form. In some embodiments, the taxane in the nanoparticles constitutes more than about any one of 50%, 60%, 70%, 80%, 90%, 95%, or 99% of the nanoparticles by weight. In some embodiments, the nanoparticles have a non-polymeric matrix. In some embodiments, the nanoparticles comprise a core of a taxane that is substantially free of polymeric materials (such as polymeric matrix).

In some embodiments, the composition comprises a carrier protein (e.g., albumin) in both nanoparticle and non-nanoparticle portions of the composition, wherein at least about any one of 50%, 60%, 70%, 80%, 90%, 95%, or 99% of the carrier protein (e.g., albumin) in the composition are in non-nanoparticle portion of the composition.

In some embodiments, the weight ratio of albumin (such as human albumin or human serum albumin) and a taxane in the nanoparticle composition is about 18:1 or less, such as about 15:1 or less, for example about 10:1 or less. In some embodiments, the weight ratio of albumin (such as human albumin or human serum albumin) and taxane in the composition falls within the range of any one of about 1:1 to about 18:1, about 2:1 to about 15:1, about 3:1 to about 13:1, about 4:1 to about 12:1, about 5:1 to about 10:1. In some embodiments, the weight ratio of albumin and taxane in the nanoparticle portion of the composition is about any one of 1:2, 1:3, 1:4, 1:5, 1:9, 1:10, 1:15, or less. In some embodiments, the weight ratio of the albumin (such as human albumin or human serum albumin) and the taxane in the composition is any one of the following: about 1:1 to about 18:1, about 1:1 to about 15:1, about 1:1 to about 12:1, about 1:1 to about 10:1, about 1:1 to about 9:1, about 1:1 to about 8:1, about 1:1 to about 7:1, about 1:1 to about 6:1, about 1:1 to about 5:1, about 1:1 to about 4:1, about 1:1 to about 3:1, about 1:1 to about 2:1, about 1:1 to about 1:1.

In some embodiments, the nanoparticle composition comprises one or more of the above characteristics.

The nanoparticles described herein may be present in a dry formulation (such as lyophilized composition) or suspended in a biocompatible medium. Suitable biocompatible media include, but are not limited to, water, buffered aqueous media, saline, buffered saline, optionally buffered solutions of amino acids, optionally buffered solutions of proteins, optionally buffered solutions of sugars, optionally buffered solutions of vitamins, optionally buffered solutions of synthetic polymers, lipid-containing emulsions, and the like.

In some embodiments, the pharmaceutically acceptable carrier comprises a carrier protein (e.g., albumin such as human albumin or human serum albumin) Examples of suitable carrier proteins include proteins normally found in blood or plasma, which include, but are not limited to, albumin, immunoglobulin including IgA, lipoproteins, apolipoprotein B, α-acid glycoprotein, β-2-macroglobulin, thyroglobulin, transferrin, fibronectin, factor VII, factor VIII, factor IX, factor X, and the like. In some embodiments, the carrier protein is non-blood protein, such as casein, α-lactalbumin, β-lactoglobulin. The proteins may either be natural in origin or synthetically prepared. In some embodiments, the protein is albumin, such as human albumin or human serum albumin. In some embodiments, the albumin is a recombinant albumin.

Human serum albumin (HSA) is a highly soluble globular protein of Mr 65K and consists of 585 amino acids. HSA is the most abundant protein in the plasma and accounts for 70-80% of the colloid osmotic pressure of human plasma. The amino acid sequence of HSA contains a total of 17 disulphide bridges, one free thiol (Cys 34), and a single tryptophan (Trp 214). Intravenous use of HSA solution has been indicated for the prevention and treatment of hypovolumic shock (see, e.g., Tullis, JAMA, 237, 355-360, 460-463, (1977)) and Houser et al., Surgery, Gynecology and Obstetrics, 150, 811-816 (1980)) and in conjunction with exchange transfusion in the treatment of neonatal hyperbilirubinemia (see, e.g., Finlayson, Seminars in Thrombosis and Hemostasis, 6, 85-120, (1980)). Other albumins are contemplated, such as bovine serum albumin Use of such non-human albumins could be appropriate, for example, in the context of use of these compositions in non-human mammals, such as the veterinary (including domestic pets and agricultural context). Human serum albumin (HSA) has multiple hydrophobic binding sites (a total of eight for fatty acids, an endogenous ligand of HSA) and binds a diverse set of taxanes, especially neutral and negatively charged hydrophobic compounds (Goodman et al., The Pharmacological Basis of Therapeutics, 9th ed, McGraw-Hill New York (1996)). Two high affinity binding sites have been proposed in subdomains IIA and IIIA of HSA, which are highly elongated hydrophobic pockets with charged lysine and arginine residues near the surface which function as attachment points for polar ligand features (see, e.g., Fehske et al., Biochem. Pharmcol., 30, 687-92 (198a), Vorum, Dan. Med. Bull., 46, 379-99 (1999), Kragh-Hansen, Dan. Med. Bull., 1441, 131-40 (1990), Curry et al., Nat. Struct. Biol., 5, 827-35 (1998), Sugio et al., Protein. Eng., 12, 439-46 (1999), He et al., Nature, 358, 209-15 (199b), and Carter et al., Adv. Protein. Chem., 45, 153-203 (1994)). Paclitaxel and propofol have been shown to bind HSA (see, e.g., Paal et al., Eur. J. Biochem., 268(7), 2187-91 (200a), Purcell et al., Biochim Biophys. Acta, 1478(a), 61-8 (2000), Altmayer et al., Arzneimittelforschung, 45, 1053-6 (1995), and Garrido et al., Rev. Esp. Anestestiol. Reanim., 41, 308-12 (1994)). In addition, docetaxel has been shown to bind to human plasma proteins (see, e.g., Urien et al., Invest. New Drugs, 14(b), 147-51 (1996)).

The carrier protein (e.g., albumin such as human albumin or human serum albumin) in the composition generally serves as a carrier for the taxane, i.e., the albumin in the composition makes the taxane more readily suspendable in an aqueous medium or helps maintain the suspension as compared to compositions not comprising a carrier protein. This can avoid the use of toxic solvents (or surfactants) for solubilizing the taxane, and thereby can reduce one or more side effects of administration of the taxane into an individual (such as a human). Thus, in some embodiments, the composition described herein is substantially free (such as free) of surfactants, such as Cremophor (or polyoxyethylated castor oil) (including Cremophor EL® (BASF)). In some embodiments, the nanoparticle composition is substantially free (such as free) of surfactants. A composition is "substantially free of Cremophor" or "substantially free of surfactant" if the amount of Cremophor or surfactant in the composition is not sufficient to cause one or more side effect(s) in an individual when the nanoparticle composition is administered to the individual. In some embodiments, the nanoparticle composition contains less than about any one of 20%, 15%, 10%, 7.5%, 5%, 2.5%, or 1% organic solvent or surfactant. In some embodiments, the carrier protein is an albumin. In some embodiments, the albumin is human albumin or human serum albumin. In some embodiments, the albumin is recombinant albumin.

The amount of a carrier protein such as albumin in the composition described herein will vary depending on other components in the composition. In some embodiments, the composition comprises a carrier protein such as an albumin in an amount that is sufficient to stabilize the taxane in an aqueous suspension, for example, in the form of a stable colloidal suspension (such as a stable suspension of nanoparticles). In some embodiments, the carrier protein such as albumin is in an amount that reduces the sedimentation rate of the taxane in an aqueous medium. For particle-containing compositions, the amount of the carrier protein such as albumin also depends on the size and density of nanoparticles of the taxane.

A taxane is "stabilized" in an aqueous suspension if it remains suspended in an aqueous medium (such as without visible precipitation or sedimentation) for an extended period of time, such as for at least about any of 0.1, 0.2, 0.25, 0.5, 1, 2, 3, 4, 5, 6, 7, 8, 9, 10, 11, 12, 24, 36, 48, 60, or 72 hours. The suspension is generally, but not necessarily, suitable for administration to an individual (such as human). Stability of the suspension is generally (but not necessarily) evaluated at a storage temperature (such as room temperature (such as 20-25° C.) or refrigerated conditions (such as 4° C.)). For example, a suspension is stable at a storage temperature if it exhibits no flocculation or particle agglomeration visible to the naked eye or when viewed under the optical microscope at 1000 times, at about fifteen minutes after preparation of the suspension. Stability can also be evaluated under accelerated testing conditions, such as at a temperature that is higher than about 40° C.

In some embodiments, the carrier protein (e.g., albumin) is present in an amount that is sufficient to stabilize the taxane in an aqueous suspension at a certain concentration. For example, the concentration of the taxane in the composition is about 0.1 to about 100 mg/ml, including for example any of about 0.1 to about 50 mg/ml, about 0.1 to about 20 mg/ml, about 1 to about 10 mg/ml, about 2 mg/ml to about 8 mg/ml, about 4 to about 6 mg/ml, or about 5 mg/ml. In some embodiments, the concentration of the taxane is at least about any of 1.3 mg/ml, 1.5 mg/ml, 2 mg/ml, 3 mg/ml, 4 mg/ml, 5 mg/ml, 6 mg/ml, 7 mg/ml, 8 mg/ml, 9 mg/ml, 10 mg/ml, 15 mg/ml, 20 mg/ml, 25 mg/ml, 30 mg/ml, 40 mg/ml, and 50 mg/ml. In some embodiments, the carrier protein (e.g., albumin) is present in an amount that avoids use of surfactants (such as Cremophor), so that the composition is free or substantially free of surfactant (such as Cremophor).

In some embodiments, the composition, in liquid form, comprises from about 0.1% to about 50% (w/v) (e.g. about 0.5% (w/v), about 5% (w/v), about 10% (w/v), about 15% (w/v), about 20% (w/v), about 30% (w/v), about 40% (w/v), or about 50% (w/v)) of carrier protein (e.g., albumin). In some embodiments, the composition, in liquid form, comprises about 0.5% to about 5% (w/v) of carrier protein (e.g., albumin).

In some embodiments, the weight ratio of a carrier protein (e.g., albumin) to the taxane in the nanoparticle composition is such that a sufficient amount of taxane binds to, or is transported by, the cell. While the weight ratio of a carrier protein (e.g., albumin) to taxane will have to be optimized for different carrier protein (e.g., albumin) and taxane combinations, generally the weight ratio of carrier protein (e.g., albumin), to taxane (w/w) is about 0.01:1 to about 100:1, about 0.02:1 to about 50:1, about 0.05:1 to about 20:1, about 0.1:1 to about 20:1, about 1:1 to about 18:1, about 2:1 to about 15:1, about 3:1 to about 12:1, about 4:1 to about 10:1, about 5:1 to about 9:1, or about 9:1. In some embodiments, the carrier protein (e.g., albumin) to taxane weight ratio is about any of 18:1 or less, 15:1 or less, 14:1 or less, 13:1 or less, 12:1 or less, 11:1 or less, 10:1 or less, 9:1 or less, 8:1 or less, 7:1 or less, 6:1 or less, 5:1 or less, 4:1 or less, and 3:1 or less. In some embodiments, the carrier protein is albumin. In some embodiments, the weight ratio of the albumin (such as human albumin or human serum albumin) to the taxane in the composition is any one of the following: about 1:1 to about 18:1, about 1:1 to about 15:1, about 1:1 to about 12:1, about 1:1 to about 10:1, about 1:1 to about 9:1, about 1:1 to about 8:1, about 1:1 to about 7:1, about 1:1 to about 6:1, about 1:1 to about 5:1, about 1:1 to about 4:1, about 1:1 to about 3:1, about 1:1 to about 2:1, about 1:1 to about 1:1.

In some embodiments, the carrier protein (e.g., albumin) allows the composition to be administered to an individual (such as human) without significant side effects. In some embodiments, the carrier protein (e.g., albumin such as human serum albumin or human albumin) is in an amount that is effective to reduce one or more side effects of administration of the taxane to a human. The term "reducing one or more side effects of administration of the taxane" refers to reduction, alleviation, elimination, or avoidance of one or more undesirable effects caused by the taxane, as well as side effects caused by delivery vehicles (such as solvents that render the taxanes suitable for injection) used to deliver the taxane. Such side effects include, for example, myelosuppression, neurotoxicity, hypersensitivity, inflammation, venous irritation, phlebitis, pain, skin irritation, peripheral neuropathy, neutropenic fever, anaphylactic reaction, venous thrombosis, extravasation, and combinations thereof. These side effects, however, are merely exemplary and other side effects, or combination of side effects, associated with taxanes can be reduced.

In some embodiments, the nanoparticle compositions described herein comprises nanoparticles comprising a taxane (such as paclitaxel) and an albumin (such as human albumin or human serum albumin), wherein the nanoparticles have an average diameter of no greater than about 200 nm. In some embodiments, the nanoparticle compositions described herein comprises nanoparticles comprising a taxane (such as paclitaxel) and an albumin (such as human albumin or human serum albumin), wherein the nanoparticles have an average diameter of no greater than about 150 nm. In some embodiments, the nanoparticle compositions described herein comprises nanoparticles comprising a taxane (such as paclitaxel) and an albumin (such as human albumin or human serum albumin), wherein the nanoparticles have an average diameter of about 130 nm. In some embodiments, the nanoparticle compositions described herein comprises nanoparticles comprising paclitaxel and human albumin (such as human serum albumin), wherein the nanoparticles have an average diameter of about 130 nm.

In some embodiments, the nanoparticle compositions described herein comprises nanoparticles comprising a taxane (such as paclitaxel) and an albumin (such as human albumin or human serum albumin), wherein the nanoparticles have an average diameter of no greater than about 200 nm, wherein the weight ratio of the albumin and the taxane in the composition is no greater than about 9:1 (such as about 9:1). In some embodiments, the nanoparticle compositions described herein comprises nanoparticles comprising a taxane (such as paclitaxel) and an albumin (such as human albumin or human serum albumin), wherein the nanoparticles have an average diameter of no greater than about 150 nm, wherein the weight ratio of the albumin and the taxane in the composition is no greater than about 9:1 (such as about 9:1). In some embodiments, the nanoparticle compositions described herein comprises nanoparticles comprising a taxane (such as paclitaxel) and an albumin (such as human albumin or human serum albumin), wherein the nanoparticles have an average diameter of about 150 nm, wherein the weight ratio of the albumin and the taxane in the composition is no greater than about 9:1 (such as about 9:1). In some embodiments, the nanoparticle compositions described herein comprises nanoparticles comprising paclitaxel and human albumin (such as human serum albumin), wherein the nanoparticles have an average diameter of about 130 nm, wherein the weight ratio of albumin and the taxane in the composition is about 9:1.

In some embodiments, the nanoparticle compositions described herein comprises nanoparticles comprising a taxane (such as paclitaxel) coated with an albumin (such as human albumin or human serum albumin). In some embodiments, the nanoparticle compositions described herein comprises nanoparticles comprising a taxane (such as paclitaxel) coated with an albumin (such as human albumin or human serum albumin), wherein the nanoparticles have an average diameter of no greater than about 200 nm. In some embodiments, the nanoparticle compositions described herein comprises nanoparticles comprising a taxane (such as paclitaxel) coated with an albumin (such as human albumin or human serum albumin), wherein the nanoparticles have an average diameter of no greater than about 150 nm. In some embodiments, the nanoparticle compositions described herein comprises nanoparticles comprising a taxane (such as paclitaxel) coated with an albumin (such as human albumin or human serum albumin), wherein the nanoparticles have an average diameter of about 130 nm. In some embodiments, the nanoparticle compositions described herein comprises nanoparticles comprising paclitaxel coated with human albumin (such as human serum albumin), wherein the nanoparticles have an average diameter of about 130 nm.

In some embodiments, the nanoparticle compositions described herein comprises nanoparticles comprising a taxane (such as paclitaxel) coated with an albumin (such as human albumin or human serum albumin), wherein the weight ratio of the albumin and the taxane in the composition is no greater than about 9:1 (such as about 9:1). In some embodiments, the nanoparticle compositions described herein comprises nanoparticles comprising a taxane (such as paclitaxel) coated with an albumin (such as human albumin or human serum albumin), wherein the nanoparticles have an average diameter of no greater than about 200 nm, wherein the weight ratio of the albumin and the taxane in the composition is no greater than about 9:1 (such as about 9:1). In some embodiments, the nanoparticle compositions described herein comprises nanoparticles comprising a taxane (such as paclitaxel) coated with an albumin (such as human albumin or human serum albumin), wherein the nanoparticles have an average diameter of no greater than about 150 nm, wherein the weight ratio of the albumin and the taxane in the composition is no greater than about 9:1 (such as about 9:1). In some embodiments, the nanoparticle compositions described herein comprises nanoparticles comprising a taxane (such as paclitaxel) coated with an albumin (such as human albumin or human serum albumin), wherein the nanoparticles have an average diameter of about 150 nm, wherein the weight ratio of the albumin and the taxane in the composition is no greater than about 9:1 (such as about 9:1). In some embodiments, the nanoparticle compositions described herein comprises nanoparticles comprising paclitaxel coated with human albumin (such as human serum albumin), wherein the nanoparticles have an average diameter of about 130 nm, wherein the weight ratio of albumin and the taxane in the composition is about 9:1.

In some embodiments, the nanoparticle compositions described herein comprises nanoparticles comprising a taxane (such as paclitaxel) stabilized by an albumin (such as human albumin or human serum albumin). In some embodiments, the nanoparticle compositions described herein comprises nanoparticles comprising a taxane (such as paclitaxel) stabilized by an albumin (such as human albumin or human serum albumin), wherein the nanoparticles have an average diameter of no greater than about 200 nm. In some embodiments, the nanoparticle compositions described herein comprises nanoparticles comprising a taxane (such as paclitaxel) stabilized by an albumin (such as human albumin or human serum albumin), wherein the nanoparticles have an average diameter of no greater than about 150 nm. In some embodiments, the nanoparticle compositions described herein comprises nanoparticles comprising a taxane (such as paclitaxel) stabilized by an albumin (such as human albumin or human serum albumin), wherein the nanoparticles have an average diameter of about 130 nm. In some embodiments, the nanoparticle compositions described herein comprises nanoparticles comprising paclitaxel stabilized by human albumin (such as human serum albumin), wherein the nanoparticles have an average diameter of about 130 nm.

In some embodiments, the nanoparticle compositions described herein comprises nanoparticles comprising a taxane (such as paclitaxel) stabilized by an albumin (such as human albumin or human serum albumin), wherein the weight ratio of the albumin and the taxane in the composition is no greater than about 9:1 (such as about 9:1). In some embodiments, the nanoparticle compositions described herein comprises nanoparticles comprising a taxane (such as paclitaxel) stabilized by an albumin (such as human albumin or human serum albumin), wherein the nanoparticles have an average diameter of no greater than about 200 nm, wherein the weight ratio of the albumin and the taxane in the composition is no greater than about 9:1 (such as about 9:1). In some embodiments, the nanoparticle compositions described herein comprises nanoparticles comprising a taxane (such as paclitaxel) stabilized by an albumin (such as human albumin or human serum albumin), wherein the nanoparticles have an average diameter of no greater than about 150 nm, wherein the weight ratio of the albumin and the taxane in the composition is no greater than about 9:1 (such as about 9:1). In some embodiments, the nanoparticle compositions described herein comprises nanoparticles comprising a taxane (such as paclitaxel) stabilized by an albumin (such as human albumin or human serum albumin), wherein the nanoparticles have an average diameter of about 150 nm, wherein the weight ratio of the albumin and the taxane in the composition is no greater than about 9:1 (such as about 9:1). In some embodiments, the nanoparticle compositions described herein comprises nanoparticles comprising paclitaxel stabilized by human albumin (such as human serum albumin), wherein the nanoparticles have an average diameter of about 130 nm, wherein the weight ratio of albumin and the taxane in the composition is about 9:1.

In some embodiments, the nanoparticle composition comprises Nab-paclitaxel (or Abraxane®). In some embodiments, the nanoparticle composition is Nab-paclitaxel (or Abraxane®). Abraxane® is a formulation of paclitaxel stabilized by human albumin USP, which can be dispersed in directly injectable physiological solution. The weight ratio of human albumin and paclitaxel is about 9:1. When dispersed in a suitable aqueous medium such as 0.9% sodium chloride injection or 5% dextrose injection, Nab-paclitaxel (or Abraxane®) forms a stable colloidal suspension of paclitaxel. The mean particle size of the nanoparticles in the colloidal suspension is about 130 nanometers. Since HSA is freely soluble in water, Nab-paclitaxel (or Abraxane®) can be reconstituted in a wide range of concentrations ranging from dilute (0.1 mg/ml paclitaxel) to concentrated (20 mg/ml paclitaxel), including for example about 2 mg/ml to about 8 mg/ml, or about 5 mg/ml.

Methods of making nanoparticle compositions are known in the art. For example, nanoparticles containing taxanes (such as paclitaxel) and carrier protein (e.g., albumin such as human serum albumin or human albumin) can be prepared under conditions of high shear forces (e.g., sonication, high pressure homogenization, or the like). These methods are disclosed in, for example, U.S. Pat. Nos. 5,916,596; 6,506,405; 6,749,868, 6,537,579 and 7,820,788 and also in U.S. Pat. Pub. Nos. 2007/0082838, 2006/0263434 and PCT Application WO08/137148.

Briefly, the taxane (such as paclitaxel) is dissolved in an organic solvent, and the solution can be added to a carrier protein solution such as an albumin solution. The mixture is subjected to high pressure homogenization. The organic solvent can then be removed by evaporation. The dispersion obtained can be further lyophilized. Suitable organic solvent include, for example, ketones, esters, ethers, chlorinated solvents, and other solvents known in the art. For example, the organic solvent can be methylene chloride or chloroform/ethanol (for example with a ratio of 1:9, 1:8, 1:7, 1:6, 1:5, 1:4, 1:3, 1:2, 1:1, 2:1, 3:1, 4:1, 5:1, 6:1, 7:1, 8:1, or 9:1).

Other Components in the Nanoparticle Compositions

The nanoparticles described herein can be present in a composition that includes other agents, excipients, or stabilizers. For example, to increase stability by increasing the negative zeta potential of nanoparticles, one or more of negatively charged components may be added. Such negatively charged components include, but are not limited to bile salts of bile acids consisting of glycocholic acid, cholic acid, chenodeoxycholic acid, taurocholic acid, glycochenodeoxycholic acid, taurochenodeoxycholic acid, litocholic acid, ursodeoxycholic acid, dehydrocholic acid and others; phospholipids including lecithin (egg yolk) based phospholipids which include the following phosphatidylcholines: palmitoyloleoylphosphatidylcholine, palmitoyllinoleoylphosphatidylcholine, stearoyllinoleoylphosphatidylcholine stearoyloleoylphosphatidylcholine, stearoylarachidoylphosphatidylcholine, and dipalmitoylphosphatidylcholine. Other phospholipids including L-α-dimyristoylphosphatidylcholine (DMPC), dioleoylphosphatidylcholine (DOPC), distearyolphosphatidylcholine (DSPC), hydrogenated soy phosphatidylcholine (HSPC), and other related compounds. Negatively charged surfactants or emulsifiers are also suitable as additives, e.g., sodium cholesteryl sulfate and the like.

In some embodiments, the composition is suitable for administration to a human. In some embodiments, the composition is suitable for administration to a mammal such as, in the veterinary context, domestic pets and agricultural animals. There are a wide variety of suitable formulations of the nanoparticle composition (see, e.g., U.S. Pat. Nos. 5,916,596, 6,096,331, and 7,820,788). The following formulations and methods are merely exemplary and are in no way limiting. Formulations suitable for oral administration can consist of (a) liquid solutions, such as an effective amount of the compound dissolved in diluents, such as water, saline, or orange juice, (b) capsules, sachets or tablets, each containing a predetermined amount of the active ingredient, as solids or granules, (c) suspensions in an appropriate liquid, and (d) suitable emulsions. Tablet forms can include one or more of lactose, mannitol, corn starch, potato starch, microcrystalline cellulose, acacia, gelatin, colloidal silicon dioxide, croscarmellose sodium, talc, magnesium stearate, stearic acid, and other excipients, colorants, diluents, buffering agents, moistening agents, preservatives, flavoring agents, and pharmacologically compatible excipients. Lozenge forms can comprise the active ingredient in a flavor, usually sucrose and acacia or tragacanth, as well as pastilles comprising the active ingredient in an inert base, such as gelatin and glycerin, or sucrose and acacia, emulsions, gels, and the like containing, in addition to the active ingredient, such excipients as are known in the art.

Examples of suitable carriers, excipients, and diluents include, but are not limited to, lactose, dextrose, sucrose, sorbitol, mannitol, starches, gum acacia, calcium phosphate, alginates, tragacanth, gelatin, calcium silicate, microcrystalline cellulose, polyvinylpyrrolidone, cellulose, water, saline solution, syrup, methylcellulose, methyl and propylhydroxybenzoates, talc, magnesium stearate, and mineral oil. The formulations can additionally include lubricating agents, wetting agents, emulsifying and suspending agents, preserving agents, sweetening agents or flavoring agents.

Formulations suitable for parenteral administration include aqueous and non-aqueous, isotonic sterile injection solutions, which can contain anti-oxidants, buffers, bacteriostats, and solutes that render the formulation compatible with the blood of the intended recipient, and aqueous and non-aqueous sterile suspensions that can include suspending agents, solubilizers, thickening agents, stabilizers, and preservatives. The formulations can be presented in unit-dose or multi-dose sealed containers, such as ampules and vials, and can be stored in a freeze-dried (lyophilized) condition requiring only the addition of the sterile liquid excipient, for example, water, for injections, immediately prior to use. Extemporaneous injection solutions and suspensions can be prepared from sterile powders, granules, and tablets of the kind previously described. Injectable formulations are preferred.

In some embodiments, the composition is formulated to have a pH range of about 4.5 to about 9.0, including for example pH ranges of any of about 5.0 to about 8.0, about 6.5 to about 7.5, and about 6.5 to about 7.0. In some embodiments, the pH of the composition is formulated to no less than about 6, including for example no less than about any of 6.5, 7, or 8 (such as about 8). The composition can also be made to be isotonic with blood by the addition of a suitable tonicity modifier, such as glycerol.

Articles of Manufacture, Kits, Compositions, and Medicines

The invention also provides kits, medicines, compositions, unit dosage forms, and articles of manufacture for use in any of the methods described herein.

Kits of the invention include one or more containers comprising taxane-containing nanoparticle compositions (or unit dosage forms and/or articles of manufacture) and/or another agent (such as at least one other agent described herein), and in some embodiments, further comprise instructions for use in accordance with any of the methods described herein. The kit may further comprise a description of selection of individual suitable for treatment. Instructions supplied in the kits of the invention are typically written instructions on a label or package insert (e.g., a paper sheet included in the kit), but machine-readable instructions (e.g., instructions carried on a magnetic or optical storage disk) are also acceptable.

For example, in some embodiments, the kit comprises a composition comprising nanoparticles comprising a taxane and a carrier protein (e.g., albumin such as human serum albumin or human albumin). In some embodiments, the kit further comprises instructions for administering the nanoparticle composition for treatment of melanoma in an individual. For another example, in some embodiments, the kit comprises a) a composition comprising nanoparticles comprising a taxane (e.g., paclitaxel) and a carrier protein (e.g., albumin such as human serum albumin or human albumin), b) an effective amount of at least one other agent described herein. In some embodiments, the kit further comprises instructions for administering the nanoparticle composition and at least one other agent for treatment of melanoma in an individual. The nanoparticles and the other agents can be present in separate containers or in a single container. For example, the kit may comprise one distinct composition or two or more compositions wherein one composition comprises nanoparticles and one composition comprises another agent. The instructions may be on a package insert or a package label. The treatment may be according to any one of the methods described herein.

The kits of the invention are in suitable packaging. Suitable packaging include, but is not limited to, vials, bottles, jars, flexible packaging (e.g., sealed Mylar or plastic bags), and the like. Kits may optionally provide additional components such as buffers and interpretative information. The present application thus also provides articles of manufacture, which include vials (such as sealed vials), unit dosages or unit dosage forms, bottles, jars, flexible packaging, and the like.

The instructions relating to the use of the nanoparticle compositions generally include information as to dosage, dosing schedule, and route of administration for the intended treatment. The containers may be unit doses, bulk packages (e.g., multi-dose packages) or sub-unit doses. For example, kits may be provided that contain sufficient dosages of the taxane (such as taxane) as disclosed herein to provide effective treatment of an individual for an extended period, such as any of a week, 8 days, 9 days, 10 days, 11 days, 12 days, 13 days, 2 weeks, 3 weeks, 4 weeks, 6 weeks, 8 weeks, 3 months, 4 months, 5 months, 7 months, 8 months, 9 months, or more. Kits may also include multiple unit doses of the taxane and pharmaceutical compositions and instructions for use and packaged in quantities sufficient for storage and use in pharmacies, for example, hospital pharmacies and compounding pharmacies.

Also provided are medicines, compositions, and unit dosage forms useful for the methods described herein. In some embodiments, there is provided a medicine (or composition or the unit dosage form) for use in treating melanoma in an individual, comprising effective amount of nanoparticles comprising a taxane (e.g., paclitaxel) and a carrier protein (e.g., an albumin such as human serum albumin or human albumin). In some embodiments, there is provided a medicine (or composition or a unit dosage form) for use in treating melanoma in an individual in conjunction with another agent, comprising nanoparticles comprising a taxane and a carrier protein (e.g., an albumin such as human serum albumin).

Additional Exemplary Embodiments

In some embodiments, there is a method of treating melanoma (such as metastatic melanoma or metastatic malignant melanoma) in a human individual comprising administering to the individual an effective amount of a composition comprising nanoparticles comprising paclitaxel and albumin (such as nanoparticles having average particle size of no greater than about 200 nm). In some embodiments, there is a method of treating cutaneous melanoma (such as metastatic cutaneous melanoma such as metastatic malignant cutaneous melanoma) in a human individual comprising administering to the individual an effective amount of a composition comprising nanoparticles comprising paclitaxel and albumin (such as nanoparticles having average particle size of no greater than about 200 nm). In some embodiments, there is a method of treating melanoma (such as metastatic melanoma or metastatic malignant melanoma) in a human individual comprising administering to the individual an effective amount of a composition comprising nanoparticles comprising paclitaxel coated with albumin (such as nanoparticles having average particle size of no greater than about 200 nm, for example Nab-paclitaxel). In some embodiments, there is a method of treating cutaneous melanoma (such as metastatic cutaneous melanoma such as metastatic malignant cutaneous melanoma) in a human individual comprising administering to the individual an effective amount of a composition comprising nanoparticles comprising paclitaxel coated with albumin (such as nanoparticles having average particle size of no greater than about 200 nm, for example Nab-paclitaxel). In some embodiments, there is a method of treating cutaneous melanoma (such as metastatic cutaneous melanoma such as metastatic malignant cutaneous melanoma) in a human individual comprising intravenously administering (for example infusing over about 30-40 minutes) to the individual an effective amount of Nab-paclitaxel (for example about 5 mg/ml Nab-paclitaxel), wherein the dose of paclitaxel in the nanoparticle composition is about 80 to about 200 mg/m$^2$ (including for example about 90 mg/m$^2$, about 120 mg/m$^2$, or about 150 mg/m$^2$). In some embodiments, there is a method of treating cutaneous melanoma (such as metastatic cutaneous melanoma such as metastatic malignant cutaneous melanoma) in a human individual comprising intravenously administering by infusing over about 30-40 minutes to the individual an effective amount of Nab-paclitaxel (for example about 5 mg/ml Nab-paclitaxel), wherein the dose of paclitaxel in the nanoparticle composition is about 150 mg/m$^2$ on days 1, 8, 15 of every 28 day cycle. In some embodiments, there is a method of treating cutaneous melanoma (such as metastatic cutaneous melanoma such as metastatic malignant cutaneous melanoma) in a human individual comprising intravenously administering by infusing over about 30-40 minutes to the individual an effective amount of Nab-paclitaxel (for example about 5 mg/ml Nab-paclitaxel), wherein the dose of paclitaxel in the nanoparticle composition is about 120 mg/m$^2$ on days 1, 8, 15 of every 28 day cycle. In some embodiments, there is a method of treating cutaneous melanoma (such as metastatic cutaneous melanoma such as metastatic malignant cutaneous melanoma) in a human individual comprising intravenously administering by infusing over about 30-40 minutes to the individual an effective amount of Nab-paclitaxel (for example about 5 mg/ml Nab-paclitaxel), wherein the dose of paclitaxel in the nanoparticle composition is about 90 mg/m$^2$ on days 1, 8, 15 of every 28 day cycle. In some embodiments, the individual is treated for at least about 2 months, including for example at least about any of 3, 4, 5, 6, 7, 8, 9, 10, 11, or 12 months. In some embodiments, the individual is chemotherapy naïve. In some embodiments, the melanoma is stage IV melanoma. In some embodiments, the individual has distant metastases. In some embodiments, the metastatic melanoma is at stage M1a. In some embodiments, the metastatic melanoma is at stage M1b. In some embodiments, the metastatic melanoma is at stage M1c. In some embodiments, the individual has measurable disease. In some embodiments, the individual has melanoma with brain metastases. In some embodiments, the individual does not have brain metastases. In some embodiments, the individual comprises a wild-type BRAF. In some embodiments, the individual comprises a mutant BRAF (such as BRAF with a V600E mutation). In some embodiments, the individual has elevated LDH level. In some embodiments, the individual is a female. In some embodiments, the individual is under about 65 years old. In some embodiments, the individual is at least about 65 years old (for example at least about any of 70, 75, or 80 years old).

In some embodiments, there is a method of treating melanoma (such as metastatic melanoma or metastatic malignant melanoma) in a human individual, wherein said individual has not previously been treated for melanoma or has not received prior cytotoxic chemotherapy such as prior adjuvant cytotoxic therapy, comprising administering to the individual an effective amount of a composition comprising nanoparticles comprising paclitaxel and albumin (such as nanoparticles having average particle size of no greater than about 200 nm). In some embodiments, there is a method of treating melanoma (such as metastatic melanoma or metastatic malignant melanoma) in a human individual, wherein said individual has not previously been treated for melanoma or has not received prior cytotoxic chemotherapy such as prior adjuvant cytotoxic therapy, comprising administering to the individual an effective amount of a composition comprising nanoparticles comprising paclitaxel coated with albumin (such as nanoparticles having average particle size of no greater than about 200 nm, for example Nab-paclitaxel). In some embodiments, there is a method of treating melanoma (such as metastatic melanoma or metastatic malignant melanoma) in a human individual, wherein said individual has not previously been treated for melanoma or has not received prior cytotoxic chemotherapy such as prior adjuvant cytotoxic therapy, comprising intravenously administering (for example infusing over about 30-40 minutes) to the individual an effective amount of Nab-paclitaxel (for example about 5 mg/ml Nab-paclitaxel), wherein the dose of paclitaxel in the nanoparticle composition is about 80 to about 200 mg/m$^2$ (including for example about 90 mg/m$^2$, about 120 mg/m$^2$, or about 150 mg/m$^2$). In some embodiments, there is a method of treating melanoma (such as metastatic melanoma or metastatic malignant melanoma) in a human individual, wherein said individual has not previously been treated for melanoma or has not received prior cytotoxic chemotherapy such as prior adjuvant cytotoxic therapy, comprising intravenously administering by intravenously administering (such as infusion over about 30-40 minutes) to the individual an effective amount of Nab-paclitaxel (for example about 5 mg/ml Nab-paclitaxel), wherein the dose of paclitaxel in the nanoparticle composition is about 80 to about 200 mg/m$^2$ (including for example about 90 mg/m$^2$, about 120 mg/m$^2$, or about 150 mg/m$^2$) on days 1, 8, 15 of every 28 day cycle. In some embodiments, there is a method of treating melanoma (such as metastatic melanoma or metastatic malignant melanoma) in a human individual, wherein said individual has not previously been treated for melanoma or has not received prior cytotoxic chemotherapy such as prior adjuvant cytotoxic therapy, comprising intravenously administering by infusing over about 30-40 minutes to the individual an effective amount of Nab-paclitaxel (for example about 5 mg/ml Nab-paclitaxel), wherein the dose of paclitaxel in the nanoparticle composition is about 150 mg/m$^2$ on days 1, 8, 15 of every 28 day cycle. In some embodiments, there is a method of treating melanoma (such as metastatic melanoma or metastatic malignant melanoma) in a human individual, wherein said individual has not previously been treated for melanoma or has not received prior cytotoxic chemotherapy such as prior adjuvant cytotoxic therapy, comprising intravenously administering by infusing over about 30-40 minutes to the individual an effective amount of Nab-paclitaxel (for example about 5 mg/ml Nab-paclitaxel), wherein the dose of paclitaxel in the nanoparticle composition is about 120 mg/m$^2$ on days 1, 8, 15 of every 28 day cycle. In some embodiments, there is a method of treating melanoma (such as metastatic melanoma or metastatic malignant melanoma) in a human individual, wherein said individual has not previously been treated for melanoma or has not received prior cytotoxic chemotherapy such as prior adjuvant cytotoxic therapy, comprising intravenously administering by infusing over about 30-40 minutes to the individual an effective amount of Nab-paclitaxel (for example about 5 mg/ml Nab-paclitaxel), wherein the dose of paclitaxel in the nanoparticle composition is about 90 mg/m$^2$ on days 1, 8, 15 of every 28 day cycle. In some embodiments, the individual is treated for at least about 2 months, including for example at least about any of 3, 4, 5, 6, 7, 8, 9, 10, 11, or 12 months. In some embodiments, the melanoma is stage IV melanoma. In some embodiments, the individual has distant metastases. In some embodiments, the metastatic melanoma is at stage M1a. In some embodiments, the metastatic melanoma is at stage M1b. In some embodiments, the metastatic melanoma is at stage M1c. In some embodiments, the individual has measurable disease. In some embodiments, the individual has melanoma with brain metastases. In some embodiments, the individual does not have brain metastases. In some embodiments, the individual comprises a wild-type BRAF. In some embodiments, the individual comprises a mutant BRAF (such as BRAF with a V600E mutation). In some embodiments, the individual has elevated LDH level. In some embodiments, the individual is a female. In some embodiments, the individual is under about 65 years old. In some embodiments, the individual is at least about 65 years old (for example at least about any of 70, 75, or 80 years old).

In some embodiments, there is a method of treating melanoma (such as metastatic melanoma or metastatic malignant melanoma) in a human individual, wherein said individual has previously been treated for melanoma or has received prior cytotoxic chemotherapy such as prior adjuvant cytotoxic therapy, comprising administering to the individual an effective amount of a composition comprising nanoparticles comprising paclitaxel and albumin (such as nanoparticles having average particle size of no greater than about 200 nm). In some embodiments, there is a method of treating melanoma (such as metastatic melanoma or metastatic malignant melanoma) in a human individual, wherein said individual has previously been treated for melanoma or has received prior cytotoxic chemotherapy such as prior adjuvant cytotoxic therapy, comprising administering to the individual an effective amount of a composition comprising nanoparticles comprising paclitaxel coated with albumin (such as nanoparticles having average particle size of no greater than about 200 nm, for example Nab-paclitaxel). In some embodiments, there is a method of treating melanoma (such as metastatic melanoma or metastatic malignant melanoma) in a human individual, wherein said individual has previously been treated for melanoma or has received prior cytotoxic chemotherapy such as prior adjuvant cytotoxic therapy, comprising intravenously administering (for example infusing over about 30-40 minutes) to the individual an effective amount of Nab-paclitaxel (for example about 5 mg/ml Nab-paclitaxel), wherein the dose of paclitaxel in the nanoparticle composition is about 80 to about 200 mg/m$^2$ (including for example about 90 mg/m$^2$, about 120 mg/m$^2$, or about 150 mg/m$^2$). In some embodiments, there is a method of treating melanoma (such as metastatic melanoma or metastatic malignant melanoma) in a human individual, wherein said individual has previously been treated for melanoma or has received prior cytotoxic chemotherapy such as prior adjuvant cytotoxic therapy, comprising intravenously administering (for example infusing over about 30-40 minutes) to the individual an effective amount of Nab-paclitaxel (for example about 5 mg/ml Nab-paclitaxel), wherein the dose of paclitaxel in the nanoparticle composition is about 80 to about 200 mg/m$^2$ (including for example about 90 mg/m$^2$, about 120 mg/m$^2$, or about 150 mg/m$^2$) on days 1, 8, 15 of every 28 day cycle. In some embodiments, there is a method of treating melanoma (such as metastatic melanoma or metastatic malignant melanoma) in a human individual, wherein said individual has previously been treated for melanoma or has received prior cytotoxic chemotherapy such as prior adjuvant cytotoxic therapy, comprising infusing over about 30-40 minutes to the individual an effective amount of Nab-paclitaxel (for example about 5 mg/ml Nab-paclitaxel), wherein the dose of paclitaxel in the nanoparticle composition is about 150 mg/m$^2$ on days 1, 8, 15 of every 28 day cycle. In some embodiments, the individual is treated for at least about 2 months, including for example at least about any of 3, 4, 5, 6, 7, 8, 9, 10, 11, or 12 months. In some embodiments, there is a method of treating melanoma (such as metastatic melanoma or metastatic malignant melanoma) in a human individual, wherein said individual has previously been treated for melanoma or has received prior cytotoxic chemotherapy such as prior adjuvant cytotoxic therapy, comprising infusing over about 30-40 minutes to the individual an effective amount of Nab-paclitaxel (for example about 5 mg/ml Nab-paclitaxel), wherein the dose of paclitaxel in the nanoparticle composition is about 120 mg/m$^2$ on days 1, 8, 15 of every 28 day cycle. In some embodiments, there is a method of treating melanoma (such as metastatic melanoma or metastatic malignant melanoma) in a human individual, wherein said individual has previously been treated for melanoma or has received prior cytotoxic chemotherapy such as prior adjuvant cytotoxic therapy, comprising infusing over about 30-40 minutes to the individual an effective amount of Nab-paclitaxel (for example about 5 mg/ml Nab-paclitaxel), wherein the dose of paclitaxel in the nanoparticle composition is about 90 mg/m$^2$ on days 1, 8, 15 of every 28 day cycle. In some embodiments, the individual is treated for at least about 2 months, including for example at least about any of 3, 4, 5, 6, 7, 8, 9, 10, 11, or 12 months. In some embodiments, the melanoma is stage IV melanoma. In some embodiments, the individual has distant metastases. In some embodiments, the metastatic melanoma is at stage M1a. In some embodiments, the metastatic melanoma is at stage M1b. In some embodiments, the metastatic melanoma is at stage M1c. In some embodiments, the individual has measurable disease. In some embodiments, the individual has melanoma with brain metastases. In some embodiments, the individual does not have brain metastases. In some embodiments, the individual comprises a wild-type BRAF. In some embodiments, the individual comprises a mutant BRAF (such as BRAF with a V600E mutation). In some embodiments, the individual has elevated LDH level. In some embodiments, the individual is a female. In some embodiments, the individual is under about 65 years old. In some embodiments, the individual is at least about 65 years old (for example at least about any of 70, 75, or 80 years old).

In some embodiments, there is a method of treating melanoma (such as metastatic melanoma or metastatic malignant melanoma) in a human individual, wherein said individual has an elevated LDH level, comprising administering to the individual an effective amount of a composition comprising nanoparticles comprising paclitaxel and albumin (such as nanoparticles having average particle size of no greater than about 200 nm). In some embodiments, there is a method of treating melanoma (such as metastatic melanoma or metastatic malignant melanoma) in a human individual, wherein said individual has an elevated LDH level, comprising administering to the individual an effective amount of a composition comprising nanoparticles comprising paclitaxel coated with albumin (such as nanoparticles having average particle size of no greater than about 200 nm, for example Nab-paclitaxel). In some embodiments, there is a method of treating melanoma (such as metastatic melanoma or metastatic malignant melanoma) in a human individual, wherein said individual has an elevated LDH level, comprising intravenously administering (for example infusing over about 30-40 minutes) to the individual an effective amount of Nab-paclitaxel (for example about 5 mg/ml Nab-paclitaxel), wherein the dose of paclitaxel in the nanoparticle composition is about 80 to about 200 mg/m$^2$ (including for example about 90 mg/m$^2$, about 120 mg/m$^2$, or about 150 mg/m$^2$). In some embodiments, there is a method of treating melanoma (such as metastatic melanoma or metastatic malignant melanoma) in a human individual, wherein said individual has an elevated LDH level, comprising intravenously administering (for example infusing over about 30-40 minutes) to the individual an effective amount of Nab-paclitaxel (for example about 5 mg/ml Nab-paclitaxel), wherein the dose of paclitaxel in the nanoparticle composition is about 80 to about 200 mg/m² (including for example about 90 mg/m², about 120 mg/m², or about 150 mg/m²) on days 1, 8, 15 of every 28 day cycle. In some embodiments, there is a method of treating melanoma (such as metastatic melanoma or metastatic malignant melanoma) in a human individual, wherein said individual has an elevated LDH level, comprising infusing over about 30-40 minutes to the individual an effective amount of Nab-paclitaxel (for example about 5 mg/ml Nab-paclitaxel), wherein the dose of paclitaxel in the nanoparticle composition is about 150 mg/m² on days 1, 8, 15 of every 28 day cycle. In some embodiments, there is a method of treating melanoma (such as metastatic melanoma or metastatic malignant melanoma) in a human individual, wherein said individual has an elevated LDH level, comprising infusing over about 30-40 minutes to the individual an effective amount of Nab-paclitaxel (for example about 5 mg/ml Nab-paclitaxel), wherein the dose of paclitaxel in the nanoparticle composition is about 120 mg/m² on days 1, 8, 15 of every 28 day cycle. In some embodiments, there is a method of treating melanoma (such as metastatic melanoma or metastatic malignant melanoma) in a human individual, wherein said individual has an elevated LDH level, comprising infusing over about 30-40 minutes to the individual an effective amount of Nab-paclitaxel (for example about 5 mg/ml Nab-paclitaxel), wherein the dose of paclitaxel in the nanoparticle composition is about 90 mg/m² on days 1, 8, 15 of every 28 day cycle. In some embodiments, the individual is treated for at least about 2 months, including for example at least about any of 3, 4, 5, 6, 7, 8, 9, 10, 11, or 12 months. In some embodiments, the individual has serum LDH at about 0.8× to about 1.1×ULN. In some embodiments, the individual has serum LDH of between greater than about 1.1× to about 2.0×ULN. In some embodiments, the individual comprises a wild-type BRAF. In some embodiments, the individual comprises a mutant BRAF (such as BRAF with a V600E mutation). In some embodiments, the individual has stage M1c metastatic melanoma. In some embodiments, the individual is a female. In some embodiments, the individual is under about 65 years old. In some embodiments, the individual is at least about 65 years old (for example at least about any of 70, 75, or 80 years old).

In some embodiments, there is a method of treating melanoma (such as metastatic melanoma or metastatic malignant melanoma) in a human individual, wherein said individual comprises wild-type BRAF, comprising administering to the individual an effective amount of a composition comprising nanoparticles comprising paclitaxel and albumin (such as nanoparticles having average particle size of no greater than about 200 nm). In some embodiments, there is a method of treating melanoma (such as metastatic melanoma or metastatic malignant melanoma) in a human individual, wherein said individual comprises wild-type BRAF, comprising administering to the individual an effective amount of a composition comprising nanoparticles comprising paclitaxel coated with albumin (such as nanoparticles having average particle size of no greater than about 200 nm, for example Nab-paclitaxel). In some embodiments, there is a method of treating melanoma (such as metastatic melanoma or metastatic malignant melanoma) in a human individual, wherein said individual comprises wild-type BRAF, comprising intravenously administering (for example infusing over about 30-40 minutes) to the individual an effective amount of Nab-paclitaxel (for example about 5 mg/ml Nab-paclitaxel), wherein the dose of paclitaxel in the nanoparticle composition is about 80 to about 200 mg/m² (including for example about 90 mg/m², about 120 mg/m², or about 150 mg/m²). In some embodiments, there is a method of treating melanoma (such as metastatic melanoma or metastatic malignant melanoma) in a human individual, wherein said individual comprises wild-type BRAF, comprising intravenously administering (for example infusing over about 30-40 minutes) to the individual an effective amount of Nab-paclitaxel (for example about 5 mg/ml Nab-paclitaxel), wherein the dose of paclitaxel in the nanoparticle composition is about 80 to about 200 mg/m² (including for example about 90 mg/m², about 120 mg/m², or about 150 mg/m²) on days 1, 8, 15 of every 28 day cycle. In some embodiments, there is a method of treating melanoma (such as metastatic melanoma or metastatic malignant melanoma) in a human individual, wherein said individual comprises wild-type BRAF, comprising infusing over about 30-40 minutes to the individual an effective amount of Nab-paclitaxel (for example about 5 mg/ml Nab-paclitaxel), wherein the dose of paclitaxel in the nanoparticle composition is about 150 mg/m² on days 1, 8, 15 of every 28 day cycle. In some embodiments, there is a method of treating melanoma (such as metastatic melanoma or metastatic malignant melanoma) in a human individual, wherein said individual comprises wild-type BRAF, comprising infusing over about 30-40 minutes to the individual an effective amount of Nab-paclitaxel (for example about 5 mg/ml Nab-paclitaxel), wherein the dose of paclitaxel in the nanoparticle composition is about 120 mg/m² on days 1, 8, 15 of every 28 day cycle. In some embodiments, there is a method of treating melanoma (such as metastatic melanoma or metastatic malignant melanoma) in a human individual, wherein said individual comprises wild-type BRAF, comprising infusing over about 30-40 minutes to the individual an effective amount of Nab-paclitaxel (for example about 5 mg/ml Nab-paclitaxel), wherein the dose of paclitaxel in the nanoparticle composition is about 90 mg/m² on days 1, 8, 15 of every 28 day cycle. In some embodiments, the individual is treated for at least about 2 months, including for example at least about any of 3, 4, 5, 6, 7, 8, 9, 10, 11, or 12 months. In some embodiments, the individual has stage M1c melanoma. In some embodiments, the individual has elevated LDH level. In some embodiments, the individual is a female. In some embodiments, the individual is under about 65 years old. In some embodiments, the individual is at least about 65 years old (for example at least about any of 70, 75, or 80 years old).

In some embodiments, there is a method of treating melanoma (such as metastatic melanoma or metastatic malignant melanoma) in a human individual, wherein said individual comprises a mutation in BRAF (such as a V600E mutation), comprising administering to the individual an effective amount of a composition comprising nanoparticles comprising paclitaxel and albumin (such as nanoparticles having average particle size of no greater than about 200 nm). In some embodiments, there is a method of treating melanoma (such as metastatic melanoma or metastatic malignant melanoma) in a human individual, wherein said individual comprises a mutation in BRAF (such as a V600E mutation), comprising administering to the individual an effective amount of a composition comprising nanoparticles comprising paclitaxel coated with albumin (such as nanoparticles having average particle size of no greater than about 200 nm, for example Nab-paclitaxel). In some embodiments, there is a method of treating melanoma (such as metastatic melanoma or metastatic malignant melanoma) in a human individual, wherein said individual comprises a mutation in BRAF (such as a V600E mutation), comprising intravenously administering (for example infusing over about 30-40 minutes) to the individual an effective amount of Nab-paclitaxel (for example about 5 mg/ml Nab-paclitaxel), wherein the dose of paclitaxel in the nanoparticle composition is about 80 to about 200 mg/m² (including for example about 90 mg/m², about 120 mg/m², or about 150 mg/m²). In some embodiments, there is a method of treating melanoma (such as metastatic melanoma or metastatic malignant melanoma) in a human individual, wherein said individual comprises a mutation in BRAF (such as a V600E mutation), comprising intravenously administering (for example infusing over about 30-40 minutes) to the individual an effective amount of Nab-paclitaxel (for example about 5 mg/ml Nab-paclitaxel), wherein the dose of paclitaxel in the nanoparticle composition is about 80 to about 200 mg/m² (including for example about 90 mg/m², about 120 mg/m², or about 150 mg/m²) on days 1, 8, 15 of every 28 day cycle. In some embodiments, there is a method of treating melanoma (such as metastatic melanoma or metastatic malignant melanoma) in a human individual, wherein said individual comprises a mutation in BRAF (such as a V600E mutation), comprising infusing over about 30-40 minutes to the individual an effective amount of Nab-paclitaxel (for example about 5 mg/ml Nab-paclitaxel), wherein the dose of paclitaxel in the nanoparticle composition is about 150 mg/m² on days 1, 8, 15 of every 28 day cycle. In some embodiments, there is a method of treating melanoma (such as metastatic melanoma or metastatic malignant melanoma) in a human individual, wherein said individual comprises a mutation in BRAF (such as a V600E mutation), comprising infusing over about 30-40 minutes to the individual an effective amount of Nab-paclitaxel (for example about 5 mg/ml Nab-paclitaxel), wherein the dose of paclitaxel in the nanoparticle composition is about 120 mg/m² on days 1, 8, 15 of every 28 day cycle. In some embodiments, there is a method of treating melanoma (such as metastatic melanoma or metastatic malignant melanoma) in a human individual, wherein said individual comprises a mutation in BRAF (such as a V600E mutation), comprising infusing over about 30-40 minutes to the individual an effective amount of Nab-paclitaxel (for example about 5 mg/ml Nab-paclitaxel), wherein the dose of paclitaxel in the nanoparticle composition is about 90 mg/m² on days 1, 8, 15 of every 28 day cycle. In some embodiments, the individual is treated for at least about 2 months, including for example at least about any of 3, 4, 5, 6, 7, 8, 9, 10, 11, or 12 months. In some embodiments, the individual has stage M1c melanoma. In some embodiments, the individual has elevated LDH level. In some embodiments, the individual is a female. In some embodiments, the individual is under about 65 years old. In some embodiments, the individual is at least about 65 years old (for example at least about any of 70, 75, or 80 years old).

In some embodiments of any of the methods described herein, the composition comprising nanoparticles comprising paclitaxel and an albumin is used as a monotherapy for treating the melanoma.

Also provided herein are methods of combination therapy comprising a therapy comprising administration of the nanoparticle compositions described herein and a second therapy. In some embodiments, the second therapy is selected from the group consisting of chemotherapy, immunotherapy, surgery, radiation therapy, targeted therapy, or a combination thereof. In some embodiments, the method comprises administration of at least one other therapeutic agent. In some embodiments, the one other therapeutic agent is a BRAF inhibitor. In some embodiments, the one other therapeutic agent is Ipilimumab. In some embodiments, the method is used as a first line therapy. In some embodiments, the method is used as a second line therapy. In some embodiments of any of the methods described herein, the composition comprising nanoparticles comprising taxane (e.g., paclitaxel) and a carrier protein (e.g., albumin) is administered intravenously. In some embodiments, the effective amount of taxane (e.g., paclitaxel) in the nanoparticle composition is about 50 mg/m² to about 400 mg/m². In some embodiments, the effective amount of taxane (e.g., paclitaxel) in the nanoparticle composition is about 100 mg/m² to about 200 mg/m². In some embodiments, the effective amount of taxane (e.g., paclitaxel) in the nanoparticle composition is about 150 mg/m². In some embodiments, the composition comprising nanoparticles comprising taxane (e.g., paclitaxel) and a carrier protein (e.g., albumin) is administered weekly. In some embodiments, the method comprises at least one 28-day treatment cycle. In some embodiments, the composition comprising nanoparticles comprising taxane (e.g., paclitaxel) and a carrier protein (e.g., albumin) is administered on days 1, 8, and 15 of the 28-day treatment cycle.

In some embodiments, the albumin is human serum albumin. In some embodiments, the albumin is human albumin. In some embodiments, the albumin is recombinant albumin. In some embodiments, the nanoparticles in the composition have an average diameter of no greater than about 200 nm. In some embodiments, the weight ratio of albumin and taxane (e.g., paclitaxel) in the nanoparticle composition is about 9:1 or less. In some embodiments, the weight ratio of albumin and taxane (e.g., paclitaxel) in the nanoparticle composition is about 9:1. In some embodiments, the taxane (e.g., paclitaxel) in the nanoparticles are coated with the albumin. In some embodiments, the taxane is paclitaxel. In some embodiments, there is provided a method of treating melanoma in an individual (e.g., human) comprising administering to the individual an effective amount of a composition comprising nanoparticles comprising paclitaxel and albumin (e.g., human albumin or human serum albumin).

The present application in some embodiments provides a method of treating melanoma in a human individual comprising administering to the individual an effective amount of a composition comprising nanoparticles comprising paclitaxel and an albumin.

In some embodiments according to (or as applied to) any of the embodiments above, the melanoma is cutaneous melanoma.

In some embodiments according to (or as applied to) any of the embodiments above, the melanoma is metastatic melanoma.

In some embodiments according to (or as applied to) any of the embodiments above, the melanoma is metastatic malignant melanoma.

In some embodiments according to (or as applied to) any of the embodiments above, the melanoma is stage IV melanoma.

In some embodiments according to (or as applied to) any of the embodiments above, the individual has distant metastases.

In some embodiments according to (or as applied to) any of the embodiments above, the metastatic melanoma is at stage M1a.

In some embodiments according to (or as applied to) any of the embodiments above, the metastatic melanoma is at stage M1b.

In some embodiments according to (or as applied to) any of the embodiments above, the metastatic melanoma is at stage M1c.

In some embodiments according to (or as applied to) any of the embodiments above, the individual has measurable disease.

In some embodiments according to (or as applied to) any of the embodiments above, the individual does not have brain metastases.

In some embodiments according to (or as applied to) any of the embodiments above, the individual has not been previously treated for melanoma.

In some embodiments according to (or as applied to) any of the embodiments above, the individual has not received prior cytotoxic chemotherapy for the metastatic malignant melanoma.

In some embodiments according to (or as applied to) any of the embodiments above, the individual has not received prior adjuvant cytotoxic chemotherapy.

In some embodiments according to (or as applied to) any of the embodiments above, the individual is a male.

In some embodiments according to (or as applied to) any of the embodiments above, the individual is a female.

In some embodiments according to (or as applied to) any of the embodiments above, the individual is under about 65 years old.

In some embodiments according to (or as applied to) any of the embodiments above, the individual is at least about 65 years old (for example at least about any of 70, 75, or 80 years old).

In some embodiments according to (or as applied to) any of the embodiments above, the individual has elevated serum lactate dehydrogenase ("LDH") level.

In some embodiments according to (or as applied to) any of the embodiments above, the individual has serum LDH of less than about 0.8× upper limit of normal ("ULN").

In some embodiments according to (or as applied to) any of the embodiments above, the individual has serum LDH at about 0.8× to about 1.1×ULN.

In some embodiments according to (or as applied to) any of the embodiments above, the individual has serum LDH of between greater than about 1.1× to about 2.0×ULN.

In some embodiments according to (or as applied to) any of the embodiments above, the melanoma comprises wild-type BRAF.

In some embodiments according to (or as applied to) any of the embodiments above, the melanoma comprises a mutation in BRAF.

In some embodiments according to (or as applied to) any of the embodiments above, the melanoma comprises a V600E mutation in BRAF.

In some embodiments according to (or as applied to) any of the embodiments above, the composition comprising nanoparticles comprising paclitaxel and an albumin is used as a monotherapy for treating the melanoma.

In some embodiments according to (or as applied to) any of the embodiments above, the method further comprises a second therapy.

In some embodiments according to (or as applied to) any of the embodiments above, the second therapy is selected from the group consisting of chemotherapy, immunotherapy, surgery, radiation therapy, targeted therapy, or a combination thereof.

In some embodiments according to (or as applied to) any of the embodiments above, the method further comprises administration of at least one other therapeutic agent.

In some embodiments according to (or as applied to) any of the embodiments above, the one other therapeutic agent is a BRAF inhibitor.

In some embodiments according to (or as applied to) any of the embodiments above, the one other therapeutic agent is Ipilimumab.

In some embodiments according to (or as applied to) any of the embodiments above, the method is used as a first line therapy.

In some embodiments according to (or as applied to) any of the embodiments above, the method is used as a second line therapy.

In some embodiments according to (or as applied to) any of the embodiments above, the composition comprising nanoparticles comprising paclitaxel and an albumin is administered intravenously.

In some embodiments according to (or as applied to) any of the embodiments above, the dose of paclitaxel in the nanoparticle composition is about 50 mg/m$^2$ to about 400 mg/m$^2$.

In some embodiments according to (or as applied to) any of the embodiments above, the dose of paclitaxel in the nanoparticle composition is about 100 mg/m$^2$ to about 200 mg/m$^2$.

In some embodiments according to (or as applied to) any of the embodiments above, the dose of paclitaxel in the nanoparticle composition is about 150 mg/m$^2$.

In some embodiments according to (or as applied to) any of the embodiments above, the composition comprising nanoparticles comprising paclitaxel and an albumin is administered weekly.

In some embodiments according to (or as applied to) any of the embodiments above, the method comprises at least one 28-day treatment cycle.

In some embodiments according to (or as applied to) any of the embodiments above, the composition comprising nanoparticles comprising paclitaxel and an albumin is administered on days 1, 8, and 15 of the 28-day treatment cycle.

In some embodiments according to (or as applied to) any of the embodiments above, the albumin is human serum albumin.

In some embodiments according to (or as applied to) any of the embodiments above, the albumin is human albumin.

In some embodiments according to (or as applied to) any of the embodiments above, the albumin is recombinant albumin.

In some embodiments according to (or as applied to) any of the embodiments above, the nanoparticles in the composition have an average diameter of no greater than about 200 nm.

In some embodiments according to (or as applied to) any of the embodiments above, the weight ratio of albumin and paclitaxel in the nanoparticle composition is about 9:1 or less.

In some embodiments according to (or as applied to) any of the embodiments above, the weight ratio of albumin and paclitaxel in the nanoparticle composition is about 9:1.

In some embodiments according to (or as applied to) any of the embodiments above, the paclitaxel in the nanoparticles are coated with the albumin.

Those skilled in the art will recognize that several embodiments are possible within the scope and spirit of this invention. The invention will now be described in greater detail by reference to the following non limiting examples. The following examples further illustrate the invention but, of course, should not be construed as in any way limiting its scope.

EXAMPLES

Example 1

A Phase 3 Study of Nab-Paclitaxel Versus Dacarbazine in Chemotherapy-Naïve Patients with Metastatic Malignant Melanoma Chemotherapy-naïve patients with stage IV cutaneous metastatic malignant melanoma were enrolled. The patients had Eastern Cooperative Oncology Group (ECOG) PS 0-1, measurable disease, and lactate dehydrogenase (LDH) levels ≤2.0× Upper Limit of Normal (ULN), and had no current brain metastases. The patient baseline characteristics are shown in Table 5. The patients were divided into two arms: (1) Nab-paclitaxel ("Nab-P," Abraxane®) 150 mg/m$^2$, intravenous, no premedication, on days 1, 8, and 15 of 28-day cycle; (2) dacarbazine (DTIC) 1000 mg/m$^2$, intravenous, on day 1 of 21-day cycle. FIG. 1 shows the phase 3 study design.

TABLE 5

Baseline Characteristics

| Variable | | Nab-paclitaxel (n = 264) | Dacarbazine (n = 265) | All Patients (N = 529) |
|---|---|---|---|---|
| Age | Median years (min, max) | 62 (21, 85) | 64 (28, 87) | 63 (21, 87) |
| Sex | Male, % | 66 | 66 | 66 |
| Region | North America, % | 44 | 44 | 44 |
| | Western Europe, % | 43 | 43 | 43 |
| | Australia, % | 13 | 13 | 13 |
| ECOG PS | 0, % | 74 | 68 | 71 |
| | 1, % | 26 | 31 | 28 |
| Metastatic stage | M1a, % | 10 | 8 | 9 |
| | M1b, % | 25 | 26 | 26 |
| | M1c, % | 65 | 66 | 65 |
| LDH category | <0.8 × ULN, % | 52 | 52 | 52 |
| | 0.8-1.1 × ULN, % | 27 | 26 | 27 |
| | >1.1-2 × ULN, % | 19 | 21 | 20 |
| BRAF Status | Known, % | 69 | 66 | 67 |
| | V600E, % | 36 | 38 | 37 |
| | Wild Type | 64 | 62 | 63 |
| Prior Therapy | Metastatic | 7 | 9 | 8 |

The primary efficacy endpoint was progression-free survival ("PFS") based on a blinded radiology assessment (according to Response Evaluation Criteria in Solid Tumors ("RECIST") v1.0). The secondary efficacy endpoint was overall survival ("OS"). Other endpoints included objective response rate ("ORR"), disease control rate ("DCR"), and safety/tolerability.

Figure 2:
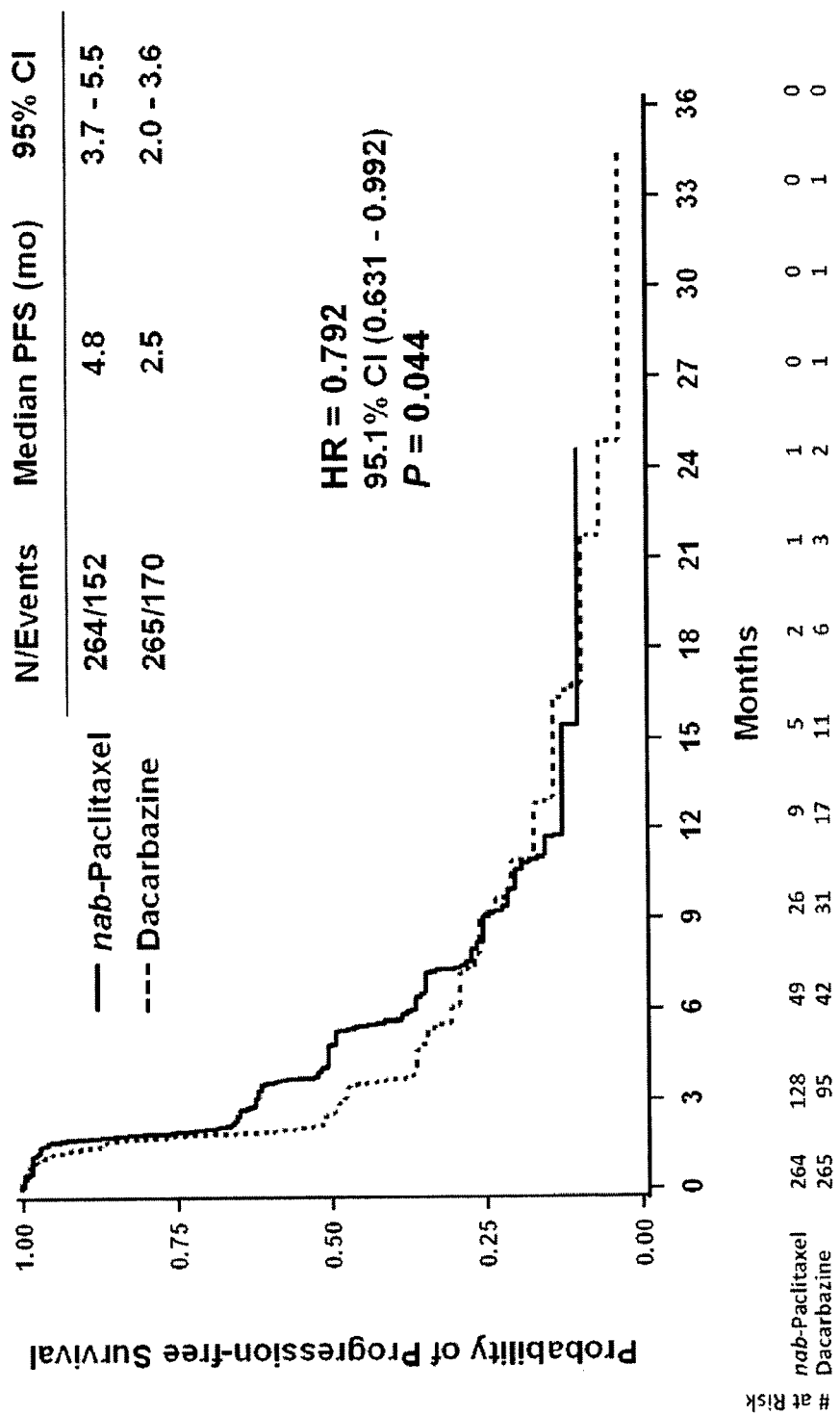
FIG. 2 shows progression free survival by independent radiology review. PFS for Nab-paclitaxel (or Abraxane®) arm: 4.8 months; PFS for dacarbazine arm: 2.5 months (P=0.044). CI, confidence interval; HR, hazard ratio.
Figure 3:
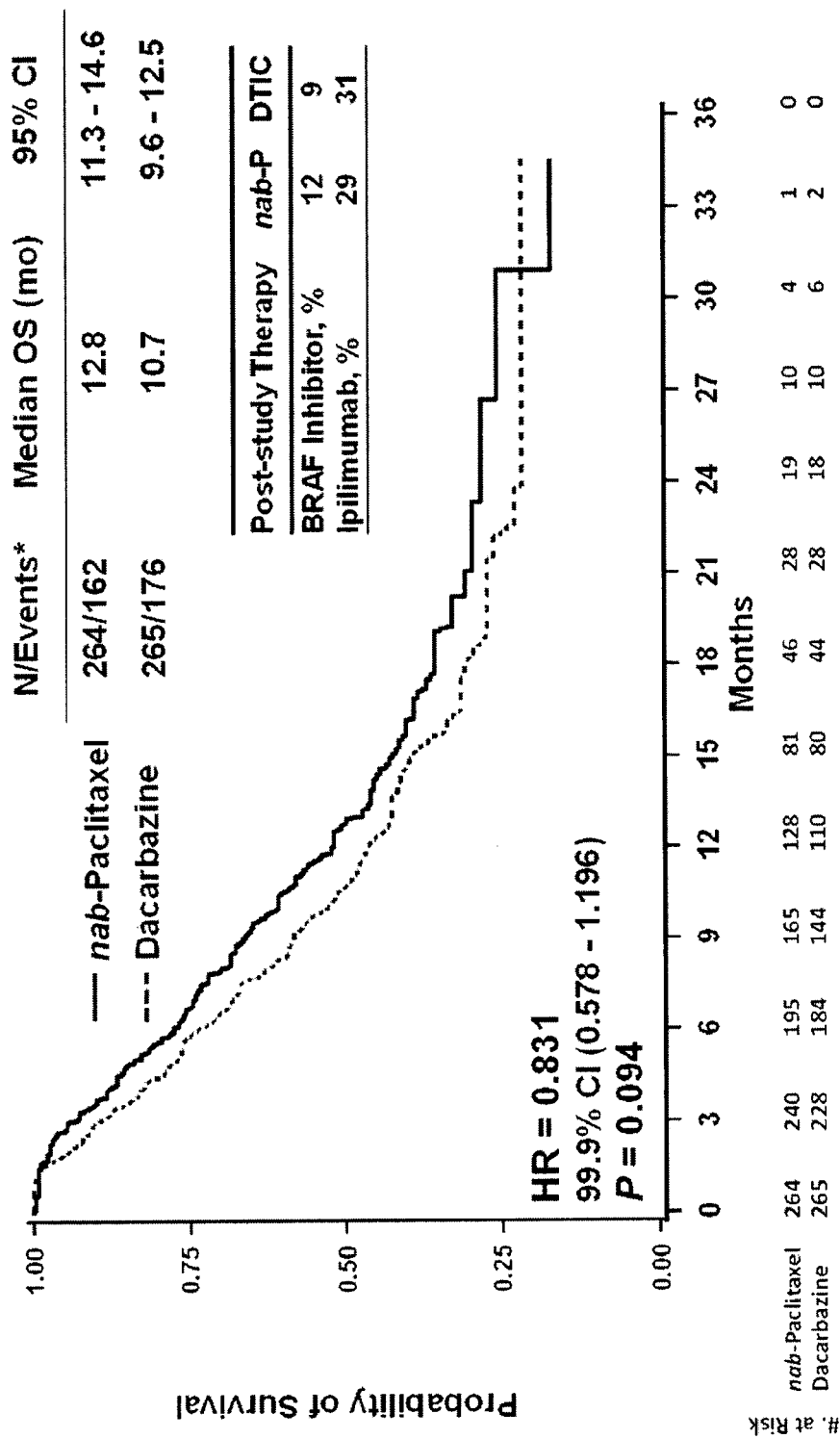
FIG. 3 shows overall survival planned interim analysis from the study. Median OS for Nab-paclitaxel (or Abraxane®) arm: 12.8 months; median OS for dacarbazine arm: 10.7 months. * indicates that at the time of PFS analysis, 64% of patients had an event.

FIG. 2 shows the PFS results of the study (PFS was conducted by independent radiology review). FIG. 3 shows the OS results of the planned interim analysis of the study. Other efficacy endpoints from the study are shown in Table 6.

TABLE 6

Other Efficacy Endpoints

| Blinded Radiology Assesment | Nab-paclitaxel (n = 264) | Dacarbazine (n = 265) | Response Rate Ratio ($P_{Nab-P}/P_{DTIC}$) | P-value |
|---|---|---|---|---|
| ORR, % | 15 | 11 | 1.305 | 0.239 |
| (95% CI) | (10.5, 19.1) | (7.5, 15.1) | (0.837, 2.035) | |
| DCR, % | 39 | 27 | 1.442 | 0.004 |
| (95% CI) | (32.8, 44.5) | (21.5, 32.1) | (1.123, 1.852) | |
| PR, % | 15 | 11 | | |
| SD ≥16 weeks, % | 24 | 15 | | |
| Best Response | | | | 0.0017* |
| PR, % | 15 | 11 | | |
| SD, % | 25 | 16 | | |
| PD, % | 35 | 48 | | |
| Not Evaluable, % | 25 | 25 | | |

*Include confirmed PR + SD + PD
P: proportion of improved patients;
PD: progressive;
PR: partial response;
SD: stable disease The PFS and interim OS analysis of the study by BRAF status is shown in Table 7.

TABLE 7

PFS and Interim OS by BRAF Status

| BRAF Status | | Nab-paclitaxel (n = 264) | Dacarbazine (n = 265) | HR (Nab-P/DTIC) | P-value |
|---|---|---|---|---|---|
| Wild Type | N | 116 | 108 | | |
| | Median PFS, months | 5.4 | 2.5 | 0.715 | 0.088 |
| | Median OS, months | 12.7 | 11.1 | 0.845 | 0.330 |
| V600E Mutation | N | 65 | 67 | | |
| | Median PFS, months | 5.3 | 3.5 | 0.883 | 0.656 |
| | Median OS, months | 16.9 | 11.2 | 0.688 | 0.132 |
| Unknown | N | 83 | 90 | | |
| | Median PFS, months | 3.7 | 2.2 | 0.684 | 0.066 |
| | Median OS, months | 11.1 | 9.9 | 0.837 | 0.381 |

Figure 4:
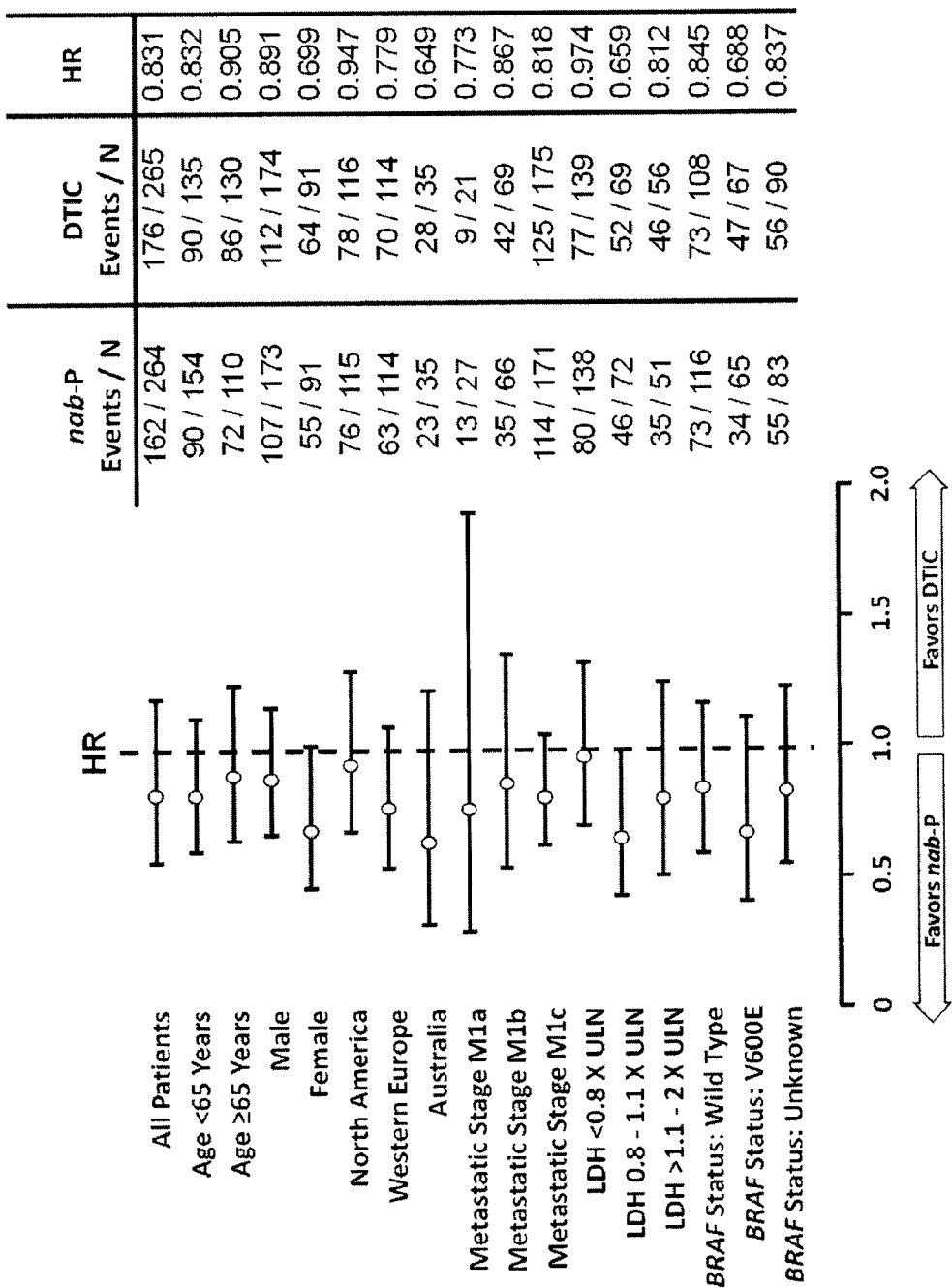
FIG. 4 shows overall survival interim analysis for specific subgroups.

FIG. 4 shows the OS interim analysis of the subgroups based on various patient characteristics. FIG. 4 shows whether a certain subgroup favors the treatment of Nab-paclitaxel versus the DTIC treatment and the extent thereof.

The adverse events from the study are shown in Table 8.

TABLE 8

Grade ≥3 Treatment-related Adverse Events (TRAEs) in ≥5% Patients

| Preferred Term | Nab-paclitaxel (n = 257) | Dacarbazine (n = 258) |
|---|---|---|
| Patients with at least 1 TRAE, % | 50 | 28 |
| Patients with at least 1 serious TRAE, % | 9 | 7 |
| Nonhematologic Adverse Events, %* | | |
| Peripheral Neuropathy** | 25 | 0 |
| Fatigue | 8 | 2 |
| Alopecia | 5 | 0 |
| Hematologic Adverse events, %* | | |
| Neutropenia | 20 | 10 |
| Leukopenia | 12 | 7 |
| Lymphocytopenia | 8 | 11 |
| Thrombocytopenia | 0 | 6 |
| Anemia | 2 | 5 |
| Neuropathy, median days | | |
| Time to Onset | 101 | — |
| Time to Improvement by 1 grade | 28 | — |
| Time to Improvement to grade ≤1 | 67 | — |

*Except for lymphocytopenia, all events P < 0.05
**All but 2 neuropathy cases were grade 3

The results showed that this study met its primary endpoint of PFS: 4.8 vs 2.5 months (P=0.044, Nab-paclitaxel vs dacarbazine). The interim OS analysis showed a trend in favor of the Nab-paclitaxel arm. Other endpoints (ORR, DCR) and subgroups showed consistent benefit in favor of the Nab-paclitaxel arm. Most notable AE was grade ≥3 neuropathy in the Nab-paclitaxel arm, which improved within a month. This study demonstrated that Nab-paclitaxel was superior to standard dacarbazine chemotherapy.

Example 2

A Phase 3 Study of Nab Paclitaxel Versus Dacarbazine in Previously Untreated Patients with Metastatic Malignant Melanoma The main purpose of this study is to compare the safety, tolerability, and anti-tumor activity of an investigational drug, Nab-paclitaxel (Abraxane®) versus dacarbazine in patients with metastatic melanoma who have not previously received chemotherapy.

Treatment arm A: Patients who receive Nab-paclitaxel would be dosed intravenously over approximately 30 minutes without steroid pre-medication and without G-CSF prophylaxis (unless modified as described below); 150 mg/m², on days 1, 8, and 15 every 4 weeks. Treatment arm B: Patients who receive dacarbazine would be dosed intravenously at 1000 mg/m² on Day 1 with steroid and antiemetic pre-medication; treatment repeated every 21 days.

The primary efficacy endpoint is progression-free survival (PFS) based on a blinded radiology assessment of response using RECIST response guidelines. The secondary outcome measures include the following: (1) patient survival as secondary efficacy endpoint; (2) progression-free survival based on investigator assessment; (3) number (%) of patients who achieve an objective confirmed complete or partial response; (4) number (%) of patients with stable disease for ≥16 weeks, or confirmed complete or partial response (i.e., total response); (5) duration of response in responding patients; (6) correlation of SPARC and other molecular biomarkers with efficacy outcomes; (7) incidence of treatment-emergent and treatment related adverse events (AEs) and serious adverse events (SAEs); (8) laboratory abnormalities; (9) nadir of myelosuppression during study drug dosing; (10) incidence of patients experiencing dose modifications, dose interruptions, and/or premature discontinuation of study drug; (11) the pharmacokinetic parameters being the maximum plasma drug concentration (Cmax), the area under the plasma concentration versus time curve (AUC and AUCinf), the half-life of the apparent terminal portion of the concentration versus time curve (T1/2), total body clearance (CL), and the volume of distribution (Vz).

The patients enrolled in the study must be 18 years or older. Both males and females are eligible for the study.

Inclusion criteria include: (1) Histologically or cytologically confirmed cutaneous malignant melanoma with evidence of metastasis (Stage IV); (2) No prior cytotoxic chemotherapy for metastatic malignant melanoma (prior treatment with kinase inhibitors or cytokines is permitted); (3) No prior adjuvant cytotoxic chemotherapy (prior adjuvant therapy with interferon, GM-CSF and/or vaccines is permitted); (4) Male or non-pregnant and non-lactating female ≥18 years of age; (5) No other current active malignancy within the past 3 years; (6) Radiographically-documented measurable disease (for example, measurable disease may refer to the presence of at least 1 radiographically documented measurable lesion.); (7) The patient has the following blood counts at Baseline: (a) ANC ≥1.5×10⁹ cells/L; (b) platelets ≥100×10⁹ cells/L; (c) Hgb ≥9 g/dL; (8) The patient has the following blood chemistry levels at Baseline: (a) AST (SGOT), ALT (SGPT) ≤2.5× upper limit of normal range (ULN) (≤5.0×ULN if hepatic metastases present); (b) total bilirubin ≤ULN; (c) creatinine ≤1.5 mg/dL; (d) LDH ≤2.0 ULNa; (9) Patient has expected survival of >12 weeks; (10) Patient has ECOG performance status 0-1; (11) Patient or his/her legally authorized representative or guardian is informed about the nature of the study, agrees to participate in the study, and signs the Informed Consent form prior to participation in any study-related activities.

Exclusion criteria include: (1) History or current evidence of brain metastases, including leptomeningeal involvement; (2) Patient has pre-existing peripheral neuropathy of NCI CTCAE Scale of Grade ≥2; (3) Prior radiation to a target lesion is permitted only if there has been clear progression of the lesion since radiation was completed; (4) Clinically significant concurrent illness; (4) Unlikely to be able to complete the study through the End of Study (EOS) visit; (5) Current enrollment in a different clinical study in which investigational therapeutic procedures are performed or investigational therapies are administered while participating in this study; (6) Serious medical factor involving any of the major organ systems such that the investigator considers it unsafe for the patient to receive an experimental research drug.

Example 3

Phase I Study of Hepatic Arterial Infusion of Nab-Paclitaxel (Abraxane®) in Patients with Metastatic Melanoma in the Liver This is an open-label, Phase I dose-escalation study to determine the response rate of metastatic melanoma to the liver when treated with Abraxane® administered via hepatic artery one day every three weeks. Secondary objectives are to determine the duration of response in the liver, survival (overall survival or progression-free survival), and safety.

Patients meeting all inclusion/exclusion criteria are enrolled in groups of 3 to 6 to receive Abraxane® infusion once every 21 days. The maximum tolerable dose is determined after two cycles of study treatment. Dose limiting toxicity is defined as: ≥grade 3 non-hematologic toxicity (or the receipt of optimal symptomatic treatment for ≥grade 3 nausea, vomiting, or diarrhea), any grade 4 transaminitis, grade 3 neutropenia with fever requiring hospitalization for parenteral antibiotics, grade 4 neutropenia lasting ≥7 days or complicated by infection, or a platelet count of <25,000/mm³. Toxicity of treatment is graded using the NCI Common Toxicity Criteria (CTC), Version 3.0. Response to therapy is measured using RECIST. Four dose levels are examined: 130 mg/m², 170 mg/m², 220 mg/m² and 285 mg/m²; these are infused via hepatic artery over 30 minutes every three weeks.

Example 4

A Phase II Study of Weekly Infusion Nab-Paclitaxel (Abraxane®) in Patients with Unresectable and Metastatic Uveal Melanoma This is a Phase II study to determine the overall response rate to single agent Nab-paclitaxel (Abraxane®) in the treatment of metastatic uveal melanoma. Secondary objectives are to determine median progression free survival and overall survival. Inclusion criteria are: (1) histologically or cytologically confirmed evidence of metastatic/unresectable uveal melanoma; (2) measurable disease, defined as at least one lesion that can be accurately measured in at least one dimension and is ≥10 mm by spiral CT scan; (3) age ≥18 years or older; (4) ECOG performance status of 0 or 1; (5) no known HIV or Hepatitis B or C; (6) normal organ/marrow function as defined by: (a) absolute neutrophil count ≥1.5×10⁹/L; (b) platelets ≥100,000×10⁹/L; (c) hemoglobin ≥9.0 gm/100 mL; (d) total bilirubin ≤1.5; (e) AST and ALT ≤2.5×ULN; (f) creatinine ≤1.8 mg/mL; (g) calcium ≤12 mg/dL when corrected for levels of serum albumin; (h) up to one prior systemic therapy. Exclusion criteria are: (1) chemotherapy or radiotherapy within 4 weeks prior to study entry; (2) simultaneous receipt of other study agents; (3) prior malignancy (except for adequately treated basal cell cancer or other cancer for which patient has been disease-free for two years); (4) serious infections or other uncontrolled medical illnesses; (5) significant psychiatric illness; (5) pregnancy; (6) peripheral neuropathy of >grade 2. Abraxane® is administered via intravenous bolus over 30 minutes at a dose of 150 mg/m² weekly for 3 of 4 weeks every 28 days.

Example 5

A Randomized Phase II Study of AB (Abraxane® Plus Bevacizumab) Versus Ipilimumab for First Line Therapy of Unresectable Stage IV Metastatic Malignant Melanoma (BRAF V600E Negative)

This is a randomized, two-arm Phase II study of the efficacy of the Abraxane® plus bevacizumab (AB) combination regimen in patients undergoing first line therapy for metastatic melanoma (BRAF V600E negative) as it compares to the current standard of care, Ipilimumab. The primary goal of this study is to assess whether the combination of Abraxane® plus bevacizumab prolongs progression-free status relative to Ipilimumab as a first line treatment in patients with unresectable stage IV melanoma. The primary endpoint is progression-free survival defined as time from randomization to the earliest documentation of progression as defined by the RECIST criteria (version 1.1) or death from any cause without the documentation of progression. The secondary endpoints include overall survival (time from randomization to death due to any cause) as well as tumor response (using RECIST criteria, v. 1.1).

Correlative goals are to examine the changes in: biomarkers of angiogenesis (Arm A) and biomarkers of immunity (Arm A and Arm B), as well as to examine the pharmacokinetics of paclitaxel when combined with bevacizumab therapy. Plasma levels of the following angiogenesis mediators are determined: angiopoietin-2, BMP-9, EGF, endoglin, endothelin-1, FGF-1, FGF-2, follistatin, G-CSF, HB-EGF, HGF, IL-8, leptin, PLGF, VEGF-A, VEGF-C, and VEGF-D. Samples of peripheral blood (pre-treatment for all cycles) are analyzed for numbers and activation status of T cells, B cells, NK cells, and dendritic cells, and peripheral blood samples are also analyzed for CD3, CD4, CD8, CD20, CD69, CD4/25, CD8/25, CD16/56, CD80, CD86, and HLA-DR.

Inclusion criteria are: (1) histologic proof of surgically unresectable stage IV malignant melanoma; (2) no prior systemic therapy for metastatic melanoma; (3) BRAF V600E wild type mutation not detected in metastatic tumor specimen; (4) measurable disease defined as at least one lesion whose longest diameter can be accurately measured as ≥2.0 cm with chest x-ray, or as ≥1.0 cm with CT scan, MRI scan, or CT component of a PET/CT scan; (5) life expectancy of ≥4 months; (6) age ≥18 years; (7) ECOG performance score of 0 or 1; (8) the following laboratory values obtained ≤14 days prior to registration or randomization: (a) ANC ≥1500 mL; (b) platelet count ≥100,000×10⁹/L; (c) hemoglobin ≥9 g/dL; (d) creatinine ≤1.5×ULN; (e) total bilirubin ≤1.5 mg/dL; (f) SGOT (AST)≤2.5×ULN; (g) absence of proteinuria at screening; (h) negative serum pregnancy test for women of childbearing potential; (i) adequate use of contraception throughout the trial and for 12 weeks after the last dose of study drug; and (j) signed informed consent.

Exclusion criteria are: (1) brain metastases per MRI or CT; (2) use of other investigational agents ≤4 weeks prior to registration; (3) use of any anti-cancer therapy ≤4 weeks prior to registration; (4) prior treatment with Ipilimumab, or taxane-based chemotherapy regimens, or agents disrupting VEGF activity or targeting VEGFR; (5) major surgical procedure, open biopsy, or significant traumatic injury ≤4 weeks prior to registration; (6) other medical conditions; (7) existence of peripheral sensory neuropathy ≥2 (from any cause); (8) palliative radiation therapy ≤2 weeks prior to randomization; (9) active or recent history of hemoptysis ≤30 days prior to registration; (10) known hypersensitivity to any of the components of Ipilimumab, bevacizumab, or Abraxane®; (11) history of inflammatory bowel disease (e.g., Crohn's ulcerative colitis); (12) patients with diagnosis of autoimmune disease, regardless of whether or not they are currently receiving treatment at the time of registration; (13); systemic use of corticosteroids ≤2 weeks prior to registration, regardless of indication.

Tables 5 and 6 describe the two arms for this study.

TABLE 5

Arm A: Abraxane ®/Bevacizumab

| Agent* | Dose | Schedule | Route | Retreatment |
|---|---|---|---|---|
| Bevacizumab | 10 mg/kg | Days 1 and 15 | IV over 90 minutes** | Every 28 days (±2 days) until progression |
| Abraxane ® | 150 mg/m² | Days 1, 8, 15 | IV over 30 minutes | |

*Drugs are administered in the order listed above. Bevacizumab is always infused first.
**Subsequent infusions of bevacizumab are administered over 60 or over 30 minutes, if tolerated.
One treatment cycle = 28 days ± 2 days.

TABLE 6

Arm B: Ipilimumab

| Drug | Dose | Schedule | Route | Retreatment |
|---|---|---|---|---|
| Ipilimumab | 3 mg/kg | Day 1 | IV over 90 minutes | Every 21 days for a maximum of 4 cycles |

One treatment cycle = 21 days ± 2 days.

Example 6

A Phase II Study of Abraxane® Plus Ipilimumab in Patients with Metastatic Melanoma This is an open-label, single-arm Phase II study to determine the efficacy and safety of Abraxane®-Ipilimumab combination administered intravenously to patients with chemotherapy naïve metastatic malignant melanoma. The primary objectives are to determine if the combination of Abraxane® and Ipilimumab can delay disease progression in patients with metastatic melanoma, and to determine the rate of progression-free survival at 6 months of the Abraxane® plus Ipilimumab combination. The secondary objectives are: (1) to determine the efficacy of the Abraxane® plus Ipilimumab combination as measured by complete and partial response rate, response duration, and overall survival in patients with metastatic unresectable stage III/IV melanoma; (2) to determine the safety of the combination of Abraxane® plus Ipilimumab when given intravenously for the treatment of patients with metastatic melanoma; and (3) to study the immunologic changes in patients who receive this therapy.

The starting dose of Abraxane® for this trial is 150 mg/m² to be administered on days 1, 8, and 15 every 28 days. Abraxane® is dosed intravenously over approximately 30 minutes without steroid premedication and without G-CSF prophylaxis. The dose of Ipilimumab for this trial is 3 mg/kg intravenously every 3 weeks for 4 doses only; this dose of Ipilimumab will not be increased.

Inclusion criteria are: (1) histologically documented diagnosis of advanced stage IV or unresectable stage III mucosal or cutaneous melanoma; (2) recurrent melanoma with measurable or evaluable sites of disease, 1.0 cm or larger, in order to assess the response to treatment by the immune-related response criteria (irRC); (3) no previous treatment with cytotoxic drugs and immunotherapeutic agents for unresectable Stage III or Stage IV disease; (4) patient is between 12 and 70 years of age with an ECOG performance status of 0 or 1; (5) normal blood counts with a white blood cell count of more than or equal to 3000/mm³, an absolute neutrophil count of more than or equal to 1500 mm³ and a platelet count of more than 100,000/mm³, hemoglobin >9.0 g/dL, no impairment of renal function (serum creatinine less than 1.1 mg/dL for females and less than 1.4 mg/dL for males), no impairment of hepatic function (serum bilirubin level of less than 1.5 mg/dL, AST and ALT ≤2.5×ULN unless there is hepatic metastasis in which case AST and ALT ≤5 ULN are acceptable), and no evidence of significant cardiac or pulmonary dysfunction; (6) no significant concurrent illness such as an active infection associated with fever lasting more than 24 hours requiring antibiotics, uncontrolled psychiatric illness, hypercalcemia (calcium greater than 11 mg), or active gastrointestinal bleeding; (7) females of child-bearing potential must use acceptable contraception and have a negative serum or urine pregnancy test within 72 hours prior to beginning treatment on this trial, and sexually active men must also use contraceptive methods for the duration of the study; (8) signed informed consent.

Exclusion criteria are: (1) metastatic uveal melanoma; (2) bone metastases only; (3) symptomatic brain or spinal cord metastases, steroid therapy or leptomeningeal disease; (4) significant cardiac illness; (5) significant impairment of pulmonary function on account of chronic bronchitis, emphysema or chronic obstructive pulmonary disease which results in impairment of vital capacity of FEV1 to less than 75% of predicted normal values; (6) symptomatic effusions on account of pleural, pericardial or peritoneal metastases of melanoma; (7) history of second malignant tumor, other than the common skin cancers—basal and squamous carcinomas—within the past 3 years; (8) ≥grade 2 sensory neuropathy at baseline.

Although the foregoing invention has been described in some detail by way of illustration and example for purposes of clarity of understanding, the descriptions and examples should not be construed as limiting the scope of the invention.

What is claimed is:

1. A method of treating melanoma in a human individual comprising administering to the individual an effective amount of a composition comprising nanoparticles comprising paclitaxel and an albumin, wherein the individual is selected for treatment based on the individual having a melanoma comprising a V600E mutation in BRAF and wherein the composition is administered intravenously and the dose of paclitaxel in the composition is about 80 mg/m² to about 200 mg/m².

2. The method of claim 1, wherein the individual is selected for treatment based on the individual having metastatic melanoma at stage M1c.

3. The method of claim 1, wherein the individual is selected for treatment based on the individual having a serum LDH level of between about 1.1× to about 2.0×ULN.

4. The method of claim 1, wherein the method further comprises a second therapy.

5. The method of claim 4, wherein the method comprises administration of at least one other therapeutic agent.

6. The method of claim 5, wherein the other therapeutic agent is a BRAF inhibitor.

7. The method of claim 5, wherein the other therapeutic agent is Ipilimumab.

8. The method of claim 1, wherein the method is used as a first line therapy.

9. The method of claim 1, wherein the method is used as a second line therapy.

10. The method of claim 1, wherein the dose of paclitaxel in the nanoparticle composition is about 150 mg/m².

11. The method of claim 1, wherein the composition comprising nanoparticles comprising paclitaxel and an albumin is administered weekly.

12. The method of claim 11, wherein the composition comprising nanoparticles comprising paclitaxel and an albumin is administered on days 1, 8, and 15 of a 28-day treatment cycle.

13. The method of claim 1, wherein the albumin is human serum albumin.

14. The method of claim 1, wherein the nanoparticles in the composition have an average diameter of no greater than about 200 nm.

15. The method of claim 1, wherein the weight ratio of albumin and paclitaxel in the nanoparticle composition is about 9:1 or less.

16. The method of claim 1, wherein the paclitaxel in the nanoparticles are coated with the albumin.

* * * * *